(12) United States Patent
Atanasio et al.

(10) Patent No.: US 11,547,101 B2
(45) Date of Patent: *Jan. 10, 2023

(54) NON-HUMAN ANIMALS HAVING A DISRUPTION IN A C9ORF72 LOCUS

(71) Applicant: Regeneron Pharmaceuticals, Inc., Tarrytown, NY (US)

(72) Inventors: Amanda Atanasio, Valhalla, NY (US); Burcin Ikiz, Santa Monica, CA (US); Guochun Gong, Pleasantville, NY (US); Michael L. Lacroix-Fralish, Yorktown Heights, NY (US); Ka-Man Venus Lai, Seattle, WA (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 852 days.

This patent is subject to a terminal disclaimer.

(21) Appl. No.: 16/366,826

(22) Filed: Mar. 27, 2019

(65) Prior Publication Data

US 2019/0216062 A1 Jul. 18, 2019

Related U.S. Application Data

(63) Continuation of application No. 15/165,307, filed on May 26, 2016, now Pat. No. 10,285,388.

(60) Provisional application No. 62/245,382, filed on Oct. 23, 2015, provisional application No. 62/232,658, filed on Sep. 25, 2015, provisional application No. 62/168,171, filed on May 29, 2015.

(51) Int. Cl.
| | |
|---|---|
| *A01K 67/027* | (2006.01) |
| *A01K 67/02* | (2006.01) |
| *C12N 15/85* | (2006.01) |
| *A61K 49/00* | (2006.01) |
| *C12N 15/90* | (2006.01) |

(52) U.S. Cl.
CPC .......... *A01K 67/0276* (2013.01); *A01K 67/02* (2013.01); *A61K 49/0008* (2013.01); *C12N 15/8509* (2013.01); *C12N 15/907* (2013.01); *A01K 2217/072* (2013.01); *A01K 2217/075* (2013.01); *A01K 2227/105* (2013.01); *A01K 2267/0318* (2013.01); *A01K 2267/0381* (2013.01); *A01K 2267/0393* (2013.01)

(58) Field of Classification Search
None
See application file for complete search history.

(56) References Cited

U.S. PATENT DOCUMENTS

| | | | |
|---|---|---|---|
| 5,670,356 A | 9/1997 | Sherf et al. | |
| 5,874,304 A | 2/1999 | Zolotukhin et al. | |
| 5,942,435 A | 8/1999 | Wheeler et al. | |
| 6,586,251 B2 | 7/2003 | Economides et al. | |
| 6,596,541 B2 | 7/2003 | Murphy et al. | |
| 7,105,348 B2 | 9/2006 | Murphy et al. | |
| 7,294,754 B2 | 11/2007 | Poueymirou et al. | |
| 7,576,259 B2 | 8/2009 | Poueymirou et al. | |
| 7,612,250 B2 | 11/2009 | Overstrom et al. | |
| 7,659,442 B2 | 2/2010 | Poueymirou et al. | |
| 8,354,389 B2 | 1/2013 | Frendewey et al. | |
| 8,518,392 B2 | 8/2013 | Frendewey et al. | |
| 8,697,359 B1 | 4/2014 | Zhang | |
| 8,697,851 B2 | 4/2014 | Frendewey et al. | |
| 10,329,582 B2 | 6/2019 | Lee et al. | |
| 10,385,359 B2 | 8/2019 | Lee et al. | |
| 10,508,289 B2 | 12/2019 | Duchateau et al. | |
| 2004/0018626 A1 | 1/2004 | Murphy et al. | |
| 2004/0177390 A1 | 9/2004 | Lewis et al. | |
| 2005/0144655 A1 | 6/2005 | Economides et al. | |
| 2006/0085866 A1 | 4/2006 | Poueymirou et al. | |
| 2008/0028479 A1 | 1/2008 | Poueymirou et al. | |
| 2008/0078000 A1 | 3/2008 | Poueymirou et al. | |
| 2008/0078001 A1 | 3/2008 | Poueymirou et al. | |

(Continued)

FOREIGN PATENT DOCUMENTS

| | | |
|---|---|---|
| WO | 1999/005266 A2 | 2/1999 |
| WO | 2002/036789 A2 | 5/2002 |

(Continued)

OTHER PUBLICATIONS

Grigg, et al. G-Quadruplex Structures Formed by Expanded Hexanucleotide Repeat RNA and DNA from the Neurodegenerative Disease-Linked C9orf72 Gene Efficiently Sequester and Activate Heme. PLOS One, 9(9): e106449, 8 pages.*

Balendra and Isaacs "C9orf72-mediated ALS and FTD: multiple pathways to disease," Nat Rev Neurol. Author manuscript; available in PMC Mar. 14, 2019. Published in final edited form as: Nat Rev Neurol. Sep. 2018; 14(9): 544-558. doi:10.1038/s41582-018-0047-2.

(Continued)

*Primary Examiner* — Christopher M Babic
*Assistant Examiner* — Kimberly A Aron
(74) *Attorney, Agent, or Firm* — Rita S. Wu; Shing-Yi Cheng; FisherBroyles, LLP

(57) ABSTRACT

A non-human animal model for neurodegenerative and/or inflammatory diseases is provided, which non-human animal comprises a disruption in a C9ORF72 locus. In particular, non-human animals described herein comprise a deletion of an entire coding sequence of a C9ORF72 locus. Methods of identifying therapeutic candidates that may be used to prevent, delay or treat one or more neurodegenerative (e.g., amyotrophic lateral sclerosis (ALS, also referred to as Lou Gehrig's disease) and frontotemporal dementia (FTD)), autoimmune and/or inflammatory diseases (e.g., SLE, glomerulonephritis) are also provided.

8 Claims, 68 Drawing Sheets
(44 of 68 Drawing Sheet(s) Filed in Color)
Specification includes a Sequence Listing.

(56) References Cited

U.S. PATENT DOCUMENTS

| | | | |
|---|---|---|---|
| 2008/0092249 | A1 | 4/2008 | Lewis et al. |
| 2009/0324559 | A1* | 12/2009 | Sakurada ............ C12N 5/0696 506/14 |
| 2010/0028931 | A1* | 2/2010 | Eggan ................... A61K 38/22 435/368 |
| 2010/0035768 | A1 | 2/2010 | Gibson et al. |
| 2013/0309670 | A1 | 11/2013 | Frendewey et al. |
| 2014/0178879 | A1 | 6/2014 | Economides et al. |
| 2014/0235933 | A1 | 8/2014 | Lee et al. |
| 2014/0309487 | A1 | 10/2014 | Lee et al. |
| 2014/0310828 | A1 | 10/2014 | Lee et al. |
| 2014/0331340 | A1 | 11/2014 | Poueymirou et al. |
| 2015/0267197 | A1 | 9/2015 | Bennett et al. |
| 2015/0376628 | A1 | 12/2015 | Schoenherr et al. |
| 2015/0376651 | A1 | 12/2015 | Frendewey et al. |
| 2016/0115486 | A1 | 4/2016 | Schoenherr et al. |
| 2016/0145646 | A1 | 5/2016 | Frendewey et al. |
| 2016/0177339 | A1 | 6/2016 | Voronina et al. |
| 2016/0273002 | A1 | 9/2016 | Duchateau et al. |
| 2016/0355796 | A1 | 12/2016 | Davidson et al. |
| 2018/0023077 | A1 | 1/2018 | Rigo |
| 2018/0094267 | A1 | 4/2018 | Heslin et al. |
| 2018/0100144 | A1 | 4/2018 | Buj Bello et al. |
| 2018/0344817 | A1 | 12/2018 | Smith et al. |
| 2019/0167814 | A1 | 6/2019 | Dion et al. |
| 2019/0167815 | A1 | 6/2019 | Holmes et al. |
| 2019/0249230 | A1 | 8/2019 | Pederson et al. |
| 2019/0270980 | A1 | 9/2019 | Ikeda et al. |

FOREIGN PATENT DOCUMENTS

| | | | |
|---|---|---|---|
| WO | 2006/044962 | A1 | 4/2006 |
| WO | 2008/017234 | A1 | 2/2008 |
| WO | 2011/020014 | A1 | 2/2011 |
| WO | 2011/020120 | A2 | 2/2011 |
| WO | 2013/030588 | A1 | 3/2013 |
| WO | 2013/041577 | A1 | 3/2013 |
| WO | 2013/163394 | A1 | 10/2013 |
| WO | 2014/062736 | A1 | 4/2014 |
| WO | 2014/130706 | | 8/2014 |
| WO | 2014/172489 | | 10/2014 |
| WO | 2015/059265 | A1 | 4/2015 |
| WO | 2015/143078 | A1 | 9/2015 |
| WO | 2015/153760 | A2 | 10/2015 |
| WO | 2015/200334 | A1 | 12/2015 |
| WO | 2015/200805 | | 12/2015 |
| WO | 2016/081923 | A2 | 5/2016 |
| WO | 2016/089692 | A1 | 6/2016 |
| WO | 2016/100819 | A1 | 6/2016 |
| WO | 2016/174056 | A1 | 11/2016 |
| WO | 2016/179112 | A1 | 11/2016 |
| WO | 2017/109757 | A1 | 6/2017 |
| WO | 2017/178590 | | 10/2017 |
| WO | 2018/078131 | | 5/2018 |
| WO | 2018/078134 | | 5/2018 |
| WO | 2018/165541 | | 9/2018 |
| WO | 2018/208972 | A1 | 11/2018 |
| WO | 2019/084140 | | 5/2019 |

OTHER PUBLICATIONS

Brevini et al., (2010) "No shortcuts to pig embryonic stem cells," Theriogenology 74:544-550.
Cao et al., (2009) "Isolation and Culture of Primary Bovine Embryonic Stem Cell Colonies by a Novel Method," Journal of Experimental Zoology, 311A:368-376.
Houdebine (2009) Methods to Generate Transgenic Animals, Genetic Engineering in Livestock, New Applications and Interdisciplinary Perspectives, Engelhard M, et al., 2009, XVI, 1 46 p. 8 illus., pp. 31-47, see p. 36.
Iyer et al., (2018) "A comparative bioinformatic analysis of C9orf72", PeerJ, 6:e4391; DOI 10.7717/peerj.4391.
Jiang et al., "Gain of toxicity from ALS/FTD-linked repeat expansions in C90RF72 is alleviated by antisense oligonucleotides targeting GGGGCC-containing RNAs," Neuron, May 4, 2016; 90(3):535-550.
Liu, et al., "C9orf72 BAC Mouse Model with Motor Deficits and Neurodegenerative Features of ALS/FTD," Neuron, May 4, 2016, 90:521-534.
Paris and Stout (2010) "Equine embryos and embryonic stem cells: Defining reliable markers of pluripotency," Theriogenology 74:516-524.
Peters, et al., "Expression of human C90RF72 hexanucleotide expansion reproduces RNA foci and dipeptide repeat proteins but not neurodegeneration in BAC transgenic mice," Neuron, Dec. 2, 2015, 88(5):902-909.
Tong, et al., "Production of p53 gene knockout rats by homologous recombination in embryonic stem cells," Nature, 467(7312):211-213 (Sep. 9, 2010).
Statement of Relatedness under MPEP 2001.06 with Respect to U.S. Appl. No. 16/366,826 dated Oct. 25, 2019.
Buchman V. et al., "Simultaneous and independent detection of C90RF72 alleles with low and high No. of GGGGCC repeats using an optimised protocol of Southern blot hybridisation," Molecular Neurodegeneration, 8:12 (2013) (6 pages).
Picher-Martel, et al. "From animal models to human disease: a genetic approach for personalized medicine in ALS," Acta Neuropathologica Communications, (2016) 4:70 (29 pages).
Statement of Relatedness under MPEP 2001.06 with Respect to U.S. Appl. No. 16/366,826 dated Jan. 12, 2021.
Abramycheva, et al., "C90RF72 hexanucleotide repeat expansion in ALS patients from the Central European Russia population," Neurobiology of Aging, 36(10):2908:e5-e9, (2015).
Abugable, et al., "DNA repair and neurological disease: From molecular understanding to the development of diagnostics and model organisms," DNA Repair (Amst.), 81:102669, 13 pages (2019).
Arogundade, et al., "Antisense RNA foci are associated with nucleoli and TDP-43 mislocalization in C9orf72-ALS/FTD: a quantitative study," Acta Neuropathologica, 137(3):527-530 (2019).
Barthold, "Genetically altered mice: phenotypes, no phenotypes, and Faux phenotypes," Genetica, 122(1):75-88 (2004).
Birling, et al., "Modeling human disease in rodents by CRISPR/Cas9 genome editing," Mamm. Genome, 28(7-8):291-301 (2017).
Brevini, et al., "Porcine embryonic stem cells: Facts, challenges and hopes," Theriogenology, 68 Suppl. 1:S206-S213 (2007).
Brown et al., "Amyotrophic Lateral Sclerosis," The New England Journal of Medicine, 377(2):162-172 (2017).
Chang et al., "Non-homologous DNA end joining and alternative pathways to double-strand break repair," Nat. Rev. Mol. Cell Biol.,18(8):495-506 (2017).
Clark, et al., "A future for transgenic livestock," Nat. Rev. Genet., 4(10):825-833 (2003).
Cleary et al., "Improved PCR based methods for detecting C9orf72 hexanucleotide repeat expansions," Mol. Cell. Probes, 30(4):218-224 (2016).
Conlon et al., "The C90RF72 Ggggcc expansion forms RNA G-quadruplex inclusions and sequesters hnRNP H to disrupt splicing in ALS brains," eLife, 5:e17820, 28 pages, (2016).
Engle, Sandra J., "Utilizing iPSC for Target Discovery in CNS," Biogen, Predict 3D, Sep. 5-6, 2019, Boston, MA, 22 pages.
Genoway, "Humanized Mouse Model," retrieved from https://www.genoway.com/services/customized-mouse/knockin models/humanisation.htm on May 12, 2018.
Gomez, et al., "Derivation of cat embryonic stem-like cells from in vitro-produced blastocysts on homologous and heterologous feeder cells," Theriogenology, 74(4): 498-515 (2010).
Graham, et al., "Resources for the design of CRISPR gene editing experiments," Genome Biol., 16:260, (2015).
Harari, et al., "Bridging the Species Divide: Transgenic Mice Humanized for Type-I Interferon Response," PLoS ONE, 9(1): e84259, (2014).
Hukema et al., "Retraction Note to: A new inducible transgenic mouse model for C9orf72-associated GGGGCC repeat expansion supports a gain-of-function mechanism in C9orf72-associated ALS and FTD," Acta Neuropathologica Communications, 4(1):129, (2016).

(56) References Cited

OTHER PUBLICATIONS

Jean, et al., "Pluripotent genes in avian stem cells," Dev. Growth Differ., 55(1): 41-51, (2013).
Kawamata, et al., "Generation of genetically modified rats from embryonic stem cells," Proc. Natl. Acad. Sci. U.S.A., 7(32):14223-14228, (2010).
Kumar, et al., "Transgenic Mouse Technology: Principles and Methods," Methods Mol. Biol., 590:335-362, (2009).
La Spada et al., "Repeat expansion disease: Progress and puzzles in disease pathogenesis," Nat Rev Genet., 11(4):247-258, (2010).
McMurray, "Mechanisms of trinucleotide repeat instability during human development," Nat. Rev. Genet., 11(11):786-799, (2010).
Mullins, et al., "Transgenesis in the rat and larger mammals," J. Clin. Invest. 97(7):1557-1560, (1996).
Munoz, et al., "Conventional pluripotency markers are unspecific for bovine embryonicderived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75 (1998).
Paulson, "Chapter 9: Repeat expansion diseases," Handbook of Clinical Neurology, 147:105-123, (2018).
Peters, et al., "Human C9ORF72 hexanucleotide expansion reproduces RNA foci and dipeptide repeat proteins but not neurodegeneration in BAC transgenic mice," Neuron, Dec. 2, 2015, 88(5):902-909.
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Schludi et al., "Distribution of dipeptide repeat proteins in cellular models and C9orf72 mutation cases suggests link to transcriptional silencing," Acta Neuropathol., 130(4):537-555, (2015).
Schludi et al., "Erratum to: Distribution of dipeptide repeat proteins in cellular models and C9orf72 mutation cases suggests link to transcriptional silencing," Acta Neuropathol., 130(4):557-558, (2015).
Sigmund, "Viewpoint: Are Studies in Genetically Altered Mice Out of Control?," Arterioscler. Thromb. Vasc. Biol., 20(6):1425-1429, (2000).
Traynor et al., "Special Issue on amyotrophic lateral sclerosis," Exp. Neurol., 262 Pt B:73-74, (2014).
Van Der Zee, et al., "A pan-European study of the C9orf72 repeat associated with FTLD: geographic prevalence, genomic instability, and intermediate repeats," Hum. Mutat., 34(2):363-373, (2013).
Wakchaure, et al., "Transgenic Animals: A Review on its Various Dimensions and Applications in Animal Biotechnology," International Journal of Emerging Technology and Advanced Engineering, 5(11):210-213, (2015).
WIPO Application No. PCT/US2019/066317, PCT International Search Report and Written Opinion of the International Searching Authority dated Mar. 11, 2020.
Statement of Relatedness under MPEP 2001.06 with Respect to U.S. Appl. No. 16/366,826 dated Apr. 1, 2020.
Adams, et al., "A genome-wide, end-sequenced 129Sv BAC library resource for targeting vector construction," Genomics, 86:753-758 (2005).
Almeida S. et al., "Modeling Key Pathological Features of Frontotemporal Dementia with C9ORF72 Repeat Expansion in iPSC-Derived Human Neurons", Acta Neuropathol 126:385-399 (2013).
Altschul, et al., "Basic Local Alignment Search Tool," J. Mol. Biol., 215(3): 403-410 (1990).
Altschul, et al., "Local Alignment Statistics," Methods in Enzymology 460-480 (1997).
Altschul, et al., "Gapped BLAST and PSI-BLAST: a new generation of protein database search programs," Nucleic Acids Res., 25(17):3389-3402 (1997).
Angrand, et al., "Simplified generation of targeting constructs using ET recombination," Nucleic Acids Res. 27(17):e16 (1999).
Atanasio A. et al., "C9orf72 Ablation Causes Immune Dysregulation Characterized by Leukocyte Expansion, Autoantibody Production, and Glomerulonephropathy in Mice", Nature 6:23204 (14 pages) (2016).
Atanasio A. et al., "C9orf72 Ablation Causes Immune Dysregulation Characterized by Leukocyte Expansion, Autoantibody Production, and Glomerulonephropathy in Mice", Nature 6:23204 (11 pages), Supplemental Material (2016).
Atkinson R.A.K. et al., "C9ORF72 Expression and Cellular Localization Over Mouse Development", Acta Neuropathologica Communications 3:59 (11 pages) (2015).
Auerbach, et al., "Establishment and Chimera Analysis of 129/SvEv- and C57BL/6-Derived Mouse Embryonic Stem Cell Lines," Biotechniques 29(5):1024-1032 (2000).
Bacchetti, et al., "Transfer of the gene for thymidine kinase to thymidine kinase-deficient human cells by purified herpes simplex viral DNA," Proc. Natl. Acad. Sci. USA 74(4): 1590-1594 (1977).
Beck, et al. "Nucleotide sequence and exact localization of the neomycin phosphotransferase gene from transposon Tn5," Gene 19(3):327-336 (1982).
Bertram "MATra—Magnet Assisted Transfection: Combining Nanotechnology and Magnetic Forces to Improve Intracellular Delivery of Nucleic Acids," Current Pharmaceutical Biotechnology 7(4):277-285 (2006).
Bieniek K.F. et al., "Expanded C9ORF72 Hexanucleotide Repeat in Depressive Pseudodementia", JAMA Neurology 71(6):775-781 (Jun. 2014).
Burberry A. et al., "Loss-of-Function Mutations in the C9ORF72 Mouse Ortholog Cause Fatal Autoimmune Disease", 8(347):1-12 (Jul. 13, 2016).
Chan et al., "RNA-mediated pathogenic mechanism in polyglutamine diseases and amyotrophic lateral sclerosis," Frontiers in Cellular Neuroscience, 8:Figure 6 (2014).
Chew J. et al., "C9ORF72 Repeat Expansions in Mice Cause TDP-43 Pathology, Neuronal Loss, and Behavioral Deficits", Science 348(6239):1151-1154 (Jun. 2015).
Ciura S. et al., "Loss of Function of C9ORF72 Causes Motor Deficits in a Zebrafish Model of Amyotrophic Lateral Sclerosis", Ann Neurol 74:180-187 (Aug. 2013).
Dechiara, et al., "Producing Fully ES Cell-Derived Mice from Eight-Cell Stage Embryo Injections," Methods Enzymol. 476:285-294 (2010).
Dechiara, et al., "VelociMouse: Fully ES Cell-Derived F0-Generation Mice Obtained from the Injection of ES Cells into Eight-Cell-Stage Embryos," Methods Mol. Biol. 530:311-324 (2009).
Dejesus-Hernandez M. et al., "Expanded GGGGCC Hexanucleotide Repeat in Noncoding Region of C9ORF72 Causes Chromosome 9p-Linked FTD and ALS", Neuron 72:245-256 (Oct. 20, 2011).
Dennis (2002) "Welfare issues of genetically modified animals," ILAR Journal, 43(2):100-109.
Egawa, et al., "Drug Screening for ALS Using Patient-Specific Induced Pluripotent Stem Cells," Science Translational Medicine, 4(145):145ra104-145ra104Figures 1-4 (2012).
Farg M.A. et al., "C9ORF72, Implicated in Amytrophic Lateral Sclerosis and Frontotemporal Dementia, Regulates Endosomal Trafficking," Human Molecular Genetics 23(13):3579-3595 (2014).
Festing, et al., "Revised nomenclature for strain 129 mice," Mammalian Genome 10:836 (1999).
Frendewey, et al., "The Loss-of-Allele Assay for ES Cell Screening and Mouse Genotyping," Methods Enzymol., 476:295-307 (2010).
GenBank Accession No. NM_145005.6 (5 pages) (Jul. 9, 2016).
GenBank Accession No. NP_659442.2 (3 pages) (Jul. 9, 2016).
GenBank Accession No. NM_018325.4 (5 pages) (Jul. 9, 2016).
GenBank Accession No. NP_060795.1 (3 pages) (Jul. 9, 2016).
GenBank Accession No. NH_001256054.2 (5 pages) (Jul. 9, 2016).
GenBank Accession No. NP_001242983.1 (3 pages) (Jul. 9, 2016).
GenBank Accession No. NM_001081343.1 (4 pages) (Dec. 12, 2015).

(56) References Cited

OTHER PUBLICATIONS

GenBank Accession No. NP_001074812.1 (2 pages) (Dec. 12, 2015).
GenBank Accession No. NM_001007702.1 (3 pages) (Aug. 10, 2014).
GenBank Accession No. NP_001007703.1 (2 pages) (Aug. 10, 2014).
Gibson, et al. "Enzymatic assembly of DNA molecules up to several hundred kilobases," Nature Methods 6(5): 343-345 (2009).
Gill, et al., "No Benefit from Chronic Lithium Dosing in a Sibling-Matched, Gender Balanced, Investigator-Blinded Trial Using a Standard Mouse Model of Familial ALS," PLoS ONE, 4(8):e6489 (2009).
Gonnet, et al., "Exhaustive Matching of the Entire Protein," Science, 256:1443-1445.
Graham, et al., "A New Technique for the Assay of Infectivity of Human Adenovirus 5 DNA," Virology, 52(2): 456-467 (1973).
Heutink P. et al., "C9orf72; Abnormal RNA Expression is the Key", Experimental Neurology 262:102-110 (Dec. 2014).
Hu, et al., "Recognition of c9orf72 Mutant RNA by Single-Stranded Silencing RNAs," Nucleic Acid Therapeutics, 2017, 27(2):87-94 DOI: 10.1089/nat.2016.0655.
Hukema R.K. et al., "A New Inducible Transgenic Mouse Model for C9orf72-Associated GGGGCC Repeat Expansion Supports a Gain-of-Function Mechanism in C9orf72-Associated ALS and FTD", Acta Neuropathologica Communications 2:166 (4 pages) (2014).
Koppers M. et al., "C9orf72 Ablation in Mice Does Not Cause Motor Neuron Degeneration or Motor Deficits", Ann Neurol 78(3):426-438 (2015).
Lagier-Tourenne C. et al., "Targeted Degradation of Sense and Antisense C9orf72 RNA Foci as Therapy for ALS and Frontotemporal Degeneration", PNAS, pp. E4530-E4539 (Oct. 29, 2013).
Lakso, et al., "Targeted oncogene activation by site-specific recombination in transgenic mice," Proc. Natl. Acad. Sci. USA, 89:6232-6236 (1992).
Liu, et al., "c9orf72 Disease-Related Foci are Each Composed of One Mutant Expanded Repeat RNA," Cell Chemical Biology, 24:141-148, (2017) http://dx.doi.org/10.1016/j.chembiol.2016.12.018.
Majounie E. et al., "Frequency of the C9orf72 Hexanucleotide Repeat Expansion in Patients With Amyotrophic Lateral Sclerosis and Frontotemporal Dementia: A Cross-Sectional Study", Lancet Neurology 11:323-330 (Apr. 2012).
Menalled, et al., "Knock-In Mouse Models of Huntington's Disease," Journal of the American Society for Experimental NeuroTherapeutics, 2(3):465-470 (2005).
Meyer, et al., "Gene targeting by homologous recombination in mouse zygotes mediated by zinc-finger nucleases," PNAS, 107(34):15022-15026 (2010).
Meyer, et al., "Modeling disease mutations by gene targeting in one-cell mouse embryos," PNAS, 109(24):9354-9359 (2012).
Mori K. et al., "The C9orf72 GGGGCC Repeat is Translated into Aggregating Dipeptide-Repeat Proteins in FTLD/ALS", Science 339(6125):1335-1338 (Mar. 15, 2013).
Muller U., "Ten Years of Gene Targeting: Targeted Mouse Mutants, from Vector Design to Phenotype Analysis", Mechanisms of Development 82:3-21 (1999).
Muyrers, et al., "Rapid modification of bacterial artificial chromosomes by ET-recombination," Nucleic Acids Res. 27(6):1555-1557 (1999).
Narayanan, et al., "Efficient and precise engineering of a 200 kb b-globin human/bacterial artificial chromosome in *E. coli* DH10B using an inducible homologous recombination system," Gene Ther., 6:442-447 (1999).
O'Gorman, et al., "Recombinase-mediated gene activation and site-specific integration in mammalian cells," Science 251(4999):1351-1355 (1991).
O'Rourke, et al., "C9orf72BAC Transgenic Mice Display Typical Pathologic Features of ALS/FTD," Neuron, 88(5):892-901 (2015).
O'Rourke J.G. et al., "C9orf72 is Required for Proper Macrophage and Microglial Function in Mice", Science 351 (6279):1324-1329 (Mar. 18, 2016).
O'Rourke J.G. et al., "C9orf72 is Required for Proper Macrophage and Microglial Function in Mice", Science 351 (6279):1324-1329, Supplementary Materials (24 pages) (2016).
Panda S.K. et al., "Highly Efficient Targeted Mutagenesis in Mice Using TALENs", Genetics 195:703-713 (Nov. 2013).
Panda S.K. et al., "Highly Efficient Targeted Mutagenesis in Mice Using TALENs", Genetics 195:703-713, Supporting Information (15 pages) (2013).
Picher-Martel, et al., "From animal models to human disease: a genetic approach for personalized medicine in Als," ATA Neuropathological Communications, 4(1):Table 5 (2016).
Poueymirou, et al., "F0 generation mice fully derived from gene-targeted embryonic stem cels allowing immediate phenotypic analysis," Nat. Biotechnol. 25:91-99 (2007).
Pribadi, et al., "CRISPR-Cas9 targeted deletion of the C9orf72 repeat expansion mutation corrects cellular phenotypes in patient-derived iPS cells," BioRXiv, pp. 13-14; figure 1 (2016) https://www.biorxiv.org/content/biorxiv/early/2016/05/02/051193.full.pdf (retrieved on Nov. 28, 2017).
Renton A.E. et al., "A Hexanucleotide Repeat Expansion in C9ORF72 is the Cause of Chromosome 9p21-Linked ALS-FTD", Neuron 72:257-268 (Oct. 20, 2011).
Renton, et al., "State of play in amyotrophic lateral sclerosis genetics," Nature Neuroscience, 17(1):17-23 (2014).
Robberecht W. et al., "The Changing Scene of Amyotrophic Lateral Sclerosis", Nature Reviews. Neuroscience 14(4):248-264 (Mar. 6, 2013).
Roberson E.D. et al., "Mouse Models of Frontotemporal Dementia", Ann Neurol. 72(6):837-849 (Dec. 2012).
Santerre, et al., "Expression of prokaryotic genes for hygromycin B and G418 resistance as dominant-selection markers in mouse L cells," Gene, 30(1-3):147-156 (1984).
Skarnes W.C. et al., "A Conditional Knockout Resource for the Genome-Wide Study of Mouse Gene Function", Nature 474(7351):337-342 (2011).
Stepto A. et al., "Modelling C9ORF72 Hexanucleotide Repeat Expansion in Amyotrophic Lateral Sclerosis and Frontotemporal Dementia", Acta Neuropathol 127:377-389 (2014).
Suda et al., (1987) "Mouse Embryonic Sterm Cells Exhibit Indefinite Proliferative Potential," Journal of Cellular Physiology, 133:197-201.
Sudria-Lopez E. et al., "Full Ablation of C9orf72 in Mice Causes Immune-System-Related Pathology and Neoplastic Events but no Motor Neuron Defects", Acta Neuropathologica 132(1):145-147 (2016).
Suzuki N. et al., "The Mouse C9ORF72 Ortholog is Enriched in Neurons Known to Degenerate in ALS and FTD" Nat Neurosci. 16(12):1725-1727 (Dec. 2013).
Thys, et al., "DNA Replication Dynamics of the GGGGCC Repeat of the C9orf72 Gene," Journal of Biological Chemistry, 290(48):28953-28962 (2015).
Valenzuela, et al., "High-throughput engineering of the mouse genome coupled with high-resolution expression analysis," Nature Biotech., 21(6):652-659 (2003).
Van Blitterswijk M. et al., "Genetic Modifiers in Carriers of Repeat Expansions in the C9ORF72 Gene", Molecular Neurodegeneration 9:38 (10 pages) (2014).
Waite A.J. et al., "Reduced C9orf72 Protein Levels in Frontal Cortex of Amyotrophic Lateral Sclerosis and Frontotemporal Degeneration Brain With the C9ORF72 Hexanucleotide Repeat Expansion", Neurobiology of Aging 35:1779.e5-1779.e13 (2014).
Xu Z. et al., "Expanded GGGGCC Repeat RNA Associated With Amyotrophic Lateral Sclerosis and Frontotemporal Dementia Causes Neurodegeneration", PNAS 110(19):7778-7783 (May 7, 2013).
Yang, et al., "Homologous recombination based modification in *Escherichia coli* and germline transmission in transgenic mice of a bacterial artificial chromsome," Nat. Biotechnol., 15:859-865 (1997).
Yu, et al., "An efficient recombination system for chromosome engineering in *Escherichia coli*" Proc. Natl. Acad. Sci. U.S.A. 97(11):5978-5983 (2000).

(56) References Cited

OTHER PUBLICATIONS

Zaias J. et al., "Reference Values for Serum Proteins of Common Laboratory Rodent Strains", Journal of American Association for Laboratory Animal Science 48(4):387-390 (Jul. 2009).

Zhang, et al., "A new logic for DNA engineering using recombination in *Escherichia coli*," Nat. Genet., 20:123-128 (1998).

Zhou et al., (2009) "Developing tTA transgenic rats for inducible and reversible gene expression," International Journal of Biological Sciences, 5:171-181.

International Search Report and Written Opinion dated Aug. 22, 2016 received in International Application No. PCT/US2016/034304.

International Search Report and Written Opinion with respect to PCT/US2017/054551 dated Dec. 11, 2017.

Statement of Relatedness under MPEP Jun. 2001 with Respect to U.S. Appl. No. 16/366,826 dated Jun. 30, 2022.

\* cited by examiner

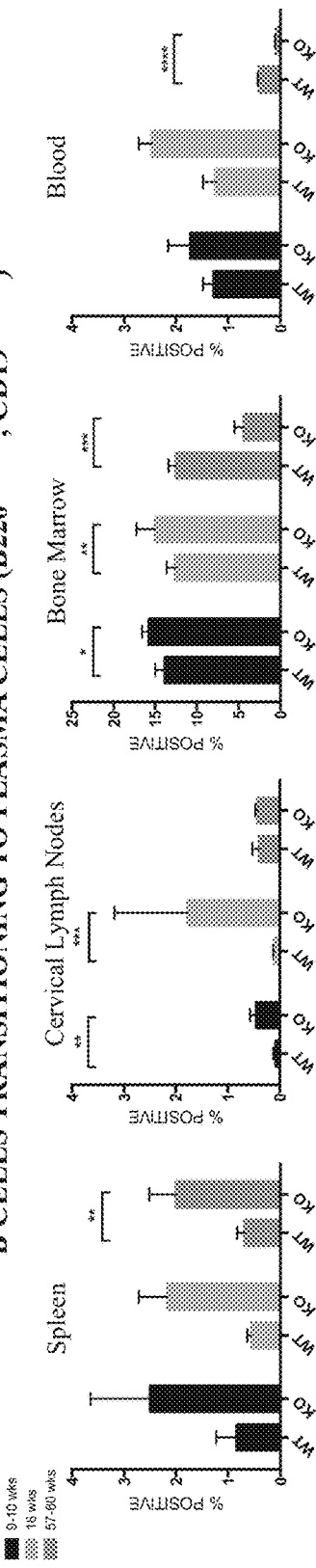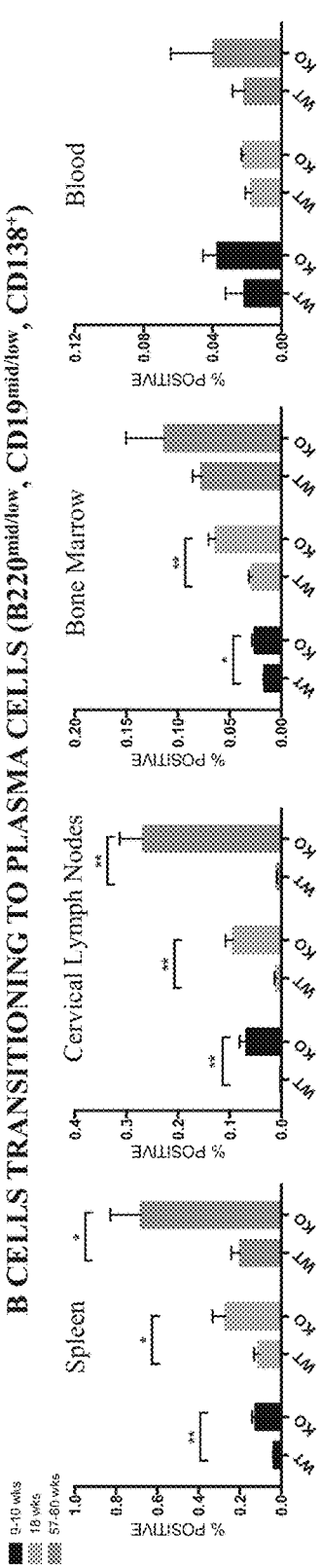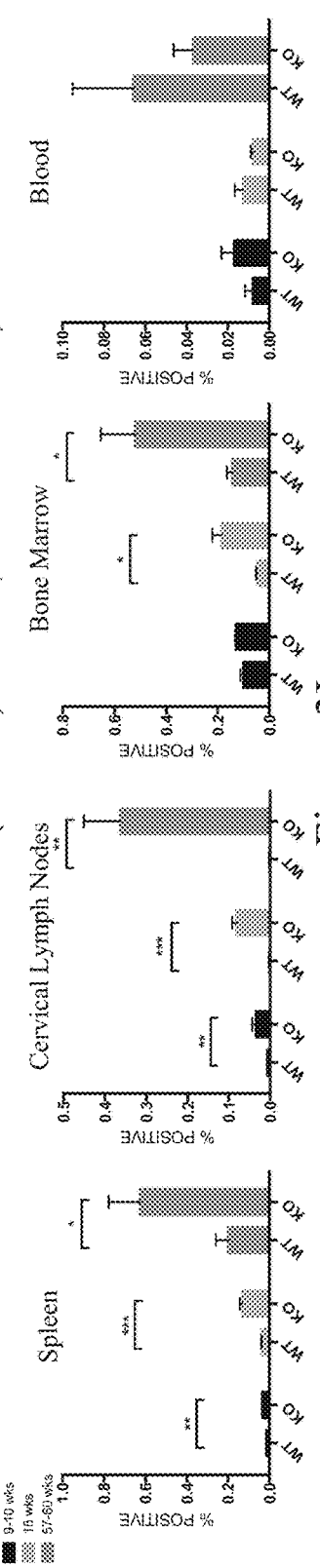
Figure 31

| Genotype | Age (wks) | Membranoproliferative Glomerulonephritis | Interstitial Mononuclear Inflammation | Hyaline Cast | Glomerulosclerosis | Basophilic Tubules |
|---|---|---|---|---|---|---|
| WT | 38 | 0 | 0 | 0 | 0 | 0 |
| WT | 38 | 0 | 0 | 0 | 0 | 0 |
| WT | 40 | 0 | 0 | 0 | 0 | 0 |
| WT | 63 | 0 | 0 | 1 | 0 | 0 |
| WT | 63 | 0 | 0 | 0 | 0 | 0 |
| WT | 63 | 0 | 0 | 1 | 0 | 0 |
| WT | 63 | 0 | 0 | 0 | 0 | 0 |
| WT | 61 | 0 | 0 | 1 | 0 | 0 |
| C9orf72-/- | 38 | 1 | 0 | 0 | 0 | 1 |
| C9orf72-/- | 38 | 2 | 2 | 3 | 2 | 2 |
| C9orf72-/- | 37 | 4 | 0 | 0 | 0 | 0 |
| C9orf72-/- | 37 | 1 | 3 | 3 | 1 | 3 |
| C9orf72-/- | 37 | 3 | 0 | 0 | 0 | 0 |
| C9orf72-/- | 35 | 1 | 0 | 1 | 0 | 0 |
| C9orf72-/- | 63 | 1 | 0 | 0 | 0 | 0 |
| C9orf72-/- | 63 | 2 | 3 | 3 | 3 | 0 |
| C9orf72-/- | 61 | 3 | 0 | 1 | 0 | 1 |
| C9orf72-/- | 61 | 2 | 0 | 0 | 0 | 0 |
| C9orf72-/- | 61 | 3 | 0 | 1 | 0 | 0 |

Figure 9B

```
                              SEQUENCE LISTING

<160> NUMBER OF SEQ ID NOS: 9

<210> SEQ ID NO 1
<211> LENGTH: 3198
<212> TYPE: DNA
<213> ORGANISM: Mus musculus

<400> SEQUENCE: 1
gtgtccgggg cggggcggtc ccggggcggg gcccggagcg ggctgcggtt gcggtccctg       60
cgccggcggt gaaggcgcag cagcggcgag tggctattgc aagcgttcgg ataatgtgag      120
acctggaatg cagtgagacc tgggatgcag ggatgtcgac tatctgcccc ccaccatctc      180
ctgctgttgc caagacagag attgctttaa gtggtgaatc acccttgttg gcggctacct      240
ttgcttactg ggataatatt cttggtccta gagtaaggca tatttgggct ccaaagacag      300
accaagtgct tctcagtgat ggagaaataa cttttcttgc caaccacact ctaaatggag      360
aaattcttcg aaatgcagag agtggggcta tagatgtaaa atttttttgtc ttatctgaaa      420 aagggggtaat tattgtttca ttaatcttcg acggaaactg gaatggagat cggagcactt      480
atggactatc aattatactg ccgcagacag agctgagctt ctacctccca cttcacagag      540
tgtgtgttga caggctaaca cacattattc gaaaaggaag aatatggatg cataaggaaa      600
gacaagaaaa tgtccagaaa attgtcttgg aaggcacaga gaggatggaa gatcagggtc      660
agagtatcat tcccatgctt actggggaag tcattcctgt aatggagctg cttgcatcta      720
tgaaatccca cagtgttcct gaagacattg atatagctga tacagtgctc aatgatgatg      780
acattggtga cagctgtcac gaaggctttc ttctcaatgc catcagctca cacctgcaga      840
cctgtggctg ttccgttgta gttggcagca gtgcagagaa agtaaataag atagtaagaa      900
cgctgtgcct ttttctgaca ccagcagaga ggaaatgctc caggctgtgt gaagcagaat      960
cgtcctttaa gtacgaatcg ggactctttg tgcaaggctt gctaaaggat gcaacaggca     1020
gttttgtcct acccttccgg caagttatgt atgcccgta ccccaccacg cacattgatg     1080
tggatgtcaa cactgtcaag cagatgccac cgtgtcatga acatatttat aatcaacgca     1140
gatacatgag gtcagagctg acagccttct ggagggcaac ttcagaagag gacatggcgc     1200
aggacaccat catctacaca gatgagagct tcactcctga tttgaatatt ttccaagatg     1260
tcttacacag agacactcta gtgaaagcct tcctggatca ggtcttccat ttgaagcctg     1320
gcctgtctct caggagtact ttccttgcac agttcctcct cattcttcac agaaaagcct     1380
tgacactaat caagtacatc gaggatgata cgcagaaggg gaaaaagccc tttaagtctc     1440
ttcggaacct gaagatagat cttgatttaa cagcagaggg cgatcttaac ataataatgg     1500
ctctagctga gaaaattaag ccaggcctac actctttcat ctttgggaga cctttctaca     1560
ctagtgtaca agaacgtgat gttctaatga ccttttgacc gtgtggtttg ctgtgtctgt     1620
```

```
ctcttcacag tcacacctgc tgttacagtg tctcagcagt gtgtgggcac atccttcctc    1680
ccgagtcctg ctgcaggaca gggtacacta cacttgtcag tagaagtctg tacctgatgt    1740
caggtgcatc gttacagtga atgactcttc ctagaataga tgtactcttt tagggcctta    1800
tgtttacaat tatcctaagt actattgctg tcttttaaag atatgaatga tggaatatac    1860
acttgaccat aactgctgat tggtttttg ttttgttttg tttgttttct tggaaactta    1920
tgattcctgg tttacatgta ccacactgaa accctcgtta gctttacaga taaagtgtga    1980
gttgacttcc tgcccctctg tgttctgtgg tatgtccgat tacttctgcc acagctaaac    2040
attagagcat ttaaagtttg cagttcctca gaaaggaact tagtctgact acagattagt    2100
tcttgagaga agacactgat agggcagagc tgtaggtgaa atcagttgtt agcccttcct    2160
ttatagacgt agtccttcag attcggtctg tacagaaatg ccgaggggtc atgcatgggc    2220
cctgagtatc gtgacctgtg acaagttttt tgttggttta ttgtagttct gtcaaagaaa    2280
gtggcatttg ttttataat tgttgccaac ttttaaggtt aattttcatt attttttgagc    2340 cgaattaaaa tgcgcacctc ctgtgccttt cccaatcttg gaaaatataa tttcttggca    2400
gagggtcaga tttcagggcc cagtcacttt catctgacca cccttttgcac ggctgccgtg    2460 tgcctggctt agattagaag tccttgttaa gtatgtcaga gtacattcgc tgataagatc    2520
tttgaagagc agggaagcgt cttgcctctt cctttggtt tctgcctgta ctctggtgtt    2580
tcccgtgtca cctgcatcat aggaacagca gagaaatctg acccagtgct attttttctag    2640 gtgctactat ggcaaactca agtggtctgt ttctgttcct gtaacgttcg actatctcgc    2700
tagctgtgaa gtactgatta gtggagttct gtgcaacagc agtgtaggag tatacacaaa    2760
cacaaatatg tgtttctatt taaaactgtg gacttagcat aaaaagggag aatatatttta    2820 tttttttacaa aagggataaa aatgggcccc gttcctcacc caccagattt agcgagaaaa    2880
agctttctat tctgaaaggt cacggtggct ttggcattac aaatcagaac aacacacact    2940
gaccatgatg gcttgtgaac taactgcaag gcactccgtc atggtaagcg agtaggtccc    3000
acctcctagt gtgccgctca ttgctttaca cagtagaatc ttatttgagt gctaattgtt    3060
gtctttgctg ctttactgtg ttgttataga aaatgtaagc tgtacagtga ataagttatt    3120
gaagcatgtg taaacactgt tatatatctt ttctcctaga tggggaattt tgaataaaat    3180 accttttgaaa ttctgtgt                                                 3198
```

<210> SEQ ID NO 2
<211> LENGTH: 481
<212> TYPE: PRT
<213> ORGANISM: Mus musculus

<400> SEQUENCE: 2

```
Met Ser Thr Ile Cys Pro Pro Ser Pro Ala Val Ala Lys Thr Glu
1               5                   10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
```

```
                    85                  90                  95
Leu Ile Phe Asp Gly Asn Trp Asn Gly Asp Arg Ser Thr Tyr Gly Leu
                100                 105                 110

Ser Ile Ile Leu Pro Gln Thr Glu Leu Ser Phe Tyr Leu Pro Leu His
                115                 120                 125

Arg Val Cys Val Asp Arg Leu Thr His Ile Ile Arg Lys Gly Arg Ile
                130                 135                 140

Trp Met His Lys Glu Arg Gln Glu Asn Val Gln Lys Ile Val Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ala Ser Met Lys Ser
                180                 185                 190

His Ser Val Pro Glu Asp Ile Asp Ile Ala Asp Thr Val Leu Asn Asp
                195                 200                 205

Asp Asp Ile Gly Asp Ser Cys His Glu Gly Phe Leu Leu Asn Ala Ile
                210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
                260                 265                 270

Lys Tyr Glu Ser Gly Leu Phe Val Gln Gly Leu Leu Lys Asp Ala Thr
                275                 280                 285

Gly Ser Phe Val Leu Pro Phe Arg Gln Val Met Tyr Ala Pro Tyr Pro
                290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
                340                 345                 350

Ile Ile Tyr Thr Asp Glu Ser Phe Thr Pro Asp Leu Asn Ile Phe Gln
                355                 360                 365

Asp Val Leu His Arg Asp Thr Leu Val Lys Ala Phe Leu Asp Gln Val
                370                 375                 380

Phe His Leu Lys Pro Gly Leu Ser Leu Arg Ser Thr Phe Leu Ala Gln
385                 390                 395                 400

Phe Leu Leu Ile Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
                420                 425                 430

Leu Lys Ile Asp Leu Asp Leu Thr Ala Glu Gly Asp Leu Asn Ile Ile
                435                 440                 445

Met Ala Leu Ala Glu Lys Ile Lys Pro Gly Leu His Ser Phe Ile Phe
                450                 455                 460

Gly Arg Pro Phe Tyr Thr Ser Val Gln Glu Arg Asp Val Leu Met Thr
465                 470                 475                 480

Phe

<210> SEQ ID NO 3
<211> LENGTH: 3435
```

```
<212> TYPE: DNA
<213> ORGANISM: Rattus norvegicus

<400> SEQUENCE: 3
cgtttgtagt gtcagccatc ccaattgcct gttccttctc tgtgggagtg gtgtctagac      60
agtccaggca gggtatgcta ggcaggtgcg tttttggttgc ctcagatcgc aacttgactc     120
cataacggtg accaaagaca aaagaaggaa accagattaa aaagaaccgg acacagaccc     180
ctgcagaatc tggagcggcc gtggttgggg gcggggctac gacggggcgg actcgggggc     240
gtgggagggc ggggccgggg cggggcccgg agccggctgc ggttgcggtc cctgcgccgg     300
cggtgaaggc gcagcggcgg cgagtggcta ttgcaagcgt ttggataatg tgagacctgg     360
gatgcaggga tgtcgactat ctgccccca ccatctcctg ctgttgccaa gacagagatt      420
gctttaagtg gtgaatcacc cttgttggcg gctacctttg cttactggga taatattctt      480
ggtcctagag taaggcacat ttgggctcca agacagacc aagtactcct cagtgatgga      540
gaaatcactt ttcttgccaa ccacactctg aatggagaaa ttcttcggaa tgcggagagt     600
ggggcaatag atgtaaagtt ttttgtctta tctgaaaagg gcgtcattat tgtttcatta     660
atcttcgacg ggaactggaa cggagatcgg agcacttacg gactatcaat tatactgccg     720
cagacggagc tgagttttcta cctcccactg cacagagtgt gtgttgacag gctaacgcac     780
atcattcgaa aaggaaggat atggatgcac aaggaaagac aagaaaatgt ccagaaaatt     840
gtcttggaag gcaccgagag gatggaagat cagggtcaga gtatcatccc tatgcttact     900
ggggaggtca tccctgtgat ggagctgctt gcgtctatga gatcacacag tgttcctgaa     960
gacctcgata tagctgatac agtactcaat gatgatgaca ttggtgacag ctgtcatgaa     1020
ggctttcttc tcaatgccat cagctcacat ctgcagacct gcggctgttc tgtggtggta     1080
ggcagcagtg cagagaaagt aaataagata gtaagaacac tgtgccttt tctgacacca     1140 gcagagagga agtgctccag gctgtgtgaa gccgaatcgt cctttaaata cgaatctgga     1200
ctctttgtac aaggcttgct aaaggatgcg actggcagtt ttgtactacc tttccggcaa     1260
gttatgtatg cccttatcc caccacacac atcgatgtgg atgtcaacac tgtcaagcag     1320
atgccaccgt gtcatgaaca tatttataat caacgcagat acatgaggtc agagctgaca     1380
gccttctgga gggcaacttc agaagaggac atggctcagg acaccatcat ctacacagat     1440
gagagcttca ctcctgattt gaatatttc caagatgtct tacacagaga cactctagtg     1500
aaagcctttc tggatcaggt cttccatttg aagcctggcc tgtctctcag gagtactttc     1560
cttgcacagt tcctcctcat tcttcacaga aaagccttga cactaatcaa gtacatagag     1620
gatgacacgc agaaggggaa aaagccctt aagtctcttc ggaacctgaa gatagatctt     1680
gatttaacag cagagggcga ccttaacata ataatggctc tagctgagaa aattaagcca     1740
ggcctacact ctttcatctt cgggagacct ttctacacta gtgtccaaga acgtgatgtt     1800
ctaatgactt tttaaacatg tggtttgctc cgtgtgtctc atgacagtca cacttgctgt     1860
tacagtgtct cagcgctttg gacacatcct tcctccaggg tcctgccgca ggacacgtta     1920
cactacactt gtcagtagag gtctgtacca gatgtcaggt acatcgttgt agtgaatgtc     1980
tcttttccta gactagatgt accctcgtag ggacttatgt ttacaaccct cctaagtact     2040
agtgctgtct tgtaaggata cgaatgaagg gatgtaaact tcaccacaac tgctggttgg     2100
ttttgttgtt tttgttttt gaacttata attcatggtt tacatgcatc acactgaaac     2160
cctagttagc ttttttacagg taagctgtga gttgactgcc tgtccctgtg ttctctggcc     2220
```

```
tgtacgatct gtggcgtgta ggatcacttt tgcaacaact aaaaactaaa gcactttgtt    2280
tgcagttcta cagaaagcaa cttagtctgt ctgcagattc gttttttgaaa gaagacatga    2340 gaaagcggag ttttaggtga agtcagttgt tggatcttcc tttatagact tagtccttta    2400
gatgtggtct gtatagacat gcccaaccat catgcatggg cactgaatat cgtgaactgt    2460
ggtatgcttt ttgttggttt attgtacttc tgtcaaagaa agtggcattg gttttttataa    2520 ttgttgccaa gttttaaggt taattttcat tattttttgag ccaaattaaa atgtgcacct    2580
cctgtgcctt tcccaatctt ggaaaatata atttcttggc agaaggtcag atttcagggc    2640
ccagtcactt tcgtctgact tccctttgca cagtccgcca tgggcctggc ttagaagttc    2700
ttgtaaacta tgccagagag tacattcgct gataaaatct tctttgcaga gcaggagagc    2760
ttcttgcctc tttcctttca tttctgcctg gactttggtg ttctccacgt tccctgcatc    2820
ctaaggacag caggagaact ctgaccccag tgctatttct ctaggtgcta ttgtggcaaa    2880
ctcaagcggt ccgtctctgt ccctgtaacg ttcgtacctt gctggctgtg aagtactgac    2940
tggtaaagct ccgtgctaca gcagtgtagg gtatacacaa acacaagtaa gtgttttatt    3000
taaaactgtg gacttagcat aaaaagggag actatattta tttttttacaa aagggataaa    3060 aatggaaccc tttcctcacc caccagattt agtcagaaaa aaacattcta ttctgaaagg    3120
tcacagtggt tttgacatga cacatcagaa caacgcacac tgtccatgat ggcttatgaa    3180
ctccaagtca ctccatcatg gtaaatgggt agatccctcc ttctagtgtg ccacaccatt    3240
gcttcccaca gtagaatctt atttaagtgc taagtgttgt ctctgctggt ttactctgtt    3300
gttttagaga atgtaagttg tatagtgaat aagttattga agcatgtgta aacactgtta    3360
tacatctttt ctcctagatg gggaatttgg aataaaatac ctttaaaatt caaaaaaaaa    3420
aaaaaaaaaa aaaaa                                                     3435
```

<210> SEQ ID NO 4
<211> LENGTH: 481
<212> TYPE: PRT
<213> ORGANISM: Rattus norvegicus

<400> SEQUENCE: 4

```
Met Ser Thr Ile Cys Pro Pro Ser Pro Ala Val Ala Lys Thr Glu
1               5                   10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Val Leu Glu
145                 150                 155                 160
```

Gly Thr Glu Arg Met Glu Asp Gln Gly Gln Ser Ile Ile Pro Met Leu
            165                 170                 175

Thr Gly Glu Val Ile Pro Val Met Glu Leu Leu Ala Ser Met Arg Ser
        180                 185                 190

His Ser Val Pro Glu Asp Leu Asp Ile Ala Asp Thr Val Leu Asn Asp
    195                 200                 205

Asp Asp Ile Gly Asp Ser Cys His Glu Gly Phe Leu Leu Asn Ala Ile
210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ala Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe His Leu Lys Pro Gly Leu Ser Leu Arg Ser Thr Phe Leu Ala Gln
385                 390                 395                 400

Phe Leu Leu Ile Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe

<210> SEQ ID NO 5
<211> LENGTH: 680
<212> TYPE: DNA
<213> ORGANISM: Artificial Sequence
<220> FEATURE:
<223> OTHER INFORMATION: Synthetic polynucleotide-prot promoter

<400> SEQUENCE: 5
ccagtagcag cacccacgtc caccttctgt ctagtaatgt ccaacacctc cctcagtcca     60
aacactgctc tgcatccatg tggctcccat ttatacctga agcacttgat ggggcctcaa    120
tgttttacta gagcccaccc ccctgcaact ctgagaccct ctggatttgt ctgtcagtgc    180

```
ctcactgggg cgttggataa tttcttaaaa ggtcaagttc cctcagcagc attctctgag    240
cagtctgaag atgtgtgctt ttcacagttc aaatccatgt ggctgtttca cccacctgcc    300
tggccttggg ttatctatca ggacctagcc tagaagcagg tgtgtggcac ttaaccccta    360
agctgagtga ctaactgaac actcaagtgg atgccatctt tgtcacttct tgactgtgac    420
acaagcaact cctgatgcca aagccctgcc caccctctc atgcccatat ttggacatgg    480
tacaggtcct cactggccat ggtctgtgag gtcctggtcc tctttgactt cataattcct    540
aggggccact agtatctata agaggaagag ggtgctggct cccaggccac agcccacaaa    600
attccacctg ctcacaggtt ggctggctcg acccaggtgg tgtccctgc tctgagccag    660 ctccccggcca agccagcacc                                                680

<210> SEQ ID NO 6
<211> LENGTH: 1052
<212> TYPE: DNA
<213> ORGANISM: Artificial Sequence
<220> FEATURE:
<223> OTHER INFORMATION: Synthetic polynucleotide-Blimp1 promoter 1kb

<400> SEQUENCE: 6
tgccatcatc acaggatgtc cttccttctc cagaagacag actggggctg aaggaaaagc     60
cggccaggct cagaacgagc cccactaatt actgcctcca acagctttcc actcactgcc    120
cccagcccaa catcccctt ttaactggga agcattccta ctctccattg tacgcacacg    180
ctcggaagcc tggctgtggg tttgggcatg agaggcaggg acaacaaaac cagtatatat    240
gattataact ttttcctgtt tccctatttc caaatggtcg aaaggaggaa gttaggtcta    300
cctaagctga atgtattcag ttagcaggag aaatgaaatc ctatacgttt aatactagag    360
gagaaccgcc ttagaatatt tatttcattg gcaatgactc caggactaca cagcgaaatt    420
gtattgcatg tgctgccaaa atactttagc tcttccttc gaagtacgtc ggatcctgta    480
attgagacac cgagtttagg tgactagggt tttcttttga ggaggagtcc cccaccccgc    540
cccgctctgc cgcgacagga agctagcgat ccggaggact tagaatacaa tcgtagtgtg    600
ggtaaacatg gagggcaagc gcctgcaaag ggaagtaaga agattcccag tccttgttga    660
aatccatttg caaacagagg aagctgccgc gggtcgcagt cggtggggg aagccctgaa    720 ccccacgctg cacggctggg ctggccaggt gcggccacgc cccatcgcg gcggctggta    780 ggagtgaatc agaccgtcag tattggtaaa gaagtctgcg gcagggcagg gagggggaag    840
agtagtcagt cgctcgctca ctcgctcgct cgcacagaca ctgctgcagt gacactcggc    900
cctccagtgt cgcggagacg caagagcagc gcgcagcacc tgtccgcccg gagcgagccc    960
ggcccgcggc cgtagaaaag gagggaccgc cgaggtgcgc gtcagtactg ctcagcccgg   1020
cagggacgcg ggaggatgtg gactgggtgg ac                                1052

<210> SEQ ID NO 7
<211> LENGTH: 2008
<212> TYPE: DNA
<213> ORGANISM: Artificial Sequence
<220> FEATURE:
<223> OTHER INFORMATION: Synthetic polynucleotide-Blimp1 promoter 2kb

<400> SEQUENCE: 7
gtggtgctga ctcagcatcg gttaataaac cctctgcagg aggctggatt tcttttgttt     60
aattatcact tggacctttc tgagaactct taagaattgt tcattcgggt ttttttgttt    120
tgttttggtt tggtttttttt gggtttttttt tttttttttttt ttttggtttt ttggagacag    180
```

```
ggtttctctg tatatagccc tggcacaaga gcaagctaac agcctgtttc ttcttggtgc    240
tagcgccccc tctggcagaa aatgaaataa caggtggacc tacaacccccc cccccccccc   300 ccagtgtatt ctactcttgt ccccggtata aatttgattg ttccgaacta cataaattgt    360
agaaggattt tttagatgca catatcattt tctgtgatac cttccacaca cccctcccccc   420 ccaaaaaaat ttttctggga aagtttcttg aaaggaaaac agaagaacaa gcctgtcttt    480
atgattgagt tgggcttttg ttttgctgtg tttcatttct tcctgtaaac aaatactcaa    540
atgtccactt cattgtatga ctaagttggt atcattaggt tgggtctggg tgtgtgaatg    600
tgggtgtgga tctggatgtg ggtggtgtg tatgccccgt gtgtttagaa tactagaaaa    660
gataccacat cgtaaacttt tgggagagat gattttttaaa aatgggggtg ggggtgaggg   720
gaacctgcga tgaggcaagc aagataaggg gaagacttga gtttctgtga tctaaaaagt   780
cgctgtgatg ggatgctggc tataaatggg cccttagcag cattgtttct gtgaattgga    840
ggatccctgc tgaaggcaaa agaccattga aggaagtacc gcatctggtt tgttttgtaa    900
tgagaagcag gaatgcaagg tccacgctct taataataaa caaacaggac attgtatgcc    960
atcatcacag gatgtccttc cttctccaga agacagactg gggctgaagg aaaagccggc   1020
caggctcaga acgagcccca ctaattactg cctccaacag cttttccactc actgccccca   1080 gcccaacatc ccctttttaa ctgggaagca ttcctactct ccattgtacg cacacgctcg   1140
gaagcctggc tgtgggtttg gcatgagag gcagggacaa caaaaccagt atatatgatt   1200 ataactttt cctgtttccc tatttccaaa tggtcgaaag gaggaagtta ggtctaccta   1260
agctgaatgt attcagttag caggagaaat gaaatcctat acgtttaata ctagaggaga   1320
accgccttag aatatttatt tcattggcaa tgactccagg actacacagc gaaattgtat   1380
tgcatgtgct gccaaaatac tttagctctt tccttcgaag tacgtcggat cctgtaattg   1440
agacaccgag tttaggtgac tagggttttc ttttgaggag gagtccccca ccccgccccg   1500
ctctgccgcg acaggaagct agcgatccgg aggacttaga atacaatcgt agtgtgggta   1560
aacatggagg gcaagcgcct gcaaagggaa gtaagaagat tcccagtcct tgttgaaatc   1620
catttgcaaa cagaggaagc tgccgcgggt cgcagtcggt ggggggaagc cctgaacccc   1680
acgctgcacg gctgggctgg ccaggtgcgg ccacgcccccc atcgcggcgg ctggtaggag   1740
tgaatcagac cgtcagtatt ggtaaagaag tctgcggcag gcagggagg gggaagagta   1800 gtcagtcgct cgctcactcg ctcgctcgca cagacactgc tgcagtgaca ctcggccctc   1860
cagtgtcgcg gagacgcaag agcagcgcgc agcacctgtc cgcccggagc gagcccggcc   1920
cgcggccgta gaaaaggagg gaccgccgag gtgcgcgtca gtactgctca gcccggcagg   1980
gacgcgggag gatgtggact gggtggac                                      2008
```

<210> SEQ ID NO 8
<211> LENGTH: 8388
<212> TYPE: DNA
<213> ORGANISM: Artificial Sequence
<220> FEATURE:
<223> OTHER INFORMATION: Polynucleotide sequence of a modified C9ORF72
      locus from lacZ through the 3' loxP site

<400> SEQUENCE: 8

```
ggtaccgatt taaatgatcc agtggtcctg cagaggagag attgggagaa tcccggtgtg     60
acacagctga acagactagc cgcccacccct ccctttgctt cttggagaaa cagtgaggaa   120
gctaggacag acagaccaag ccagcaactc agatctttga acggggagtg gagatttgcc   180
```

| | |
|---|---|
| tggtttccgg caccagaagc ggtgccggaa agctggctgg agtgcgatct tcctgaggcc | 240 |
| gatactgtcg tcgtcccctc aaactggcag atgcacggtt acgatgcgcc catctacacc | 300 |
| aacgtgacct atcccattac ggtcaatccg ccgtttgttc ccacggagaa tccgacgggt | 360 |
| tgttactcgc tcacatttaa tgttgatgaa agctggctac aggaaggcca gacgcgaatt | 420 |
| attttgatg gcgttaactc ggcgtttcat ctgtggtgca acgggcgctg ggtcggttac | 480 |
| ggccaggaca gtcgtttgcc gtctgaattt gacctgagcg catttttacg cgccggagaa | 540 |
| aaccgcctcg cggtgatggt gctgcgctgg agtgacggca gttatctgga agatcaggat | 600 |
| atgtggcgga tgagcggcat tttccgtgac gtctcgttgc tgcataaacc gactacacaa | 660 |
| atcagcgatt ccatgttgc cactcgcttt aatgatgatt tcagccgcgc tgtactggag | 720 |
| gctgaagttc agatgtgcgg cgagttgcgt gactacctac gggtaacagt ttctttatgg | 780 |
| cagggtgaaa cgcaggtcgc cagcggcacc gcgcctttcg gcggtgaaat tatcgatgag | 840 |
| cgtggtggtt atgccgatcg cgtcacacta cgtctgaacg tcgaaaaccc gaaactgtgg | 900 |
| agcgccgaaa tcccgaatct ctatcgtgcg gtggttgaac tgcacaccgc cgacggcacg | 960 |
| ctgattgaag cagaagcctg cgatgtcggt ttccgcgagg tgcggattga aaatggtctg | 1020 |
| ctgctgctga acggcaagcc gttgctgatt cgaggcgtta accgtcacga gcatcatcct | 1080 |
| ctgcatggtc aggtcatgga tgagcagacg atggtgcagg atatcctgct gatgaagcag | 1140 |
| aacaactta cgccgtgcg ctgttcgcat tatccgaacc atccgctgtg gtacacgctg | 1200 |
| tgcgaccgct acggcctgta tgtggtggat gaagccaata ttgaaaccca cggcatggtg | 1260 |
| ccaatgaatc gtctgaccga tgatccgcgc tggctaccgg cgatgagcga acgcgtaacg | 1320 |
| cgaatggtgc agcgcgatcg taatcacccg agtgtgatca tctggtcgct ggggaatgaa | 1380 |
| tcaggccacg gcgctaatca cgacgcgctg tatcgctgga tcaaatctgt cgatccttcc | 1440 |
| cgcccggtgc agtatgaagg cggcggagcc gacaccacgg ccaccgatat tatttgcccg | 1500 |
| atgtacgcgc gcgtggatga agaccagccc ttcccggctg tgccgaaatg gtccatcaaa | 1560 |
| aaatggcttt cgctacctgg agagacgcgc ccgctgatcc tttgcgaata cgcccacgcg | 1620 |
| atgggtaaca gtcttggcgg tttcgctaaa tactggcagg cgtttcgtca gtatcccgt | 1680 |
| ttacagggcg gcttcgtctg ggactgggtg gatcagtcgc tgattaaata tgatgaaaac | 1740 |
| ggcaacccgt ggtcggctta cggcggtgat tttggcgata cgccgaacga tcgccagttc | 1800 |
| tgtatgaacg gtctggtctt tgccgaccgc acgccgcatc cagcgctgac ggaagcaaaa | 1860 |
| caccagcagc agttttcca gttccgttta tccgggcaaa ccatcgaagt gaccagcgaa | 1920 |
| tacctgttcc gtcatagcga taacgagctc ctgcactgga tggtggcgct ggatggtaag | 1980 |
| ccgctggcaa gcgtgaagt gcctctggat gtcgctccac aagtaaaca gttgattgaa | 2040 |
| ctgcctgaac taccgcagcc gggagagcgcc gggcaactct ggctcacagt acgcgtagtg | 2100 |
| caaccgaacg cgaccgcatg gtcagaagcc gggcacatca gcgcctggca gcagtggcgt | 2160 |
| ctggcggaaa acctcagtgt gacgctcccc gccgcgtccc acgccatccc gcatctgacc | 2220 |
| accagcgaaa tggattttg catcgagctg ggtaataagc gttggcaatt taaccgccag | 2280 |
| tcaggctttc tttcacagat gtggattggc gataaaaaac aactgctgac gccgctgcgc | 2340 |
| gatcagttca cccgtgcacc gctggataac gacattggcg taagtgaagc gacccgcatt | 2400 |
| gaccctaacg cctgggtcga acgctggaag gcggcgggcc attaccaggc cgaagcagcg | 2460 |
| ttgttgcagt gcacggcaga tacacttgct gatgcggtgc tgattacgac cgctcacgcg | 2520 |

```
tggcagcatc aggggaaaac cttatttatc agccggaaaa cctaccggat tgatggtagt    2580
ggtcaaatgg cgattaccgt tgatgttgaa gtggcgagcg ataccgca tccggcgcgg     2640 attggcctga actgccagct ggcgcaggta gcagagcggg taaactggct cggattaggg    2700
ccgcaagaaa actatcccga ccgccttact gccgcctgtt ttgaccgctg ggatctgcca    2760
ttgtcagaca tgtataccc gtacgtcttc ccgagcgaaa acggtctgcg ctgcgggacg     2820
cgcgaattga attatggccc acaccagtgg cgcggcgact tccagttcaa catcagccgc    2880
tacagtcaac agcaactgat ggaaaccagc catcgccatc tgctgcacgc ggaagaaggc    2940
acatggctga atatcgacgg tttccatatg gggattggtg cgacgactc ctggagcccg     3000 tcagtatcgg cggaattcca gctgagcgcc ggtcgctacc attaccagtt ggtctggtgt    3060
caaaaataat aataaccggg cagggggat ctaagctcta gataagtaat gatcataatc     3120
agccatatca catctgtaga ggttttactt gctttaaaaa acctcccaca cctcccctg      3180 aacctgaaac ataaaatgaa tgcaattgtt gttgttaact tgtttattgc agcttataat    3240
ggttacaaat aaagcaatag catcacaaat ttcacaaata aagcattttt tcactgcat      3300 tctagttgtg gtttgtccaa actcatcaat gtatcttatc atgtctggat ccccggcta     3360 gagtttaaac actagaacta gtggatcccc gggctcgata actataacgg tcctaaggta    3420
gcgactcgag ataacttcgt ataatgtatg ctatacgaag ttatatgcat ggcctccgcg    3480
ccgggttttg gcgcctcccg cgggcgcccc cctcctcacg gcgagcgctg ccacgtcaga    3540
cgaagggcgc agcgagcgtc ctgatccttc gcccggacg ctcaggacag cggcccgctg     3600
ctcataagac tcggccttag aaccccagta tcagcagaag gacatttag gacgggactt     3660 gggtgactct agggcactgg ttttctttcc agagagcgga acaggcgagg aaaagtagtc    3720
ccttctcggc gattctgcgg agggatctcc gtggggcggt gaacgccgat gattatataa    3780
ggacgcgccg ggtgtggcac agctagttcc gtcgcagccg ggatttgggt cgcggttctt    3840
gtttgtggat cgctgtgatc gtcacttggt gagtagcggg ctgctgggct ggccggggct    3900 tcgtggccg ccgggccgct cggtgggacg gaagcgtgtg gagagaccgc caagggctgt     3960
agtctgggtc cgcgagcaag gttgccctga actgggggtt gggggagcg cagcaaaatg     4020 gcggctgttc ccgagtcttg aatggaagac gcttgtgagg cgggctgtga ggtcgttgaa    4080
acaaggtggg gggcatggtg gcggcaaga acccaaggtc ttgaggcctt cgctaatgcg    4140
ggaaagctct tattcgggtg agatgggctg gggcaccatc tggggaccct gacgtgaagt     4200
ttgtcactga ctggagaact cggttttgtcg tctgttgcgg gggcggcagt tatggcggtg    4260
ccgttgggca gtgcacccgt acctttggga gcgcgcgccc tcgtcgtgtc gtgacgtcac    4320
ccgttctgtt ggcttataat gcagggtggg gccacctgcc ggtaggtgtg cggtaggctt    4380
ttctccgtcg caggacgcag ggttcgggcc tagggtaggc tctcctgaat cgacaggcgc    4440
cggacctctg gtgaggggag ggataagtga ggcgtcagtt tctttggtcg gttttatgta    4500
cctatcttct taagtagctg aagctccggt tttgaactat gcgctcgggg ttggcgagtg    4560
tgttttgtga agttttttag gcaccttttg aaatgtaatc atttgggtca atatgtaatt    4620
ttcagtgtta gactagtaaa ttgtccgcta aattctggcc gttttggct tttttgttag     4680 acgtgttgac aattaatcat cggcatagta tatcggcata gtataatacg acaaggtgag    4740
gaactaaacc atgggatcgg ccattgaaca agatggattg cacgcaggtt ctccggccgc    4800
ttgggtggag aggctattcg gctatgactg ggcacaacag acaatcggct gctctgatgc    4860
cgccgtgttc cggctgtcag cgcaggggcg cccggttctt tttgtcaaga ccgacctgtc    4920
```

```
cggtgccctg aatgaactgc aggacgaggc agcgcggcta tcgtggctgg ccacgacggg    4980
cgttccttgc gcagctgtgc tcgacgttgt cactgaagcg ggaagggact ggctgctatt    5040
gggcgaagtg ccggggcagg atctcctgtc atctcacctt gctcctgccg agaaagtatc    5100
catcatggct gatgcaatgc ggcggctgca tacgcttgat ccggctacct gcccattcga    5160
ccaccaagcg aaacatcgca tcgagcgagc acgtactcgg atggaagccg tcttgtcga     5220 tcaggatgat ctggacgaag agcatcaggg gctcgcgcca gccgaactgt tcgccaggct    5280
caaggcgcgc atgcccgacg gcgatgatct cgtcgtgacc catggcgatg cctgcttgcc    5340
gaatatcatg gtgaaaatg gccgcttttc tggattcatc gactgtggcc ggctgggtgt     5400
ggcggaccgc tatcaggaca tagcgttggc tacccgtgat attgctgaag agcttggcgg    5460
cgaatgggct gaccgcttcc tcgtgcttta cggtatcgcc gctcccgatt cgcagcgcat    5520
cgccttctat cgccttcttg acgagttctt ctgagggat ccgctgtaag tctgcagaaa     5580
ttgatgatct attaaacaat aaagatgtcc actaaaatgg aagttttcc tgtcatactt     5640 tgttaagaag ggtgagaaca gagtacctac attttgaatg aaggattgg agctacgggg     5700 gtggggtgg ggtgggatta gataaatgcc tgctctttac tgaaggctct ttactattgc     5760
tttatgataa tgtttcatag ttggatatca aatttaaac aagcaaaacc aaattaaggg     5820
ccagctcatt cctcccactc atgatctata gatctataga tctctcgtgg gatcattgtt    5880
tttctcttga ttcccacttt gtggttctaa gtactgtggt ttccaaatgt gtcagtttca    5940
tagcctgaag aacgagatca gcagcctctg ttccacatac acttcattct cagtattgtt    6000
ttgccaagtt ctaattccat cagacctcga cctgcagccc ctagtcgagc gccagtagca    6060
gcacccacgt ccaccttctg tctagtaatg tccaacacct ccctcagtcc aaacactgct    6120
ctgcatccat gtggctccca tttatacctg aagcacttga tggggcctca atgttttact    6180
agagcccacc ccctgcaac tctgagaccc tctggatttg tctgtcagtg cctcactggg     6240
gcgttggata atttcttaaa aggtcaagtt ccctcagcag cattctctga gcagtctgaa    6300
gatgtgtgct tttcacagtt caaatccatg tggctgtttc acccacctgc ctggccttgg    6360
gttatctatc aggacctagc ctagaagcag gtgtgtggca cttaacacct aagctgagtg    6420
actaactgaa cactcaagtg gatgccatct ttgtcacttc ttgactgtga cacaagcaac    6480
tcctgatgcc aaagccctgc ccacccctct catgcccata tttggacatg gtacaggtcc    6540
tcactggcca tggtctgtga ggtcctggtc ctctttgact tcataattcc tagggccac     6600 tagtatctat aagaggaaga gggtgctggc tcccaggcca cagcccacaa aattccacct    6660
gctcacaggt tggctggctc gacccaggtg gtgtcccctg ctctgagcca gctcccggcc    6720
aagccagcac catgggaacc cccaagaaga gaggaaggt gcgtaccgat ttaaattcca     6780
atttactgac cgtacaccaa aatttgcctg cattaccggt cgatgcaacg agtgatgagg    6840
ttcgcaagaa cctgatggac atgttcaggg atcgccaggc gttttctgag catacctgga    6900
aaatgcttct gtccgtttgc cggtcgtggg cggcatggtg caagttgaat aaccggaaat    6960
ggtttcccgc agaacctgaa gatgttcgcg attatcttct atatcttcag gcgcgcggtc    7020
tggcagtaaa aactatccag caacatttgg gccagctaaa catgcttcat cgtcggtccg    7080
ggctgccacg accaagtgac agcaatgctg tttcactggt tatgcggcgg atccgaaaag    7140
aaaacgttga tgccggtgaa cgtgcaaaac aggctctagc gttcgaacgc actgatttcg    7200
accaggttcg ttcactcatg gaaaatagcg atcgctgcca ggatatacgt aatctggcat    7260
```

| | |
|---|---|
| ttctggggat tgcttataac accctgttac gtatagccga aattgccagg atcagggtta | 7320 |
| aagatatctc acgtactgac ggtgggagaa tgttaatcca tattggcaga acgaaaacgc | 7380 |
| tggttagcac cgcaggtgta gagaaggcac ttagcctggg ggtaactaaa ctggtcgagc | 7440 |
| gatggatttc cgtctctggt gtagctgatg atccgaataa ctacctgttt tgccgggtca | 7500 |
| gaaaaaatgg tgttgccgcg ccatctgcca ccagccagct atcaactcgc gccctggaag | 7560 |
| ggatttttga agcaactcat cgattgattt acggcgctaa ggtaaatata aaatttttaa | 7620 |
| gtgtataatg tgttaaacta ctgattctaa ttgtttgtgt attttaggat gactctggtc | 7680 |
| agagatacct ggcctggtct ggacacagtg cccgtgtcgg agccgcgcga gatatggccc | 7740 |
| gcgctggagt ttcaataccg gagatcatgc aagctggtgg ctggaccaat gtaaatattg | 7800 |
| tcatgaacta tatccgtaac ctggatagtg aaacaggggc aatggtgcgc ctgctggaag | 7860 |
| atggcgattg atctagataa gtaatgatca taatcagcca tatcacatct gtagaggttt | 7920 |
| tacttgcttt aaaaaacctc ccacacctcc ccctgaacct gaaacataaa atgaatgcaa | 7980 |
| ttgttgttgt taaacctgcc ctagttgcgg ccaattccag ctgagcgtga gctcaccatt | 8040 |
| accagttggt ctggtgtcaa aaataataat aaccgggcag gggggatcta agctctagat | 8100 |
| aagtaatgat cataatcagc catatcacat ctgtagaggt tttacttgct ttaaaaaacc | 8160 |
| tcccacacct cccctgaac ctgaaacata aatgaatgc aattgttgtt gttaacttgt | 8220 |
| ttattgcagc ttataatggt tacaaataaa gcaatagcat cacaaatttc acaaataaag | 8280 |
| catttttttc actgcattct agttgtggtt tgtccaaact catcaatgta tcttatcatg | 8340 |
| tctggatcct cgacataact tcgtataatg tatgctatac gaagttat | 8388 |

<210> SEQ ID NO 9
<211> LENGTH: 17210
<212> TYPE: DNA
<213> ORGANISM: Artificial Sequence
<220> FEATURE:
<223> OTHER INFORMATION: Polynucleotide sequence of a modified C9ORF72
      locus from Exon 1a through 3' UTR

<400> SEQUENCE: 9

| | |
|---|---|
| cgtttgtagt gacagccatc ccaattgccc tttccttcta ggtggaaagt ggtgtctaga | 60 |
| cagtccaggg agggtgtgcg agggaggtgc gttttggttg cctcagctcg caacttaact | 120 |
| ccacaacggt gaccaaggac aaaagaagga aacaagactg cagagatccg caccggggag | 180 |
| ccctgcagat tctgggtctg ctgtggactg ggggcgggac tgcgactggg cgggcctggg | 240 |
| ggcgtgtccg gggcggggcg gtcccggggc ggggcccgga gcgggctgcg gttgcggtcc | 300 |
| ctgcgccggc ggtgaaggcg cagcagcggc gagtgggtga gtgagacgcg cgggcggagg | 360 |
| ggggctgctg ccacggtcgg ctcgcgggcc ggccggctcc gggtaccagc ggggttttt | 420 |
| tctccttcga ggtgaactcc tccctgtccc ccggcgaaa gagcccttgg ccttgcagga | 480 |
| gttgcggggg ccgcggcgt gcggagggga tgggatggg cctcatcttt gctgtccgcc | 540 |
| cgcgctcccc gatcccgacc cggagcgtct cccgggccct tgagggaacc ctccgggagt | 600 |
| acggcgagcg cggccccac cgccacaagc ctgggcccca ggggcctggc ccggcgacag | 660 |
| ctggtgggtc ctgcgaccca gtcaggtctc ccgagggtcc ccgcccggga ggagaaagcg | 720 |
| ccggtgggat ggagtaagga cggacagaac aacacgcagg caggatttcg cagaagtttg | 780 |
| caaggagtgc ggatgcccac ttacatgggc tgctactctt accaggttgt tcccagttc | 840 |
| tgtgggacgt gacctggttg cctcacagct ccgcggttgt acagacttat taaaggaagt | 900 |

```
gaccattgtg acttgggcat cacttgactg atggtaatca gttgcagaga gagaagtgca    960
ctgattaagt ctgtccacac agggtctgtc tggccaggag tgcatttgcc tgggagggat   1020
tggttgcgct ttctggtgtg gggactatta ggctcttgta gagttttgtc ccggcagatg   1080
gataaatttc ttgttacact gttcccgttc gtcaccagtt gagaaaaacg ggtacacagt   1140
ctgtctcagt agtactttta ctttatatta agggcccaaa agggactgga aaatacttta   1200
agatagaatc gttagtccac ttggaaaact aaaatatga gagagagagg ggggggggag   1260
agagagagag agagagagag agaaaggaag gaagaaggag gaagaggagg aggaaagaga   1320
ttgagattat gttaataata tggaatcaga atatttgaaa tatagtaagc gtcccctcag   1380
ttaaagagga cattccagga ggcccccagt atagcctgaa atctcaggaa acgcctacat   1440
acacccatcg tgtggatata ggtgttttcc cttcattaca tttcatacac agatgttaaa   1500
gtttagaaag taggcacaat aagagattac aaataactga taataaagtc gagccattgc   1560
agctgctctg taaaagtcct gtgaatgtga tcgctttgtg tttcaaagta acttactgta   1620
cttcaccccct gttaagcaaa acaagattca cctgaacgca ggcaccttgg taccttggca   1680
gacaccagat ctgataacca agaggatgga gaagtagtgg cagacagtgt ggagagcatg   1740
aatatgctag acaaaagggt gaatcataac ctaggagcag aaagcaggta tttcatcatc   1800
ctccacagta aaaacctatg tcacgtaaaa aacctacaag tagttttttct tttactcttt   1860
ttgaatgaaa gcttgctaca ggcactgaaa gttaaaataa tctgtggatc aggaggaaca   1920
ggggttttct gtctgagtca ctgctgacta gcacctcagt gaccattggc actgtgggaa   1980
accccagagt cagttggaaa cttcgaaact aaaggtgacg tgttcttat ttcatagaac   2040
acaaaaaata gaggggtta cagcctgcgc tgcagactgg acattcaaca agcatttaaa   2100
tttctgggag acaaatgtaa atataacttt aaaagttggt aaaatactct gtttggctat   2160
gttggccatc caatgtttgc ttttagaaaa tgactgaatg gataaaacgt ctatcttttg   2220
agcctgccct agaccccccat gttgagtgaa tactgtccaa gtgttaggtt agccggcctg   2280
agaaacttgg atctaggcaa gatggcacag tcctggtgtc atgagtatgc atgtgagttt   2340
tggctgaaat tgaacatttg tagagaatga caaaggctgg tctggcaagt agtccactgt   2400
ctttacagtg gtcttggtta gttcctgttt ggctgagagg gctggttgat ggctgtcctg   2460
cccctcttcc cacaagtgga agccttatgg tataattctt gatcacagta gcagtaggca   2520
aatgaacttc ctcaaagcag cctggaaagc tgattttttt ttctttcttt ctcttttttt   2580
tttttttttc acaaggttaa agaaaaaaca aagggcttca aatgtgccag tctgctaaca   2640
gtgttaacat gtttattaac ataaataaac tttattagtt tttggaagta ttggttaagc   2700
cctcgtgacc cctgaactcg gtttatagag tgatgagtcg tagcctcact ctggtttgga   2760
ctctggcttc tctcagaaga ctctgtggct aatgttaacc ttctgaagta gccagaaaac   2820
atataagcaa aagtctgtga ggttgaaatg aatttttttgg ccacatttgt atatgggttc   2880
ccaccaatgc taacttcagg tgttagtaat atcagactca cagcttccct gattacactt   2940
cgctataaga ctttatttttt taggtcatag gaatttcccc tttttcatga ttcctaaatc   3000
atgaaataac atagtctaaa aatacggtat tcctgaaata aacaatttct aagttttaag   3060
ctgcgtgcta ttctgaacag tctgatgccc tcttgtagct tttactgtgt cctaccccgg   3120
gcatggttga ttcctttgtc caaacatctg tctgttgtat ccacactgga ttgcaccacc   3180
tgcgtgctag tcagtcactc agacatttta gttataaggt agcttatatt tactccttat   3240
tttatttaat aatggcctca tagcaaggcg gtaatgatac tggtaatttg ggtttgctta   3300
```

```
agaggagcca tgaagtagtt ttaaatgaaa aggtgaaaat tcccactata gtttggaggg    3360
ggaggctata ctggtactac tacgattcac ggtaagacta atcttctgt gaaattatga     3420 aggagaaaaa gttacactgg tctggtcttg ctgttggatt aattttatag ttataaccac    3480
tgtacatgat aaataaccct aaaacaatga atttgtaggt ggatggcata atctgaaaac    3540
catgttctga gcagttgatg gcagcaggct gtgctggaag tgttaggcat atttatagat    3600
ttcagcccaa gttctgaaga ggctggagag atggctcagt ggttaagagt gcttgctatt    3660
gcagaggacc taggttcctc tacaggcacc aggcaagcgt gggacacact gagatacata    3720
cagacaaaac ataaaattaa ataaattgtg cataataata ctagtaatat atgagtaaaa    3780
taaggataaa tacacatcat aattaaataa ataaattgta aagttcccta gaagtgaggg    3840
tcaccaagcc attcacaaga tggctgcgct gatgcaggga tatatgtgaa ctagaaaaag    3900
gtcaaactta acagagaagt tccaaggcat gctactgcag gcttggctag catgcttgac    3960
ctgcagaaat gctgacggcc actgggaggt tttcacaaat gaggaattag aagaactttt    4020
tttactaatc tccagaaaaa aaaaagggaa gaagaaactg aagcagcctg tgatgtggac    4080
cagaaacgca gtgacagtaa catgtgtgac attgcaaagg catgaaagga cagagctgtg    4140
gaatacagac ctcaggtgga gctcagcata gagtcattcg gggattatgc ctgctgcagc    4200
aacaaaagga tgagctcaaa agagacaccg acttctgaat gcagtgggtg tttgttttgt    4260
tttgtttcaa atgaattggg cagaaaactt tccagctgtg gaagcttctg aaccgtccct    4320
tgctgctgac atctaagcgt ccgctgtgtc ccagctcagt gatctagggt cttccaaaca    4380
gatggtccgg tgctgagcac tttgaatctc aatcctgagt ttctaccacg cctttggcca    4440
tttaattccc agataaaaga cacatacaac ctttatattt ataataaacc ttagtcagca    4500
caagagctga gcaaatatct gtcctctatg ctattatatc tattacccag ccaataaccc    4560
cattctataa tttgctgtgc ttcatctggg ctgctcttaa cttcagtcag ccagcccacg    4620
tggccattat tttaagattt ttttacccca tagtgtcttc tcactttact ttacattttt    4680
ctctctctcc tcatggttct cctctgaccc caagcctagg aaccctaaac cccacccatg    4740
tctcttctgc ccatctattg gctgtaggca tctttattca ccaatcagga taacttggag    4800
gcaaggttaa gtagtctcct gggtctaggt gctgtctctg ggagcaacca gtatttagca    4860
tagcaaaaga ccagacctcc acaatgatca ctctgaccat cggggcagaa ggcacctact    4920
agcctgtgcc actcacctca ctttgttgaa tcacatctta tcctgtagtg tgtatcactg    4980
cctgttatca caggaaaaag tgagtcccat caaataagat gtttcagaaa gagaccatgt    5040
tcatataatt atcattctgg taagctttta atggttatat tttgttatta atctctttgt    5100 tcctatttttg caaattatac cttacagtaa atatatatgc atccaatggg gtctttgaat    5160
tcctccccgg ggagtaggag gactctttga ggatgggctg catttaaagc taaacaacgc    5220
aacatgacct ttagtcctta tagatagcct agagatgaga ctaaataaaa gaatggtat     5280 ataatgcttt aagtttccca atcagcttaa aagcttttcc tataaatctt taagattatg    5340
ctctggggct caatactgct tcaagaaggg cttttctttt gtatttagaa ttattcacct    5400
ttttaaacaa aggagaaaaa tggaatagaa atatgtttgc aacataattt tatgactatg    5460
tgtttatttc gcgtgttctg tgggcctgca gtttgctgct gttaatgagg acaacagtgg    5520
caccaataca gttccactc agattacatt ctctgttccc tttctgaaag ctgccctctc     5580
cactgggccc aaaagagtca gtatcttaaa caagctgtac aacttagata accatggtct    5640
```

```
cttcagacta gttaattgac atatattaaa aagtaaatag taccaaagtg aatttctgaa    5700
attaaaaatg aacatttaaa aactctaggt aaactattcc ttagagttaa gtgttttgcc    5760
aagttctgta atcataatat gatagaaacg ctcactcagc attctaaata tagaagttac    5820
tccttcgcat gacactctaa ttcttgataa ggtggagaaa gagagagaga gaggggggaga    5880 gacagaaaat atggtggttc aaggaccatt tgagggaatt agttatgttc ttccgtcctc    5940
tgtggatctt aggggttgaa tacagtcatt gagctcggtg gatggctgtc ctgttgaaag    6000
gtctgcccag cagagcaaat agactttttt atttacatgg acatccgttt gtgactaatc    6060
taatgttcac tcccaaagta atcacacaga cagagaggta gcttccttca gtactcttac    6120
cttacatgaa tcctaccatt tgttatttt ttttccactt taaatctttg attatgtgtt    6180
tttaattaga aaatttgcat acaaatttcc atacagtatg tagaattgac tgtgtttgaa    6240
tgggtgaaga tccacatgtg taaccctagc tctggactgg ctctgagctt gtttgctctt    6300
ctcttttgtg ttctgagtaa ctgaaactct ttcattttag cagcttagta tgcgcccttc    6360
acattgctgt gctgcctgct gcactaacat tactcctttg cttatgttcc ccttcctgat    6420
tcagtgtcat tttaagcagt agtactggac ctcagtacct tagccggagc tcactgaggt    6480
gacagggctg aggctctgct gctgtctttt gagcttacct cttttttaatg ttttatggta    6540 tttctgctgc caggtttggg ggttttgttt tgttttgttt tttgttttttt gttttttta    6600 attttctagg aacacctaga aaacacaaac taggaaactt aaaagagcag cgtcttgttc    6660
cctgcgttct agaaagtcca agcctaatgc cagtgtcatg gttgtcagga acatgagcct    6720
ctgaaggctt cttgggaaac ctttcttgtc tcaacacctc tggtggcaag cagtagtcca    6780
tggtactctc tctgtccacg gtcagcatcc cagtccctgc cctttatctt tgtgcagccg    6840
accagctttg ctttagtctg tctccttctc aggtctcctt ccccgctcct cttaagcaca    6900
gcagtcattg gattagagcc catccttccc tcggatggcc catttgacct aattttacgt    6960
atttgtaact aaggtcccat ttacttacac agggccctcc ccttcctgtt tgttctttta    7020
gctgaaatgg tttggagacc aaatatccaa tcattacaat tgtgcacaag ctatgttcat    7080
ttggaggtaa taaaggctca ttcttttgctt ctattggtat gtgacatttt tctaagtcac    7140 ttgggggtttg atagatatct ttaaatggct gaacctgatc actgttcttt tgtatgtccc    7200
tgtttagcta ttgcaagcgt tcggataatg tgagacctgg aatgcagtga acctgggat     7260 gcagggatgg gtaccgattt aaatgatcca gtggtcctgc agaggagaga ttgggagaat    7320
cccggtgtga cacagctgaa cagactagcc gcccacccctc cctttgcttc ttggagaaac    7380
agtgaggaag ctaggacaga cagaccaagc cagcaactca gatctttgaa cggggagtgg    7440
agatttgcct ggtttccggc accagaagcg gtgccggaaa gctggctgga gtgcgatctt    7500
cctgaggccg atactgtcgt cgtcccctca aactggcaga tgcacggtta cgatgcgccc    7560
atctacacca acgtgaccta tcccattacg gtcaatccgc cgtttgttcc cacggagaat    7620
ccgacgggtt gttactcgct cacatttaat gttgatgaaa gctggctaca ggaaggccag    7680
acgcgaatta ttttttgatgg cgttaactcg gcgtttcatc tgtggtgcaa cgggcgctgg    7740
gtcggttacg gccaggacag tcgtttgccg tctgaatttg acctgagcgc attttttacgc    7800 gccggagaaa accgcctcgc ggtgatggtg ctgcgctgga gtgacggcag ttatctggaa    7860
gatcaggata tgtggcggat gagcggcatt ttccgtgacg tctcgttgct gcataaaccg    7920
actacacaaa tcagcgattt ccatgttgcc actcgcttta atgatgattt cagccgcgct    7980
gtactggagg ctgaagttca gatgtgcggc gagttgcgtg actacctacg ggtaacagtt    8040
```

```
tctttatggc agggtgaaac gcaggtcgcc agcggcaccg cgcctttcgg cggtgaaatt    8100
atcgatgagc gtggtggtta tgccgatcgc gtcacactac gtctgaacgt cgaaaacccg    8160
aaactgtgga gcgccgaaat cccgaatctc tatcgtgcgg tggttgaact gcacaccgcc    8220
gacggcacgc tgattgaagc agaagcctgc gatgtcggtt ccgcgaggt gcggattgaa     8280 aatggtctgc tgctgctgaa cggcaagccg ttgctgattc gaggcgttaa ccgtcacgag    8340
catcatcctc tgcatggtca ggtcatggat gagcagacga tggtgcagga tatcctgctg    8400
atgaagcaga acaactttaa cgccgtgcgc tgttcgcatt atccgaacca tccgctgtgg    8460
tacacgctgt gcgaccgcta cggcctgtat gtggtggatg aagccaatat tgaaacccac    8520
ggcatggtgc caatgaatcg tctgaccgat gatccgcgct ggctaccggc gatgagcgaa    8580
cgcgtaacgc gaatggtgca gcgcgatcgt aatcacccga gtgtgatcat ctggtcgctg    8640
gggaatgaat caggccacgg cgctaatcac gacgcgctgt atcgctggat caaatctgtc    8700
gatccttccc gcccggtgca gtatgaaggc ggcggagccg acaccacggc caccgatatt    8760
atttgcccga tgtacgcgcg cgtggatgaa gaccagccct tcccggctgt gccgaaatgg    8820
tccatcaaaa aatggctttc gctacctgga gagacgcgcc cgctgatcct ttgcgaatac    8880
gcccacgcga tgggtaacag tcttggcggt ttcgctaaat actggcaggc gtttcgtcag    8940
tatccccgtt tacagggcgg cttcgtctgg gactgggtgg atcagtcgct gattaaaatat   9000 gatgaaaacg gcaacccgtg gtcggcttac ggcggtgatt ttggcgatac gccgaacgat    9060
cgccagttct gtatgaacgg tctggtctttt gccgaccgca cgccgcatcc agcgctgacg    9120
gaagcaaaac accagcagca gttttttccag ttccgtttat ccgggcaaac catcgaagtg   9180
accagcgaat acctgttccg tcatagcgat aacgagctcc tgcactggat ggtggcgctg    9240
gatggtaagc cgctggcaag cggtgaagtg cctctggatg tcgctccaca aggtaaacag    9300
ttgattgaac tgcctgaact accgcagccg gagagcgccg ggcaactctg gctcacagta    9360
cgcgtagtgc aaccgaacgc gaccgcatgg tcagaagccg ggcacatcag cgcctggcag    9420
cagtggcgtc tggcggaaaa cctcagtgtg acgctccccg ccgcgtccca cgccatcccg    9480
catctgacca ccagcgaaat ggatttttgc atcgagctgg gtaataagcg ttggcaattt    9540
aaccgccagt caggctttct ttcacagatg tggattggcg ataaaaaaca actgctgacg    9600
ccgctgcgcg atcagttcac ccgtgcaccg ctggataacg acattggcgt aagtgaagcg    9660
acccgcattg accctaacgc ctgggtcgaa cgctggaagg cggcgggcca ttaccaggcc    9720
gaagcagcgt tgttgcagtg cacggcagat acacttgctg atgcggtgct gattacgacc    9780
gctcacgcgt ggcagcatca ggggaaaacc ttatttatca gccggaaaac ctaccggatt    9840
gatggtagtg gtcaaatggc gattaccgtt gatgttgaag tggcgagcga tacaccgcat    9900
ccggcgcgga ttggcctgaa ctgccagctg gcgcaggtag cagagcgggt aaactggctc    9960
ggattagggc gcaagaaaaa ctatcccgac cgccttactg ccgcctgttt tgaccgctgg   10020
gatctgccat tgtcagacat gtataccccg tacgtcttcc cgagcgaaaa cggtctgcgc   10080
tgcgggacgc gcgaattgaa ttatggccca caccagtggc gcggcgactt ccagttcaac   10140
atcagccgct acagtcaaca gcaactgatg aaaccagcc atcgccatct gctgcacgcg    10200
gaagaaggca catggctgaa tatcgacggt ttccatatgg ggattggtgg cgacgactcc   10260
tggagccccg cagtatcggc ggaattccag ctgagcgccg tcgctaccca ttaccagttg   10320
gtctggtgtc aaaaataata ataaccgggc agggggatc taagctctag ataagtaatg    10380
```

```
atcataatca gccatatcac atctgtagag gttttacttg ctttaaaaaa cctcccacac    10440 ctcccccctga acctgaaaca taaaatgaat gcaattgttg ttgttaactt gtttattgca    10500
gcttataatg gttacaaata aagcaatagc atcacaaatt tcacaaataa agcattttt     10560 tcactgcatt ctagttgtgg tttgtccaaa ctcatcaatg tatcttatca tgtctggatc    10620
ccccggctag agtttaaaca ctagaactag tggatcccccg ggctcgataa ctataacggt    10680
cctaaggtag cgactcgaga taacttcgta taatgtatgc tatacgaagt tatatgcatg    10740
gcctccgcgc cgggttttgg cgcctccccgc gggcgccccc ctcctcacgg cgagcgctgc    10800
cacgtcagac gaagggcgca gcgagcgtcc tgatccttcc gcccggacgc tcaggacagc    10860
ggcccgctgc tcataagact cggccttaga accccagtat cagcagaagg acattttagg    10920
acgggacttg ggtgactcta gggcactggt tttctttcca gagagcggaa caggcgagga    10980
aaagtagtcc cttctcggcg attctgcgga gggatctccg tggggcggtg aacgccgatg    11040
attatataag gacgcgccgg gtgtggcaca gctagttccg tcgcagccgg gatttgggtc    11100
gcggttcttg tttgtggatc gctgtgatcg tcacttggtg agtagcgggc tgctgggctg    11160 gccgggggctt tcgtggccgc cgggccgctc ggtgggacgg aagcgtgtgg agagaccgcc    11220
aagggctgta gtctgggtcc gcgagcaagg ttgccctgaa ctgggggttg ggggagcgc    11280 agcaaaatgg cggctgttcc cgagtcttga atggaagacg cttgtgaggc gggctgtgag    11340
gtcgttgaaa caaggtgggg ggcatggtgg gcggcaagaa cccaaggtct tgaggccttc    11400
gctaatgcgg gaaagctctt attcgggtga gatgggctgg ggcaccatct ggggaccctg    11460
acgtgaagtt tgtcactgac tggagaactc ggtttgtcgt ctgttgcggg ggcggcagtt    11520
atggcggtgc cgttgggcag tgcacccgta cctttgggag cgcgcgccct cgtcgtgtcg    11580
tgacgtcacc cgttctgttg gcttataatg cagggtgggg ccacctgccg gtaggtgtgc    11640 ggtaggctt tctccgtcgc aggacgcagg gttcgggcct agggtaggct ctcctgaatc    11700
gacaggcgcc ggacctctgg tgaggggagg gataagtgag gcgtcagttt ctttggtcgg    11760
ttttatgtac ctatcttctt aagtagctga agctccggtt ttgaactatg cgctcggggt    11820
tggcgagtgt gtttttgtgaa gttttttagg caccttttga aatgtaatca tttgggtcaa    11880 tatgtaatttt tcagtgttag actagtaaat tgtccgctaa attctggccg ttttttggctt    11940 ttttgttaga cgtgttgaca attaatcatc ggcatagtat atcggcatag tataatacga    12000
caaggtgagg aactaaacca tgggatcggc cattgaacaa gatggattgc acgcaggttc    12060
tccggccgct tgggtggaga ggctattcgg ctatgactgg gcacaacaga caatcggctg    12120
ctctgatgcc gccgtgttcc ggctgtcagc gcaggggcgc ccggttcttt ttgtcaagac    12180
cgacctgtcc ggtgccctga atgaactgca ggacgaggca gcgcggctat cgtggctggc    12240
cacgacgggc gttccttgcg cagctgtgct cgacgttgtc actgaagcgg gaagggactg    12300
gctgctattg ggcgaagtgc cggggcagga tctcctgtca tctcaccttg ctcctgccga    12360
gaaagtatcc atcatggctg atgcaatgcg gcggctgcat acgcttgatc cggctacctg    12420
cccattcgac caccaagcga aacatcgcat cgagcgagca cgtactcgga tggaagccgg    12480
tcttgtcgat caggatgatc tggacgaaga gcatcagggg ctcgcgccag ccgaactgtt    12540
cgccaggctc aaggcgcgca tgcccgacgg cgatgatctc gtcgtgaccc atggcgatgc    12600
ctgcttgccg aatatcatgg tggaaaatgg ccgcttttct ggattcatcg actgtggccg    12660
gctgggtgtg gcggaccgct atcaggacat agcgttggct acccgtgata ttgctgaaga    12720
gcttggcggc gaatgggctg accgcttcct cgtgctttac ggtatcgccg ctcccgattc    12780
```

```
gcagcgcatc gccttctatc gccttcttga cgagttcttc tgaggggatc cgctgtaagt  12840
ctgcagaaat tgatgatcta ttaaacaata aagatgtcca ctaaaatgga agtttttcct  12900
gtcatacttt gttaagaagg gtgagaacag agtacctaca ttttgaatgg aaggattgga  12960
gctacggggg tgggggtggg gtgggattag ataaatgcct gctctttact gaaggctctt  13020
tactattgct ttatgataat gtttcatagt tggatatcat aatttaaaca agcaaaacca  13080
aattaagggc cagctcattc ctcccactca tgatctatag atctatagat ctctcgtggg  13140
atcattgttt ttctcttgat tcccactttg tggttctaag tactgtggtt tccaaatgtg  13200
tcagtttcat agcctgaaga acgagatcag cagcctctgt tccacataca cttcattctc  13260
agtattgttt tgccaagttc taattccatc agacctcgac ctgcagcccc tagtcgagcg  13320
ccagtagcag cacccacgtc caccttctgt ctagtaatgt ccaacacctc cctcagtcca  13380
aacactgctc tgcatccatg tggctcccat ttatacctga agcacttgat ggggcctcaa  13440
tgttttacta gagcccaccc ccctgcaact ctgagaccct ctggatttgt ctgtcagtgc  13500
ctcactgggg cgttggataa tttcttaaaa ggtcaagttc cctcagcagc attctctgag  13560
cagtctgaag atgtgtgctt ttcacagttc aaatccatgt ggctgtttca cccacctgcc  13620
tggccttggg ttatctatca ggacctagcc tagaagcagg tgtgtggcac ttaacaccta  13680
agctgagtga ctaactgaac actcaagtgg atgccatctt tgtcacttct tgactgtgac  13740
acaagcaact cctgatgcca aagccctgcc caccctctc atgcccatat ttggacatgg  13800
tacaggtcct cactggccat ggtctgtgag gtcctggtcc tctttgactt cataattcct  13860 agggccact agtatctata agaggaagag ggtgctggct cccaggccac agcccacaaa  13920
attccacctg ctcacaggtt ggctggctcg acccaggtgg tgtccctgc tctgagccag  13980 ctcccggcca agccagcacc atgggaaccc ccaagaagaa gaggaaggtg cgtaccgatt  14040
taaattccaa tttactgacc gtacaccaaa atttgcctgc attaccgtc gatgcaacga  14100 gtgatgaggt tcgcaagaac ctgatggaca tgttcagggga tcgccaggcg ttttctgagc  14160
atacctggaa aatgcttctg tccgtttgcc ggtcgtgggc ggcatggtgc aagttgaata  14220
accggaaatg gtttcccgca gaacctgaag atgttcgcga ttatcttcta tatcttcagg  14280
cgcgcggtct ggcagtaaaa actatccagc aacatttggg ccagctaaac atgcttcatc  14340
gtcggtccgg gctgccacga ccaagtgaca gcaatgctgt ttcactggtt atgcggcgga  14400
tccgaaaaga aaacgttgat gccggtgaac gtgcaaaaca ggctctagcg ttcgaacgca  14460
ctgatttcga ccaggttcgt tcactcatgg aaaatagcga tcgctgccag gatatacgta  14520
atctggcatt tctggggatt gcttataaca ccctgttacg tatagccgaa attgccagga  14580
tcagggttaa agatatctca cgtactgacg gtggagaat gttaatccat attggcagaa  14640
cgaaaacgct ggttagcacc gcaggtgtag agaaggcact tagcctgggg gtaactaaac  14700
tggtcgagcg atggatttcc gtctctggtg tagctgatga tccgaataac tacctgtttt  14760
gccgggtcag aaaaaatggt gttgccgcgc catctgccac cagccagcta tcaactcgcg  14820
ccctggaagg gattttgaa gcaactcatc gattgattta cggcgctaag gtaaatataa  14880 aattttaag tgtataatgt gttaaactac tgattctaat tgtttgtgta ttttaggatg  14940
actctggtca gagataccctg gcctggtctg gacacagtgc ccgtgtcgga gccgcgcgag  15000
atatggcccg cgctggagtt tcaataccgg agatcatgca agctggtggc tggaccaatg  15060
taaatattgt catgaactat atccgtaacc tggatagtga aacagggagca atggtgcgcc  15120
```

-continued

| | |
|---|---|
| tgctggaaga tggcgattga tctagataag taatgatcat aatcagccat atcacatctg | 15180 |
| tagaggtttt acttgcttta aaaaacctcc cacacctccc cctgaacctg aaacataaaa | 15240 |
| tgaatgcaat tgttgttgtt aaacctgccc tagttgcggc caattccagc tgagcgtgag | 15300 |
| ctcaccatta ccagttggtc tggtgtcaaa ataataata accgggcagg ggggatctaa | 15360 |
| gctctagata agtaatgatc ataatcagcc atatcacatc tgtagaggtt ttacttgctt | 15420 |
| taaaaaacct cccacacctc ccctgaacct gaaacataa aatgaatgca attgttgttg | 15480 |
| ttaacttgtt tattgcagct tataatggtt acaaataaag caatagcatc acaaatttca | 15540 |
| caaataaagc attttttca ctgcattcta gttgtggttt gtccaaactc atcaatgtat | 15600 |
| cttatcatgt ctggatcctc gacataactt cgtataatgt atgctatacg aagttattgc | 15660 |
| tagcgtgtct cagcagtgtg tgggcacatc cttcctcccg agtcctgctg caggacaggg | 15720 |
| tacactacac ttgtcagtag aagtctgtac ctgatgtcag gtgcatcgtt acagtgaatg | 15780 |
| actcttccta gaatagatgt actcttttag ggccttatgt ttacaattat cctaagtact | 15840 |
| attgctgtct tttaaagata tgaatgatgg aatatacact tgaccataac tgctgattgg | 15900 |
| tttttttgttt tgttttgttt gttttcttgg aaacttatga ttcctggttt acatgtacca | 15960 |
| cactgaaacc ctcgttagct ttacagataa agtgtgagtt gacttcctgc ccctctgtgt | 16020 |
| tctgtggtat gtccgattac ttctgccaca gctaaacatt agagcattta agtttgcag | 16080 |
| ttcctcagaa aggaacttag tctgactaca gattagttct tgagagaaga cactgatagg | 16140 |
| gcagagctgt aggtgaaatc agttgttagc ccttccttta tagacgtagt ccttcagatt | 16200 |
| cggtctgtac agaaatgccg aggggtcatg catgggccct gagtatcgtg acctgtgaca | 16260 |
| agttttttgt tggtttattg tagttctgtc aaagaaagtg gcatttgttt ttataattgt | 16320 |
| tgccaacttt taaggttaat tttcattatt tttgagccga attaaaatgc gcacctcctg | 16380 |
| tgcctttccc aatcttggaa aatataattt cttggcagag ggtcagattt cagggcccag | 16440 |
| tcactttcat ctgaccaccc tttgcacggc tgccgtgtgc ctggcttaga ttagaagtcc | 16500 |
| ttgttaagta tgtcagagta cattcgctga taagatcttt gaagagcagg gaagcgtctt | 16560 |
| gcctctttcc tttggtttct gcctgtactc tggtgtttcc cgtgtcacct gcatcatagg | 16620 |
| aacagcagag aaatctgacc cagtgctatt tttctaggtg ctactatggc aaactcaagt | 16680 |
| ggtctgtttc tgttcctgta acgttcgact atctcgctag ctgtgaagta ctgattagtg | 16740 |
| gagttctgtg caacagcagt gtaggagtat acacaaacac aaatatgtgt ttctatttaa | 16800 |
| aactgtggac ttagcataaa aagggagaat atatttattt tttacaaaag ggataaaaat | 16860 |
| gggccccgtt cctcacccac cagatttagc gagaaaaagc tttctattct gaaaggtcac | 16920 |
| ggtggctttg gcattacaaa tcagaacaac acacactgac catgatggct tgtgaactaa | 16980 |
| ctgcaaggca ctccgtcatg gtaagcgagt aggtcccacc tcctagtgtg ccgctcattg | 17040 |
| ctttacacag tagaatctta tttgagtgct aattgttgtc tttgctgctt tactgtgttg | 17100 |
| ttatagaaaa tgtaagctgt acagtgaata agttattgaa gcatgtgtaa acactgttat | 17160 |
| atatcttttc tcctagatgg ggaattttga ataaaatacc tttgaaattc | 17210 |

NON-HUMAN ANIMALS HAVING A DISRUPTION IN A C9ORF72 LOCUS

CROSS REFERENCE TO RELATED APPLICATIONS

This application is a continuation application of U.S. Application Ser. No. 15/165,307, filed May 26, 2016 (now allowed), which application claims the benefit of priority from U.S. Provisional Application No. 62/168,171, filed May 29, 2015, U.S. Provisional Application No. 62/232,658, filed Sep. 25, 2015, and U.S. Provisional Application No. 62/245,382, filed Oct. 23, 2015, the entire contents of which are incorporated herein by reference.

INCORPORATION BY REFERENCE OF SEQUENCE LISTING

The sequence listing in an ASCII text file, named as 32698_10152US01_SequenceListing of 56 kb, created on May 19, 2016, and submitted to the United States Patent and Trademark Office via EFS-Web, is incorporated herein by reference.

BACKGROUND

Neurodegenerative diseases are major contributors to disability and disease. In particular, amyotrophic lateral sclerosis (ALS, also referred to as Lou Gehrig's disease) and frontotemporal dementia (FTD) are rare nervous system disorders characterized by progressive neuronal loss and/or death. Although aging is viewed as the greatest risk factor for neurodegenerative disease, several genetic components have been discovered. For example, mutations in the copper-zinc superoxide dismutase (SODI) gene have long been associated with ALS. Also, expanded hexanucleotide repeats of GGGGCC within a non-coding region of the C9ORF72 gene have been linked to both ALS and FTD. Currently, there is no cure for either disease, yet treatments that help to manage and/or alleviate symptoms do exist.

Inflammatory diseases include a vast variety of diseases that are often characterized by genetic mutation(s) that result in an impaired or dysfunctional immune system. Although the mechanisms of, for example, rheumatoid arthritis, inflammatory bowl disease and glomerulonephritis are not completely understood, several genetic components have been linked to the various signs and symptoms presented by patients. Such diseases are characterized by systemic inflammation and display various abnormalities throughout the patient body. As with ALS and FTD, treatments for inflammatory diseases aim only to improve symptoms and slow disease progress.

While various laboratory animal models are extensively used in the development of most therapeutics, few exist that address neurodegenerative and inflammatory diseases in ways that provide for elucidation of the exact molecular mechanism by which identified genetic components cause disease. Thus, the manner in which genetic mutations cause neurodegenerative and/or inflammatory disease remains largely unknown. Ideal animal models would contain the same genetic components and represent similar characteristics of human disease. Given the genetic differences between species, there is a high unmet need for the development of improved animal models that closely recapitulate human neurodegenerative and/or inflammatory disease. Of course, such improved animal models provide significant value in the development of effective therapeutic and/or prophylactic agents.

SUMMARY

The present invention encompasses the recognition that it is desirable to engineer non-human animals to permit improved in vivo systems for identifying and developing new therapeutics and, in some embodiments, therapeutic regimens, which can be used for the treatment of neurodegenerative diseases, disorders and conditions. In some embodiments, the in vivo systems as described herein can be used for identifying and developing new therapeutics for treating inflammatory diseases, disorders, and conditions. In some embodiments, the in vivo systems as described herein can also be used for identifying and developing new therapeutics for treating autoimmune diseases, disorders, and conditions. Further, non-human animals described herein that comprise a, disruption in a C9ORF72 locus and/or otherwise functionally silenced C9ORF72 locus, such that a C9ORF72 polypeptide is not expressed or produced, are desirable, for example, for use in identifying and developing therapeutics that target a GGGGCC hexanucleotide repeat, C9ORF72 transcription and regulation, and/or increasing or decreasing levels of C9ORF72, which have been associated with disease in humans. In some embodiments, non-human animals as described herein provide improved in vivo systems (or models) for neurodegenerative diseases, disorders and conditions (e.g., ALS and/or FTD). In some embodiments, non-human animals described herein provide improved in vivo systems (or models) for inflammatory disease, disorders, and conditions.

The present invention provides non-human animal models for amyotrophic lateral sclerosis (ALS), frontotemporal dementia (FTD), and/or glomerulonephritis. In various embodiments, non-human animal models for ALS and/or FTD are provided, which are characterized by a disruption (e.g., a deletion of an entire coding region) in a C9ORF72 locus. In some embodiments, a disruption in a C9ORF72 locus affects one or more neurons of a non-human animal comprising said disruption. In some embodiments, a disruption in a C9ORF72 locus affects one or more of the spleen, cervical lymph nodes, bone marrow, kidney and blood of a, non-human animal comprising said disruption.

In some embodiments, a disruption in a C9ORF72 locus of a non-human animal as described herein results in one or more of the following phenotypes: an ALS-like phenotype; splenomegaly; lymphadenopathy; glomerulonephritis; an infiltration of one or more of macrophages, monocytes and granulocytes into the spleen, cervical lymph nodes, bone marrow and/or blood; an infiltration of F4/80$^+$ macrophages in the kidney and/or liver; a depletion of B and/or T cells in the bone marrow; a decrease of lymphocytes in the blood; and an increase in expression of one or more cytokines (e.g., IL-17, IL-10, TNF-α and IL-12) in the serum.

In some embodiments, a disruption (e.g., a deletion) in a non-human C9ORF72 locus results from an insertion of a nucleic acid sequence that, in some certain embodiments, comprises a reporter gene.

In some embodiments, a non-human animal is provided comprising in its genome a deletion of the entire coding sequence in a C9ORF72 locus, i.e., a deletion of a genomic sequence coding for all C9ORF72 isoforms (i.e., isoforms V1, V2 and V3).

In some embodiments, a deletion is of a genomic segment of about 26 kb in a C9ORF72 locus of a non-human animal.

In some embodiments, a deletion is of a genomic segment encompassing at least exons 2-11 (e.g., exons 2-11 of V1), in whole or in part. In some embodiments, a deletion includes exons 1-11. In some embodiments, a C9ORF72 locus having a deletion comprises a reporter gene. In some embodiments, a reporter gene is operably linked to a C9ORF72 promoter. In some embodiments, a C9ORF72 promoter is an endogenous promoter.

In some embodiments, a C9ORF72 locus of a non-human animal described herein lacks the coding region of exon 2 through the coding region of exon 11, and comprises a reporter gene. In some embodiments, the reporter gene is operably linked to a C9ORF72 promoter. In some embodiments, the reporter gene is operably linked to the non-coding region of exon 2 (i.e., part of the 5' UTR) of a C9ORF72 gene, thereby placing the reporter gene in an operable linkage to exon 1 (i.e., exon 1a or exon 1b) and the upstream regulatory sequences (including the promoter) of a C9ORF72 locus of a non-human animal. In specific embodiments, the operable linkage between a reporter gene and the non-coding portion of exon 2 is achieved by targeted deletion of a C9ORF72 genomic sequence from the codon immediately after the ATG start codon in exon 2 through the coding region of exon 11, and insertion of a reporter coding sequence without an ATG start codon into the site of the C9ORF72 locus immediately after the remaining ATG start codon in exon 2 of the C9ORF72 gene. In some embodiments, expression of a reporter gene resembles the expression pattern (or profile) of a C9ORF72 locus.

In some embodiments, a reporter gene is selected from the group consisting of β-galactosidase (lacZ), luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP. In some certain embodiments, a reporter gene is lacZ.

In some embodiments, a non-human animal as described herein is homozygous or heterozygous for a deletion of the entire coding sequence in a C9ORF72 locus.

In some embodiments, a non-human animal as described herein develops one or more phenotypes as described herein; in some certain embodiments, phenotypes are detectable after about 8 weeks of age.

In some embodiments, a non-human animal as described herein develops one or more symptoms of ALS and/or FTD during development; in some certain embodiments, after about 36 weeks of age; in some certain embodiments, after about 40 weeks of age. In some embodiments, a non-human animal as described herein develops progressive motor deficits after about 36 weeks of age. In some embodiments, a non-human animal as described herein develops lower motor neuron pathology after about 40 weeks of age. In some embodiments, a non-human animal as described herein develops a decrease in body weight after about 36 weeks of age. In some embodiments, a non-human animal as described herein develops mitochondrial dysfunction in motor neurons during development; in some certain embodiments, mitochondrial dysfunction is characterized by a decrease in one or more of mitochondrial respiration, basal respiration, maximal respiration, spare respiratory capacity, ATP production and proton leak; in some certain embodiments, mitochondrial dysfunction is characterized by an increase in the mitochondrial to nuclear DNA ratio as compared to the mitochondrial to nuclear DNA ratio of the motor neurons from a control or reference non-human animal.

In some embodiments, a non-human animal as described herein develops one or more symptoms of glomerulonephritis during development; in some certain embodiments, after about 35 weeks of age, after about 35-41 weeks of age inclusive or after about 35-60 weeks of age inclusive. In some embodiments, a non-human animal as described herein develops splenomegaly after about 8 weeks of age. In some embodiments, a non-human animal as described herein develops lymphadenopathy after about 8 weeks of age. In some embodiments, lymphadenopathy is palpable after about 12-18 weeks of age inclusive or after about 18-60 weeks of age inclusive. In some embodiments, a non-human animal as described herein is characterized by an infiltration of one or more of plasma cells, monocytes, granulocytes and F4/80$^+$ macrophages; in some certain embodiments, infiltration is detectable after about 8 weeks of age; in some certain embodiments, infiltration is detectable up to 60 weeks of age. In some embodiments, a non-human animal as described herein develops an infiltration of F4/80$^+$ macrophages in the kidney and/or liver after about 8 weeks of age.

In some embodiments, a non-human animal as described herein develops an increased serum cytokine level of one or more of IL-10, IL-12, IL-17, IFN-γ, TNF-α and MCP-1 after about 8 weeks of age. In some embodiments, a non-human animal as described herein develops an increased serum level of IL-12 after about 8 weeks of age that is about 6-fold or more as compared to a reference or control non-human animal.

In some embodiments, a non-human animal as described herein develops kidney disease characterized by a thickened basement membrane, cast formation (or hyaline cast formation), immune complex deposition, membranoproliferative glomerulonephritis, interstitial mononuclear inflammation, glomerulosclerosis, basophilic tubules, or combinations thereof after about 28-35 weeks of age inclusive, after about 35-41 weeks of age inclusive, or after about 35-60 weeks of age inclusive.

In some embodiments, a non-human animal as described herein develops an increased myeloid dendritic cell population in one or more of the spleen, lymph nodes, bone marrow, kidney and blood after about 28-35 weeks of age inclusive. In some embodiments, a myeloid dendritic cell population is characterized as CD45$^+$CD45b$^+$CD11c$^+$MHCII$^+$.

In some embodiments, a non-human animal as described herein develops an increased serum level of one or more autoantibodies after about 8 weeks of age; in some certain embodiments, after about 28-35 weeks of age inclusive. In some embodiments, a non-human animal as described herein develops an increased serum level of one or more autoantibodies between about 8 weeks to about 60 weeks of age inclusive. In some embodiments, one or more autoantibodies are selected from anti-Rheumatoid Factor (anti-RF) antibodies, anti-dsDNA antibodies, anti-nuclear antibodies (ANA), anti-Smith (anti-Sm) antibodies, anti-Cardiolipin antibodies, and combinations thereof.

In some embodiments, a non-human animal as described herein develops an increased level of F4/80$^+$ macrophages in one or more of the spleen, lymph nodes, bone marrow, kidney and blood after about 28-35 weeks of age inclusive. In some embodiments, F4/80$^+$ macrophages are characterized as CD45$^+$CD11b$^+$F4/80$^+$Ly6G$^-$.

In some embodiments, a non-human animal as described herein develops an increased T cell population in one or more of the spleen, lymph nodes, bone marrow, kidney and blood after about 28-35 weeks of age inclusive. In some embodiments, T cells are characterized as CD8$^+$CD44$^+$, CD8+CD69+, CD8+PD1+, CD4+CD44+, CD4+CD69+ or CD4+PD1+. In some embodiments, a non-human animal as described herein develops an increased regulatory T cell population in the spleen and/or lymph nodes after about 28-35 weeks of age inclusive, and wherein the regulatory T cell population is characterized as CD4+FoxP3+. In some embodiments, a non-human animal as described herein develops an increased T follicular helper (Tfh) cells in the spleen, lymph nodes (e.g., cervical lymph nodes or "CLN", and mesenteric lymph nodes or "MLN"), and/or blood after about 26 weeks of age, and wherein the Tfh cell population is characterized as CD4+CXCR5+CD44+ICOS+PD-1+Bcl-6+.

In some embodiments, a non-human animal as described herein develops an increased plasma cell population in one or more of the spleen, lymph nodes and bone marrow after about 8-60 weeks of age inclusive. In some embodiments, a plasma cell population is characterized as CD45+CD19−B220−CD138+ or CD45+CD19$^{int}$B220$^{int}$CD138+.

In some embodiments, a non-human animal as described herein develops autoimmune lymphoproliferative syndrome (ALPS) during development. In some embodiments, a non-human animal as described herein develops lupus nephritis during development. In some embodiments, a non-human animal as described herein develops proliferative glomerulonephropathy. In some embodiments, a non-human animal as described herein develops one or more phenotypes associated with systemic lupus erythematosus (SLE) during development. In some embodiments, a non-human animal as described herein develops one or more phenotypes or symptoms selected from the group consisting of elevated autoantibody titers and serum cytokines, lymphadenopathy, splenomegaly and select expansions of myeloid and lymphoid compartments, or a combination thereof. In some embodiments, one or more phenotypes or symptoms are observed as early as 8 weeks. In some embodiments, one or more phenotypes or symptoms are observed between about 18 weeks to about 24 weeks inclusive.

In some embodiments, an isolated non-human cell or tissue of a non-human animal as described herein is provided. In some embodiments, an isolated cell or tissue comprises a C9ORF72 locus as described herein. In some embodiments, a cell is a neuronal cell or a cell from a neuronal lineage. In some embodiments, a cell is from a, lymphoid or myeloid lineage. In some embodiments, a cell is selected from a B cell, dendritic cell, macrophage, monocyte, and a T cell. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, an immortalized cell line is provided, which is made from an isolated cell of a non-human animal as described herein.

In some embodiments, a non-human embryonic stem cell is provided whose genome comprises a C9ORF72 locus as described herein or a deletion in a C9ORF72 locus as described herein. In some embodiments, a non-human embryonic stem cell is a rodent embryonic stem cell. In some certain embodiments, a rodent embryonic stem cell is a mouse embryonic stem cell and is from a 129 strain, C57BL strain, or a mixture thereof. In some certain embodiments, a rodent embryonic stem cell is a mouse embryonic stem cell and is a mixture of 129 and C573BL strains.

In some embodiments, the use of a non-human embryonic stem cell as described herein is provided to make a, genetically modified non-human animal. In some certain embodiments, a non-human embryonic stem cell is a mouse embryonic stem cell and is used to make a mouse comprising a C9ORF72 locus as described herein. In some certain embodiments, a non-human embryonic stem cell is a rat embryonic stem cell and is used to make a rat comprising a C9ORF72 locus as described herein.

In some embodiments, a non-human embryo is provided comprising, made from, obtained from, or generated from a non-human embryonic stem cell comprising a C9ORF72 locus as described herein. In some certain embodiments, a non-human embryo is a rodent embryo; in some embodiments, a mouse embryo; in some embodiments, a rat embryo.

In some embodiments, the use of a, non-human embryo as described herein is provided to make a genetically modified non-human animal. In some certain embodiments, a non-human embryo is a mouse embryo and is used to make a mouse comprising a C9ORF72 locus as described herein. In some certain embodiments, a non-human embryo is a rat embryo and is used to make a rat comprising a C9ORF72 locus as described herein.

In some embodiments, a nucleic acid construct (or targeting construct, or targeting vector) as described herein is provided.

In some embodiments, a nucleic acid construct as described herein comprises, from 5' to 3', a non-human targeting arm comprising a polynucleotide that is homologous to a 5' portion of a non-human (e.g., a rodent such as a mouse or a rat) C9ORF72 locus, a first recombinase recognition site; a first promoter operably linked to a recombinase gene, a second promoter operably linked to a selectable marker, a second recombinase recognition site, a reporter gene as described herein, and a non-human targeting arm comprising a polynucleotide that is homologous to a 3' portion of a non-human (e.g., a rodent such as a mouse or a rat) C9ORF72 locus. In some embodiments, the 3 portion of a non-human C9ORF72 locus includes a genomic sequence downstream of the stop codon in exon 11 of a non-human (e.g., a rodent such as a mouse or a rat) C9ORF72 gene. In some embodiments, the 5' portion of a C9ORF72 locus includes a genomic sequence upstream of the start codon in exon 2 of a non-human (e.g., rodent such as mouse or rat) C9ORF72 gene. In many embodiments, first and second recombinase recognition sites are oriented to direct an excision. In many embodiments, a recombinase gene encodes a recombinase that recognizes first and second recombinase recognition sites. In many embodiments, a first promoter drives expression of the recombinase gene in differentiated cells and does not drive expression of the recombinase gene in undifferentiated cells. In many embodiments, a first promoter is transcriptionally competent and developmentally regulated.

In some embodiments, recombinase recognition sites include loxP, lox511, lox2272, lox2372, lox66, lox71, loxM2, lox5171, FRT, FRT11, FRT71, attp, att, FRT, Dre, rox, or a combination thereof. In some embodiments, a recombinase gene is selected from the group consisting of Cre, Flp (e.g., Flpe, Flpo), and Dre. In some certain embodiments, first and second recombinase recognition sites are lox (e.g., loxP) sites, and a recombinase gene encodes a Cre recombinase.

1 In some embodiments, a first promoter is selected from the group consisting of protamine (Prot; e.g., Prot1 or Prot5), Blimp1, Blimp1 (1 kb fragment), Blimp1 (2 kb fragment), Gata6, Gata4, Igf2, Lhx2, Lhx5, and Pax3. In some certain embodiments, a first promoter is selected from a promoter that appears in Table 2. In some certain embodiments, a first promoter is or comprises SEQ ID NO:5, SEQ ID NO:6 or SEQ ID NO:7.

In some embodiments, a selectable marker is selected from group consisting of neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and Herpes simplex virus thymidine kinase (HSV-tk).

In some embodiments, a second promoter is selected from the group consisting of an UbC promoter, Ubi promoter, hCMV promoter, mCM V promoter, CAGGS promoter, EF1 promoter, pgk1 promoter, beta-actin promoter, and a ROSA26 promoter. In some certain embodiments, a selectable marker is neo$^r$ and a second promoter is Ubi.

In some embodiments, a method of making a non-human animal is provided whose genome comprises a deletion of the entire coding sequence in a C9ORF72 locus, the method comprising (a) introducing a nucleic acid sequence into a non-human embryonic stem cell so that the entire coding sequence in a C9ORF72 locus is deleted, which nucleic acid comprises a polynucleotide that is homologous to the C9ORF72 locus; (b) obtaining a genetically modified non-human embryonic stem cell from (a); and (c) creating a non-human animal using the genetically modified non-human embryonic stem cell of (b). In some embodiments, a method of making a non-human animal described herein further comprises a step of breeding a non-human animal generated in (c) so that a non-human animal homozygous for a deletion is created.

In some embodiments, a nucleic acid sequence is, comprises, or appears in a nucleic acid construct as described herein. In some embodiments, a nucleic acid sequence comprises one or more selection markers. In some embodiments, a nucleic acid sequence comprises one or more site-specific recombination sites. In some embodiments, a nucleic acid sequence comprises a recombinase gene and a selection marker flanked by recombinase recognition sites, which recombinase recognition sites are oriented to direct an excision. In some embodiments, a nucleic acid sequence further comprises a reporter gene that is downstream of a selection marker. In some embodiments, a nucleic acid sequence comprises a recombinase gene that is operably linked to a promoter that drives expression of the recombinase gene in differentiated cells and does not drive expression of the recombinase gene in undifferentiated cells. In some embodiments, a nucleic acid sequence comprises a recombinase gene that is operably linked to a promoter that is transcriptionally competent and developmentally regulated. In some embodiments, a nucleic acid sequence comprises a recombinase gene that is operably linked to a promoter that is or comprises SEQ ID NO:5, SEQ ID NO:6 or SEQ ID NO:7.

In some embodiments, a method for making a non-human animal whose genome comprises a deletion of the entire coding sequence in a C9ORF72 locus is provided, the method comprising modifying the genome of a non-human animal so that it comprises a deletion of the entire coding sequence in a C9ORF72 locus, thereby making said non-human animal.

In some embodiments, a non-human animal is provided which is obtainable by, generated from, or produced from a method as described herein.

In some embodiments, a non-human animal model of amyotrophic lateral sclerosis (ALS) or frontotemporal dementia (FTD) is provided, which non-human animal has a genome comprising a deletion of the entire coding sequence in a C9ORF72 locus.

In some embodiments, a non-human animal model of amyotrophic lateral sclerosis (ALS) or frontotemporal dementia (FTD) is provided, which is obtained by a deletion of the entire coding sequence in a C9ORF72 locus, wherein the non-human animal develops one or more symptoms of ALS and/or FTD during development.

In some embodiments, a non-human animal model of glomerulonephritis is provided, which non-human animal has a genome comprising a deletion of the entire coding sequence in a C9ORF72 locus.

In some embodiments, a non-human animal model of glomerulonephritis is provided, which is obtained by a deletion of the entire coding sequence in a C9ORF72 locus, wherein the non-human animal develops one or more symptoms of glomerulonephritis during development.

In some embodiments, a non-human animal model of lynphoproliferative disease is provided, which non-human animal has a genome comprising a deletion of the entire coding sequence in a C9ORF72 locus.

1 In some embodiments, a non-human animal model of lymphoproliferative disease is provided, which is obtained by a deletion of the entire coding sequence in a C9ORF72 locus, wherein the non-human animal develops one or more symptoms of immune system dysregulation or dysfunction during development.

In some embodiments, a method for identifying a therapeutic candidate for the treatment of a disease, disorder or condition in a non-human animal is provided, the method comprising (a) administering a candidate agent to a non-human animal whose genome comprises a deletion of the entire coding sequence in a C9ORF72 locus; (b) performing one or more assays to determine if the candidate agent has an effect on one or more signs, symptoms and/or conditions associated with the disease, disorder or condition; and (c) identifying the candidate agent that has an effect on the one or more signs, symptoms and/or conditions associated with the disease, disorder or condition as the therapeutic candidate.

In some embodiments, a disease, disorder or condition in a non-human animal is a neurodegenerative disease, disorder or condition. In some embodiments, a disease, disorder or condition in a non-human animal is an inflammatory disease, disorder or condition. In some embodiments, a disease, disorder or condition in a non-human animal is an autoimmune disease, disorder or condition.

In some embodiments, a disease, disorder or condition in a non-human animal is autoimmune lymphoproliferative syndrome (ALPS; also known as Canale-Smith syndrome). In some embodiments, ALPS is characterized by an increased serum level of IL-10, anti-Rheumatoid Factor (anti-RF) antibodies, anti-nuclear antibodies (ANA) or combinations thereof.

In some embodiments, a disease, disorder or condition in a non-human animal is lupus nephritis. In some embodiments, lupus nephritis is characterized by mesangeal proliferation and/or expansion. In some embodiments, lupus nephritis is characterized by one or more tubular abnormalities. In some embodiments, one or more tubular abnormalities are selected from dilatation, cast formation, basophilia, and combinations thereof.

In some embodiments a disease, disorder or condition in a non-human animal is Systemic Lupus Erythematosus (SLE). In some embodiments, SLE is characterized by one or more of lymphoid hyperplasia, T cell activation, elevated serum antinuclear antibodies (ANA), and systemic inflammation affecting heart, lungs, liver, skin, joints, nervous system, and kidneys.

In some embodiments, use of a non-human animal as described herein is provided in the manufacture of a medicament for the treatment of a neurodegenerative disease, disorder or condition.

In some embodiments, use of a non-human animal as described herein is provided in the manufacture of a medicament for the treatment of an inflammatory disease, disorder or condition.

In some embodiments, use of a non-human animal as described herein is provided in the manufacture of a medicament for the treatment of an autoimmune disease, disorder or condition.

In some embodiments, use of a non-human animal as described herein is provided in the manufacture of a medicament for the treatment of a lymphoproliferative disease, disorder or condition.

In some embodiments, use of a non-human animal as described herein is provided in the manufacture of a medicament for the treatment of autoimmune lymphoproliferative syndrome (ALPS).

In some embodiments, use of a non-human animal as described herein is provided in the manufacture of a medicament for the treatment of lupus nephritis.

In some embodiments, a neurodegenerative disease, disorder or condition is amyotrophic lateral sclerosis (ALS). In some embodiments, a neurodegenerative disease, disorder or condition is frontotemporal dementia (FTD). In some embodiments, an inflammatory disease, disorder or condition is glomerulonephritis. In some embodiments, an autoimmune disease, disorder or condition is glomerulonephritis, autoimmune lymphoproliferative syndrome (ALPS), lupus nephritis or systemic lupus erythematosus (SLE).

In some embodiments, an autoimmune disease, disorder or condition as described herein is characterized by a significant increase in serum autoantibody concentration. In some embodiments, an autoimmune disease, disorder or condition as described herein is characterized by a significant increase in the serum level of one or more cytokines (e.g., IL-10, IL-12, IL-17, TNF-$\alpha$, etc.).

In some embodiments, a lymphoproliferative disease, disorder or condition as described herein is characterized by a significant increase in one or more immune cells in one or more of the spleen, bone marrow, lymph node(s), kidney or blood. In some embodiments, a lymphoproliferative disease, disorder or condition as described herein is characterized by deregulation or dysregulation of one or more lymphocytes.

1 In various embodiments, a deletion of the entire coding sequence in a C9ORF72 locus includes deletions as described herein. In various embodiments, a non-human C9ORF72 locus includes a non-human C9ORF72 locus as described herein. In various embodiments, a non-human C9ORF72 locus is a murine C9orf72 locus (e.g., a mouse or a rat C9orf72 locus).

In various embodiments, one or more phenotypes as described herein is or are as compared to a reference or control. In some embodiments, a reference or control includes a non-human animal having a modification as described herein, a modification that is different than a modification as described herein, or no modification (e.g., a wild type non-human animal).

In various embodiments, a non-human animal described herein is a rodent; in some embodiments, a mouse; in some embodiments, a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of non-human animals, cells and methods provided herein are apparent in the detailed description of certain embodiments that follows. It should be understood, however, that the detailed description, while indicating certain embodiments, is given by way of illustration only, not limitation. Various changes and modifications within the scope of the invention will become apparent to those skilled in the art from the detailed description.

BRIEF DESCRIPTION OF THE DRAWING

The Drawing included herein, which is composed of the following Figures, is for illustration purposes only and not for limitation. The patent or application file contains at least one drawing executed in color. Copies of this patent or patent application publication with color drawing(s) will be provided by the Office upon request and payment of the necessary fee.

FIG. 2A: exemplary percent survival (y-axis) over time (x-axis, weeks); FIG. 2B: exemplary body weight change (y-axis, in grams) over time (x-axis, weeks); FIG. 2C: exemplary mean motor impairment score over time (x-axis, weeks); FIG. 2D: exemplary mean tremor score over time (x-axis, weeks); FIG. 2E: exemplary mean rigidity score over time (x-axis, weeks); FIG. 2F: exemplary maximum time at rotarod (y-axis, in seconds) over time (x-axis, weeks); FIG. 2G: exemplary open field locomotor behavior, e.g., immobility (left; y-axis, in seconds) and rearing time (right; y-axis, in seconds) over time (x-axis, weeks); FIG. 2H: exemplary catwalk behavior, e.g., mean stride length (top left, y-axis, centimeters [cm]), interlimb coordination (top right) presented as percent regularity index (y-axis) over time (x-axis, weeks), and stance phase (bottom center) presented as mean stand (y-axis, in seconds) over time (x-axis, weeks); FIG. 2I: exemplary images of motor neurons from 60 week old wild type (WT, n=5) and C9orf72$^{-/-}$ mice (n=5), and exemplary motor neuron count (bottom left), mean area (in $\square m^2$, bottom middle, p<0.0001) and cell body area (in number of cells, bottom right) for wild type (WT) and C9orf72$^{-/-}$ mice; 10 motor neurons were measured for cell body area per slide (three slides per group), swelling indicated hypoxia and cell damage; FIG. 2J: exemplary percent survival over time (top left), body weight change in grams (top right), mean motor impairment score over time (bottom left), mean tremor score over time (bottom middle), and mean rigidity score over time (bottom right) in 32-60 week old wild type (C9orf72$^{+/+}$; n=14) and C9orf72$^{-/-}$ (n=17) mice; FIG. 2K: exemplary maximum time at rotarod over time (top left), open field locomotor behavior, e.g., immobility over time (top middle) and rearing time over time (top right), catwalk behavior, e.g., mean stride length over time (bottom left) and interlimb coordination presented as percent regularity index over time (bottom middle), and total distance traveled over time (bottom right) in 32-60 week old wild type (C9orf72$^{+/+}$; n=14) and C9orf72$^{-/-}$ (n=17) mice; FIG. 2L: exemplary mean motor impairment score over time (top left), mean tremor score over time (top middle), mean rigidity score over time (top right) and grip strength (in grains of force) in wild type (C9orf72$^{+/+}$), heterozygous (C9orf72$^{+/-}$) and homozygous (C9orf72$^{-/-}$) mice. Statistical significance was determined using Student's unpaired t-test and one-way analysis of variance (ANOVA) test.

FIG. 3A: exemplary images of dissected female wild type (WT) and C9orf72$^{-/-}$ mice showing enlarged cervical lymph nodes (arrows) in C9orf72$^{-/-}$ mice, and spleen weights (right, in grams) in female wild type (WT), C9orf72$^{+/-}$ (HI-ET), and C9orf72$^{-/-}$ (KO) mice at 8 (top row) and 18 (bottom row) weeks; FIG. 3I: exemplary plasma cells at various stages expressing specific cell surface antigens isolated from spleen, cervical lymph nodes, bone marrow and blood of male wild type (WT) and C9orf72$^{-/-}$ (KO) mice at 9-10 weeks (black bars), 18 weeks (light grey bars) and 57-60 weeks (dark grey bars);

FIG. 3AA: exemplary percent positive (top row) and total cell count (bottom row) for CD4+PD1+ T cells in various tissues of wild type (WT) and C9orf72−/− mice; FIG. 3AB: exemplary percent positive (top row) and total cell count (bottom row) for CD4+FoxP3+ T cells in various tissues of wild type (WT) and C9orf72−/− mice; FIG. 3AC: exemplary percent positive (left in each pair) and total cell count (right in each pair) for CD8+CD62L+ (top left), CD4+CD62L+ (bottom left), CD8+CD127+ (top right) and CD4+CD127+ (bottom right) T cell populations in spleen of wild type (WT) and C9orf72−/− mice; FIG. 3A): exemplary cytokine panel showing expression of various cytokines in 18 week old male wild type (WT), C9orf72+/− (Het), and C9orf72−/− (KO) mice (cytokines are indicated above each graph); FIG. 3AE: exemplary cytokine panel showing expression of various cytokines in 8-58 week old male wild type (WT), C9orf72−/− (Het), and C9orf72−/− (KO) mice (cytokines are indicated above each graph); FIG. 3AF: exemplary cytokine panel showing expression of various cytokines in 8-38 week old female wild type (WT), C9orf72+/− (Het), and C9orf72−/− (KO) mice (cytokines are indicated above each graph); FIG. 3AG: exemplary levels of blood urea nitrogen (y-axis, mg/dL), globulin (y-axis, g/dL) and serum immunoglobulin (y-axis, IgG, U/mL (left); y-axis, IgM, U/mL (right)) in wild type (WT), C9orf72+/−, and C9orf72−/− mice (blood urea nitrogen and globulin measurement is from 45-56 week old male mice; serum IgM and IgG rheumatoid factor measurement is from 8-58 week old male mice; significant increase in IgG and IgM RF was observed in C9orf72−/− mice at all time points starting from 8 weeks of age); FIG. 3AH: exemplary levels of IgG and IgM Rheumatoid Factor in female (top row) and male (bottom row) wild type (WT), C9orf72+/− (Het) and C9orf72−/− (KO) mice; serum measurement 8-10 week (male: 7 WT, 5 Het, 9 KO; female: 7 WT, 5 Het, 8 KO), 18 week (male: 9 WT, 6 Het, 13 KO; female: 5 WT, 12 Het, 15 KO), 30-41 week (male: 3WT, 4 Het, 4 KO; female: 10 WT, 9 Het, 9 KO) and 54-65 week (male: 6WT, 9 Het, 5 KO) old mice; FIG. 3AI: exemplary levels of circulating IgG and IgM (in µg/mL, y-axis) in female (top row) and male (bottom row) wild type (WT), C9orf72+/− (Het) and C9orf72−/− (KO) mice; FIG. 3AJ: exemplary levels of circulating autoantibodies (in U/mL, y-axis) in female, 26-34 weeks old, (top row) and male, 26-34 weeks old, (bottom row) wild type (WT), C9orf72+/− (Het) and C9orf72−/− (KO) mice; FIG. 3AK: exemplary images of sectioned kidney (top) and liver (bottom) from wild type (WT) and C9orf72−/− mice at 100× and 20× power, respectively, stained with hematoxylin and eosin (H&E) or F4/80 via immunohistochemistry (F4/80 IHC); FIG. 3AL: exemplary images of sectioned kidney tissue from 8-63 week old wild type (WT) and C9orf72−/− mice stained with hematoxylin and eosin (H&E, top panel), IgG ($2^{nd}$ panel from top), IgM ($3^{rd}$ panel from top) and Complement C3 (bottom panel). Statistical significance was determined using Student's unpaired t-test and one-way analysis of variance (ANOVA) test.

FIG. 5A: top illustrates experimental design and time points for treatment, body weight measurement, and behavioral studies, bottom shows exemplary body weight change (y-axis, in grams) over time (x-axis, weeks) in control (black) and BMAA-treated mice (grey); FIG. 5B: exemplary maximum time at rotarod (y-axis, seconds) over time (x-axis, weeks) in control (black) and BMAA-treated mice (grey); FIG. 5C: exemplary open field locomotor behavior, e.g., immobility (left; y-axis, in seconds) and rearing time (right; y-axis; in seconds) over time (x-axis, weeks) in control (black) and BMAA-treated mice (grey);

FIG. 5D: exemplary catwalk behavior, e.g., mean stride length (top left, y-axis, centimeters [cm]), interlimb coordination (top right) presented as percent regularity index (y-axis) over time (x-axis, weeks), and stance phase (bottom center) presented as mean stand (y-axis, in seconds) over time (x-axis, weeks) in control (black) and BMAA-treated mice (grey). Statistical significance was determined using Student's unpaired t-test and one-way analysis of variance (ANOVA) test.

FIG. 6A: top illustrates experimental design and time points for treatment, body weight measurement, and behavioral studies, bottom left shows exemplary percent survival (y-axis) over time (x-axis, weeks), bottom right shows exemplary body weight change (y-axis, in grams) over time (x-axis, weeks); FIG. 6B: top left shows exemplary mean motor impairment score over time (x-axis, weeks), top right shows exemplary mean tremor score over time (x-axis, weeks), bottom shows exemplary mean rigidity score over time (x-axis, weeks); FIG. 6C: exemplary maximum time at rotarod (y-axis, seconds) over time (x-axis, weeks); FIG. 6D: exemplary open field locomotor behavior, e.g., immobility (left; y-axis, in seconds) and rearing time (right; y-axis, in seconds) over time (x-axis, weeks); FIG. 6E: exemplary catwalk behavior, e.g., mean stride length (top left, y-axis, centimeters [cm]), interlimb coordination (top right) presented as percent regularity index (y-axis) over time (x-axis, weeks), and stance phase (bottom center) presented as mean stand (y-axis, in seconds) over time (x-axis, weeks). Statistical significance was determined using Student's unpaired t-test and one-way analysis of variance (ANOVA) test.

FIGS. 9A-9C show progressive glomerulonephropathy in C9orf72$^{-/-}$ mice. FIG. 9A shows weighted graphs of histopathological scoring that demonstrate that the most significant renal changes observed in null mice are associated with membranoproliferative glomerulonephritis. FIG. 9B shows individual histopathological scores corresponding to weighted graphs depicted in FIG. 9A. Briefly, H&E stained kidney sections were blindly scored for categories of renal disease associated with immune mediated glomerulonephropathy: membranoproliferative glomerulonephritis, interstitial mononuclear inflammation, hyaline cast formation, glomerulosclerosis, and basophilic tubules. Score of 0=none, 1=minimal, 2=mild, 3=moderate and 4=severe. All null mice displayed minimal to severe membranoproliferative glomerulonephritis with occasional evidence of additional disease categories in more severely affected animals. FIG. 9C shows urine ACR measurements assayed at 14 week (FIG. 9C, top) and 24 week (FIG. 9C, bottom) time points from the same cohort of mice indicate onset of albuminuria in C9orf72$^{-/-}$ mice with age. Heterozygous mice displayed values comparable to WT consistent with the absence of an observed phenotype.

DEFINITIONS

Figure 1A:
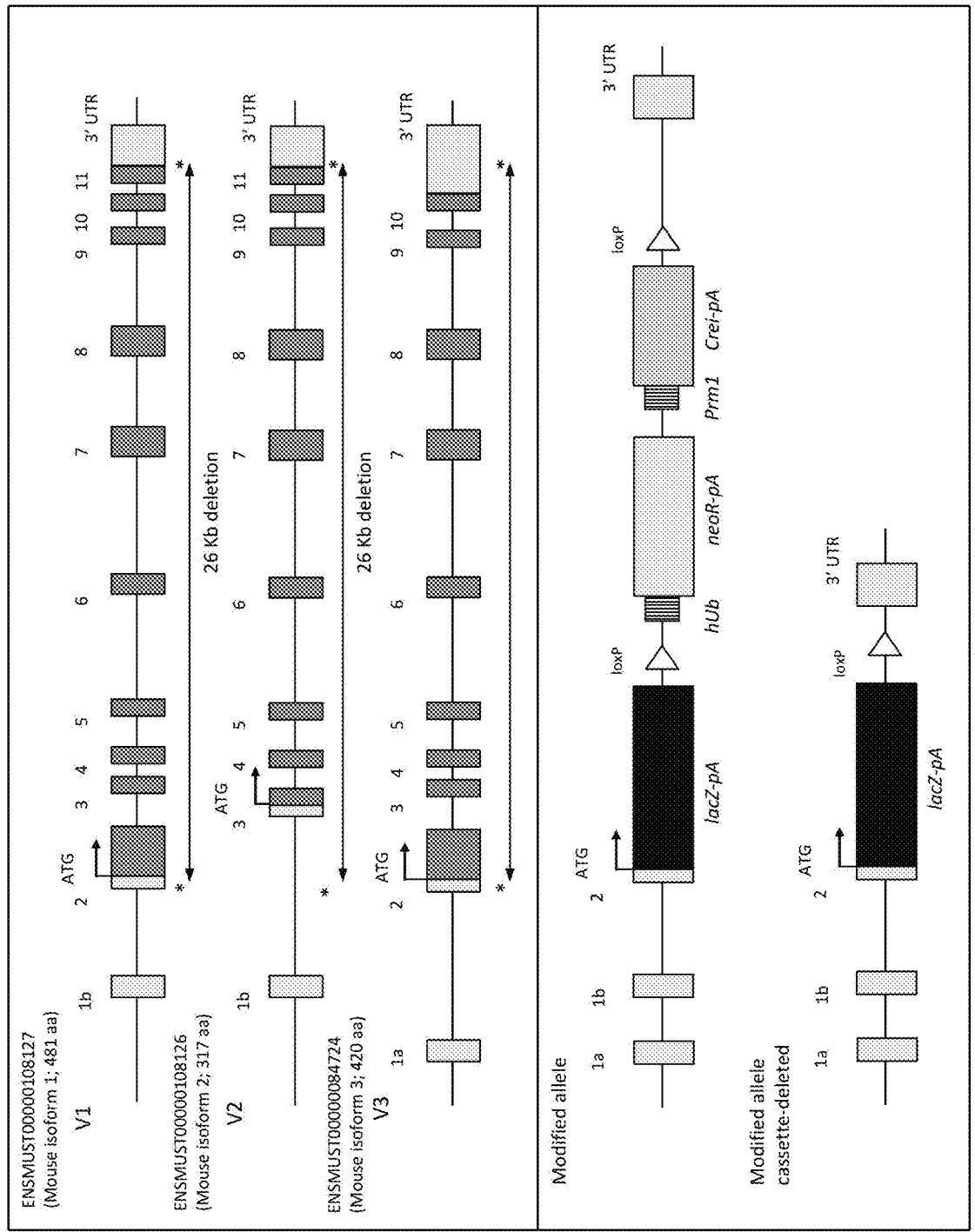
FIG. 1A, top box, shows a schematic illustration, not to scale, of the three reported mouse C9orf72 transcript isoforms (V1, V2 and V3) and a targeted deletion strategy for disruption of the mouse C9orf72 locus. A targeting vector was generated that includes a mouse homology arm upstream (or "mHU)", containing a genomic sequence upstream of and inclusive of the start codon in exon 2 of the mouse C9ORF72 gene), a lacZ reporter gene (without the ATG start codon), a self-deleting drug selection cassette (which includes a neomycin resistance gene, and a Cre recombinase gene linked to a mouse protamine 1 (Prm1) promoter, flanked by loxP sites), and a mouse homology arm downstream (or "mHD", containing a genomic sequence 49 bp downstream of the stop codon of exon 11 of the mouse C9ORF72 gene). Upon homologous recombination, a mouse genomic region of about 26 kb, including the C9orf72 coding sequence for all predicted mouse C9orf72 isoforms (i.e., the coding sequence beginning from the codon immediately after the ATG start codon in exon 2 of mouse C9orf72, through exons 3-10, intervening introns and 49 bp of the 3'UTR in exon 11 of mouse C9orf72), was removed; and the lacZ reporter gene (without the ATG start codon) was inserted immediately after the remaining, endogenous ATG start codon of mouse C9orf72. The resulting modified mouse C9orf72 locus is depicted in FIG. 1A, bottom box. Self-deleting technology was employed to remove the neomycin cassette prior to phenotypic analysis, leaving the lacZ reporter and one loxP site under control of the mouse C9orf72 promoter. The modified mouse C9orf72 locus after the neomycin cassette having been deleted is depicted in FIG. 1A, bottom box. The nucleotide sequence of the modified C9orf72 locus beginning from inserted lacZ sequence through the 3' loxP site is set forth in SEQ ID NO: 8; and the nucleotide sequence of the modified C9orf72 locus beginning from exon 1a through the 3' UTR is set forth in SEQ ID NO: 9.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned herein are hereby incorporated by reference.

"Administration" includes the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. For example, in certain embodiments, administration to an animal subject (e.g., to a human or a rodent) may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

"Amelioration" includes the prevention, reduction or palliation of a state, or improvement of the state of a subject. Amelioration includes, but does not require complete recovery or complete prevention of a disease, disorder or condition (e.g., radiation injury).

"Approximately", as applied to one or more values of interest, includes to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Biologically active" includes a characteristic of any agent that has activity in a biological system, in vitro or in vivo (e.g., in an organism). For instance, an agent that, when present in an organism, has a biological effect within that organism is considered to be biologically active. In particular embodiments, where a protein or polypeptide is biologically active, a portion of that protein or polypeptide that shares at least one biological activity of the protein or polypeptide is typically referred to as a "biologically active" portion.

"Comparable" includes two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conservative", when describing a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a, receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445. In some embodiments, a substitution is a moderately conservative substitution wherein the substitution has a nonnegative value in the PAM250 log-likelihood matrix.

"Control" includes the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild type animal). In one experiment, a "test" (i.e., a variable being tested) is applied. In a second experiment, the "control," the variable being tested is not applied. In some embodiments, a control is a, historical control (i.e., of a test or assay performed previously, or an amount or result that is previously known). In some embodiments, a control is or comprises a printed or otherwise saved record. A control may be a positive control or a negative control.

"Disruption" includes the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product. In some such embodiments, a disruption may achieve assembly of a fusion protein. In some embodiments, a disruption may affect level, but not activity, of a gene or gene product. In some embodiments, a disruption may affect activity, but not level, of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

"Determining", "measuring", "evaluating", "assessing", "assaying" and "analyzing" includes any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

"Endogenous locus" or "endogenous gene" includes a genetic locus found in a parent or reference organism prior to introduction of a disruption, deletion, replacement, alteration, or modification as described herein. In some embodiments, the endogenous locus has a sequence found in nature. In some embodiments, the endogenous locus is a wild type locus. In some embodiments, the reference organism is a wild type organism. In some embodiments, the reference organism is an engineered organism. In some embodiments, the reference organism is a laboratory-bred organism (whether wild type or engineered).

"Endogenous promoter" includes a promoter that is naturally associated, e.g., in a wild type organism, with an endogenous gene.

"Gene" includes a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity we note that, as used in the present application, the term "gene" generally refers to a portion of a nucleic acid that encodes a polypeptide; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

"Heterologous" includes an agent or entity from a different source. For example, when used in reference to a polypeptide, gene, or gene product present in a, particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type). "Heterologous" also includes a polypeptide, gene or gene product that is normally present in a particular native cell or organism, but has been modified, for example, by mutation or placement under the control of non-naturally associated and, in some embodiments, non-endogenous regulatory elements (e.g., a promoter).

"Host cell" includes a cell into which a nucleic acid or protein has been introduced. Persons of skill upon reading this disclosure will understand that such terms refer not only to the particular subject cell, but also is used to refer to the progeny of such a cell, Because certain modifications may occur in succeeding generations due to either mutation or environmental influences, such progeny may not, in fact, be identical to the parent cell, but are still included within the scope of the phrase "host cell". In some embodiments, a host cell is or comprises a prokaryotic or eukaryotic cell. In general, a host cell is any cell that is suitable for receiving and/or producing a, heterologous nucleic acid or protein, regardless of the Kingdom of life to which the cell is designated. Exemplary cells include those of prokaryotes and eukaryotes (single-cell or multiple-cell), bacterial cells (e.g., strains of *Escherichia coli, Bacillus* spp., *Streptomyces* spp., etc.), mycobacteria cells, fungal cells, yeast cells (e.g., *Saccharomyces cerevisiae, Schizosaccharomrnyces pombe, Pichia pastoris, Pichia methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a, retinal cell that expresses a viral gene (e.g., a PER.C6® cell). In some embodiments, a host cell is or comprises an isolated cell. In some embodiments, a host cell is part of a tissue. In some embodiments, a host cell is part of an organism.

"Identity", in connection with a comparison of sequences, includes identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

"Improve", "increase", "eliminate", or "reduce" includes indicated values that are relative to a baseline measurement, such as a measurement in the same individual (or animal) prior to initiation of a treatment described herein, or a measurement in a control individual (or animal) or multiple control individuals (or animals) in the absence of the treatment described herein.

"Isolated" includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. In some embodiments, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

"Locus" or "Loci" includes a specific location(s) of a gene (or significant sequence), DNA sequence, polypeptide-encoding sequence, or position on a chromosome of the genome of an organism. For example, a "C9ORF72 locus" may refer to the specific location of a C9ORF72 gene, C9ORF72 DNA sequence, C9ORF72-encoding sequence, or C9ORF72 position on a chromosome of the genome of an organism that has been identified as to where such a sequence resides. A C9ORF72 locus may comprise a regulatory element of a C9ORF72 gene, including, but not limited to, an enhancer, a promoter, 5' and/or 3' UTR, or a combination thereof. Those of ordinary skill in the art will appreciate that chromosomes may, in some embodiments, contain hundreds or even thousands of genes and demonstrate physical co-localization of similar genetic loci when comparing between different species. Such genetic loci can be described as having shared synteny.

"Non-human animal" includes any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human mammal is a primate, a goat, a sheep, a pig, a dog, a cow, or a rodent. In some embodiments, a non-human animal is a rodent such as a rat or a mouse.

"Nucleic acid" includes any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid"

refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" includes one or more exons. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

"Operably linked" includes a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" includes polynucleotide sequences, which are necessary to affect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaiyotes, such control sequences generally include promoter, ribosomal binding site and transcription termination sequence, while in eukaryotes typically such control sequences include promoters and transcription termination sequence. The term "control sequences" is intended to include components whose presence is essential for expression and processing, and can also include additional components whose presence is advantageous, for example, leader sequences and fusion partner sequences.

"Phenotype" includes a trait, or to a class or set of traits displayed by a cell or organism. In some embodiments, a, particular phenotype may correlate with a particular allele or genotype. In some embodiments, a phenotype may be discrete; in some embodiments, a phenotype may be continuous.

"Physiological conditions" includes its art-understood meaning referencing conditions under which cells or organisms live and/or reproduce. In some embodiments, the term includes conditions of the external or internal mileu that may occur in nature for an organism or cell system. In some embodiments, physiological conditions are those conditions present within the body of a, human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

"Polypeptide" includes any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

"Prevent" or "prevention" in connection with the occurrence of a disease, disorder, and/or condition, includes reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

"Reference" includes a standard or control agent, animal, cohort, individual, population, sample, sequence or value against which an agent, animal, cohort, individual, population, sample, sequence or value of interest is compared. In some embodiments, a reference agent, animal, cohort, individual, population, sample, sequence or value is tested and/or determined substantially simultaneously with the testing or determination of the agent, animal, cohort, individual, population, sample, sequence or value of interest. In some embodiments, a reference agent, animal, cohort, individual, population, sample, sequence or value is a historical reference, optionally embodied in a tangible medium. In some embodiments, a reference may refer to a control. A "reference" also includes a "reference animal". A "reference animal" may have a modification as described herein, a modification that is different as described herein or no modification (i.e., a wild type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

"Response" includes any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a neuron's response. Neuron or subject response may be measured according to a wide variety of criteria, including clinical criteria and objective criteria. Examination of the motor system of a subject may include examination of one or more of strength, tendon reflexes, superficial reflexes, muscle bulk, coordination, muscle tone, abnormal movements, station and gait. Techniques for assessing response include, but are not limited to, clinical examination, stretch flex (myotatic reflex), Hoffmann's reflex, and/or pressure tests. Methods and guidelines for assessing response to treatment are discussed in Brodal, A.: Neurological Anatomy in Relation to Clinical Medicine, ed. 2, New York, Oxford University Press, 1969; Medical Council of the U.K.: Aids to the Examination of the Peripheral Nervous System, Palo Alto, Calif., Pendragon House, 1978; Monrad-Krohn, G. H., Refsum, S.: The Clinical Examination of the Nervous System, ed. 12, London, H. K. Lewis & Co., 1964; and Wolf, J. K.: Segmental Neurology, A Guide to the Examination and interpretation of Sensory and Motor Function, Baltimore, University Park Press, 1981. The exact response criteria can be selected in any appropriate manner, provided that when comparing groups of neurons and/or patients, the groups to be compared are assessed based on the same or comparable criteria for determining response rate. One of ordinary skill in the art will be able to select appropriate criteria.

"Risk", as will be understood from context, of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 and up to 100%. In some embodiments, risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0, 1, 2, 3, 4, 5, 6, 7, 8, 9, 10, or more.

"Substantially" includes the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantial homology" includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al, 1990, J. Mol. Biol., 215(3): 403-410; Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinforratics Methods and Protocols (Methods in Molecular Biology, Vol. 132), Humana Press, 1998. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence, for example, noncontiguous residues brought together by the folded conformation of a polypeptide or a portion thereof. In some embodiments, the relevant stretch is at least 10, 15, 20, 25, 30, 35, 40, 45, 50, or more residues.

"Substantial identity" includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

"Targeting vector" or "targeting construct" includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct as described herein further comprises a nucleic acid sequence or gene (e.g., a reporter gene or homologous or heterologous gene) of particular interest, a selectable marker, control and or regulatory sequences, and other nucleic acid sequences that encodes a recombinase or recombinogenic protein. In some embodiments, a targeting construct may comprise a gene of interest in whole or in part, wherein the gene of interest encodes a polypeptide, in whole or in part, that has a similar function as a protein encoded by an endogenous sequence. In some embodiments, a targeting construct may comprises a humanized gene of interest, in whole or in part, wherein the humanized gene of interest encodes a polypeptide, in whole or in part, that has a similar function as a polypeptide encoded by an endogenous sequence. In some embodiments, a targeting construct may comprise a reporter gene, in whole or in part, wherein the reporter gene encodes a polypeptide that is easily identified and/or measured using techniques known in the art.

"Transgenic animal", "transgenic non-human animal" or "Tg" includes any non-naturally occurring non-human animal in which one or more of the cells of the non-human animal contain heterologous nucleic acid and/or gene encoding a polypeptide of interest, in whole or in part. In some embodiments, a heterologous nucleic acid and/or gene is introduced into the cell, directly or indirectly by introduction into a precursor cell, by way of deliberate genetic manipulation, such as by microinjection or by infection with a recombinant virus. The term genetic manipulation does not include classic breeding techniques, but rather is directed to introduction of recombinant DNA molecule(s). This molecule may be integrated within a chromosome, or it may be extrachromosomally replicating DNA. The term "$Tg^+$" includes animals that are heterozygous or homozygous for a heterologous nucleic acid and/or gene, and/or animals that have single or multi-copies of a heterologous nucleic acid and/or gene.

"Treatment", "Treat" or "Treating" includes any administration of a substance (e.g., a, therapeutic candidate) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

"Variant" includes an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, or 2% of the residues in the variant are substituted as compared with the parent. In some embodiments, a "variant" has 10, 9, 8, 7, 6, 5, 4, 3, 2, or 1 substituted residue(s) as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a, plurality of variants of a, particular polypeptide of interest may commonly be found in nature, particularly when the polypeptide of interest is an infectious agent polypeptide.

"Vector" includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operably linked genes are referred to herein as "expression vectors."

"Wild type" includes an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

Non-human animals are provided having a disruption in a C9OORF72 locus. In particular, non-human animals described herein have a deletion of an entire coding sequence in a C9ORF72 locus, i.e., a deletion of a genomic segment coding for all C9ORF72 isoforms (e.g., a deletion of the coding portion of exon 2 through the coding portion of exon 11 of isoform V1). Non-human animals as described herein demonstrate weight loss and ALS-like motor abnormalities such as, for example, motor inactivity and gait impairment. Also, non-human animals described herein demonstrate splenomegaly and/or lymphadenopathy at about eight (8) weeks of age. Further, non-human animals described herein demonstrate glomerulonephritis at about 35 weeks of age. Therefore, provided non-human animals are particularly useful for the development and identification of therapeutic candidates for the treatment and/or amelioration of neurodegenerative diseases, disorders and conditions and, in some embodiments, autoimmune and/or inflammatory diseases, disorders and conditions. In particular, non-human animals described herein encompasses the introduction of a reporter gene into an endogenous C9ORF72 locus resulting in expression of the reporter gene (i.e., a reporter polypeptide) in the nervous and immune systems of the non-human animal. Such transgenic non-human animals provide a source of cells for determnnining the efficacy of therapeutic candidates to ameliorate ALS and/or FTD. Further, such transgenic non-human animals provide a useful animal model system for the development of therapeutics for the treatment of neurodegenerative, autoimmune and/or inflammatory diseases, disorders and conditions.

In some embodiments, non-human animals described herein develop ALS- and/or FTD-like disease due to the absence of, lack of, or decreased level of C9ORF72 (e.g., RNA, polypeptide, etc.) in cells of the non-human animals. In some embodiments, non-human animals described herein develop glomerulonephritis due to the absence of, lack of, or decrease level of C9ORF72 (e.g., RNA, polypeptide, etc.). In some embodiments, non-human animals described herein are heterozygous for a disruption in a C9ORF72 locus as described herein. In some embodiments, non-human animals described herein are homozygous for a disruption in a 9ORF72 locus as described herein. In some embodiments, non-human animals as described herein comprise a reporter gene, in whole or in part, wherein said reporter gene is operably linked to a C9ORF72 promoter. In some embodiments, C9ORF72 promoters include endogenous C9ORF72 promoters.

The present disclosure provides a comprehensive phenotypic analysis of a non-human animal line with global C9orf72 ablation and the discovery of a unique role for C9orf72 in immune system homeostasis. The present disclosure specifically demonstrates that a complete ablation of C9orf72 resulted in gait abnormalities and an indication towards hindlimb weakness that suggests possible onset of lower motor neuron pathology beginning at about 40 weeks of age. As described herein, the immune phenotype exhibited by C9orf72$^{-/-}$ non-human animals consisted of select expansions in both myeloid and lymphoid compartments, with increased activation of T cells and elevated plasma cells. Neutrophilia and monocytosis resulted in mixed infiltrates in immune organs that expanded, but did not obliterate basic architecture. C9orf72$^{-/-}$ non-human animals demonstrated elevated serum cytokines (e.g., IL-12) and tissue RNA signatures consistent with myeloid upregulation. Renal disease with accompanying pathological changes such as, for example, thickened basement membrane and cast formation, was present in the majority of non-human animals by about 35 weeks of age. At a microscopic level, glomeruli stained heavily with IgG and IgM antibody and complement C3 in a pattern indicating deposition of immune complexes. Also described herein, C9orf72$^{-/-}$ non-human animals demonstrated high titer of autoantibodies including anti-RF, ANA, anti-Sm, and anti-cardiolipin, which indicated that loss of C9orf72 expression profoundly disrupts immune homeostasis. None of the immune-related phenotype characteristics were observed in wild type or C9orf72$^{+/-}$ (heterozygous) non-human animals. Thus, the present invention provides, among other things, the creation of an improved in vivo system for the development of new therapies and/or identification of new therapeutic targets for the treatment of various diseases, disorders or conditions that are not achievable through the use of established in vivo systems due, in part, to the nonexistence of particular phenotypes in such established systems.

Various aspects of the invention are described in detail in the following sections. The use of sections is not meant to limit the invention. Each section can apply to any aspect of the invention. In this application, the use of "or" means "and/or" unless stated otherwise.

C9ORF72

Amyotrophic lateral sclerosis (ALS), also referred to as Lou Gehrig's disease, is the most frequent adult-onset paralytic disorder, characterized by the loss of upper and/or lower motor neurons. ALS occurs in as many as 20,000 individuals across the United States with about 5,000 new cases occurring each year. Frontotemporal dementia (FTD), originally referred to as Pick's disease after physician Arnold Pick, is a group of disorders caused by progressive cell degeneration in the frontal or temporal lobes of the brain. FTD is reported to count for 10-15% of all dementia cases. GGGGCC hexanucleotide repeat expansion between two non-coding exons of C9ORF172 have been linked to both ALS and FTD (DeJesus-Hernandez, M. et al., 2011, Neuron 72:245-256; Renton, A. E. et al., 2011, Neuron 72:257-268; Majounie, E. et al., 2012, Lancet Neurol. 11:323-330; Waite, A. J. et al., 2014, Neurobiol. Aging 35:1779.e5-1779.e13). However, the mechanism through which such repeat mutations cause disease, whether through a loss- or gain-of-function of toxicity, remains unclear. For example, zebrafish with reduced C9ORF72 expression from targeted reduction or knockdown demonstrate axonopathy and deficits in locomotor function (Ciura, S. et al., 2013, Ann. Neurol. 74(42):180-187), while mice with reduced C9ORF72 expression do not show any behavioral or pathological features associated with ALS disease (Lagier-Tourenne, C. et al., 2013, Proc. Nat. Acad. Sci. U.S.A. E4530-E4539). Further, knock-in mice that have been generated to contain 66 C9ORF72 repeat expansions exhibit RNA foci and dipeptide protein aggregates in their neurons. These mice showed cortical neuron loss and exhibited behavior and motor deficits at 6 months of age (Chew, J. et al., 2015, Science May 14. Pii:aaa9344).

Many pathological aspects related to GGGGCC hexanucleotide repeat expansions in C9ORF72 have been reported such as, for example, repeat length-dependent formation of RNA foci, sequestration of specific RNA-binding proteins, and accumulation and aggregation of dipeptide repeat proteins (e.g., reviewed in Stepto, A. et al., 2014, Acta Neuropathol. 127:377-389; see also Almreida, S. et al., 2013, Acta Neuropathol. 126:385-399; Bieniek, K. F. et al., 2014, JAMA Neurol. 71(6): 775-781; van Blitterswijk, M. et al., 2014, Mol. Neurodegen. 9:38, 10 pages). Although C9ORF72 has been reported to regulate endosomal trafficking (Farg, M. A. et al., 2014, Human Mol. Gen. 23(13): 3579-3595), much of the cellular function of C9ORF72 remains unknown. Indeed, C9ORF72 is a gene that encodes an uncharacterized protein with unknown function. Despite the lack of understanding surrounding C9ORF72, several animal models, including engineered cell lines, for ALS and/or FTD have been developed (Roberson, E. D., 2012, Ann. Neurol. 72(6):837-849; Panda, S. K. et al., 2013, Genetics 195:703-715; Suzuki, N. et al., 2013, Nature Neurosci. 16(12):1725-1728; Xu, Z. et al., 2013, Proc. Nat. Acad. Sci. U.S.A. 110(19):7778-7783; Hukema, R. K. et al., 2014, Acta Neuropathol. Comm. 2:166, 4 pages). For example, transgenic mice having a lacZ gene insertion that replaced exons 2-6 of C9orf72 (311004O21Rik) have been produced by gene targeting efforts from the Knockout Mouse Project (see FIG. 1d of Suzuki, N. et al., 2013, supra; for KOMP, see Skarnes, W. C. et al., 2011, Nature 474 (7351):337-342). X-gal staining was observed in the brain, spinal cord, testis and germinal centers of the spleen in these mice, however, not in muscle (tibialis anterior), heart, lung, liver, and kidney. It is unclear, however, if the remaining undeleted exons (i.e., 7-11) yield any expression and, consequently, function. Another report using a transgenic mouse strain containing 80 GGGGCC repeats operably linked with a fluorescent reporter and controlled by a tetracycline responsive element without any surrounding C9orf72 sequences demonstrated neuronal cytoplasmic inclusions similar to those seen in ALS-FTD patients, which suggests that the repeat expansion itself may be responsible for disease (Hukema, R. K. et al., 2014, Acta Neuropathol. Comm. 2:166, 4 pages). These mice have been useful to establish an initial (9orf72 expression profile in cells of the CNS and provide some understanding of the mechanism of action associated with the repeat expansion; however, it remains unclear if the specific design of these constructs in these mice indicate specific functions that can be confidently attributed to C9orf72 or are a result of something else, unrelated to C9orf72 function.

In some cases, however, construct design can influence the phenotype of the resulting transgenic animal (see, e.g., Muller, U., 1999, Mech. Develop. 81:3-21). Because the C9orf72-disrupted mice as described above utilized a targeting vector with a promoter-driven selection cassette (see FIG. 1d of Suzuki, N. et al., 2013, supra; FIG. 1 of Skarnes, W. C. et al., 2011, supra), it is not clear if the displayed expression pattern correctly correlates with normal C9ORF72 expression. Indeed, expression of the remaining exons 7-11 driven by the selection cassette-associated promoter or C9ORF72 promoter itself has not been determined. As a result, phenotypes, and perhaps C9ORF72 expression via lacZ, observed in such mice may be modified or otherwise skewed due to aspects of the targeting vector. Further, a transgenic mouse strain containing an inducible GGGGCC repeat (Hukema, 2014, supra) was designed without human flanking sequence presumably due to the fact that such surrounding sequence was thought to affect translation of repeat sequences. Thus, such in vivo systems exploiting C9ORF72-mediated biology for therapeutic applications are incomplete.

As described herein, the present disclosure specifically describes a non-human animal model for ALS and/or FTD, which non-human animal comprises a disruption in a C9ORF72 locus. In particular, the present disclosure specifically describes a rodent model for ALS and/or FTD, wherein the rodent comprises a deletion of the entire coding sequence for all C9orf72 isoforms (e.g., the coding portion of exon 2 through the coding portion of exon 11 of V1) of a C9orf72 gene via insertion of a lacZ reporter gene. The targeting vector employed by the present inventors was designed to contain a self-deleting drug selection cassette (see e.g., U.S. Pat. Nos. 8,697,851, 8,518,392 and 8,354,389, all of which are herein incorporated by reference), which allows for removal of the drug selection cassette in a development-dependent manner, thereby removing any chance of promoter affects or aberrant expression of remaining exons or effects from the selection cassette itself. As described herein, the present inventors achieved complete ablation of C9orf72. Further, the present inventors measured the motor behaviors of these rodents using rotarod, open field and CatWalk assays up to 60 weeks of age and neurological deficits throughout the same period. Without wishing to be bound by any particular theory, the present disclosure demonstrates that only 40% of C9orf72 knockout rodents survived past 60 weeks of age and the rodents ceased gaining body weight beginning around 40 weeks of age. While rotarod tests did not show significant changes due to C9orf72 deletion, rodents described herein demonstrated significant hind limb paresis, motor impairment, decreased mobility and gait abnormalities at around 50 weeks of age. Further, the present disclosure specifically demonstrates that genetic silencing of murine C9orf72 results in multiple motor and neurological abnormalities similar to those found in human motor neuron diseases. Thus, rodents described herein provide, at least in some embodiments, improved in vivo systems for development of therapeutic candidates for the treatment of neurodegenerative disease such as, for example, ALS and/or FTD. Further, rodents described herein overcome deficits in existing animal models characterized by suboptimal C9orf72 deletion for the development of C9orf72-targeted therapies.

C9ORF72 Sequences

Mouse C9ORF72 transcript variants have been reported in the art (e.g., Koppers et al., Ann Neurol (2015); 78: 426-438; Atkinson et al., Acta Neuropathologica Communications (2015) 3: 59), and are also depicted in FIG. 1A. The genomic information for the three reported mouse C9ORF72 transcript variants is also available at the Ensembl web site under designations of ENSMUST00000108127 (V1), ENSMUST00000108126 (V2), and ENSMUST00000084724 (V3). Exemplary non-human (e.g., rodent) C9ORF72 mRRNA and amino acid sequences are set forth in Table 1. For mRLNA sequences, bold font contained within parentheses indicates coding sequence and consecutive exons, where indicated, are separated by alternating lower and upper case letters. For amino acid sequences, mature polypeptide sequences, where indicated, are in bold font.

Human C9ORF72 transcript variants are known in the art. One human C9ORF72 transcript variant lacks multiple exons in the central and 3' coding regions, and its 3' terminal exon extends beyond a splice site that is used in variant 3 (see below), which results in a novel 3' untranslated region (UTR) as compared to variant 3. This variant encodes a significantly shorter polypeptide and its C-terminal amino acid is distinct as compared to that which is encoded by two other variants. The mRNA and amino acid sequences of this variant can be found at GenBank accession numbers NM_145005.6 and NP_659442.2, respectively, and are hereby incorporated by reference. A second human C9ORF72 transcript variant (2) differs in the 5' untranslated region (UTR) compared to variant 3. The mRNA and amino acid sequences of this variant can be found at GenBank accession numbers NM_018325.4 and NP_060795.1, respectively, and are hereby incorporated by reference. A third human C9ORF72 transcript variant (3) contains the longest sequence among three reported variants and encodes the longer isoform. The mRNA and amino acid sequences of this variant can be found at GenBank accession numbers NM_001256054.2 and NP_001242983.1, respectively, and are hereby incorporated by reference, Variants 2 and 3 encode the same protein.

TABLE 1

```
Mus musculus C9orf72 mRNA (NM_001081343; SEQ ID NO: 1)
gtgtccgggcggggcggtcccggggcggggcccggagcgggctgcggttgcggtccctgcgccggcggtgaaggcgcagc
agcggcgagtggCTATTGCAAGCGTTCGGATAATGTGAGACCTGGAATGCAGTGAGAC
CTGGGATGCAGGG(ATGTCGACTATCTGCCCCCCACCATCTCCTGCTGTTGC
CAAGACAGAGATTGCTTTAAGTGGTGAATCACCCTTGTTGGCGGCTACCTT
TGCTTACTGGGATAATATTCTTGGTCCTAGAGTAAGGCATATTTGGGCTCC
AAAGACAGACCAAGTGCTTCTCAGTGATGGAGAAATAACTTTTCTTGCCAA
CCACACTCTAAATGGAGAAATTCTTCGAAATGCAGAGAGTGGGGCTATAGA
TGTAAAATTTTTTGTCTTATCTGAAAAAGGGGTAATTATTGTTTCATTAATC
TTCGACGGAAACTGGAATGGAGATCGGAGCACTTATGGACTATCAATTATA
CTGCCGCAGACAGAGCTGAGCTTCTACCTCCCACTTCACAGAGTGTGTGTT
GACAGGCTAACACACATTATTCGAAAAGGAAGAATATGGATGCATAAGgaaa
gacaagaaaatgtccagaaaattgtcttggaaggcacagagaggatggaagatcagGGTCAGAGTATCATT
CCCATGCTTACTGGGGAAGTCATTCCTGTAATGGAGCTGCTTGCATCTATG
AAATCCCACAGTGTTCCTGAAGACATTGATatagctgatacagtgctcaatgatgatgacattgg
tgacagctgtcacgaaggctttcttctcaaTGCCATCAGCTCACACCTGCAGACCTGTGGCTG
TTCCGTTGTAGTTGGCAGCAGTGCAGAGAAAGTAAATAAGatagtaagaacgctgtgc
cttttctgacaccagcagagagagaaatgctccaggctgtgtgaagcagaatcgtcctttaagtacgaatcgggactctttgtg
caaggcttgctaaagGATGCAACAGGCAGTTTTGTCCTACCCTTCCGGCAAGTTATG
TATGCCCCGTACCCCACCACCCACATTGATGTGGATGTCAACACTGTCAAG
CAGATGCCACCGTGTCATGAACATATTTATAATCAACGCAGATACATGAGG
TCAGAGCTGACAGCCTTCTGGAGGGCAACTTCAGAAGAGGACATGGCGCA
GGACACCATCATCTACACAGATGAGAGCTTCACTCCTGATTTgaatattttccaagat
gtcttacacagagacactctagtgaaagccttcctggatcagGTCTTCCATTTTGAAGCCTGGCCTGT
CTCTCAGGAGTACTTTCCTTGCACAGTTCCTCCTCATTCTTCACAGAAAAGC
CTTGACACTAATCAAGTACATCGAGGATGAGGATGATACgcagaagggaaaaagccctttaagtctc
ttcggaacctgaagatagatcttgatttaacagcagagggcgatcttaacataataatggctctagctgagaaaattaagcc
aggcctacactctttcatctttgggagaccttctcacactagtgtacaagaacgtgatgttctaatgaccttttga)ccgtgtggtt
tgctgtgtctgtctcttcacagtcacacctgctgttacagtgtctcagcagtgtgtgggcacatccttcctcccgagtcctgctgcaggac
agggtacactacacttgtcagtagaagtctgtacctgatgtcaggtgcatcgttacagtgaatgactcttcctagaatagatgtactcttttt
agggccttatgtttacaattatcctaagtactattgctgtcttttaaagatatgaatgatggaatatacacttgaccataactgctgattggttt
tttgttttgttttgtttgttttcttggaaacttatgattcctggtttacatgtaccacactgaaaccctcgttagctttacagataaagtgtgagtt
gacttcctgccctctgtgttctgtggtatgtccgattacttctgccacagctaaacattagagcatttaaagtttgcagttcctcagaaag
gaacttagtctgactacagattagttcttgagagaagacactgataggggcagagctgtaggtgaaatcagttgttagcccttcctttatag
acgtagtccttcagattcggtctgtacagaaatgccgaggggtcatgcatgggccctgagtatcgtgacctgtgacaagttttttgttgg
```

TABLE 1-continued

```
tttattgtagttctgtcaaagaaagtggcatttgtttttataattgttgccaacttttaaggttaattttcattattttttgagccgaattaaaatgcg
cacctcctgtgcctttcccaatcttggaaaatataatttcttggcagagggtcagatttcagggcccagtcactttcatctgaccacccttt
gcacggctgccgtgtgcctggcttagattagaagtccttgttaagtatgtcagagtacattcgctgataagatctttgaagagcaggga
agcgtcttgcctctttcctttggtttctgcctgtactctggtgtttcccgtgtcacctgcatcataggaacagcagagaaatctgacccagt
gctattttctaggtgctactatggcaaactcaagtggtctgtttctgttcctgtaacgttcgactatctcgctagctgtgaagtactgattag
tggagttctgtgcaacagcagtgtaggagtatacacaaacacaaatatgttttctatttaaaactgtggacttagcataaaaagggaga
atatatttattttttacaaaagggataaaaatgggccccgttcctcacccaccagatttagcgagaaaaagctttctattctgaaaggtcac
ggtggctttggcattacaaatcagaacaacacacactgaccatgatggcttgtgaactaactgcaaggcactccgtcatggtaagcga
gtaggtcccacctcctagtgtgccgctcattgctttacacagtagaatcttatttgagtgctaattgttgtctttgctgcttactgtgttgttat
agaaaatgtaagctgtacagtgaatgaattagtcattgaagcatgtgtaaacactgttatatatcttttctcctagatggggaattttgaataaaat
acctttgaaattctgtgt
```

*Mus musculus* C9orf72 amino acid (NM_001081343; SEQ ID NO: 2)
**MSTICPPPSPAVAKTEIALSGESPLLAATFAYWDNILGPRVRHIWAPKTDQVLLS
DGEITFLANHTLNGEILRNAESGAIDVKFFVLSEKGVIIVSLIFDGNWNGDRSTY
GLSILLPQTELSFYLPLHRVCVDRLTHIIRKGRIWMHKERQENVQKIVLEGTER
MEDQGQSIIPMLTGEVIPVMELLASMKSHSVPEDIDIADTVLNDDDIGDSCHEG
FLLNAISSHLQTCGCSVVVGSSAEKVNKIVRTLCLFLTPAERKCSRLCEAESSFK
YESGLFVQGLLKDATGSFVLPFRQVMYAPYPTTHIDVDVNTVKQMPPCHEHIY
NQRRYMRSELTAFWRATSEEDMAQDTIIYTDESFTPDLNIFQDVLHRDTLVKAF
LDQVFHLKPGLSLRTFLAQFLLILHRKALTLIKYIEDDT**QKGKKPFKSLRNLKID
LDLTAEGDLNIIMALAEKIKPGLHSFIFGRPFYTSVQEDVLMTF

*Rattus norvegicus* C9orf72 mRNA (NM_001007702: SEQ ID NO: 3)
```
CGTTTGTAGTGTCAGCCATCCCAATTGCCTGTTCCTTCTCTGTTGGGAGTGGTGTC
TAGACAGTCCAGGCAGGGTATGCTAGGCAGGTGCGTTTTGGTTGCCTCAGATCG
CAACTTGACTCCATAACGGTGACCAAAGACAAAGAAGGAAACCAGATTAAAA
AGAACCGGACACAGACCCCTGCAGAATCTGGAGCGGCCGTGGTTGGGGGCGGG
GCTACGACGGGGCGGACTCGGGGGCGTGGGAGGGCGGGGCCGGGGCGGGGCCC
GGAGCCGGCTGCCGGTTGCGGTCCCTGCGCCGGCGGTGAAGGCGCAGCGGCGGC
GAGTGGCTATTGCAAGCGTTTGGATAATGTGAGACCTGGGATGCAGGG(ATGTC
GACTATCTGCCCCCCACCATCTCCTGCTGTTGCCAAGACAGAGATTGCTTT
AAGTGGTGAATCACCCTTGTTGGCGGCTACCTTTGCTTACTGGGATAATAT
TCTTGGTCCTGAGTAAGGCACATTTGGGCTCCAAAGACAGACCAAGTACT
CCTCAGTGATGGAGAAATCACTTTTCTTGCCAACCACACTCTGAATGGAGA
AATTCTTCGGAATGCGGAGAGTGGGCAATAGATGTAAAGTTTTTTGTCTT
ATCTGAAAAGGGCGTCATTATTGTTTCATTAATCTTCGACGGGAACTGGAA
CGGAGATCGGAGCACTTACGGACTATCAATTATACTGCCGCAGACGGAGCT
GAGTTTCTACCTCCCACTGCACAGAGTGTGTGTTGACAGGCTAACGCACAT
CATTCGAAAAGGAAGGATATGGATGCACAAGGAAAGACAAGAAAATGTCCA
GAAAATTGTCTTGGAAGGCACCGAGAGGATGGAAGATCAGGGTCAGAGTA
TCATCCCTATGCTTACTGGGGAGGTCATCCCTGTGATGGAGCTGCTTGCGT
CTATGAGATCACACAGTGTTCCTGAAGACCTCGATATAGCTGATACAGTAC
TCAATGATGATGACATTGGTGACAGCTGTCATGAAGGCTTTCTTCTCAATG
CCATCAGCTCACATCTGCAGACCTGCGGCTGTTCTGTGGTGGTAGGCAGCA
GTGCAGAGAAAGTAAATAAGATAGTAAGAACACTGTGCCTTTTTCTGACAC
CAGCAGAGAGGAAGTGCTCCAGGCTGTGTGAAGCCGAATCGTCCTTTAAAT
ACGAATCTGGACTCTTTGTACAAGGCTTGCTAAAGGATGCGACTGGCAGTT
TTGTACTACCTTTCCGGCAAGTTATGTATGCCCCTTATCCCACCACACACAT
CGATGTGGATGTCAACACTGTCAAGCAGATGCCACCGTGTCATGAACATAT
TTATAATCAACGCAGATACATGAGGTCAGAGCTGACAGCCTTCTGGAGGGC
AACTTCAGAAGAGGACATGGCTCAGGACACCATCATCTACACAGATGAGAG
CTTCACTCCTGATTTGAATATTTTCCAAGATGTCTTACACAGAGACACTCTA
GTGAAAGCCTTTCTGGATCAGGTCTTCCATTTGAAGCCTGGCCTGTCTCTC
AGGAGTACTTTCCTTGCACAGTTCCTCCTCATTCTTCACAGAGCCTTGA
CACTAATCAAGTACATAGAGGATGACACGCAGAAGGGGAAAAAGCCCTTTA
AGTCTCTTCGGAACCTGAAGATAGATCTTGATTTAACAGCAGAGGGCGACC
TTAACATAATAATGGCTCTAGCTGAGAAAATTAAGCCAGGCCTACACTCTTT
CATCTTCGGGAGACCTTTCTACACTAGTGTCCAAGAACGTGATGTTCTAAT
GACTTTTAA)ACATGTGGTTTGCTCGTGTGTCTCATGACAGTCACACTTGCTG
TTACAGTGTCTCAGCGCTTTGGACACATCCTTCCTCCAGGGTCCTGCCGCAGGAC
ACGTTACACTACACTTGTCAGTAGAGGTCTGTACCAGATGTCAGGTACATCGTT
GTAGTGAATGTCTCTTTTCCTAGACTAGATGTACCCTCGTAGGGACTTATGTTTA
CAACCCTCCTAAGTACTAGTGCTGTCTTGTAAGGATACGAATGAAGGGATGTAA
ACTTCACCACAACTGCTGGTTGGTTTTGTTGTTTTTGTTTTTTGAAACTTATAATT
CATGGTTTACATGCATCACACTGAAACCCTAGTTAGCTTTTTACAGGTAAGCTGT
GAGTTGACTGCCTGTCCCTGTGTTCTCTGGCCTGTACGATCTGTGGCGTGTAGGA
TCACTTTTGCAACAACTAAAAACTAAAGCACTTTGTTTGCAGTTCTACAGAAAG
CAACTTAGTCTGTCTGCAGATTCGTTTTTGAAAGAAGACATGAGAAAGCGGAGT
TTTAGGTGAAGTCAGTTGTTGGATCTTCCTTTATAGACTTAGTCCTTTAGATGTG
GTCTGTATAGACATGCCCAACCATCATGCATGGGCACTGAATATCGTGAACTGT
GGTATGCTTTTTGTTGGTTTATTGTACTTCTGTCAAAGAAAGTGGCATTGGTTTTT
ATAATTGTTGCCAAGTTTTAAGGTTAATTTTCATTATTTTTGAGCCAAATTAAAA
TGTGCACCTCCTGTGCCTTTCCCAATCTTGGAAAATATAATTTCTTGGCAGAAGG
TCAGATTTCAGGGCCCAGTCACTTTCGTCTGACTTCCCTTTGCACAGTGCGCCAT
GGGCCTGGCTTAGAAGTTCTTGTAAACTATGCCAGAGAGTACATTCGCTGATAA
AATCTTCTTTGCAGAGCAGGAGAGCTTCTTGCCTCTTTCCTTTCATTTCTGCCTGG
ACTTTGGTGTTCTCCACGTTCCCTGCATCCTAAGGACAGCAGGAGAACTCTGAC
CCCAGTGCTATTTCTCTAGGTGCTATTGTGGCAAACTCAAGCGGTCCGTCTCTGT
CCCTGTAACGTTCGTACCTTGCTGGCTGTGAAGTACTGACTGGTAAAGCTCCGTG
```

TABLE 1-continued

```
CTACAGCAGTGTAGGGTATACACAAACACAAGTAAGTGTTTTATTTAAAACTGT
GGACTTAGCATAAAAAGGGAGACTATATTTATTTTTTACAAAAGGGATAAAAAT
GGAACCCTTTCCTCACCCACCAGATTTAGTCAGAAAAAAACATTCTATTCTGAA
AGGTCACAGTGGTTTTGACATGACACATCAGAACAACGCACACTCTTCCATGATG
GCTTATGAACTCCAAGTCACTCCATCATGGTAAATGGGTAGATCCCTCCTTCTAG
TGTGCCACACCATTGCTTCCCACAGTAGAATCTTATTTAAGTGCTAAGTGTTGTC
TCTGCTGGTTTACTCTGTTGTTTTAGAGAATGTAAGTTGTATAGTGAATAAGTTA
TTGAAGCATGTGTAAACACTGTTATACATCTTTTCTCCTACTATGGGGAATTTGGA
ATAAAATACCTTTAAAATTCAAAAAAAAAAAAAAAAAAAAAAAAA
```

*Rattus norvegicus* C9orf72 amino acid (NP_001007703; SEQ ID NO: 4)
```
MSTICPPPSPAVAKTEIALSGESPLLAATFAYWDNILGPRVRHIWAPKTDQVLLSDGE
ITFLANHTLNGEILRNAESGAIDVKFFVLSEKGVIIVSLIFDGNWNGDRSTYGLSIILP
QTELSFYLPLHRVCVDRLTHIIRKGRIWMHKERQENVQKIVLEGTERMEDQGQSIIP
MLTGEVIPVMELLASMRSHSVPEDLDIADTVLNDDDIGDSCHEGFLLNAISSHLQTC
GCSVVVGSSAEKVNKIVRTLCLFLTPAERKCSRLCEAESSFKYESGLFVQGLLKDAT
GSFVLPFRQVMYAPYPTTHIDVNTVKQMPPCHEHIYNQRRYMRSELTAFWRAT
SEEDMAQDTIIYTDESFTPDLNIFQDVLHRDTLVKAFLDQVFHLKPGLSLRSTFLAQF
LLILHRKALTLIKYIEDDTQKGKKPFKSLRNLKIDLDLTAEGDLNIIMALAEKIKPGL
HSFIFGRPFYTSVQERDVLMTF
```

C9ORF72 Targeting Vectors and Production of Non-Human Animals Having a Disruption in a C9ORF72 Locus Provided herein are targeting vectors or targeting constructs for the production of non-human animals having a disruption in a C9ORF72 locus as described herein.

DNA sequences can be used to prepare targeting vectors for knockout animals (e.g., an C9ORF72 KO). Typically, a polynucleotide molecule (e.g., an insert nucleic acid) encoding a reporter gene and/or a selectable marker is inserted into a vector, preferably a DNA vector, in order to replicate the polynucleotide molecule in a suitable host cell.

A polynucleotide molecule (or insert nucleic acid) comprises a, segment of DNA that one desires to integrate into a target locus. In some embodiments, an insert nucleic acid comprises one or more polynucleotides of interest. In some embodiments, an insert nucleic acid comprises one or more expression cassettes. In some certain embodiments, an expression cassette comprises a polynucleotide of interest, a polynucleotide encoding a selection marker and/or a reporter gene along with, in some certain embodiments, various regulatory components that influence expression. Virtually any polynucleotide of interest may be contained within an insert nucleic acid and thereby integrated at a target genomic locus. Methods disclosed herein, provide for at least 1, 2, 3, 4, 5, 6 or more polynucleotides of interest to be integrated into a targeted C9ORF72 genomic locus.

In some embodiments, a polynucleotide of interest contained in an insert nucleic acid encodes a reporter. In some embodiments, a polynucleotide of interest encodes a selectable marker.

In some embodiments, a polynucleotide of interest is flanked by or comprises site-specific recombination sites (e.g., loxP, Frt, etc.). In some certain embodiments, site-specific recombination sites flank a DNA segment that encodes a reporter and/or a DNA segment that encodes a selectable marker. Exemplary polynucleotides of interest, including selection markers and reporter genes that can be included within insert nucleic acids are described herein.

Various methods employed in preparation of plasmids, DNA constructs and/or targeting vectors and transformation of host organisms are known in the art. For other suitable expression systems for both prokaryotic and eukaryotic cells, as well as general recombinant procedures, see Molecular Cloning: A Laboratory Manual, 2nd Ed., ed. by Sambrook, J. et al., Cold Spring Harbor Laboratory Press: 1989.

As described above, exemplary non-human (e.g., rodent) C9ORF72 nucleic acid and amino acid sequences for use in constructing targeting vectors for knockout animals are provided in Table 1. Other non-human C9ORF72 sequences can also be found in the GenBank database. C9ORF72 targeting vectors, in some embodiments, comprise DNA sequences encoding a reporter gene and/or a selectable marker, flanked by sequences that are identical or substantially homologous to flanking sequences of a target region (also referred to as "homology arms") for insertion into the genome of a transgenic non-human animal. To give but one example, a deletion start point may be set upstream (5') of a first exon, a first coding exon, or the first or second codon, to allow an insert nucleic acid to be operably linked to an endogenous regulatory sequence (e.g., a promoter). FIG. 1A illustrates a targeting strategy for making a targeted deletion of the entire coding sequence of a murine C9orf72 gene and replacement with a cassette that contains a sequence from a lacZ gene that encodes β-galactosidase and a drug selection cassette (Neo) that encodes neomycin phosphotransferase for the selection of G418-resistant embryonic stem (ES) cell colonies. The targeting vector also includes a sequence encoding a recombinase (e.g., Cre) regulated by an ES-cell specific miRNAs or a germ-cell specific promoter (e.g., protamine 1 promoter; Prot-Cre-SV40). The drug selection cassette and Cre recombinase-encoding sequences are flanked by loxP (LP) recombinase recognition sites that enable Cre-mediated excision of the drug selection cassette in a development-dependent manner, e.g., progeny derived from rodents whose germ cells containing the disrupted C9orf72 gene described above will shed the selectable marker (Neo) during development (see U.S. Pat. Nos. 8,697,851, 8,518,392, 8,354,389, 8,946,505, and 8,946,504, all of which are herein incorporated by reference). This allows for, among other things, automatic excision of the selection cassette from either differentiated cells or germ cells. Thus, prior to phenotypic analysis the drug selection cassette is removed leaving only the lacZ reporter gene operably linked to the murine C9orf72 promoter.

As described herein, disruption of a C9orf72 locus can comprise a replacement of or an insertion/addition to the C9orf72 locus or a portion thereof with an insert nucleic acid. In some embodiments, an insert nucleic acid comprises a reporter gene. In some certain embodiments, a reporter gene is positioned in operable linkage with an endogenous C9orf72 promoter. Such a modification allows for the expression of a reporter gene driven by an endogenous C9orf72 promoter. Alternatively, a reporter gene is not placed in operable linkage with an endogenous C9orf72 promoter.

A variety of reporter genes (or detectable moieties) can be used in targeting vectors described herein. Exemplary reporter genes include, for example, β-galactosidase (encoded lacZ gene), Green Fluorescent Protein (GFP), enhanced Green Fluorescent Protein (eGFP), MmGFP, blue fluorescent protein (BFP), enhanced blue fluorescent protein (eBFP), mPlum, mCherry, tdTomato, mStrawberry, J-Red, DsRed, mOrange, mnKO, mCitrine, Venus, YPet, yellow fluorescent protein (YFP), enhanced yellow fluorescent protein (eYFP), Emerald, CyPet, cyan fluorescent protein (CFP), Cerulean, T-Sapphire, luciferase, alkaline phosphatase, or a combination thereof. The methods described herein demonstrate the construction of targeting vectors that employ the use of a lacZ reporter gene that encodes β-galactosidase, however, persons of skill upon reading this disclosure will understand that non-human animals described herein can be generated in the absence of a reporter gene or with any reporter gene known in the art.

Where appropriate, the coding region of the genetic material or polynucleotide sequence(s) encoding a reporter polypeptide, in whole or in part, may be modified to include codons that are optimized for expression in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a reporter polypeptide (e.g. lacZ), in whole or in part, may include an altered sequence to optimize codon usage for a particular cell type (e.g., a rodent cell). For example, the codons of the reporter gene to be inserted into the genome of a non-human animal (e.g., a rodent) may be optimized for expression in a cell of the non-human animal. Such a sequence may be described as a codon-optimized sequence.

Compositions and methods for making non-human animals that comprises a disruption in a C9ORF72 locus as described herein are provided, including compositions and methods for making non-human animals that express a reporter gene from a C9ORF72 promoter and a C9ORF72 regulatory sequence. In some embodiments, compositions and methods for making non-human animals that express a reporter gene from an endogenous promoter and an endogenous regulatory sequence are also provided. Methods include inserting a targeting vector, as described herein, encoding a reporter gene (e.g., lacZ) into the genome of a non-human animal so that an entire coding sequence of a C9ORF72 locus is deleted, in whole or in part. In some embodiments, methods include inserting targeting vector into the genome of a non-human animal so that the entire coding sequence for all C9ORF72 isoforms at a, C9ORF72 locus is deleted.

Insertion of a reporter gene operably linked to a C9ORF72 promoter (e.g., an endogenous C9ORF72 promoter) employs a relatively minimal modification of the genome and results in expression of reporter polypeptide in a C9ORF72-specific manner in the non-human animal. In some embodiments, a non-human animal described herein comprises a C9ORF72 locus that comprises a targeting vector as described herein.

Targeting vectors described herein may be introduced into ES cells and screened for ES clones harboring a disruption in a C9orf72 locus as described in Frendewey, D., et al., 2010, Methods Enzymol. 476:295-307. A variety of host embryos can be employed in the methods and compositions disclosed herein. For example, the pluripotent and/or totipotent cells having the targeted genetic modification can be introduced into a pre-morula stage embryo (e.g., an 8-cell stage embryo) from a corresponding organism. See, e.g., U.S. Pat. Nos. 7,576,259, 7,659,442, 7,294,754, and US 2008/0078000 A1, all of which are incorporated by reference herein in their entireties. In other cases, the donor ES cells may be implanted into a host embryo at the 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo, an uncompacted morula stage embryo, or a compacted morula stage embryo.

In some embodiments, the VELOCIMOUSE® method (Poueymirou, W. T. et al., 2007, Nat. Biotechnol. 25:91-99) may be applied to inject positive ES cells into an 8-cell embryo to generate fully ES cell-derived F0 generation heterozygous mice ready for lacZ expression profiling or breeding to homozygosity. Exemplary methods for generating non-human animals having a disruption in a C9orf72 locus are provided in Example 1.

Methods for generating transgenic non-human animals, including knockouts and knock-ins, are well known in the art (see, e.g., Gene Targeting: A Practical Approach, Joyner, ed., Oxford University Press, Inc. (2000)). For example, generation of transgenic rodents may optionally involve disruption of the genetic loci of an endogenous rodent gene and introduction of a reporter gene into the rodent genome, in some embodiments, at the same location as the endogenous rodent gene.

A schematic illustration (not to scale) of the genomic organization of a, mouse C9orf72 is provided in FIG. 1A. An exemplary targeting strategy for deletion of an entire coding sequence of murine C9orf72 locus using a reporter gene is also provided in FIG. 1A. As illustrated, genomic DNA containing the coding portion of exon 2 through the coding portion of exon 11 of a murine C9orf72 locus is deleted and replaced with a reporter gene and a drug selection cassette flanked by site-specific recombinase recognition sites. The targeting vector used in this strategy includes a recombinase-encoding sequence that is operably linked to a promoter that is developmentally regulated such that the recombinase is expressed in undifferentiated cells. Exemplary promoters than can be included in targeting vectors described herein are provided in Table 2. Additional suitable promoters that can be used in targeting vectors described herein include those described in U.S. Pat. Nos. 8,697,851, 8,518,392 and 8,354,389; all of which are herein incorporated by reference). Upon homologous recombination, the entire coding sequence (e.g., the coding portion of exon 2 through the coding portion of exon 11) of an endogenous murine C9orf72 locus is replaced by the sequence contained in the targeting vector. The drug selection cassette is removed in a development-dependent manner, i.e., progeny derived from mice whose germ line cells containing a disruption in a C9orf72 locus described above will shed the selectable marker from differentiated cells during development (see U.S. Pat. Nos. 8,697,851, 8,518,392 and 8,354, 389, all of which are herein incorporated by reference).

TABLE 2

Prot promoter (SEQ ID NO: 5)
CCAGTAGCAGCACCCACGTCCACCTTCTGTCTAGTAATGTCCAACACCTCCCTCA
GTCCAAACACTGCTCTGCATCCATGTGGCTCCCATTTATACCTGAAGCACTTGAT
GGGGCCTCAATGTTTACTAGAGCCCACCCCCCTGCAACTCTGAGACCCTCTGG
ATTTGTCTGTCAGTGCCTCACTGGGGCGTTGGATAATTTCTTAAAAGGTCAAGTT
CCCTCAGCAGCATTCTTCTGAGCAGTCTGAAGATGTGTGCTTTTTCACAGTTCAAAT
CCATGTGGCTGTTTCACCCACCTGCCTGGCCTTGGGTTATCTATCAGGACCTAGC
CTAGAAGCAGGTGTGTGGCACTTAACACCTAAGCTGAGTGACTAACTGAACACT
CAAGTGGATGCCATCTTTGTCACTTCTTGACTGTGACACAAGCAACTCCTGATGC
CAAAGCCCTGCCCACCCCTCTCATGCCCATATTTGGACATGGTACAGGTCCTCAC
TGGCCATGGTCTGTGAGGTCCTGGTCCTCTTTGACTTCATAATTCCTAGGGGCCA
CTAGTATCTATAAGAGGAAGAGGGTGCTGGCTCCCAGGCCACAGCCCACAAAA
TTCCACCTGCTCACAGGTTGGCTGGCTCGACCCAGGTGGTGTCCCCTGCTCTGAG
CCAGCTCCCGGCCAAGCCAGCACC Blimp1 promoter 1 kb (SEQ ID NO: 6)
TGCCATCATCACAGGATGTCCTTCCTTCTCCAGAAGACAGACTGGGGCTGAAGG
AAAAGCCGGCCAGGCTCAGAACGAGCCCCACTAATTACTGCCTCCAACAGCTTT
CCACTCACTGCCCCAGCCCAACATCCCCTTTTTAACTGGGAAGCATTCCTACTC
TCCATTGTACGCACACGCTCGGAAGCCTGGCTGTGGGTTTGGGCATGAGAGGCA
GGGACAACAAAACCAGTATATATGATTATAACTTTTTCCTGTTTCCCTATTTCCA
AATGGTCGAAAGGAGGAAGTTAGGTCTACCTAAGCTGAATGTATTCAGTTAGCA
GGAGAAATGAAATCCTTACGTTTAATACTAGAGGAGAACCGCCTTAGAATATT
TATTTCATTGGCAATGACTCCAGGACTACACAGCGAAATTGTATTGCATGTGCT
GCCAAAATACTTTAGCTCTTTCCTTCGAATACGTCGGATCCTGTAATTGAGACA
CCGAGTTTAGGTGACTAGGGTTTTCTTTTGAGGAGGAGTCCCCCACCCCGCCCC
GCTCTGCCGCGACAGGAAGCTAGCGATCCGGAGGACTTAGAATACAATCGTAGT
GTGGGTAAACATGGAGGGCAAGCGCCTGCAAAGGGAAGTAAGAAGATTCCCAG
TCCTTGTTGAAATCCATTTGCAAACAGAGGAAGCTGCCGCGGGTCGCAGTCGGT
GGGGGGAAGCCCTGAACCCCACGCTGCACGGCTGGGCTGGCCAGGTGCGGCCA
CGCCCCCATCGCGGCGGCTGGTAGGAGTGAATCAGACCGTCAGTATTGGTAAAG
AAGTCTGCGGCAGGGCAGGGAGGGGGAAGAGTAGTCAGTCGCTCGCTCACTCG
CTCGCTCGCACAGACACTGCTGCAGTGACACTCGGCCCTCCAGTGTCGCGGAGA
CGCAAGAGCAGCGCGCAGCACCTGTCCGCCCGGAGCGAGCCCGGCCCGCGGCC
GTAGAAAAGGAGGGACCGCCGAGGTGCGCGTCAGTACTGCTCAGCCCGGCAGG
GACGCGGGAGGATGTGGACTGGGTGGAC Blimp1 promoter 2 kb (SEQ ID NO: 7)
GTGGTGCTGACTCAGCATCGGTTAATAAACCCTCTGCAGGAGGCTGGATTTCTTT
TGTTTAATTATCACTTGGACCTTTCTGAGAACTCTTAAGAATTGTTCATTCGGGT
TTTTTTGTTTTGTTTTGGTTTGGTTTTTTTGGGTTTTTTTTTTTTTTTTTTTTTTTGGT
TTTTGGAGACAGGGTTTCTCTGTATATAGCCCTGGCACAAGAGCAAGCTAACAG
CCTGTTTCTTCTTGGTGCTAGCGCCCCCTCTGGCAGAAAATGAAATAACAGGTG
GACCTACAACCCCCCCCCCCCCCCCAGTGTATTCTACTCTTGTCCCCGGTATAA
ATTTGATTGTTCCGAACTACATAAATTGTAGAAGGATTTTTTAGATGCACATATC
ATTTTCTGTGATACCTTCCACACACCCCTCCCCCCCAAAAAAATTTTTCTGGGAA
AGTTTCTTGAAAGGAAAACAGAAGAACAAGCCTGTCTTTATGATTGAGTTGGGC
TTTTGTTTTGCTGTGTTTCATTTCTTCCTGTAAACAAATACTCAAATGTCCACTTC
ATTGTATGACTAAGTTGGTATCATTAGGTTGGGTCTGGGTGTGTGAATGTGGGT
GTGGATCTGGATGTGGGTGGGTGTGTATGCCCCGTGTGTTTAGAATACTAGAAA
AGATACCACATCGTAAACTTTTGGGAGAGATGATTTTTAAAAATGGGGGTGGGG
GTGAGGGGAACCTGCGATGAGGCAAGCAAGATAAGGGGAAGACTTGAGTTTCT
GTGATCTAAAAAGTCGCTGTGATGGGATGCTGGCTATAAATGGGCCCTTAGCAG
CATTGTTTCTGTGAATTGGAGGATCCCTGCTGAAGGCAAAAGACCATTGAAGGA
AGTACCGCATCTGGTTTGTTTTGTAATGAGAAGCAGGAATGCAAGGTCCACGCT
CTTAATAATAAACAAACAGGACTTGTATGCCATCATCACAGGATGTCCTTCCT
TCTCCAGAAGACAGACTGGGGCTGAAGGAAAAGCCGGCCAGGCTCAGAACGAG
CCCCACTAATTACTGCCTCCAACAGCTTTCCACTCACTGCCCCCAGCCCAACATC
CCCTTTTTAACTGGGAAGCATTCCTACTCTCCATTGTACGCACACGCTCGGAAGC
CTGGCTGTGGGTTTGGGCATGAGAGGCAGGGACAACAAAACCAGTATATATGA
TTATAACTTTTTCCTGTTTCCCTATTTCCAAATGGTCGAAAGGAGGAAGTTAGGT
CTACCTAAGCTGAATGTATTCAGTTAGCAGGAGAAATGAAATCCTATACGTTTA
ATACTAGAGGAGAACCGCCTTAGAATATTTATTTCATTGGCAATGACTCCAGGA
CTACACAGCGAAATTGTATTGCATGTGCTGCCAAAATACTTTAGCTCTTTCCTTC
GAAGTACGTCGGATCCTGTAATTGAGACACCGAGTTTAGGTGACTAGGGTTTTC
TTTTGAGGAGGAGTCCCCCACCCCGCCCCGCTCTGCCGCGACAGGAAGCTAGCG
ATCCGGAGGACTTAGAATACAATCGTAGTGTGGGTAAACATGGAGGGCAAGCG
CCTGCAAAGGGAAGTAAGAAGATTCCCAGTCCTTGTTGAAATCCATTTGCAAAC
AGAGGAAGCTGCCGCGGGTCGCAGTCGGTGGGGGGAAGCCCTGAACCCCACGC
TGCACGGCTGGGCTGGCCAGGTGCGGCCACGCCCCCATCGCGGCGGCTGGTAGG
AGTGAATCAGACCGTCAGTATTGGTAAAGAAGTCTGCGGCAGGGCAGGGAGGG
GGAAGAGTAGTCAGTCGCTCGCTCACTCGCTCGCTCGCACAGACACTGCTGCAG
TGACACTCGGCCCTCCAGTGTCGCGGAGACGCAAGAGCAGCGCGCAGCACCTGT
CCGCCCGGAGCGAGCCCGGCCCGCGGCCGTAGAAAAGGAGGGACCGCCGAGGT
GCGCGTCAGTACTGCTCAGCCCGGCAGGGACGCGGGAGGATGTGGACTGGGTG
GAC A transgenic founder non-human animal can be identified based upon the presence of a reporter gene (or absence of C9ORF72) in its genome and/or expression of a reporter in tissues or cells of the non-human animal (or lack of expression of C9ORF72). A transgenic founder non-human animal can then be used to breed additional non-human animals carrying the reporter gene thereby creating a series of non-human animals each carrying one or more copies of a C9ORF72 locus as described herein.

Transgenic non-human animals may also be produced to contain selected systems that allow for regulated or directed expression of the transgene. Exemplary systems include the Cre/loxP recombinase system of bacteriophage P1 (see, e.g., Lakso, M. et al., 1992, Proc. Natl. Acad. Sci, USA 89:6232-6236) and the FLP/Frt recombinase system of *S. cerevisiae* (O'Gorman, S. et al, 1991, Science 251:1351-1355). Such animals can be provided through the construction of "double" transgenic animals, e.g., by mating two transgenic animals, one containing a transgene encoding a selected polypeptide (e.g., a reporter gene) and the other containing a transgene encoding a recombinase (e.g., a Cre recombinase).

Although embodiments employing a disruption in a C9ORF72 locus in a mouse (i.e., a mouse with a deletion of an entire C9orf72-coding sequence) are extensively discussed herein, other non-human animals that comprise a disruption in a C9ORF72 locus are also provided. In some embodiments, such non-human animals comprise a disruption in a C9ORF72 locus characterized by insertion of a reporter operably linked to an endogenous C9ORF72 promoter. Such non-human animals include any of those which can be genetically modified to delete an entire coding sequence of a C9ORF72 locus as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Briefly, methods for nuclear transfer include steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes may be matured in a variety of medium known to persons of skill in the art prior to enucleation. Enucleation of the oocyte can be performed in a variety of ways known to persons of skill in the art. Insertion of a donor cell or nucleus into an enucleated oocyte to form a, reconstituted cell is typically achieved by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium known to persons of skill in the art and then transferred to the womb of an animal. See, e.g., U.S. Patent Application Publication No. 2008-0092249 A1, WO 1999/005266 A2, U.S. Patent Application Publication No. 2004-0177390 A1, WO 2008/017234 A1, and U.S. Pat. No. 7,612,250, each of which is herein incorporated by reference.

Methods for modifying a non-human animal genome (e.g., a pig, cow, rodent, chicken, etc.) include, e.g., employing a zinc finger nuclease (ZFN) or a transcription activator-like effector nuclease (TALEN) to modify a genome to include a disruption in a C9ORF72 locus as described herein.

In some embodiments, a non-human animal described herein is a mammal. In some embodiments, a non-human animal described herein is a small mammal, e.g., of the superfamily Dipodoidea or Muroidea. In some embodiments, a genetically modified animal described herein is a rodent. In some embodiments, a rodent described herein is selected from a mouse, a rat, and a hamster. In some embodiments, a rodent described herein is selected from the superfamily Muroidea. In some embodiments, a genetically modified animal described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with—tailed rats, *Malagasy* rats and mice), Platacanthomyidae (e.g., spiny dormice), and Spalacidae (e.g., mole rates, bamboo rats, and zokors). In some certain embodiments, a genetically modified rodent described herein is selected from a true mouse or rat (family Muridae), a gerbil, a spiny mouse, and a crested rat. In some certain embodiments, a genetically modified mouse described herein is from a member of the family Muridae. In some embodiment, a non-human animal described herein is a rodent. In some certain embodiments, a rodent described herein is selected from a mouse and a rat. In some embodiments, a non-human animal described herein is a mouse.

In some embodiments, a non-human animal described herein is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse described herein is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032). In some certain embodiments, a genetically modified mouse described herein is a mix of an aforementioned 129 strain and an aforementioned C57BL/6 strain. In some certain embodiments, a mouse described herein is a mix of aforementioned 129 strains, or a mix of aforementioned BL/6 strains. In some certain embodiments, a 129 strain of the mix as described herein is a 129S6 (129/SvEvTac) strain. In some certain embodiments, a mouse described herein is a BALB strain, e.g., BALB/c strain. In some embodiments, a mouse described herein is a mix of a BALB strain and another aforementioned strain.

In some embodiments, a non-human animal described herein is a rat. In some certain embodiments, a rat described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

A rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, the rat pluripotent and/or totipotent cell can be from a DA strain or an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is an ACLC.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of a rat ES cell line from a DA rat are the DA.2B rat ES cell line and the DA.2C rat ES cell line. In some cases, the rat pluripotent and/or totipotent cells are from an inbred rat strain. See, e.g., U.S. 2014/0235933 A1, filed on Feb. 20, 2014, and herein incorporated by reference in its entirety.

Non-human animals are provided that comprise a disruption in a C9ORF72 locus. In some embodiments, a disruption in a C9ORF72 locus results in a loss-of-function. In particular, loss-of-function mutations include mutations that result in a decrease or lack of expression of C9ORF72 and/or a decrease or lack of activity/function of C9ORF72. In some embodiments, loss-of-function mutations result in one or more phenotypes as described herein. Expression of C9ORF72 may be measured directly, e.g., by assaying the level of C9ORF72 in a cell or tissue of a non-human animal as described herein.

Typically, expression level and/or activity of C9ORF72 is decreased if the expression and/or activity level of C9ORF72 is statistically lower (p≤0.05) than the level of C9ORF72 in an appropriate control cell or non-human animal that does not comprises the same disruption (e.g., deletion). In some embodiments, concentration and/or activity of C9ORF72 is decreased by at least 1%, 5%, 10%, 20%, 30%, 40%, 50%, 60%, 70%, 80%, 90%, 95%, 99% or more relative to a control cell or non-human animal which lacks the same disruption (e.g., deletion).

In other embodiments, cells or organisms having a disruption in a C9ORF72 locus that reduces the expression level and/or activity of C9ORF72 are selected using methods that include, but not limited to, Southern blot analysis, DNA sequencing, PCR analysis, or phenotypic analysis. Such cells or non-human animals are then employed in the various methods and compositions described herein.

In some embodiments, an endogenous C9ORF72 locus is not deleted (i.e., intact). In some embodiments, an endogenous C9ORF72 locus is altered, disrupted, deleted or replaced with a heterologous sequence (e.g., a reporter gene encoding sequence). In some embodiments, all or substantially all of an endogenous C9ORF72 locus is replaced with an insert nucleic acid; in some certain embodiments, replacement includes replacement of an entire coding sequence of an endogenous C9ORF72 locus with a, lacZ reporter gene so that the lacZ reporter gene is in operable linkage with a C9ORF72 promoter (e.g., an endogenous C9ORF72 promoter). In some embodiments, a portion of a reporter gene (e.g., a function fragment thereof) is inserted into an endogenous non-human C9ORF72 locus. In some embodiments, the reporter gene is a lacZ gene. In some embodiments, a reporter gene is inserted into one of the two copies of the endogenous C9ORF72 locus, giving rise to a, non-human animal that is heterozygous with respect to the reporter gene. In some embodiments, a non-human animal is provided that is homozygous for a reporter gene.

Methods Employing Non-Human Animals Having Disruption in a C9ORF72 Locus

Non-human animals as described herein provide improved animal models for neurodegenerative diseases, disorders and conditions. In particular, non-human animals as described herein provide improved animal models that translate to human diseases such as, for example, ALS and/or FTD, characterized by upper motor neuron symptoms and/or non-motor neuron loss.

For example, a disruption in a C9ORF72 locus as described herein may result in various symptoms (or phenotypes) in the non-human animals provided herein. In some embodiments, deletion of a C9ORF72 locus results in non-human animals that are grossly normal at birth, but that develop ALS-like symptoms upon aging, e.g., after about 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, etc. In some embodiments, deletion of a C9ORF72 locus results in abnormal functions of one or more cell types, e.g., a neuron and/or a portion thereof. A neuron includes a sensory neuron or a motor neuron. Other phenotypes associated with ALS and/or FTD may be present in non-human animals described herein. For example, an ALS-like phenotype may involve impairment of one or more neurons, e.g., motor neurons and/or sensory neurons. Further, an ALS-like phenotype involving upper motor neurons may result in spasticity (e.g., spastic paralysis, rigidity), increased and/or abnormal reflexes (e.g., Babinski's sign), tremors and a combination thereof. An ALS-like phenotype involving impairment of lower motor neurons may result in muscle weakness and wasting, fasciculations, and a combination thereof, and/or impairment of the bulbar resulting in an inability to swallow and tongue fasciculations. An ALS-like symptom may also comprise one or more of the following phenotypes: a) kyphosis; b) abnormal hind limb clasping, dragging or toe curling; c) deficiency in motor coordination and motor learning ability, deficiency in rotarod, catwalk and/or open field test(s); d) motor neuron loss in the spinal cord; e) astrocytosis in the spinal cord; f) weight loss compared with a control rodent; g) accumulation of poly-ubiquitinated proteins and/or (h) increased neurological scoring using the ALS-TDI neurological scoring system (Table 3).

TABLE 3

| ALS-TDI neurological scoring system | |
|---|---|
| Score of 0: | Full extension of hind legs away from lateral midline when mouse is suspended by its tail, and mouse can hold this for two seconds, suspended two to three times. |

TABLE 3-continued

ALS-TDI neurological scoring system

Score of 1: Collapse or partial collapse of leg extension towards lateral midline (weakness) or trembling of hind legs during tail suspension.
Score of 2: Toes curl under at least twice during walking of 12 inches, or any part of foot is dragging along cage bottom/table.
Score of 3: Rigid paralysis or minimal joint movement, foot not being used for generating forward motion.
Score of 4: Mouse cannot right itself within 30 seconds after being placed on either side.

Thus, in at least some embodiments, non-hum animals described herein provide improved animal models for neurodegenerative diseases, disorders or conditions (e.g., ALS and/or FTD) and can be used for the development and/or identification of therapeutic agents for the treatment, prevention and/or inhibiting one or more phenotypes (or symptoms) of neurodegenerative diseases, disorders or conditions. In some embodiments, one or more symptoms (or phenotypes) in non-human animals described herein appear in Table 3.

Non-human animals as described herein also provide an in vivo system for identifying a therapeutic agent for treating, preventing and/or inhibiting one or more symptoms of neurodegenerative diseases, disorders or conditions (e.g., ALS and/or FTD). In some embodiments, an inhibitory effect of a therapeutic agent is determined in vivo, by administering said therapeutic agent to a non-human animal that has a C9ORF72 disruption as described herein, and develops neurodegenerative symptoms after 38 weeks of age.

Non-human animals as described herein also provide improved animal models for inflammatory or autoimmune diseases, disorders and conditions. In particular, non-human animals as described herein provide improved animal models that translate to human inflammatory disease characterized by infiltration of immune cells in various organs (e.g. kidney, liver, spleen, etc.). In addition, non-human animals as described herein provide improved animal models that translate to human autoimmune disease characterized by the increased presence of autoantibodies (e.g., IgG and IgM) in the serum.

For example, a disruption in a C9ORF72 locus as described herein may result in various conditions (or phenotypes) in the non-human animals provided herein. In some embodiments, deletion of a, C9ORF72 locus results in non-human animals that are grossly normal at birth, but that develop inflammatory and/or autoimmune conditions upon aging, e.g., after about 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, etc. In some embodiments, deletion of a C9ORF72 locus results in an infiltration of one or more immune cell types, e.g., plasma cells, monocytes, granulocytes and/or macrophages. Other phenotypes associated with an inflammatory and/or autoimmune condition may be present in non-human animals described herein. For example, an inflammatory or autoimmune condition may involve enlargement of one or more of the spleen, lymph nodes, kidney, and/or liver. Further, an inflammatory or autoimmune condition involving the blood may result in an increase presence of autoantibodies. An inflammatory or autoimmune condition involving the liver may result in hepatitis.

Thus, in at least some embodiments, non-human animals as described herein provide improved animal models for inflammatory and/or autoimmune diseases, disorders or conditions and can be used for the development and/or identification of therapeutic agents for the treatment, prevention and/or inhibiting one or more phenotypes (or symptoms) of an inflammatory and/or autoimmune disease, disorder or condition. In some embodiments, an inflammatory and/or autoimmune disease, disorder or condition is present in one or more organs or tissues of a non-human animal described herein. In some certain embodiments, one or more organs or tissues includes spleen, liver, lymph nodes, kidney, bone marrow, and blood.

Non-human animals as described herein also provide an in vivo system for identifying a therapeutic agent for treating, preventing and/or inhibiting one or more symptoms of an inflammatory and/or autoimmune disease, disorder or condition. In some embodiments, an inhibitory effect of a therapeutic agent is determined in vivo, by administering said therapeutic agent to a non-human animal that has a C9ORF72 disruption as described herein, and develops an inflammatory and/or autoimmune disease, disorder or condition after 8 weeks of age. In various embodiments, an inflammatory and/or autoimmune disease, disorder or condition is or comprises glomerulonephritis or hepatitis.

Non-human animals may be administered a therapeutic agent to be tested by any convenient route, for example by systemic injection, pumps for long-term exposure, or direct intracerebral injection. Such animals may be included in a behavior study, so as to determine the effect of the therapeutic agent on the behavior, e.g., motor behavior, of the non-human animals compared to appropriate control non-human animals that did not receive the therapeutic agent. A biopsy or anatomical evaluation of animal spinal cord, muscle and/or brain tissue may also be performed, and/or a sample of blood or CSP may be collected.

Non-human animals as described herein provide an improved in vivo system and source of biological materials (e.g., cells) that lack expression of C9ORF72 that are useful for a variety of assays. In various embodiments, non-human animals described herein are used to develop therapeutics that treat, prevent and/or inhibit one or more symptoms associated with a lack of C90ORF72 expression and/or activity. In various embodiments, non-human animals described herein are used to identify, screen and/or develop candidate therapeutics (e.g., antibodies, siRNA, etc.) that bind C9ORF72. In various embodiments, non-human animals described herein are used to screen and develop candidate therapeutics (e.g., antibodies, siRNA, etc.) that block activity of C9ORF72. In various embodiments, non-human animals described herein are used to determine the binding profile of antagonists and/or agonists of a C9ORF72 poly-peptide (or transcript) of a non-human animal as described herein. In some embodiments, non-human animals described herein are used to determine the epitope or epitopes of one or more candidate therapeutic antibodies that bind C90ORF72.

In various embodiments, non-human animals described herein are used to determine the pharmacokinetic profiles of a drug targeting C9ORF72. In various embodiments, one or more non-human animals described herein and one or more control or reference non-human animals are each exposed to one or more candidate drugs targeting C9OORF72 at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered drugs targeting C9ORF72 using samples obtained from non-human animals as described herein including, but not limited to, total IgG, anti-therapeutic antibody response, agglutination, etc.

In various embodiments, non-human animals as described herein are used to measure the therapeutic effect of blocking, modulating, and/or inhibiting C9ORF72 activity (or C9ORF72 signaling, or C9ORF72-mediated interactions) and the effect on gene expression as a result of cellular changes. In various embodiments, a, non-human animal as described herein or cells isolated therefrom are exposed to a drug targeting C9ORF72 of the non-human animal and, after a subsequent period of time, analyzed for effects on C9ORF72-dependent processes (or interactions), for example, endosomal trafficking, immune homeostasis, or motor neuron and/or non-motor neuron function.

Cells from non-human animals as described herein can be isolated and used on an ad hoc basis, or can be maintained in culture for many generations. In various embodiments, cells from a non-human animal as described herein are immortalized (e.g., via use of a virus) and maintained in culture indefinitely (e.g., in serial cultures).

In various embodiments, cells and/or non-human animals as described herein are used in various immunization regimens to determine the C9ORF72-mediated functions in the immune response to an antigen (e.g., a B cell response). In some embodiments, candidate therapeutics that bind, or block one or more functions of, C9ORF72 are characterized in a non-human animal described herein. Suitable measurements include various cellular assays, proliferation assays, serum immunoglobulin analysis (e.g., antibody titer), cytotoxicity assays, characterization of ligand-receptor interactions (e.g., immunoprecipitation assays) and characterization of ligand-ligand interactions. In some embodiments, non-human animals described herein are used to characterize the C9ORF72-mediated functions regulating an immune response to an antigen. In some embodiments, the antigen is associated with an autoimmune disease, disorder or condition. In some embodiments, the antigen is associated with an inflammatory disease, disorder or condition. In some embodiments, that antigen is associated with a neurological disease, disorder or condition. In some embodiments, the antigen is associated with an infectious agent (e.g., a bacterium). In some embodiments, the antigen is a test antigen (e.g., ovalbumin or OVA). In some embodiments, the antigen is a target associated with a disease or condition suffered by one or more human patients in need of treatment.

In various embodiments, non-human animals as described herein are used for challenge with one or more antigens to determine the therapeutic potential of compounds or biological agents to modulate C9ORF72-dependent regulation of an immune response, including but not limited to, the specific B cell-dependent responses to a given antigen.

Non-human animals as described herein provide an in vivo system for the analysis and testing of a drug or vaccine. In various embodiments, a candidate drug or vaccine may be delivered to one or more non-human animals described herein, followed by monitoring of the non-human animals to determine one or more of the immune response to the drug or vaccine, the safety profile of the drug or vaccine, or the effect on a disease or condition and/or one or more symptoms of a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Vaccine efficacy may be determined in a number of ways. Briefly, non-human animals described herein are vaccinated using methods known in the art and then challenged with a vaccine or a vaccine is administered to already-infected non-human animals. The response of a non-human animal(s) to a vaccine may be measured by monitoring of, and/or performing one or more assays on, the non-human animal(s) (or cells isolated therefrom) to determine the efficacy of the vaccine. The response of a non-human animal(s) to the vaccine is then compared with control animals, using one or more measures known in the art and/or described herein.

Vaccine efficacy may further be determined by viral neutralization assays. Briefly, non-human animals as described herein are immunized and serum is collected on various days post-immunization. Serial dilutions of serum are pre-incubated with a virus during which time antibodies in the serum that are specific for the virus will bind to it. The virus/serum mixture is then added to permissive cells to determine infectivity by a plaque assay or microneutralization assay. If antibodies in the serum neutralize the virus, there are fewer plaques or lower relative luciferase units compared to a control group.

Non-human animals described herein provide an in vivo system for assessing the pharmacokinetic properties and/or efficacy of a drug (e.g., a drug targeting C9ORF72). In various embodiments, a drug may be delivered or administered to one or more non-human animals as described herein, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, but not limited to, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs (e.g., C9ORF72 modulators) are monitored in or through the use of non-human animals described herein.

In some embodiments, performing an assay includes determining the effect on the phenotype and/or genotype of the non-human animal to which the drug is administered. In some embodiments, performing an assay includes determining lot-to-lot variability for a drug (e.g., a C9ORF72 modulator such as, e.g., an antagonist or an agonist). In some embodiments, performing an assay includes determining the differences between the effects of a drug administered to a non-human animal described herein and a reference non-human animal. In various embodiments, reference non-human animals may have a modification as described herein, a modification that is different as described herein (e.g., one that has a altered, disrupted, deleted, inserted, modified, etc. or otherwise non-functional C9ORF72 locus) or no modification (i.e., a wild type non-human animal).

Exemplary parameters that may be measured in non-human animals (or in and/or using cells isolated therefrom) for assessing the pharmacokinetic properties of a drug include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity, and the like. In various embodiments, non-human animals described herein are used to determine a pharmaceutically effective dose of a drug (e.g., a drug targeting C9ORF72).

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Generation of a Disruption in a Non-Human C9ORF72 Locus

This example illustrates a targeted disruption in a, C9orf72 locus of a rodent. In particular, this example specifically describes the deletion of the entire coding sequence of a mouse C9orf72 locus using a lacZ reporter construct placed in operable linkage with a mouse C9orf72 promoter. The C9orf72-lacZ targeting vector for creating a disruption in an endogenous mouse C9orf72 locus was made as previously described (see, e.g., U.S. Pat. No. 6,586,251; Valenzuela et al., 2003, Nature Biotech. 21(6):652-659; and Adams, N.C. and N. W. Gale, in Mammalian and Avian Transgenesis-New Approaches, ed. Lois, S.P.a.C., Springer Verlag, Berlin Heidelberg, 2006). The resulting modified C9orf72 locus is depicted in FIG. 1A, bottom box.

Briefly, a targeting vector was generated using bacterial artificial chromosome (BAC) clones from a mouse RP23 BAC library (Adams, D. J. et al., 2005, Genomics 86:753-758) and introduced into F1 hybrid (129S6SvEvTac/C57BL6NTac) embryonic stem (ES) cells followed by culturing in selection medium containing G418. Drug-resistant colonies were picked 10 days after electroporation and screened for correct targeting as previously described (Valenzuela et al., supra; Frendewey, D. et al., 2010, Methods Enzymol. 476:295-307). The VELOCIMOUSE® method (DeChiara, T. M. et al., 2010, Methods Enzymol. 476:285-294; Dechiara, T. M., 2009, Methods Mol. Biol. 530:311-324; Poueymirou et al., 2007, Nat. Biotechnol. 25:91-99) was used, in which targeted ES cells were injected into uncompacted 8-cell stage Swiss Webster embryos, to produce healthy fully ES cell-derived F0 generation mice heterozygous for the C9orf72 deletion. F0 generation heterozygous male were crossed with C57B16/NTac females to generate F1 heterozygotes that were intercrossed to produce F2 generation C9orf72$^{-/-}$, C9orf72$^{+/-}$ and wild type mice for phenotypic analyses. A second cohort of N2F2 generation mice was generated via in vitro fertilization (IVF) using frozen F1 heterozygous sperm and oocytes from C57B16/NTac donor females. N2F1 heterozygous offspring were then intercrossed to generate N2F2 C9orf72$^{-/-}$, C9orf72$^{+/-}$ and wild type mice for phenotypic analysis.

Phenotypic studies of F2 and N2F2 mice began at six (6) weeks of age. Mice were observed from birth for various developmental milestones (runting, breathing, facial and limb abnormalities, skin color, posture, righting and eye opening) until 6 weeks of age, when they were housed 2-5 per cage in 12 hours of light per day at 20-23° C., and 40-60% humidity for study. Mice were housed in 95.6× 309.1×133.4 mm cages (Thoren) with cob bedding (The Andersons Lab Bedding) and a cotton nestlet for enrichment (Ancare). In housing, the mice were monitored twice daily for health status and had access to normal chow (LabDiet) and water ad libitum. All animal procedures were carried out in strict accordance with the recommendations in the Guide for the Care and Use of Laboratory Animals of the National Institutes of Health. The protocol was approved by the Regeneron Pharmaceuticals Institutional Animal Care and Use Committee (IACUC), and all efforts were made to minimize suffering.

TAQMAN® Expression Analysis:

Axillary, brachial and cervical lymph nodes, gonadal fat pad, frontal cortex, diaphragm, spinal cord, spleen and thymus tissues were dissected fresh into RNALater stabilization reagent (QIAgen) and stored at −20'C. Tissues were homogenized in TRIZOL® reagent and phase separated with chloroform. The aqueous phase, containing total RNA, was purified using miRNeasy Mini Kit (QIAgen) according to manufacturer's specifications. Genomic DNA was removed using MAGMAX™ TURBO™ DNase Buffer and TURBO™ DNase (Ambion). mRNA was reverse-transcribed into cDNA using SUPERSCRIPT® VILO™ Master Mix (SuperScript® III RT, RNaseOUT™, recombinant ribonuclease inhibitor, proprietary helper protein, random primers, MgCl$_2$, dNTPs; Invitrogen by Life Technologies). cDNA was amplified with the TAQMAN® Gene Expression Master Mix (Applied Biosystems) using the ABI 79001HT Sequence Detection System (Applied Biosystems). Beta-Actin was used as an internal control gene to normalize cDNA input differences. Thymus from wild type mice was used as a reference sample to calculate fold difference of mRNA between samples (n=5 females per tissue per genotype). Exemplary results are set forth in FIG. 1B.

LacZ Expression Profiling:

Mice were deeply anesthetized via Ketamine/Xylazine (120/5 mg/kg) IP injection and fixed by cardiac perfusion using a 0.2% glutaraldehyde, 4% paraformaldehyde solution. Brain, ribcage, lymph nodes, salivary glands, thymus, heart, lung, liver, spleen, stomach, kidney, intestine, urogenital, muscle, and hind limb tissues were dissected, rinsed in PBS and post-fixed for 30 minutes in a 0.2% glutaraldehyde, 4% paraformaldehyde solution. Tissues were washed and incubated in X-gal (1 mg/mL) staining solution for 1-24 hours at 37° C. Alter staining, tissues were washed, post-fixed in 4% paraformaldehyde and cleared in a glycerol series of 50%, 70% and 100%. Photographs were taken with a Nikon SMZ1500 stereomicroscope and Nikon DS-Ri1 digital camera using NIS-Elements D Imaging Software (Nikon).

Expression profiling was recorded at embryonic day 12.5 (E12.5), 6 weeks, and 28 weeks. Representative data of the relative expression profile of β-galactosidase (lacZ) in E12.5 embryos (Table 4) and 6- and 28-week old C9orf72$^{-/-}$ mice (Table 5) are provided below (−=: no expression; +=low expression; ++=moderate expression; +++=high expression; wt=wild type C57BL/6N; nd=not determined).

Figure 1B:
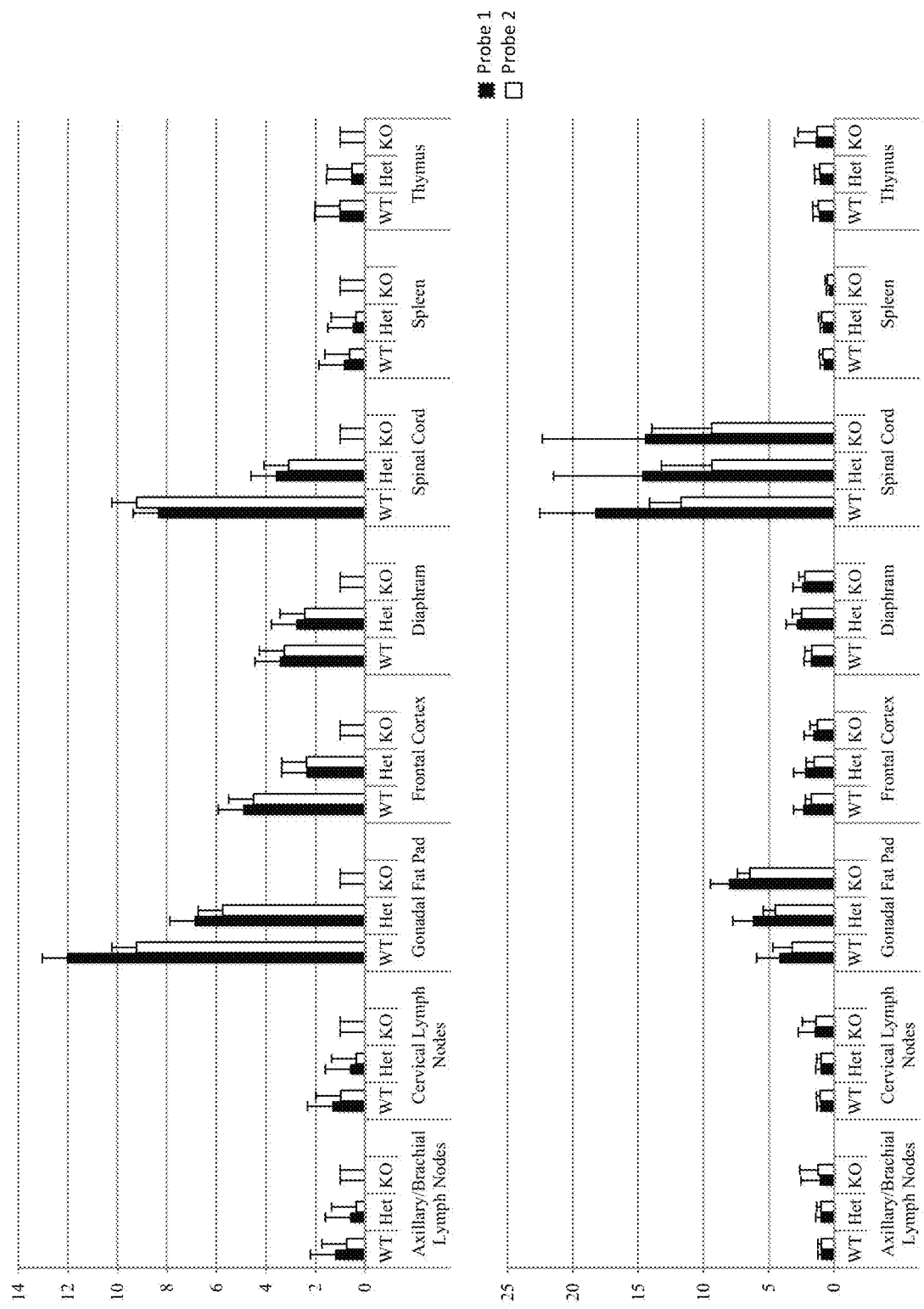
FIG. 1B shows TAQMAN® expression analysis of C9orf72 (top; also known as 3110043O21RIK) and MOB kinase activator 3B (Mob3b; bottom) for wild type (WT), C9orf72$^{+/-}$ (Het) and C9orf72$^{-/-}$ (KO) mice.

As shown in FIG. 1B, high levels of C9orf72 expression was detected in wild type (WT) gonadal fat pad, frontal cortex and spinal cords, with lower levels in the thymus, spleen, and lymph node. C9orf72$^{+/-}$ (Het) mice had roughly half the expression level of wild type (WT), as expected, and C9orf72$^{-/-}$ (KO) mice had no detectable C9orf72 expression. No difference in transcription levels of nearby loci Mob3b, Ak045932, and Ifnk among tested genotypes was observed, which indicated that insertion of lacZ alone (i.e., coding sequence ablation) affected expression of C9orf72.

Consistent with data shown in FIG. 1B, lacZ staining in 6 and 28 week C9orf72$^{-/-}$ (KO) animals revealed enzyme activity in several regions of the brain and spinal cord, as well as in spleen, testes, and kidney (Tables 4 and 5), which is consistent with other reports (Suzuki, N. et al., 2013, Nat. Neurosci. 16(12):1725-8; Koppers, M. et al., 2015, Am. Neurol. 78(3):425-38). Further, less prominent staining in other tissues was observed. Reporter activity was more limited in intensity and scope in C9orf72$^{+/-}$ tissues, as expected for a single lacZ replacement allele.

Taken together, this example demonstrates that murine C9orf72 is expressed in various tissues of the nervous and immune systems. Further, this example demonstrates that at least in some tissues, expression increases with age of the animal and directly correlates with neurological and immunological phenotypes described in the following examples (see below).

TABLE 4

| Embyro genotype | lacZ expression |
| --- | --- |
| wt | − |
| C9orf72$^{+/-}$ | +++ |
| C9orf72$^{-/-}$ | +++ |

TABLE 5

| | | C9orf72$^{-/-}$ | |
| --- | --- | --- | --- |
| Tissue | wt | 6-wk male | 28-wk male |
| Brain | − | +++ | +++ |
| Spinal cord | − | +++ | +++ |
| Heart | − | + | +++ |
| Ribcage | − | + | +++ |
| Hindlimb | − | ++ | +++ |
| Liver | − | ++ | +++ |
| Lung | − | ++ | +++ |
| Thymus | − | + | ++ |
| Spleen | − | + | +++ |

Example 2. Behavioral Analysis of Non-Human Animals Having a Disruption in a C9orf72 Locus This example demonstrates, among other things, that non-human animals (e.g., rodents) described herein develop ALS-like symptoms such as, for example, decreased body weight and significant motor abnormalities resulting from a disruption in a, rodent (e.g., mouse) C9orf72 locus as described in Example 1.

Phenotypic studies of mice having a disruption in a C9orf72 as described above were performed at 8, 18, 37 (female) and 57-60 weeks (male). Body weight was measured on a bi-weekly basis, and body composition was analyzed by uCT scan (Dynamic 60). Standard 24 scan was used to visualize mass of the cervical region of the spine. All animal procedures were conducted in compliance with protocols approved by the Regeneron Pharmaceuticals Institutional Animal Care and Use Committee.

Assessment of overall motor function was performed using blinded subjective scoring assays. Analysis of motor impairment was conducted using rotarod, open field locomotor, and catwalk testing. Motor impairment score was measure using the system developed by the ALS Therapy Development Institute (ALSTDI, Gill A. et al., 2009, PLoS One 4:e6489). During catwalk testing, subjects walk across an illuminated glass platform while a video camera records from below. Gait related parameters such as stride pattern, individual paw swing speed, stance duration, and pressure are reported for each animal. This test is used to phenotype mice and evaluate novel chemical entities for their effect on motor performance. CatWalk XT is a system for quantitative assessment of footfalls and gait in rats and mice. It is used to evaluate the locomotor ability of rodents in almost any kind of experimental model of central nervous, peripheral nervous, muscular, or skeletal abnormality.

CatWalk Gait Analysis:

Animals are placed at the beginning of the runway of Noldus CatWalk XT 10, with the open end in front of them. Mice spontaneously run to the end of the runway to attempt to escape. The camera records and the software of the system measures the footprints. The footprints are analyzed for abnormalities in paw placement.

Open Field Test:

Mice are placed in the Kinder Scientific open field system and evaluated for 60 minutes. The apparatus uses infrared beams and computer software to calculate fine movements, X+Y ambulation, distance traveled, number of rearing events, time spent rearing, and immobility time.

Rotorod:

The rotorod test (IITC Life Science, Woodland Hills, Calif.) measures the latency for a mouse to fall from a rotating beam. The rotorod is set to the experimental regime that starts at 1 rpm and accelerates up to 15 rpm over 180 seconds. Then, the animals' latency to fall following the incremental regime is recorded. The average and maximum of the three longest durations of time that the animals stay on the beam without falling off are used to evaluate falling latency. Animals that manage to stay on the beam longer than 180 seconds are deemed to be asymptomatic.

Upper motor neuron impairment presents as spasticity (i.e., rigidity), increased reflexes, tremor, bradykinesia, and Babinski signs. Lower motor neuron impairment presents as muscle weakness, wasting, clasping, curling and dragging of feet, and fasciculations. Bulbar impairment presents as difficulty swallowing, slurring and tongue fasciculations. Table 6 sets forth the scoring methodology related to motor impairment, tremor and rigidity of animals during testing. Exemplary results are set forth in FIGS. 2A-2H.

Figure 2A:
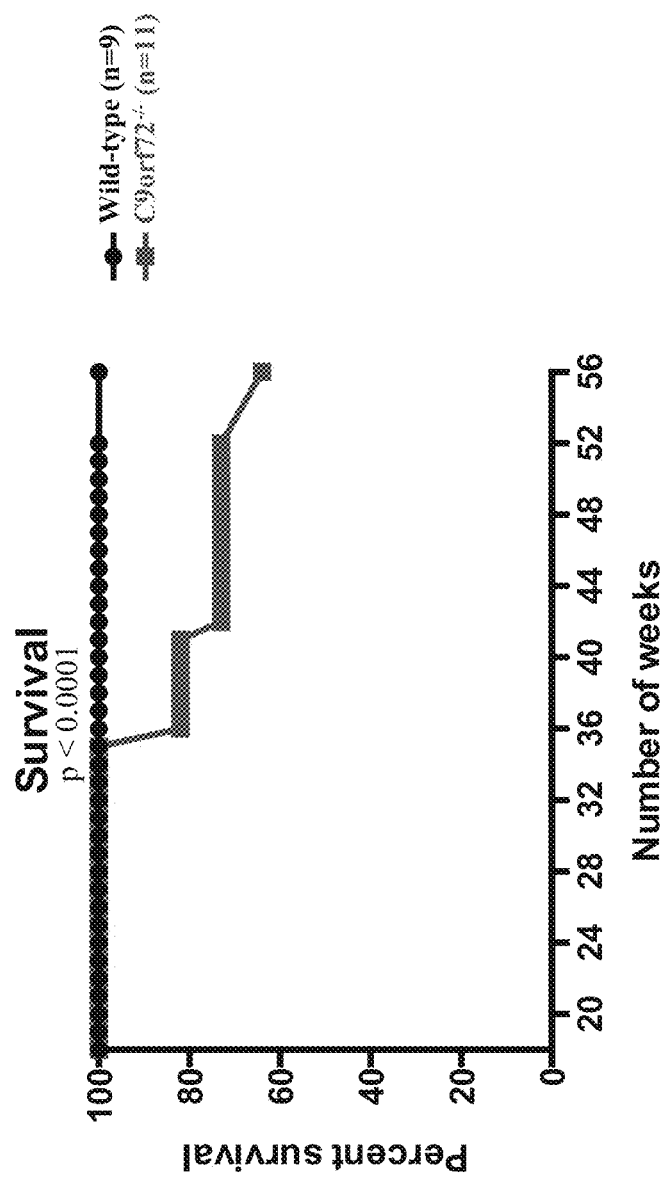
FIGS. 2A-2L show ALS-like phenotypes measured in wild type (n=9) and C9orf72$^{-/-}$ (n=11) mice.
Figure 2B:
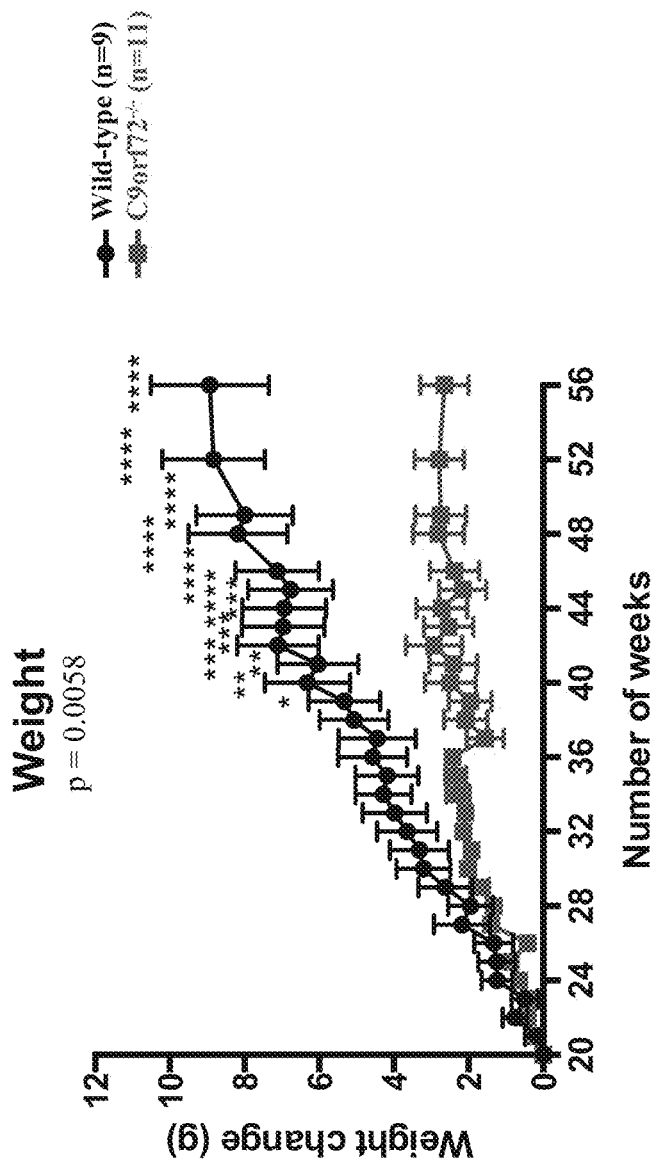
Figure 2C:
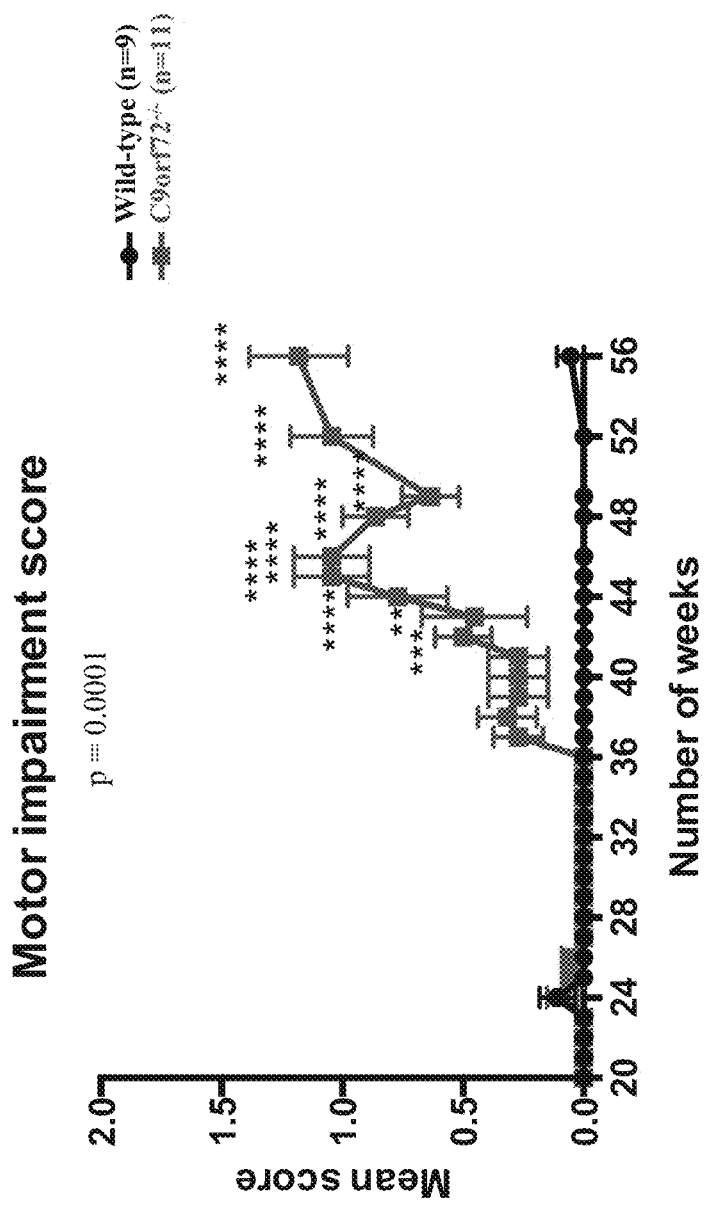
Figure 2D:
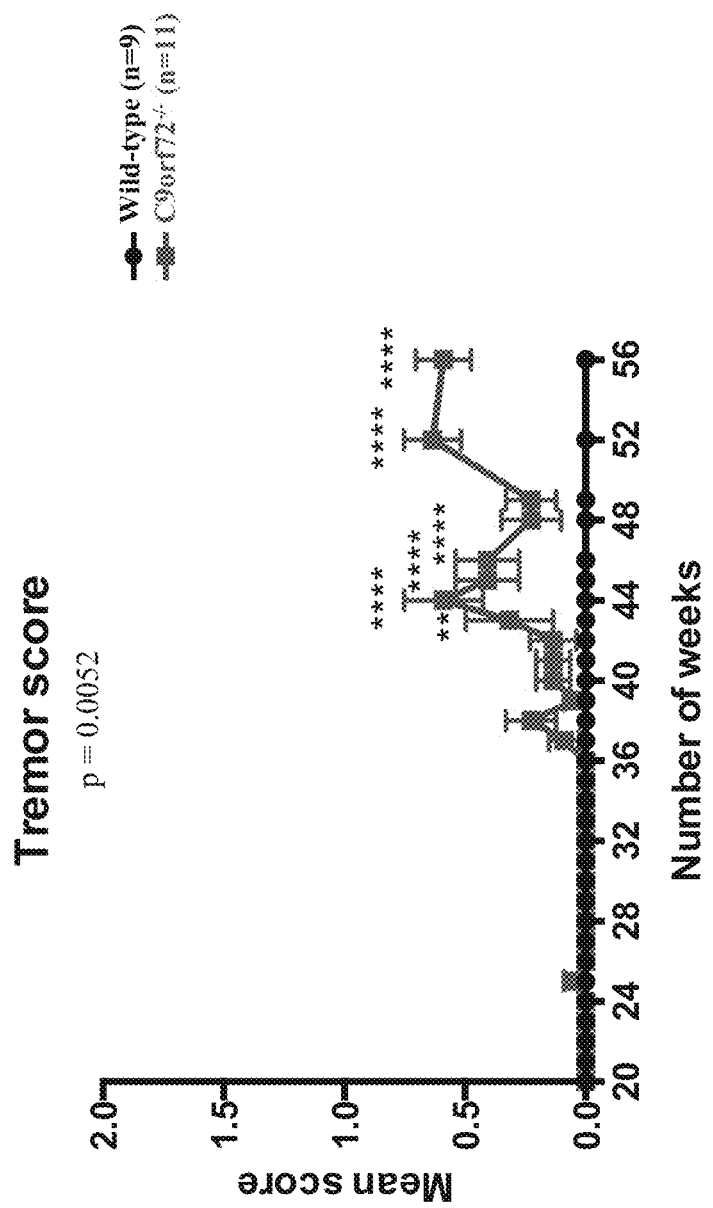
Figure 2E:
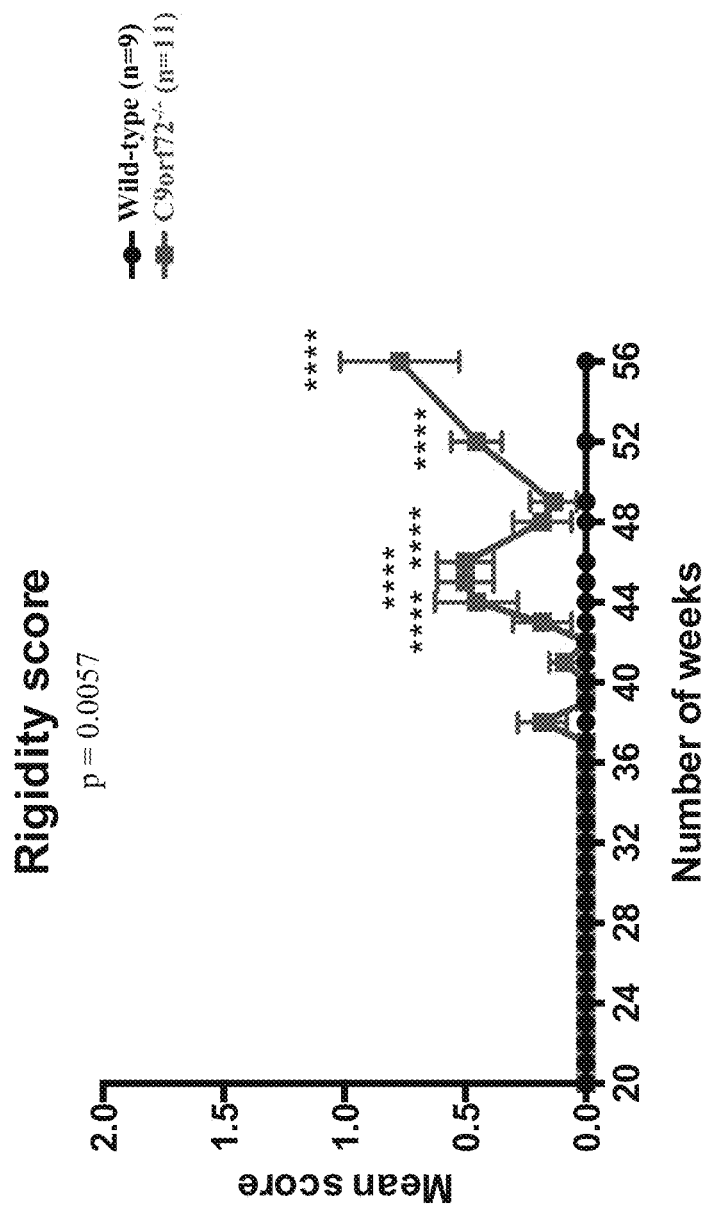
Figure 2F:
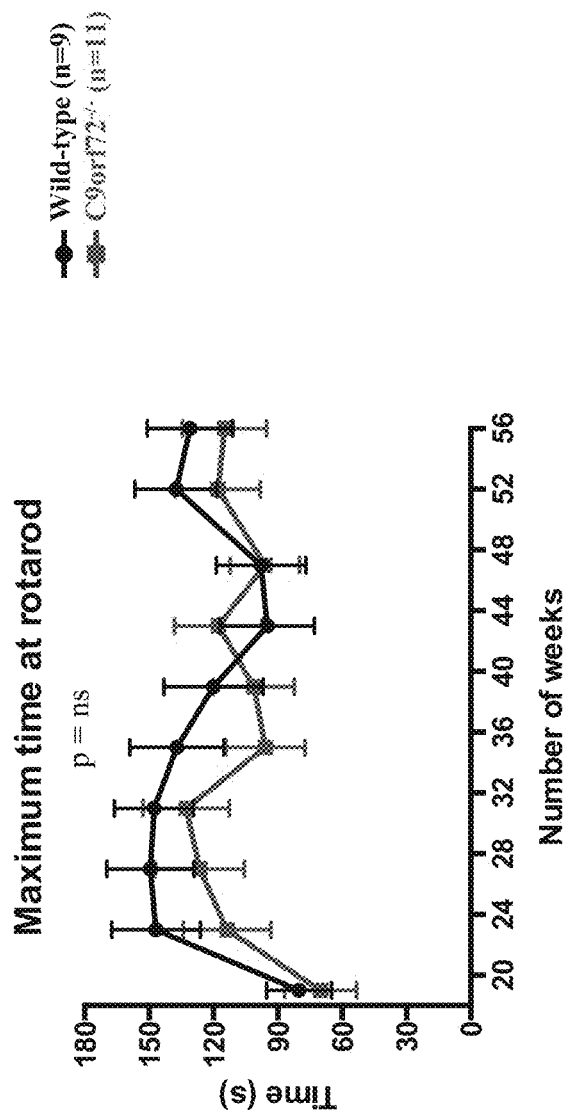
Figure 2G:
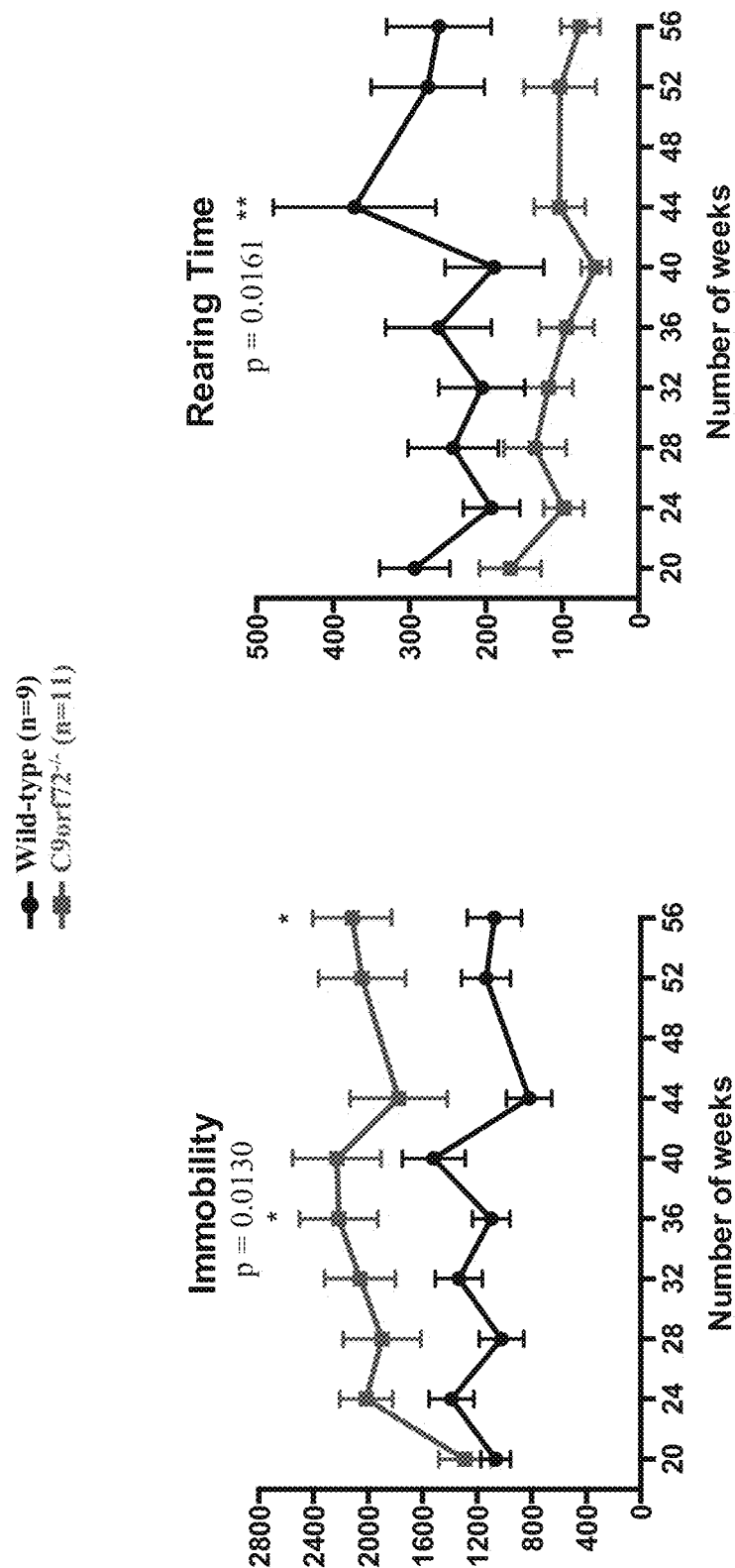
Figure 2H:
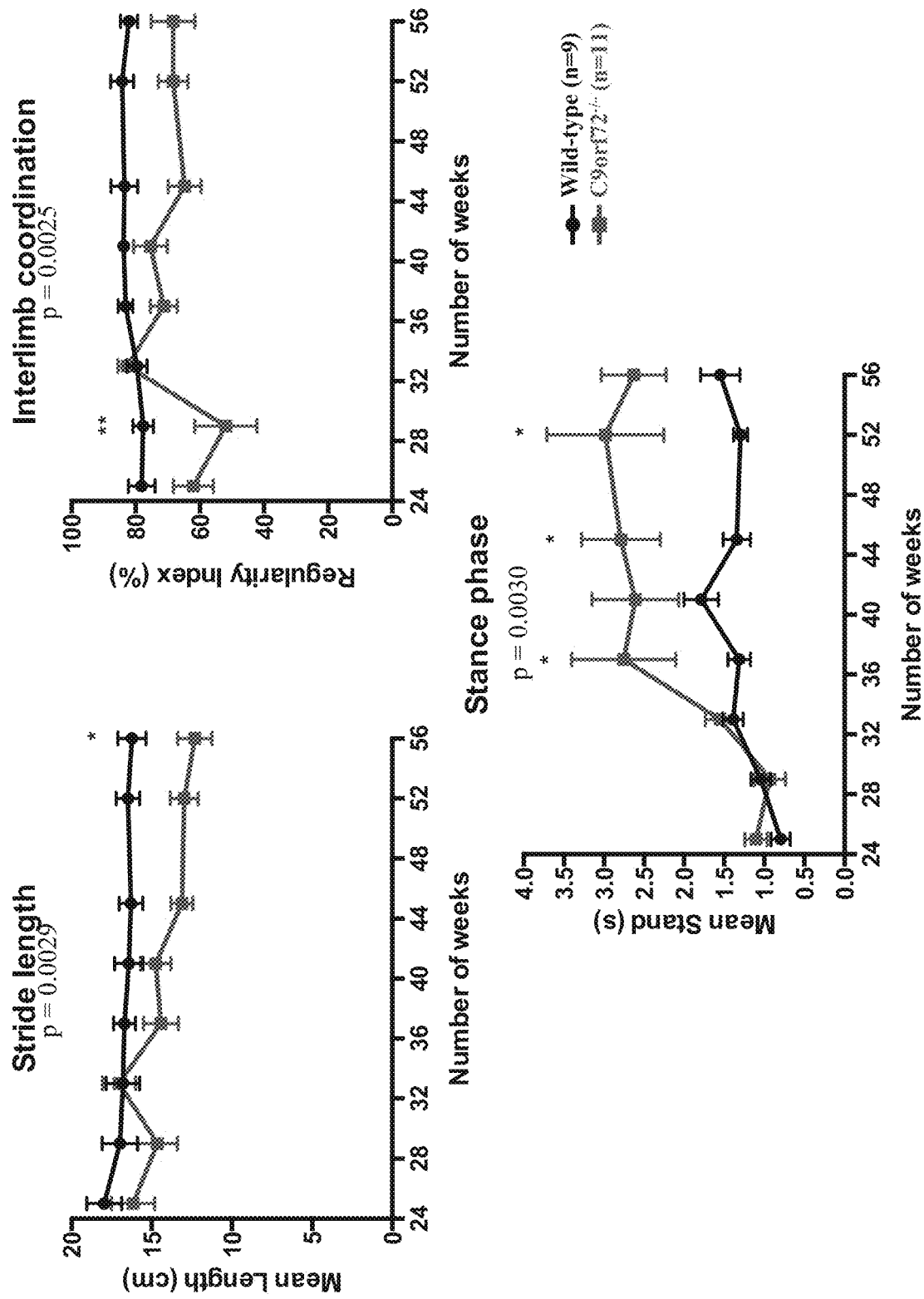

As shown in FIGS. 2A-2H, C9orf72$^{-/-}$ mice demonstrated ALS-like phenotypes such as, for example, decreased body weight, motor inactivity and gait impairment. In particular, decreased body weight in C9orf72$^{-/-}$ mice as compared to wild type control mice began at about 30 weeks of age (FIG. 2B). Further, with the exception of rotarod, significant motor impairment (e.g., significant weakness and collapsing of hind limbs towards lateral midline, as well as mild tremor and rigid hind limb muscles, p<0.0001) was observed for C9orf72$^{-/-}$ mice in all types of testing (FIGS. 2C-2H) beginning at about 40 weeks of age, which indicated the onset of upper and lower motor neuron pathology. Similar defects were not observed in wild type or heterozygous (C9orf72$^{+/-}$) animals.

Rotarod and CatWalk gait analysis on C9orf72$^{-/-}$ mice demonstrated significantly decreased loco-motor behaviors and fewer rearing events, indicating hind limb impairment. CatWalk gait analyses revealed signs of impaired lower inter-limb coordination and reduced stride length, as well as bradykinesia and dragging of hind limbs. These data indicated significant gait abnormalities as compared to wild type. No difference between wild type and C9orf72$^{-/-}$ mice was observed in regard to maximum time on the rotarod. As early as 36 weeks of age, C9orf72$^{-/-}$ mice demonstrated significant and progressive motor deficits.

Figure 2I:
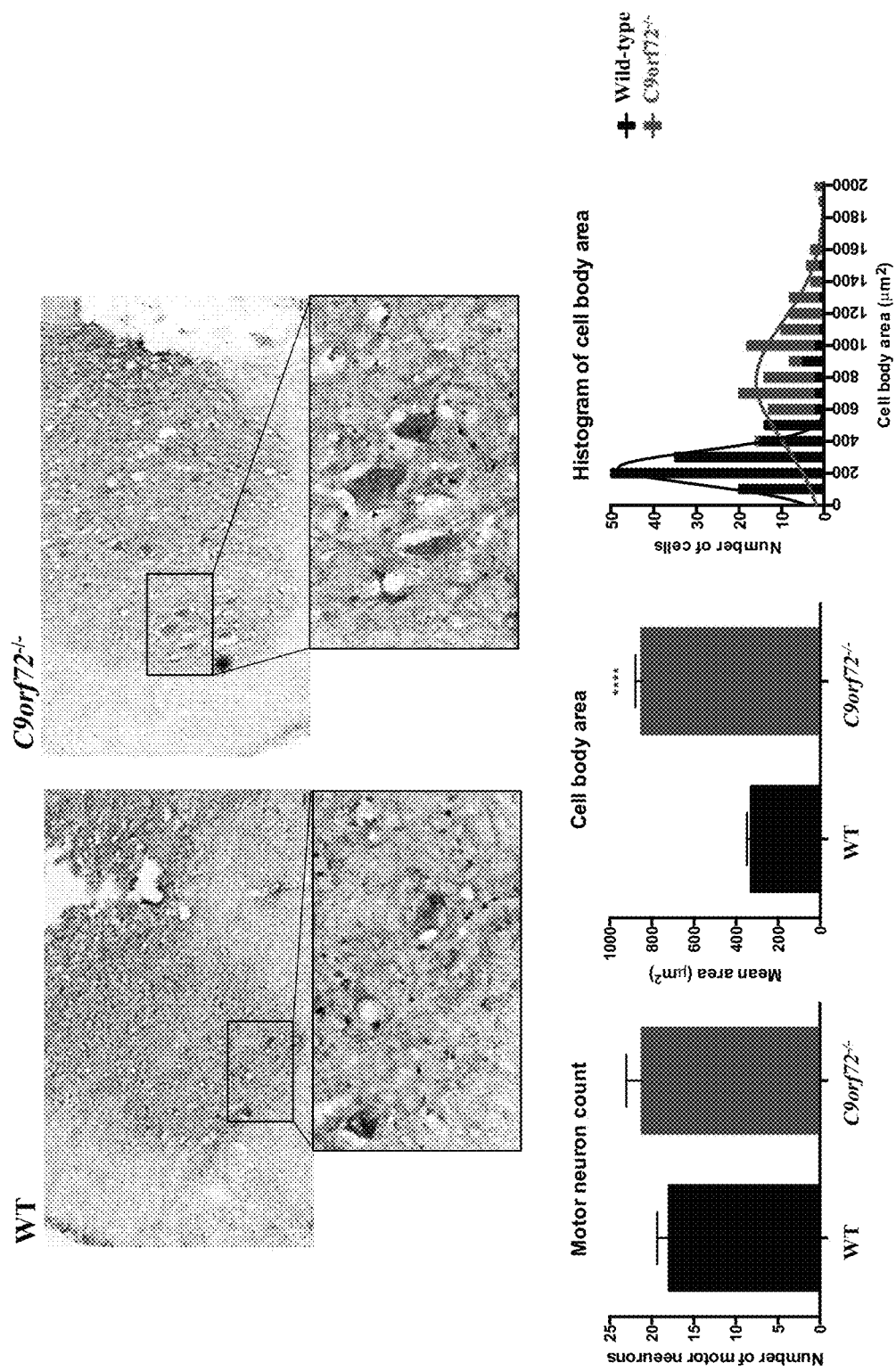

In another experiment, the lumbar portion of spinal cords from wild type and C9orf72$^{-/-}$ mice (n=5, 60 weeks old) were collected for histopathological analysis. No difference in total number of motor neurons in the spinal cords was observed (FIG. 2I). However, the mean cell body area of C9orf72$^{-/-}$ motor neurons was significantly larger as compared to wild type (p<0.0001). In particular, the motor neurons of C9orf72$^{-/-}$ mice demonstrated hypertrophic characteristics evidenced by significantly larger mean cell body area as compared to wild type (FIG. 2I). Thus, these data indicated a possible onset of lower motor neuron pathology beginning at 40 weeks of age.

Figure 2J:
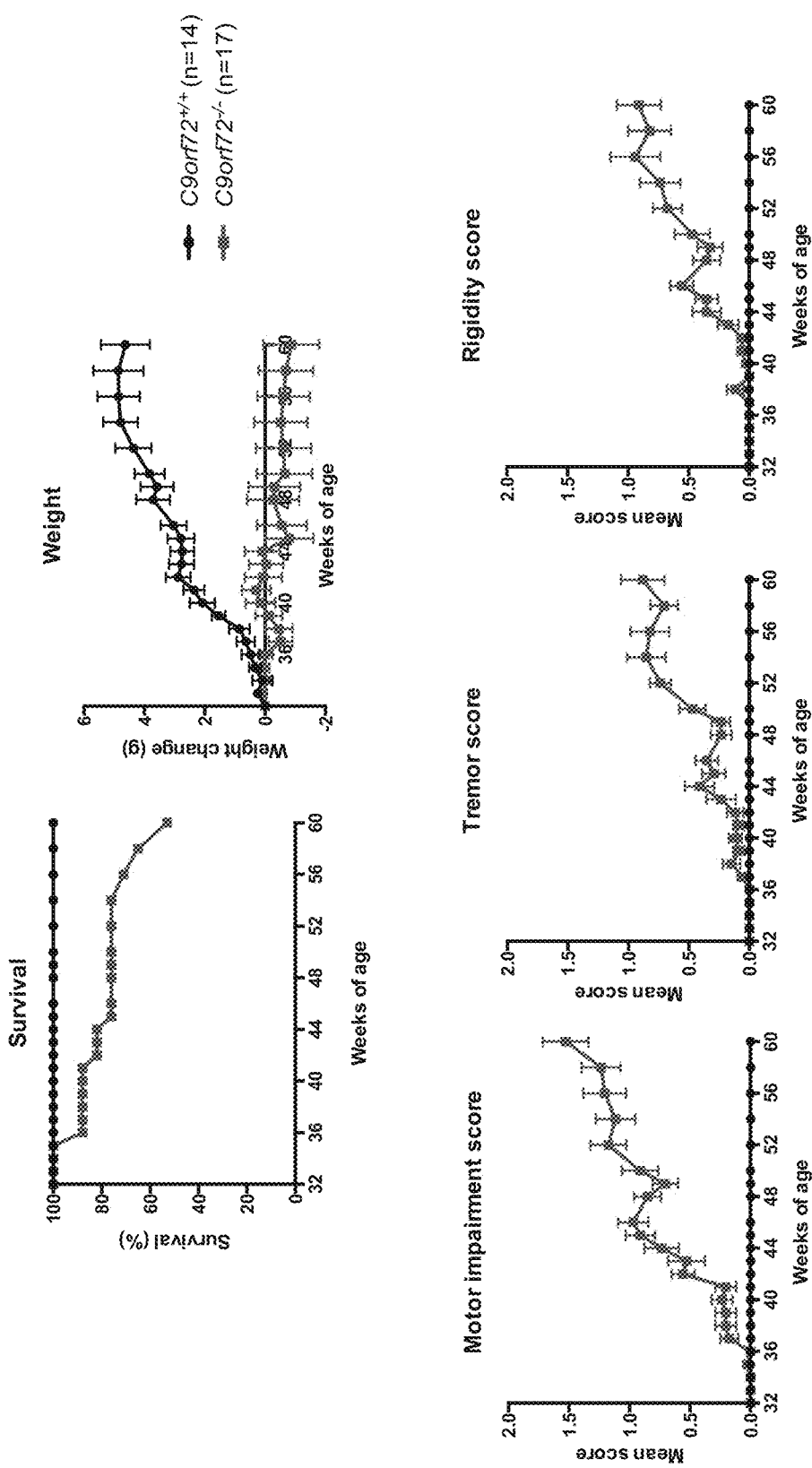

In a similar experiment, motor abnormalities were assessed in wild type (C9orf72$^{+/+}$, n=14; 11 female, 3 male) and C9orf72$^{-/-}$ (n=17; 12 female, 5 male) starting at 32 weeks up to 60 weeks of age as percent of living animals at a given week. Mice were weighed weekly and assessment of overall motor function was performed using blinded subjective scoring assays (as described above). Weekly or bi-monthly clinical neurological exams were performed on the two groups of mice looking at their motor impairment, tremor and rigidity of their hind limb muscles. For motor impairment, we followed a blinded neurological scoring scale (described above) from of zero (no symptoms) to four (mouse cannot right themselves within 30 seconds of being placed on their side). For tremor and rigidity, we created a scoring system with a scale from zero (no symptoms) to three (severe). All data reported as mean±SEM. Representative results are set forth in FIG. 2J.

Figure 2K:
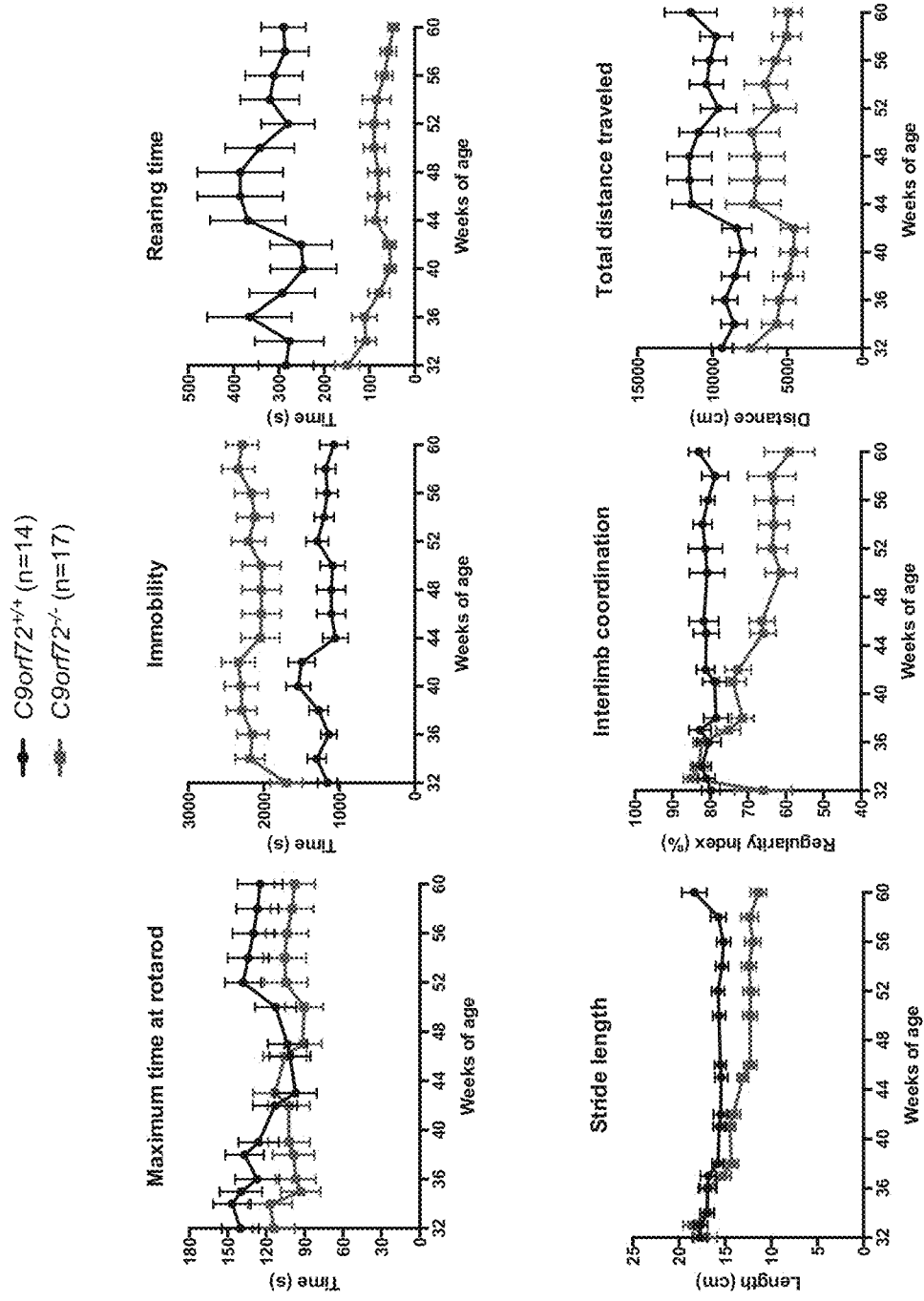

Locomotor behaviors were evaluated for 60 minutes every other week using the automated Open Field system (Kinder Scientific), rotarod test (Rota Rod, IITC Life Science, Woodland Hills, Calif.) and gait analysis (CatWalk XT 10, Noldus) as described above. All data reported as mean±SEM. Representative results are set forth in FIG. 2K.

Using the scoring scales described above, the inventors observed that at around 40 weeks of age, the C9orf72$^{-/-}$ mice started showing significant weakness and collapsing of their hind legs towards lateral midline, as well as mild tremor and rigid hind limb muscles (P<0.0001), suggesting the onset of upper and lower motor neuron pathology. Further, all of the wild-type mice lived past 60 weeks of age, but only ~53% C9orf72$^{-/-}$ mice (9 of 17; 5 female, 4 male) were alive at 60 weeks of age (FIG. 2.1, top left). Beginning at around 36 weeks of age, C9orf72$^{-/-}$ mice ceased gaining body weight, in contrast with the cohort of wild-type mice.

From the open field assay, the inventors observed that C9orf72$^{-/-}$ mice display significantly decreased locomotor behaviors compared to their wild-type counterparts (P=0.0008). These mice also displayed significantly less rearing behaviors (P=0.0009), which indicated impairment of their hind limbs. No significant change in the maximum time mice would stay on a rotating beam at any time during the study was observed between wild type and C9orf72$^{-/-}$ mice. From the CatWalk gait analysis, the inventors observed that C9orf72$^{-/-}$ mice have significantly impaired lower interlimb coordination (P=0.0005) and stride length (P=0.0013), as well as bradykinesia and dragging of hind limbs. These data indicated significant gait abnormalities in C9orf72$^{-/-}$ mice as compared to wild type. Thus, the example demonstrates that, starting at around 36 weeks of age, C9orf72$^{-/-}$ mice show significant and progressive motor deficits as compared to wild type.

In another experiment, heterozygous (C9orf72$^{+/-}$) and homozygous (C9orf72$^{-/-}$) mice were examined using a grip strength test. Briefly, the grip strength measures the neuromuscular function as maximal muscle strength of forelimbs, and is assessed by the grasping applied by a mouse on a grid that is connected to a sensor. Three trials were carried out in succession measuring forelimb-strength only. All grip strength values obtained were normalized against mouse body weight. The grip strength test was performed thirteen wild-type, seven C9orf72$^{+/-}$ and eighteen C9orf72$^{-/-}$ mice at 20 weeks of age (before the onset of motor symptoms) and on twelve wild-type, four C9orf72$^{+/-}$, and thirteen C9orf72$^{-/-}$ mice at 60 weeks of age. Representative data is set forth in FIG. 2L.

Figure 2L:
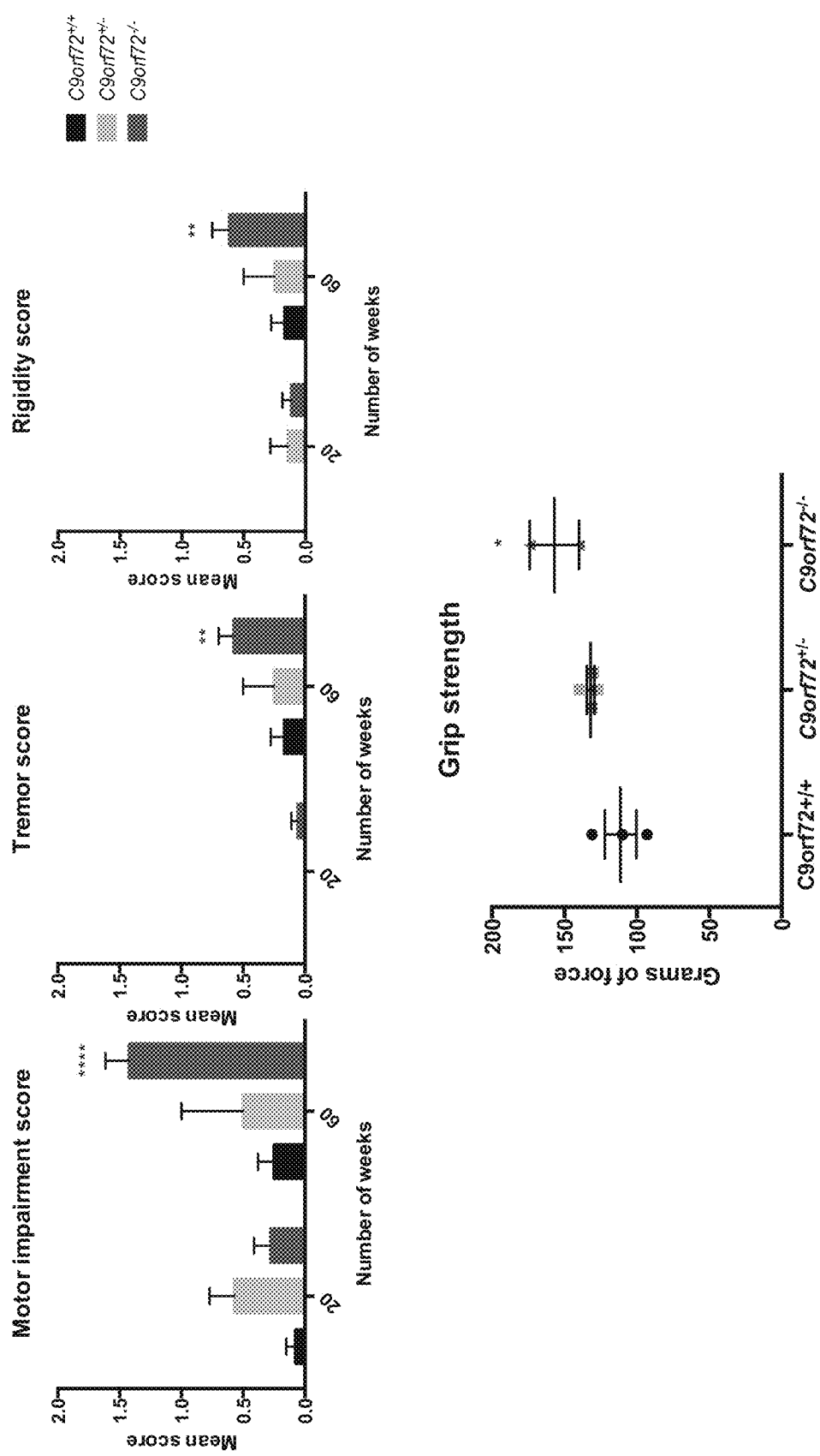

As shown in FIG. 2L, heterozygous (C9orf72$^{+/-}$) mice did not show any significant motor impairment, tremor or rigidity at 60 weeks. Further, heterozygous (C9orf72$^{+/-}$) mice did not show any change in grip strength at 60 weeks as compared to wild type.

Taken together, this example demonstrates that non-human animals described above demonstrate a measurable neurodegenerative phenotype and, therefore, provide useful models of amyotrophic lateral sclerosis (ALS) and/or frontotemporal dementia (FTD), which non-human animals have a genome comprising a deletion of the entire coding sequence (i.e., exons 2-10) of an endogenous C9orf72 locus resulting from insertion of a reporter gene (e.g., lacZ). Such animal models provide a useful in vivo system for the development and screening of therapeutic candidates for the treatment of ALS and/or FTD.

TABLE 6

| Motor impairment | 0<br>no phenotype | 1<br>clasping | 2<br>clasping & dragging | 3<br>paralysis |
|---|---|---|---|---|
| Tremor | none | mild | moderate | severe |
| Rigidity | none | mild | moderate | severe |

Example 3. Immunophenotype Analysis of Non-Human Animals Having a Disruption in a C9orf72 Locus This example demonstrates that non-human animals made according to Example 1 demonstrate an immunological phenotype characterized by, in some embodiments, splenomegaly and lymphadenopathy resulting from infiltration of various immune cell populations. Further, this example specifically demonstrates such non-human animals develop glomerulonephritis characterized by infiltration of immune cell populations in the kidney. Without wishing to be bound by any particular theory, the present inventors propose that the C9ORF72 locus product plays a critical role in immune function and the loss of C9ORF72 polypeptide in non-human animals described herein is not the prominent mechanism of ALS and/or FTD disease. Various tissues were harvested from C9orf72$^{-/-}$ and wild type mice for analysis (n=4-6 animals per genotype at 8, 18, and 37 weeks for females, and 9-10, 18, and 57-60 weeks for males).

Cell Preparation and Flow Cytometry Analysis:

Maximum blood volume was collected into EDTA coated tubes by cardiac puncture immediately following $CO_2$ euthanization and approximately 200 µL was transferred into heparin-coated tubes for FACS preparation. Spleen, bone marrow, and cervical lymph nodes were harvested, dissociated into single cell suspensions in Dulbecco's 1×PBS with 2% fetal bovine serum (Stem Cell Technologies) plus 2 mM EDTA (Ambion) and filtered using methods known in the art. Red blood cell (RBC) lysis was performed on blood, spleen, and bone marrow using RBC lysis buffer (eBioscience) or ACK Lysing Buffer (Life Technologies). Lymph node, spleen, and bone marrow cells were counted using a Cellometer Auto T4 Cell Viability Counter (Nexcelom Bioscience) and plated for approximately 10 million cells per well for spleen, and 1 million cells per well or maximum volume for lymph nodes and bone marrow. Blood was plated at maximum volume (approximately 250 µL) per well. Cells were treated with LIVE/DEAD Fixable Aqua stain, (Life Technologies) at room temperature, spun down, and re-suspended in blocking solution (purified anti-mouse CD16/CD32 mAb, BD Pharmingen, 1:100 in FACS buffer) for 15 minutes on ice. Cells were stained with conjugated antibodies for 30 minutes on ice, washed, fixed (BD Cytofix/cytoperm kit) and washed again. Cells were finally resuspended in FACS buffer (Dulbecco's 1×PBS with 2% fetal bovine serum, Stem Cell Technologies, plus 2 mM EDTA, Ambion) and analyzed on a BD FACSCanto Flow Cytometer II or LSRFortessa Flow Cytometer (BD Biosciences). Foxp3 staining (eBioscience) was performed according to manufacturer's specifications.

Plasma cell staining panel: CD11b (M1/70; Biolegend), CD11c (N418; Biolegend), CD3 (145-2C11; Biolegend), B220 (RA3-6B2; Biolegend), CD19 (1D3; BD Pharmingen), CD138 (281-2; BD Pharmingen), and CD45 (30-F11; BD Pharmingen). Myeloid cell staining panel: F4/80 (BM8; Biolegend), CD115 (AFS98; eBioscience), Ly6G (RB6-8C5; eBioscience), CD11b (M1/70; eBioscience), CD45 (30-F11; BD Biosciences), and Ly6C (AL-21; BD Biosciences). Antibodies to CD8, CD25, CD62L, CD69, CD127, PD1 (RPMI-30), NKp46 were obtained from BioLegend (San Diego, Calif.). Foxp3 antibody was obtained from eBioscience (San Diego, Calif.). CD49b antibody was obtained from BD Biosciences (San Jose, Calif.). Data, were analyzed using FlowJo Software (Tree Star). Counts for perent positive and total cell number were performed for spleen, cervical lymph nodes, bone marrow, and kidney of 30-35 week old females (wild type: n=4; C9orf72$^{-/-}$ n=4) on a Nexelcom Bioscience Cellometer Auto 2000 Cell Viability Counter with AO/PI Viability dye (acridine orange and propidium iodide). Cell counts were used to determine absolute number of cell populations observed by surface staining and graphed accordingly.

Histology:

Tissues were harvested into 4% paraformaldehyde (PFA, Electron Microscopy Sciences) or collected following transcardial perfusion with 50 mL saline solution, 50 mL 4% PFA in acetate buffer at pH6.5 and finally 50 mL 4% PFA solution in borate buffer at pH9.5. Spinal cords were collected into 15% followed by 30% sucrose solution in borate buffer until they dropped. All other tissues were post-fixed in 4% PFA and transferred to 70% ethanol after 24 or 48 hours. Paraffin embedding, sectioning, and hematoxylin and eosin (H&E) staining were performed by a commercial histology laboratory (Histoserv, Inc.; Germantown, Md.). Immunohistochemistry for IgM, IgG, complement factor C3, CD45R, CD3, CD138, and F4/80 was completed by a commercial laboratory (Histotox Labs; Boulder, Colo.). Motor neuron cell count and cell body area were quantified using Image J. Motor neuron count represents the average from three slides per animal, n=5 mice and cell body area represents the average from three slides per animal, 10 motor neurons per slide, n=5 mice. Complement Factor C3 IHC was quantified using Halo.

Hematology Assays:

Blood samples were collected via retro-orbital eye bleeds under isoflurane anesthesia or by cardiac puncture after euthanasia by $CO_2$ inhalation in accordance with Regeneron IACUC protocol. Complete Blood Count (CBC) with differential was performed on 20 µL of whole blood using Hemavet 950 (Drew Scientific Group) and clinical chemistry was run on serum samples using ADVIA 1800 Chemistry System (Siemans Medical Solutions USA). ELISAs were performed on plasma samples using the following: Mouse IgG Rheumatoid Factor ELISA Kit and Mouse IgM Rheumatoid Factor ELISA Kit (Shibayagi Co., Ltd.), Mouse Anti-dsDNA Total Ig ELISA kit, Mouse Anti-Nuclear Antibodies (ANA) Total Ig ELISA kit, Mouse Anti-Sm (Smith Antigen) Total Ig ELISA kit, Mouse Anti-Cardiolipin Total Ig ELISA kit (Alpha Diagnostic Intl.), and IgG and IgM mouse EISA kit (Abcam) according to manufacturer's specifications. Samples were read on a Spectramax M5 Microplate Reader at 450 nm (Molecular Devices). Samples were analyzed in duplicate and averaged for mean value. IFN-γ, IL-1β, IL-2, IL-4, IL-6, IL-10, IL-12 total, IL-17, MCP-1, and TNF-α were measured in plasma samples using a Multi-Spot® 10-plex electrochemiluminescence detection assay (Meso Scale Discovery) according to manufacturer's specifications and read on a Meso Sector S 600 plate reader at 620 nm (Meso Scale Discovery). Samples were analyzed in duplicate and averaged for mean value.

RNA Isolation, Sequencing and Analysis:

Spleen and cervical lymph nodes were dissected fresh into RNALater stabilization reagent (Qiagen) and stored at −20° C. Total RNA was isolated using MagMAX™ Nucleic Acid Isolation Kit (Ambion) per manufacturer's specifications. RNA was quantified using UV spectrophotometer and RNA integrity was evaluated by Qiaxcel (Qiagen). PolyA mRNA was purified from total RNA using Dynabeads mRNA kit (Invitrogen) and strand specific RNA-Seq libraries were prepared with the ScriptSeq RNA-seq Library Preparation kit (Illumina). RNA-Seq libraries were sequenced to a length of 33 bp using Hiseq 2000 NGS sequencer (Illumina). Gene expression levels were derived from raw sequencing reads using Nimbus2, an RNA-Seq software developed by Regeneron Pharmaceuticals, Inc.

Urinalysis Method; Urine samples were obtained via spot collection and urinary albumin concentration was determined with Albuwell M indirect competitive ELISA kit (Exocell, Philadelphia, Pa.). Urinary creatinine concentration was assayed using the Creatinine Companion kit (Exocell). Assays were performed according to manufacturer's instructions and data obtained were used to calculate the urine albumin-to-creatinine ratio (ACR).

Statistical Analysis:

Statistical and graphical analyses were performed using GraphPad Prism software (version 3.0). Data were analysed using Student's unpaired t-test and one-way analysis of variance (ANOVA). Results were considered statistically significant at p values <0.05 (error bars depict s.e.m.). Exemplary results are set forth in FIGS. 3A-3A L.

Figure 3A:
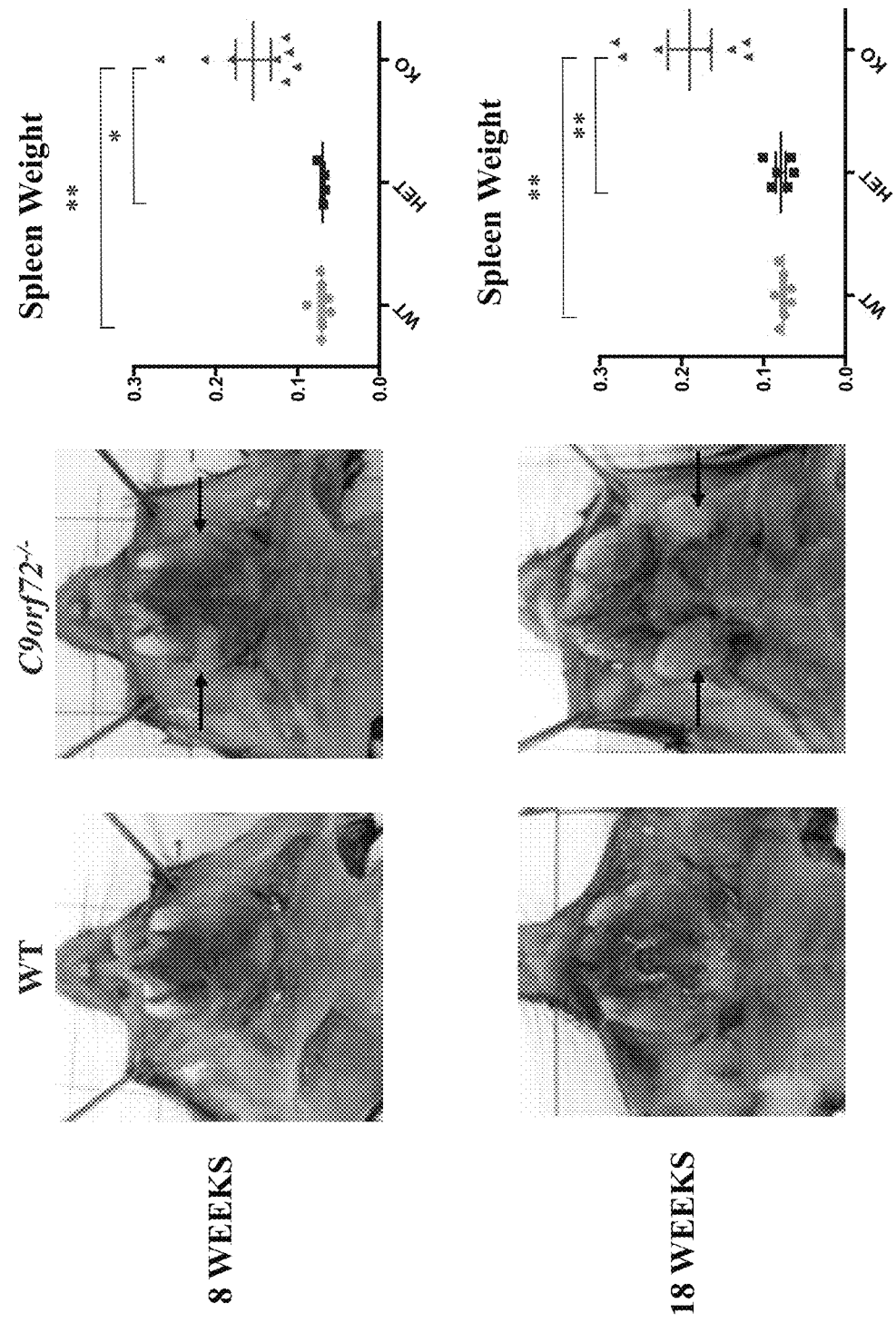
FIGS. 3A-3AL show immunophenotyping results measured in wild type mice (n=≥4) and mice having a disruption in a C9orf72 locus (n=≥4).
Figure 3B:
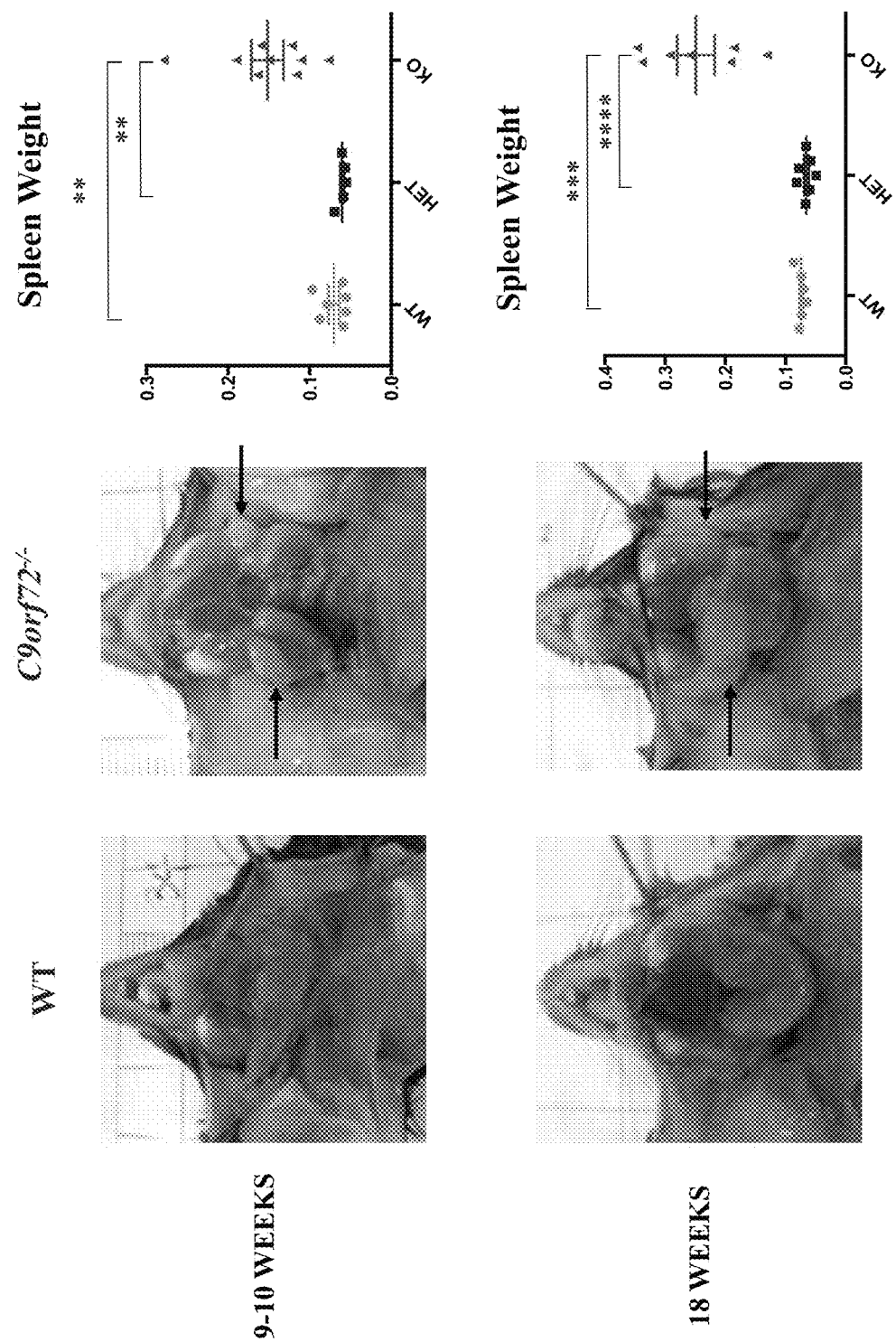
FIG. 3B: exemplary images of dissected male wild type (WT) and C9orf72$^{-/-}$ mice showing enlarged cervical lymph nodes (arrows) in C9orf72$^{-/-}$ mice, and spleen weights (right, in grams) in male wild type (WT), C9orf72$^{+/-}$ (HET), and C9orf72$^{-/-}$ (KO) mice at 9-10 (top row) and 18 (bottom row) weeks.
Figure 3C:
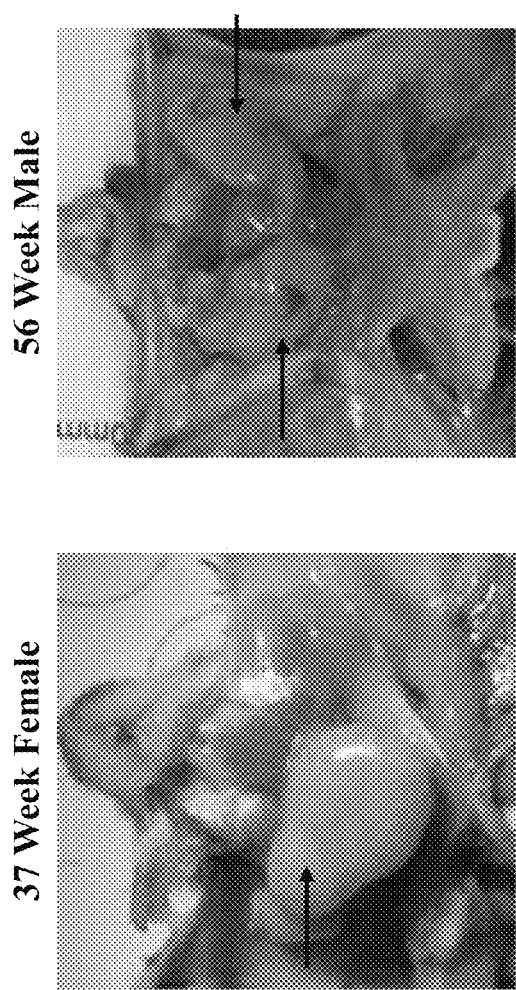
FIG. 3C: exemplary images of 37 week female and 56 week male C9orf72$^{-/-}$ mice showing enlarged cervical lymph nodes (arrows)
Figure 3D:
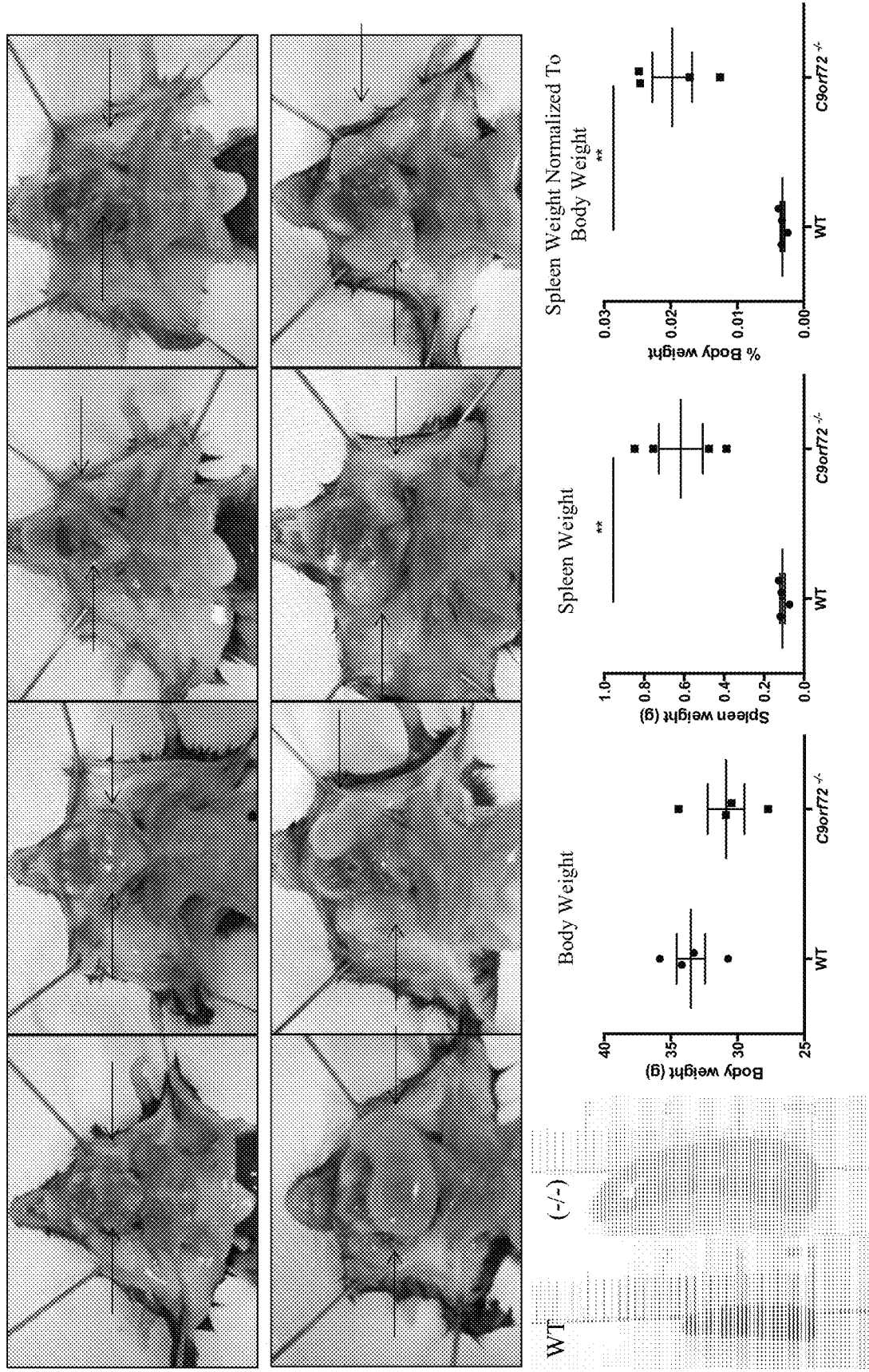
FIG. 3D: exemplary images of dissected 30-35 week old female wild type (top row) and C9orf72$^{-/-}$ (middle row) mice showing enlarged cervical lymph nodes (arrows), and body weights (in grams), spleen weights (in grams) and spleen weight normalized to body weight (as % Body weight) (bottom row); exemplary image of dissected spleen (bottom left) from wild type (WT) and C9orf72$^{-/-}$ (–/–) mice.

As shown in FIGS. 3A-3D, C9orf72$^{-/-}$ mice developed significant enlargement of the spleen as compared to wild type and C9orf72$^{+/-}$ mice. Further, cervical lymph nodes were progressively larger with age (FIGS. 3A-3D). Thus, as early as 8 weeks of age, C9orf72$^{-/-}$ mice demonstrate enlarged spleens and cervical lymph nodes. Such enlargements were palpable in the cervical regions of all C9orf72$^{-/-}$ mice, but not wild type or C9orf72$^{+/-}$ mice. Upon further investigation, such masses were palpable by 12 weeks of age in female C9orf72$^{-/-}$ mice, and in both male and female C9orf72$^{-/-}$ mice by 18 weeks. Upon dissection, the masses proved to originate from cervical lymph nodes, with enlargement observed as early as 8 weeks of age (FIG. 3A). A full dissection also revealed additional enlarged lymph nodes throughout the body, most notably mesenteric lymph nodes in older C9orf72$^{-/-}$ mice (>35 weeks). Peyer's patches were also notably enlarged and splenomegaly was apparent in C9orf72$^{-/-}$ mice by 8 weeks of age (FIG. 3D, bottom left). Only nine of 17 C9orf72$^{-/-}$ mice lived past 60 weeks of age, whereas all wild type mice subjected to periodic neurological function tests survived to the end of the experimental period. At about 18-24 weeks of age, splenomegaly and cervical lymph node hyperplasia were well-established in all C9orf72$^{-/-}$ mice and C9orf72$^{-/-}$ body weight curves began to flatten as compared to wild type and C9orf72$^{+/-}$ mice (e.g., FIG. 2B).

Figure 3E:
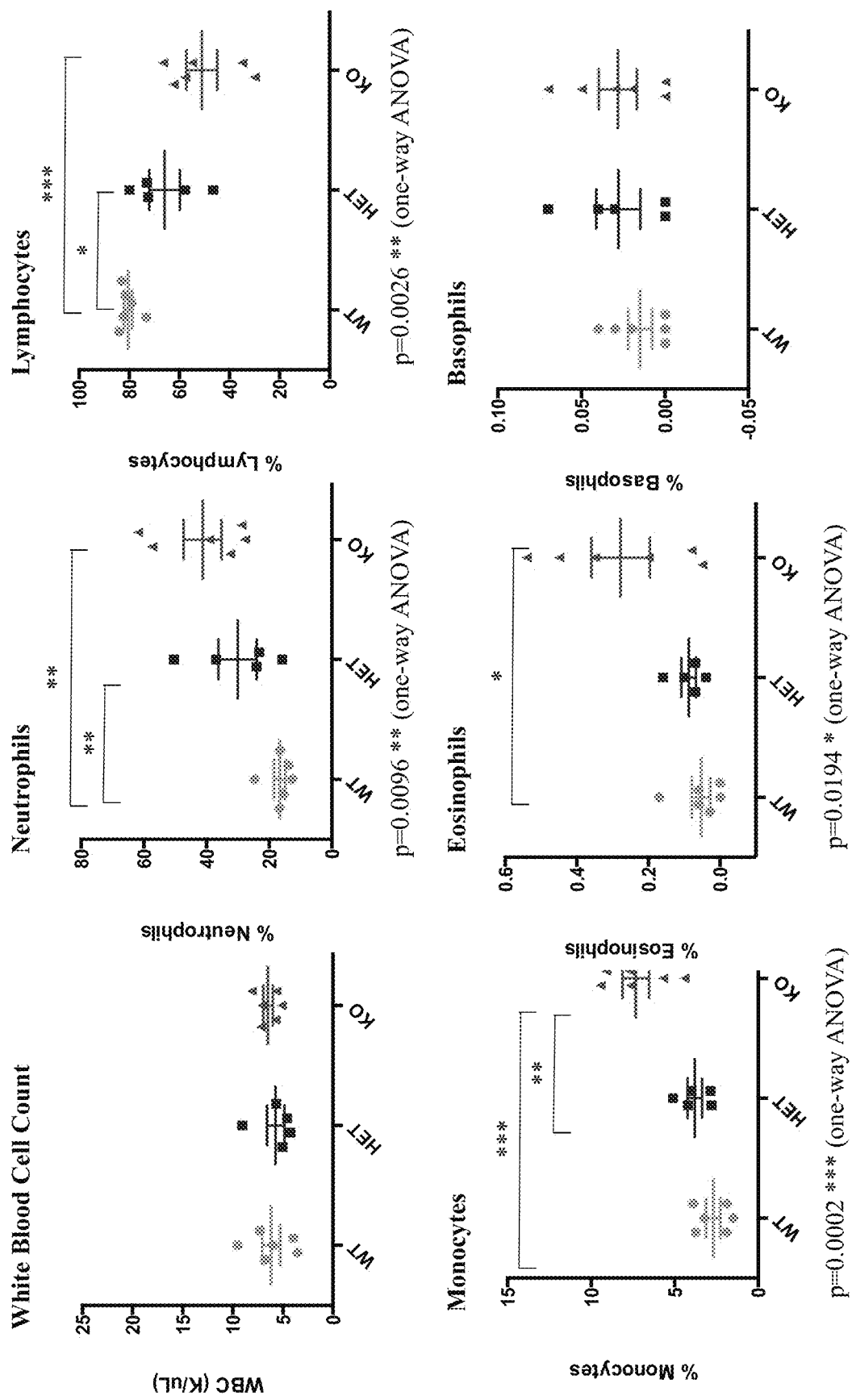
FIG. 3E: exemplary CBC data with differential showing total white blood count and circulating populations of various immune cell types in 34-38 week old male wild type (WT), C9orf72$^{+/-}$ (HET), and C9orf72$^{-/-}$ (KO) mice (cell type is indicated above each graph)

CBC data with differential of whole blood shows that C9orf72$^{-/-}$ mice develop a significant increase in circulating neutrophils, eosinophils and monocytes as compared to wild type, while demonstrating a significant decrease in circulating lymphocytes (FIG. 3E). CBC data from C9orf72$^{-/-}$ mice (e.g., 34-38 weeks old) also demonstrated that circulating white blood cell differential was altered as compared to wild type mice. The inventors observed that the significant increase in monocytes and neutrophils, and a decrease in lymphocytes in C9orf72$^{-/-}$ mice as compared to wild type mice were detectable as early as 8 weeks of age.

Figure 3F:
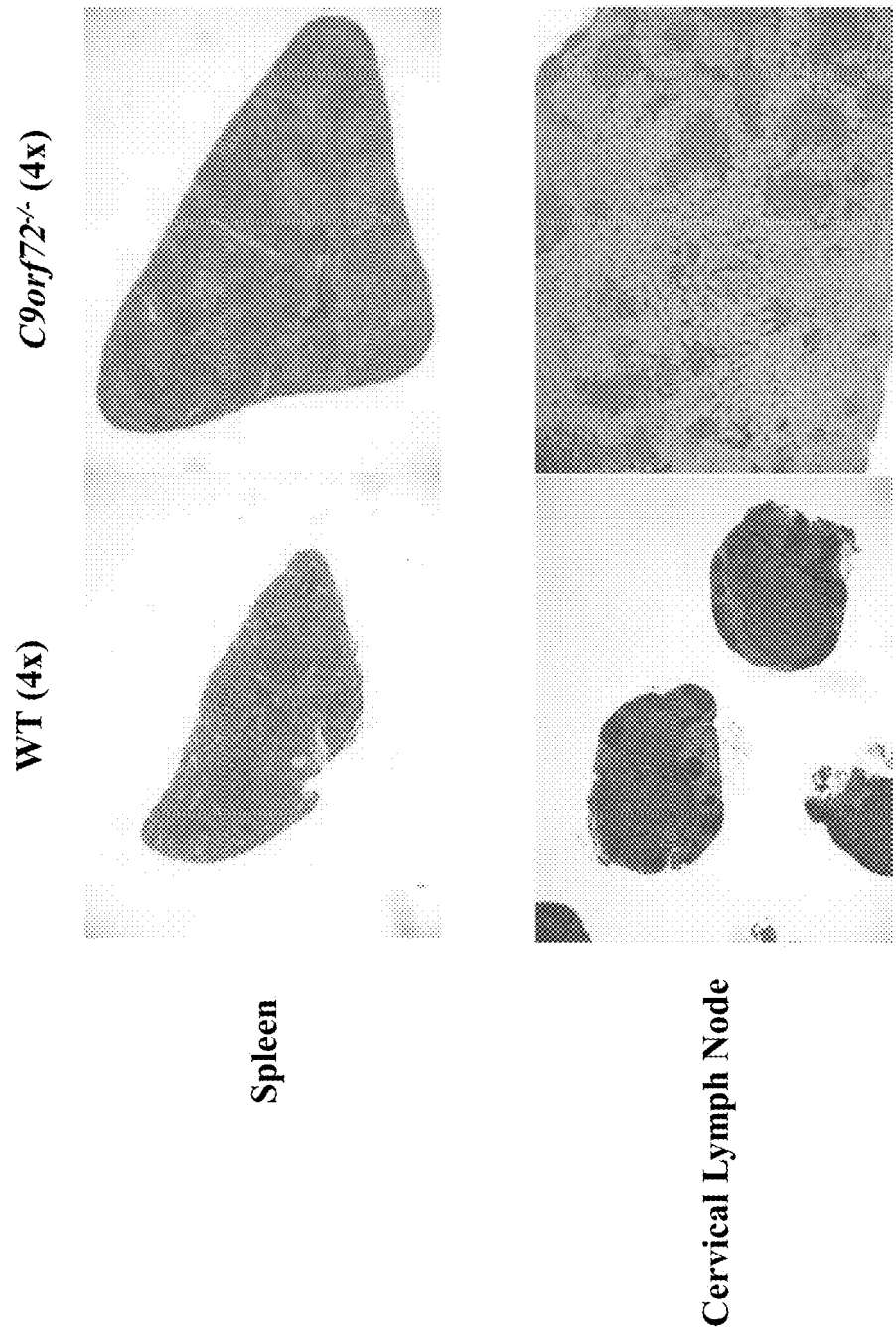
FIG. 3F: exemplary images of sectioned spleen and cervical lymph node tissue from wild type (WT) and C9orf72$^{-/-}$ mice at 4× power stained with hematoxylin and eosin.
Figure 3G:
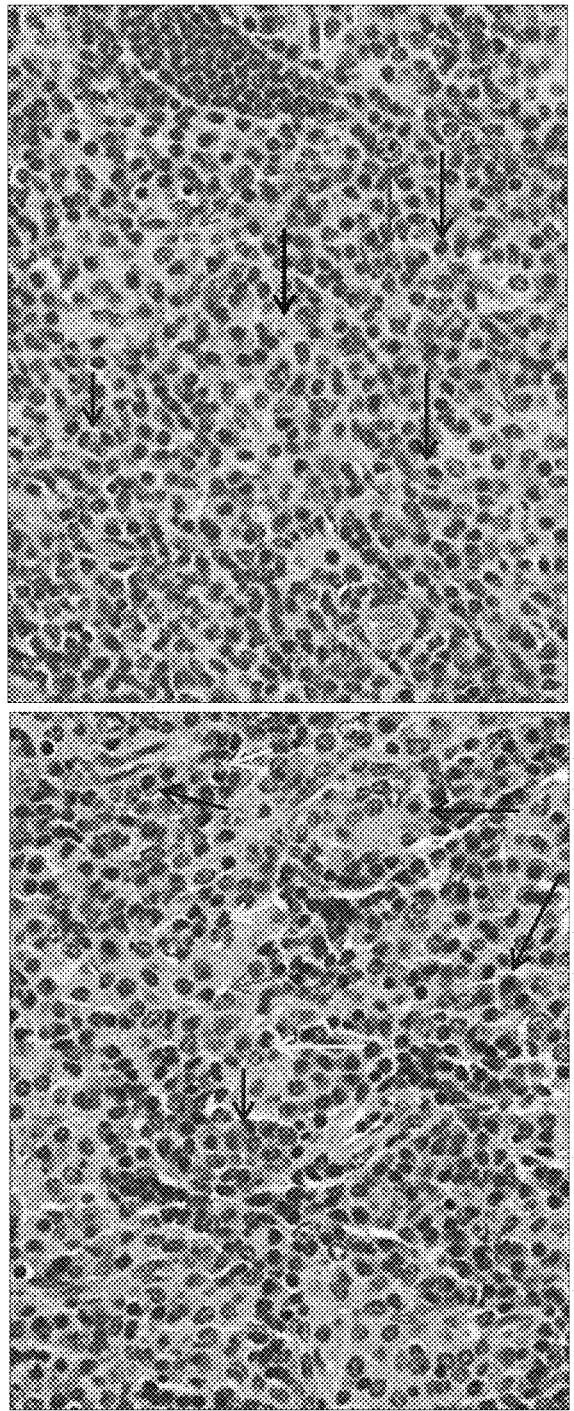
FIG. 3G: exemplary images of sectioned cervical lymph node tissue from C9orf72$^{-/-}$ mice at 60× power stained with hematoxylin and eosin (blue arrows: cells with plasmacytoid morphology; yellow arrows: neutrophils; green arrows: macrophage-type cells; red arrow: Mott cell)

H&E staining revealed a mixed population of cells with multiple morphologies in the spleen and cervical lymph nodes of C9orf72$^{-/-}$ mice (FIGS. 3F, 3G). Specifically, cervical lymph nodes viewed at 4× power showed an abundance of large round cells characterized by variably distinct cell borders and with moderate to abundant eosinophilic characteristics (FIG. 3F). Occasionally, foamy cytoplasm was observed in the expanded cell population. When viewed at 60× power, cells within cervical lymph nodes demonstrated plasmacytoid morphology (blue arrows) intermixed with neutrophils (yellow arrows) and other mature lymphocytes (FIG. 3G). Cells that appeared to be consistent with macrophages (green arrows) were also present as were Mott cells (intermittently, red arrow; abnormal plasma cells with condensed immunoglobulins), all of which indicated chronic inflammation in cervical lymph nodes of C9orf72$^{-/-}$ mice (FIG. 3G).

The observed enlargement of spleens and lymph nodes in C9orf72$^{-/-}$ mice indicated a neoplastic or immune dysregulation disease process, which has not been previously reported in ALS-FTD) patients. Histopathological analysis on C9orf72$^{-/-}$ lymphoid tissues (i.e., staining lymph node and spleen sections from 8-60 week old mice with hematoxylin and eosin (H&E)) confirmed that the basic cellular organization of enlarged lymph nodes was preserved. Further, IHC staining confirmed the presence of 13 cells (CD45R$^+$) in the cortex and T cells (CD3$^+$) between the follicles and in the paracortex zone. However, there was expansion of the cortical and medullary nodal architecture by a cell population consisting mostly of large round cells with variably distinct borders, and with a single round nucleus surrounded by eosinophilic and foamy cytoplasm. A similar cellular infiltrate was also present in the spleen, predominantly located within the red pulp, which expanded the splenic architecture and, as a result, splenic weights in C9orf72$^{-/-}$ mice. It was also noted that an abundance of plasmacytoid cells containing perinuclear halos, consistent with plasma cell morphology, along with occasional Mott cells were present. Similar mixed infiltrates were not observed in wild type and C9orf72$^{+/-}$ (heterozygous) mice.

The large, round cell population did not stain consistently with CD45R, CD3, or CD138, but was strongly positive for F4/80, a macrophage lineage marker. IHC signal was predominant on the cell membrane but scant in the cytoplasm due to the highly vacuolated cytoplasm. In contrast, WT and heterozygous control F4/80 staining was characteristic of cytoplasmic and membranous staining pattern expected for macrophages, with overall F4/80 signal more intense than that observed in C9orf72$^{-/-}$ mice (see below, e.g., FIG. 3P).

H&E and IHC analyses of additional organs from mice aged 8-60 weeks revealed sporadic thymus medullary hyperplasia and bone marrow focal fibrosis and/or myeloid hyperplasia in certain C9orf72$^{-/-}$ mice. A more common observation was the presence of a prominent population of dendritic cells found in the liver and kidneys of null mice. These elongated to angular cells were F4/80$^+$ and morphologically resembled typical dendritic cells (DC), though larger in size and more numerous. They were more pronounced in C9orf72$^{-/-}$ liver as early as 8 weeks compared with wild type, though there was no evidence of associated liver disease. We also observed an increase in F4/80$^+$ cells in C9orf72$^{-/-}$ kidney at 8 weeks that became more prominent with age. DC were located primarily within the outer medulla, where they formed aggregates in the vicinity of the macula densa and adjacent tubules, along with prominent cuffs around glomeruli in association with lymphocytes. We noted increasing infiltrates of mixed leukocytes in the kidney as mice aged, accompanied by varying degrees of immune-mediated glomerular disease that was well-established by 35-60 weeks of age. No evidence of inflammation in brain or spinal cord tissue was observed in any animals examined. Thus, the spleen and lymph nodes were the major sites of immune pathology in C9orf72$^{-/-}$ mice with indications of secondary progressive glomerular disease in the kidney.

Figure 3H:
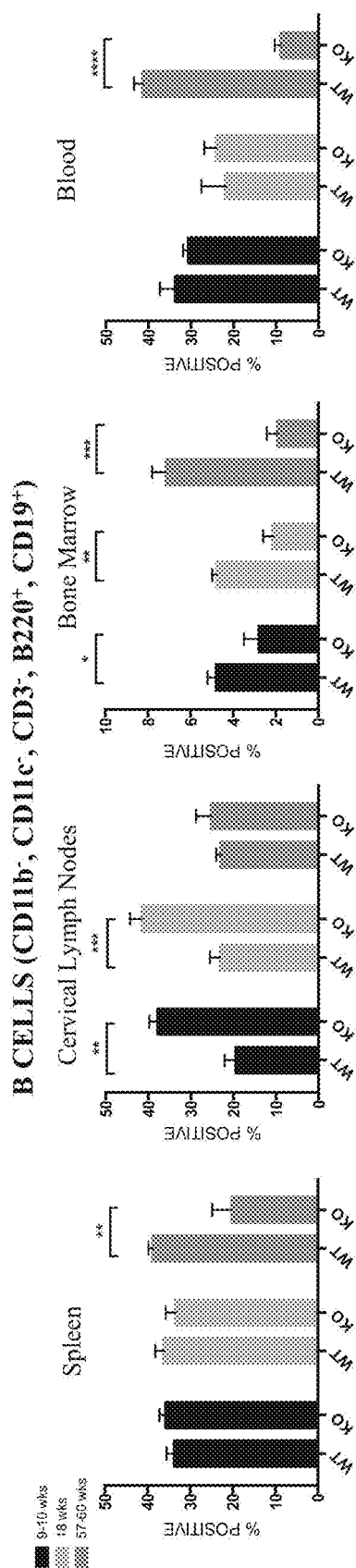
FIG. 3H: exemplary percent positive B cells (CD11b$^-$, CD11c$^-$, CD3$^-$, B220$^+$, CD19$^+$) from spleen, cervical lymph nodes, bone marrow and blood in wild type (WT) and C9orf72$^{-/-}$ (KO) male mice.

As shown in FIG. 3H, C9orf72$^{-/-}$ male mice demonstrate increasing numbers of CD11b$^-$CD11c$^-$CD3$^-$B220$^+$CD19$^+$ B cells in the cervical lymph nodes, while showing comparable or decreased percentages of these same B cells in spleen, bone marrow and blood as compared to wild type. B cells that are transitioning to plasma cells (B220$^{mid/low}$CD19$^{mid/low}$) and mature plasma cells (B220$^{low/-}$CD19$^{low/-}$CD45$^+$CD138$^{mid/+}$) appeared to increase with age in the spleen, cervical lymph nodes, and bone marrow of C9orf72$^{-/-}$ male mice as compared to wild type (FIG. 3I).

Figure 3J:
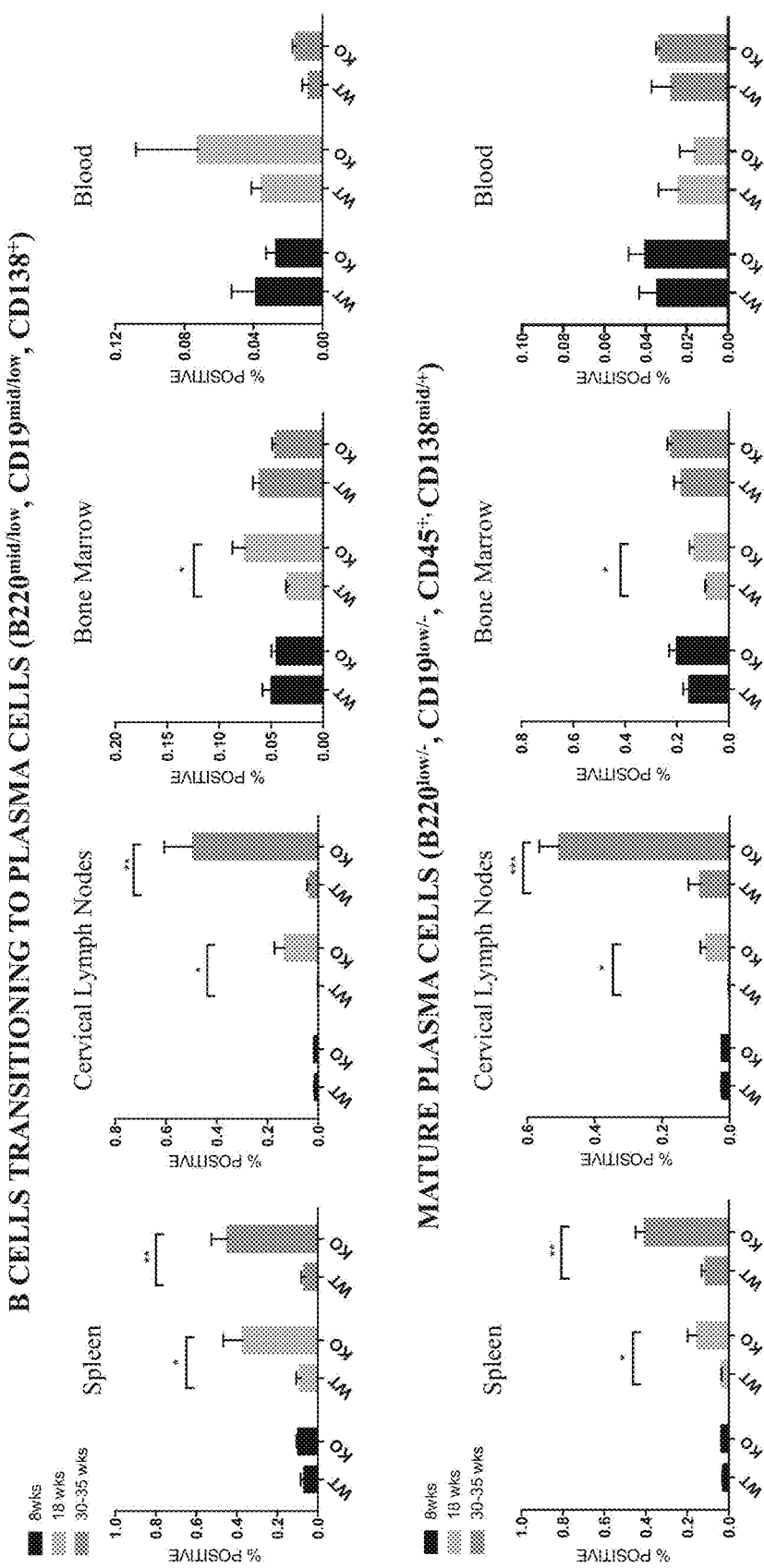
FIG. 3J: exemplary plasma cells at various stages expressing specific cell surface antigens isolated from spleen, cervical lymph nodes, bone marrow and blood of female wild type (WT) and C9orf72$^{-/-}$ (KO) mice at 8 weeks (black bars), 18 weeks (light grey bars) and 30-35 weeks (dark grey bars)

The percentage of B cells (CD45$^+$CD19$^+$) was either unchanged or reduced in female C9orf72$^{-/-}$ mice as compared to wild type, depending on the organ examined (e.g., cervical lymph nodes). C9orf72$^{-/-}$ female mice demonstrate increasing percentages of B cells transitioning to plasma cells/plasma blasts (CD45$^+$CD19$^{int}$B220$^{int}$CD138$^+$) and mature plasma cells (CD45$^+$CD19$^-$B220$^-$CD138$^+$) in spleen, lymph node and bone marrow as compared to wild type (FIG. 3J). We did not observe any consistent differences between C9orf72$^{-/-}$ and control mice in these cell types in the blood. Taken together, these data demonstrated an advancing adaptive immune response in C9orf72$^{-/-}$ mice.

Figure 3K:
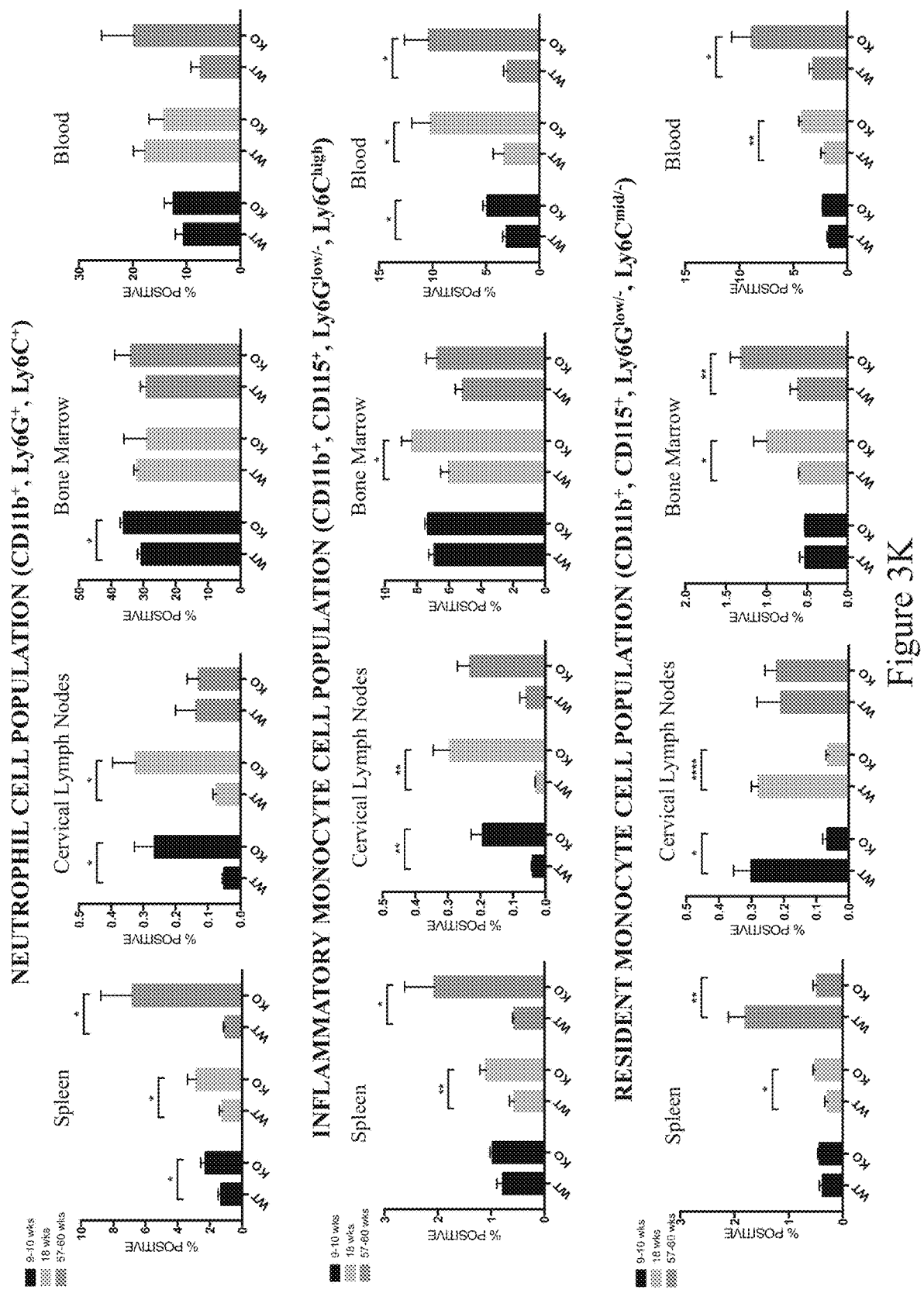
FIG. 3K: exemplary percent positive myeloid cells at various stages expressing specific cell surface antigens isolated from spleen, cervical lymph nodes, bone marrow and blood of male wild type (WT) and C9orf72$^{-/-}$ (KO) mice at 9-10 weeks (black bars), 18 weeks (light grey bars) and 57-60 weeks (dark grey bars)
Figure 3L:
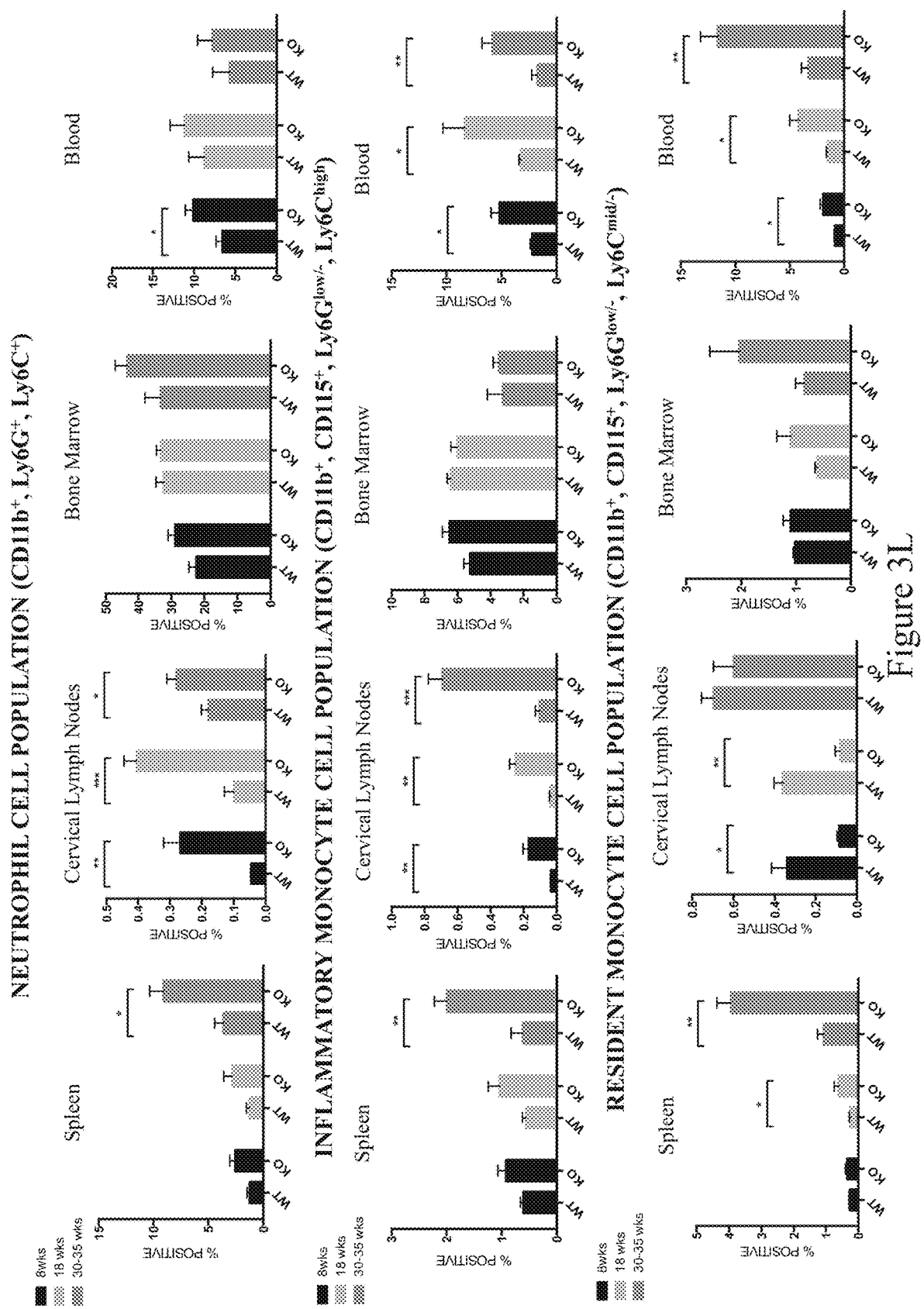
FIG. 3L: exemplary percent positive myeloid cells at various stages expressing specific cell surface antigens isolated from spleen, cervical lymph nodes, bone marrow and blood of female wild type (WT) and C9orf72$^{-/-}$ (KO) mice at 8 weeks (black bars), 18 weeks (light grey bars) and 30-35 weeks (dark grey bars)
Figure 3M:
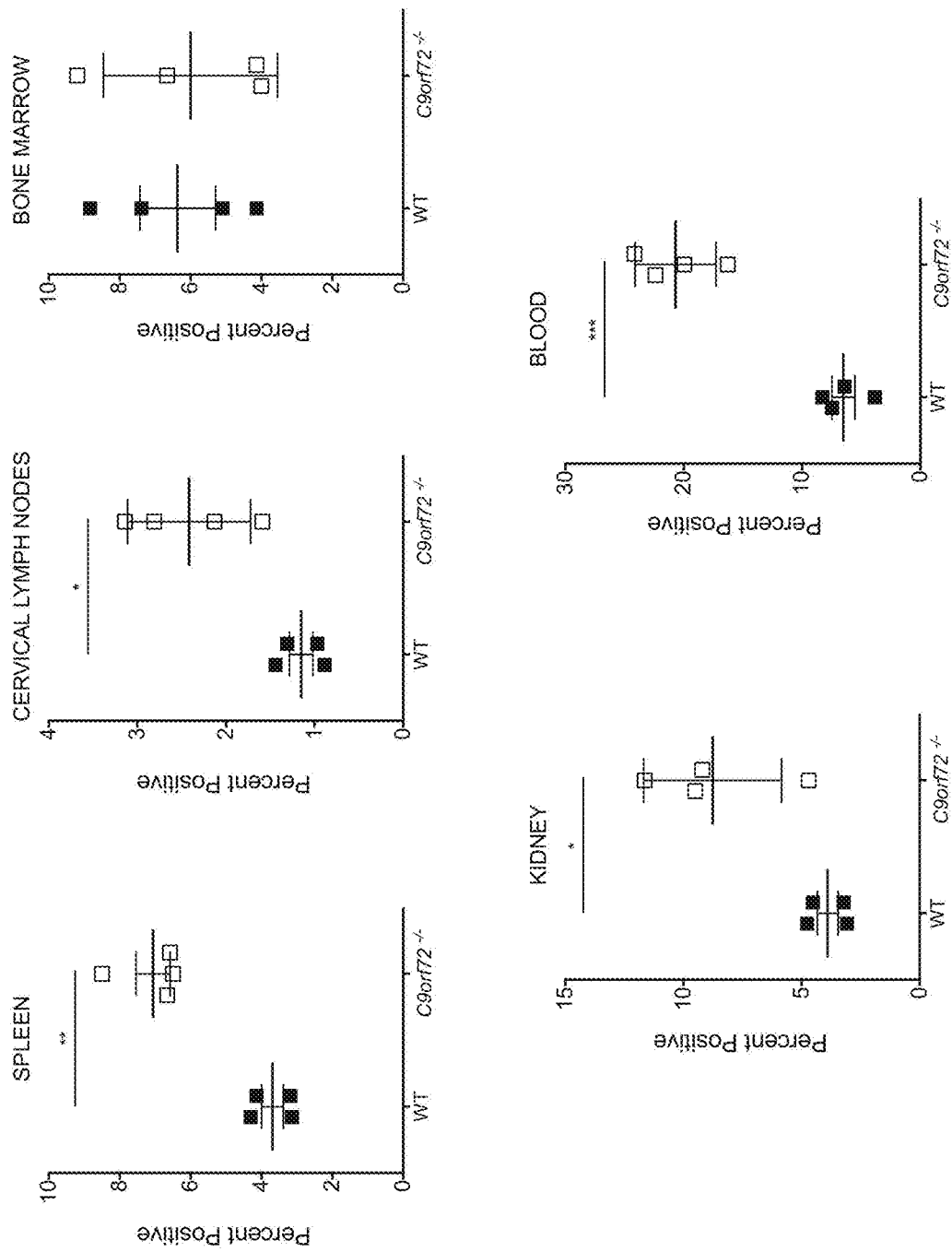
FIG. 3M: exemplary percent positive macrophage (CD45$^+$, CD11b$^+$, F4/80$^+$, Ly6G$^-$) cells in spleen, cervical lymph nodes, bone marrow, kidney and blood of 30-35 week female wild type (WT) and C9orf72$^{-/-}$ mice.

As shown in FIGS. 3K and 3L, increasing percentages of neutrophils (CD11b$^+$Ly6G$^+$Ly6C$^+$) were observed in the spleen of male and female C9orf72$^{-/-}$ mice as they aged. Increases were also observed in the cervical lymph nodes of C9orf72$^{-/-}$ male mice between 9-18 weeks and C9orf72$^{-/-}$ female mice at all time points examined. Granulocyte populations were also increased in bone marrow and blood with varying significance at most time points. Inflammatory monocytes (CD11b$^+$, CD115$^+$, Ly6G$^{low/-}$, Ly6C$^{high}$) were significantly increased in C9orf72$^{-/-}$ mice as compared to wild type for spleen, cervical lymph nodes, bone marrow and blood during at least one time point of testing (FIGS. 3K and 3L, middle row). Similar increases of resident monocytes (CD11b$^+$CD115$^+$Ly6G$^{low/-}$Ly6C$^{mid/-}$) over time was also observed in C9orf72$^{-/-}$ mice in spleen, bone marrow and blood, with decreases noted in the cervical lymph nodes (FIGS. 3K and 3L, bottom row, respectively). As shown in FIG. 3M, increased populations of F4/80$^+$ macrophages in the spleen, cervical lymph nodes, kidney and bone marrow were observed in C9orf72$^{-/-}$ mice as compared to wild type.

Figure 3N:
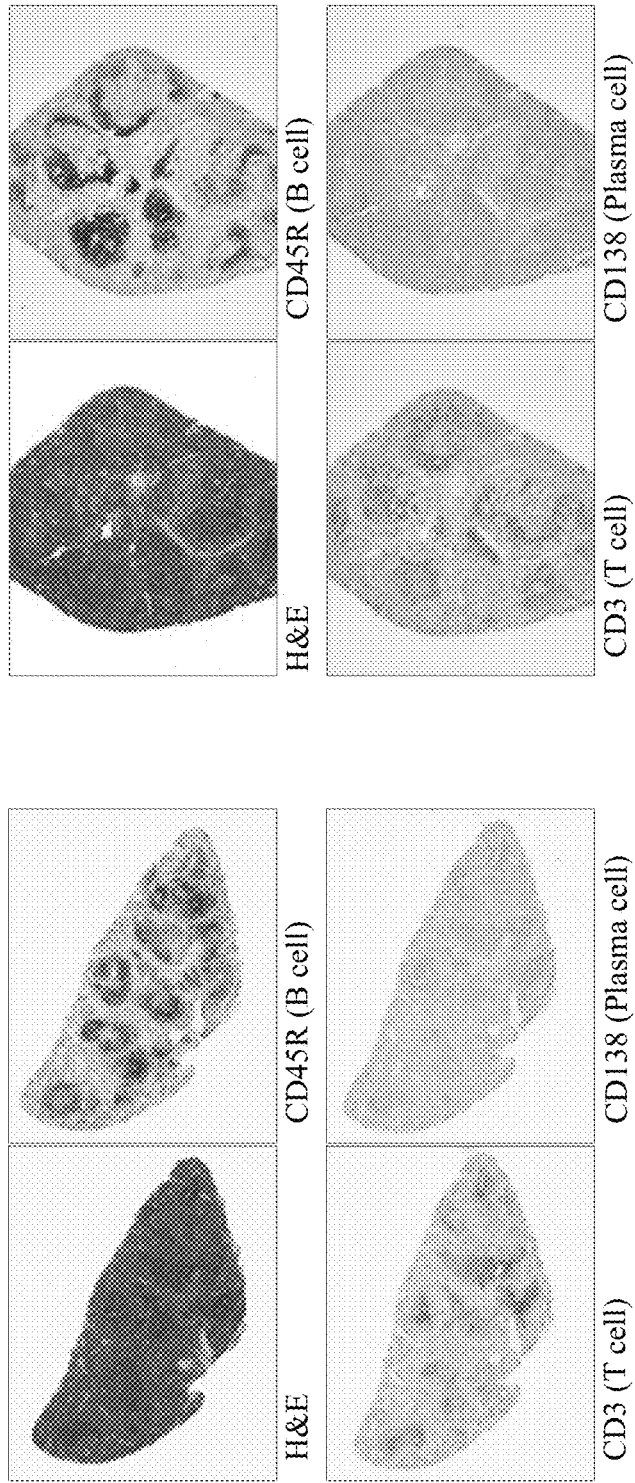
FIG. 3N: exemplary images of sectioned spleen from wild type (WT) and C9orf72$^{-/-}$ mice at 4× power stained with various markers (indicated beneath each image)
Figure 3O:
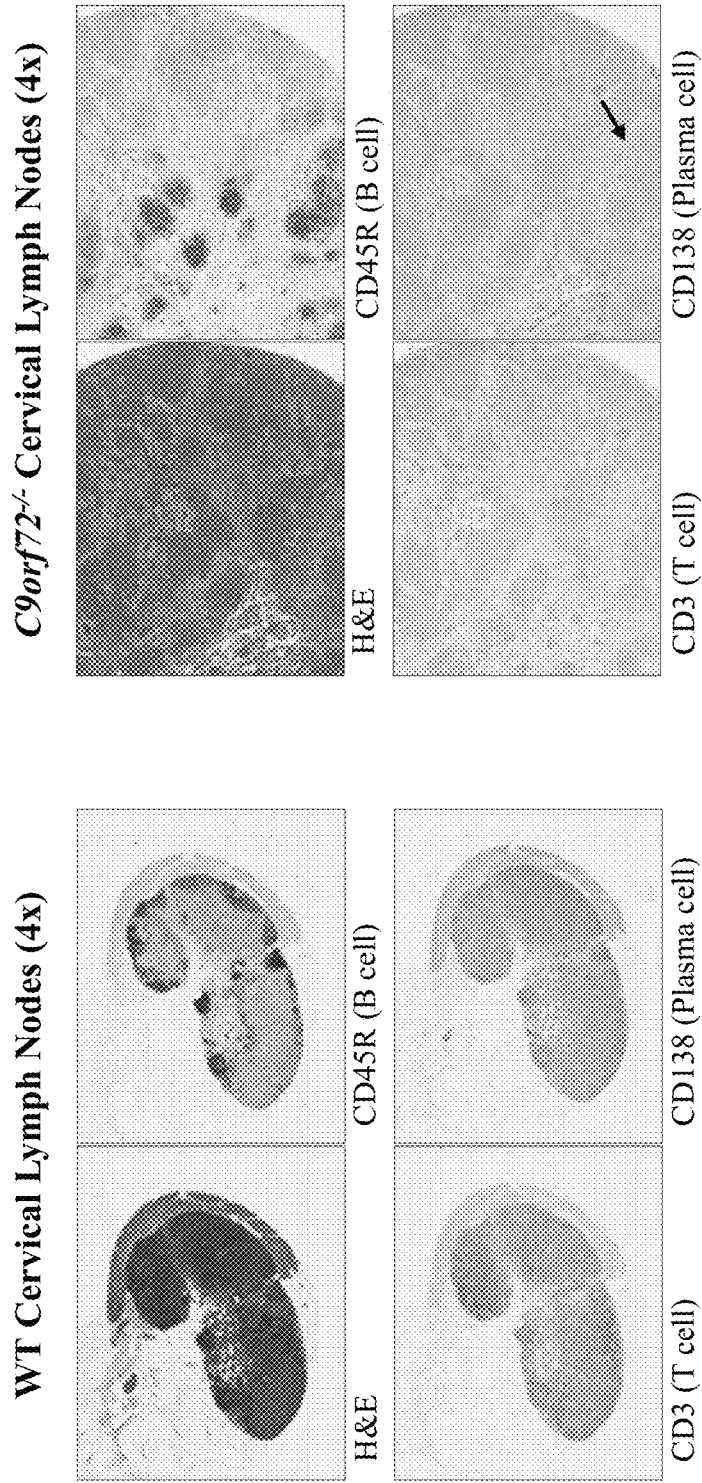
FIG. 3O: exemplary images of sectioned cervical lymph node from wild type (WT) and C9orf72$^{-/-}$ mice at 4× power stained with various markers (indicated beneath each image; arrow: cells intermittently stained with CD138)

Histopathological analysis in the context of CD45R, CD3 and CD138 expression was also analyzed in the spleen and cervical lymph nodes of wild type and C9orf72$^{-/-}$ mice (FIGS. 3N, 3O). Sections were viewed at 4× and 60× power. In the spleen, C9orf72$^{-/-}$ mice demonstrated a loss of normal follicular morphology (FIG. 3N). The white pulp areas were enlarged and dysplastic with ill-defined borders. Accumulation of cells with abundant light pink cytoplasm (plasma-like cells) was observed. CD138 staining did not differ markedly from wild type mice and some of the proliferating cells in the center of the white pulp did not stain with CD45R, CD3, or CD138. The spleens of wild type mice demonstrated essentially normal morphology with white pulp areas composed of central T cells (anti-CD3 IHC) surrounded by a rim of B cells (anti-CD45R IHC), and CD138 staining for plasma cells was minimal (FIG. 3N, left).

In the cervical lymph nodes, C9orf72$^{-/-}$ mice demonstrated islands of lymphoid tissues scattered amongst large aggregates of round cells with a, single nucleus and abundant eosinophilic cytoplasm (FIG. 3O). These cells replaced the normal architecture, but relatively normal B cell and T cell areas remained (evident in the center of CD3 and CD45R stained sections). The abnormal cells intermittently stained with CD3, CD138 (arrow in bottom right image of FIG. 3O), and CD45R but were generally negative for all three markers. Wild type mice showed normal lymph node morphology (FIG. 3O, right). CD45R immunostaining (B cell) was found at the periphery surrounding T cell (CD3) zones and CD138 rarely stained cells in the medulla.

Figure 3P:
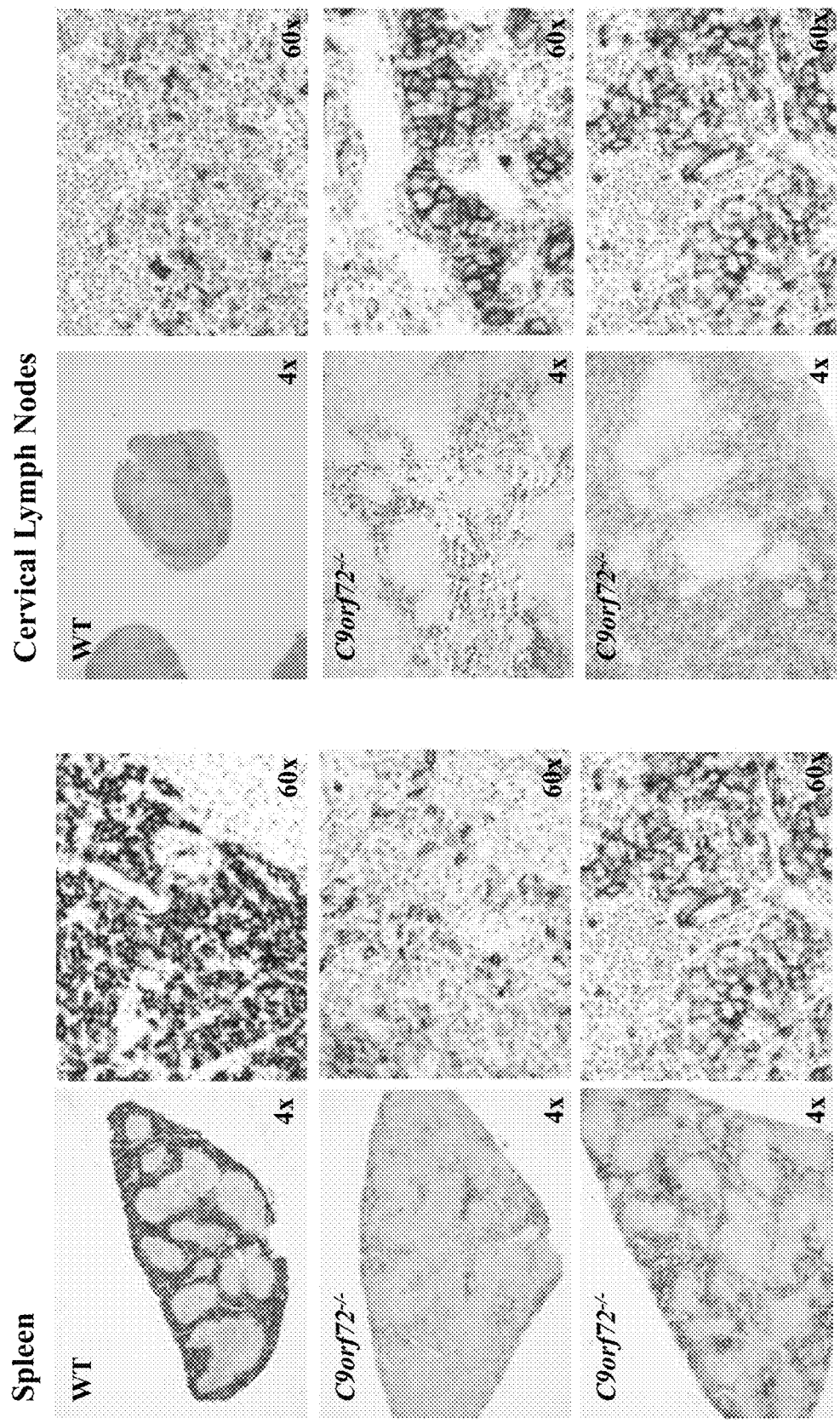
FIG. 3P: exemplary images of sectioned spleen and cervical lymph node from wild type (WT) and C9orf72$^{-/-}$ mice at 4× and 60× power stained with F4/80.

Histopathological analysis in the context of F4/80 expression was also analyzed in the spleen and cervical lymph nodes of wild type and C9orf72$^{-/-}$ mice (FIG. 3P). Sections were viewed at 4× and 60× power. The data demonstrated positive F4/80 staining (macrophages) in C9orf72$^{-/-}$ mice, which correlates with the large foamy cell infiltrate observed in H&E staining (described above). Extracellular F4/80 staining was also observed in the red pulp of spleen in C9orf72_mice. F4/80$^+$ cell number increased with age from 8-58 weeks in C9orf72$^{-/-}$ mice, and was increased in C9orf72$^{-/-}$ lymph nodes as compared to wild type lymph nodes.

Figure 3Q:
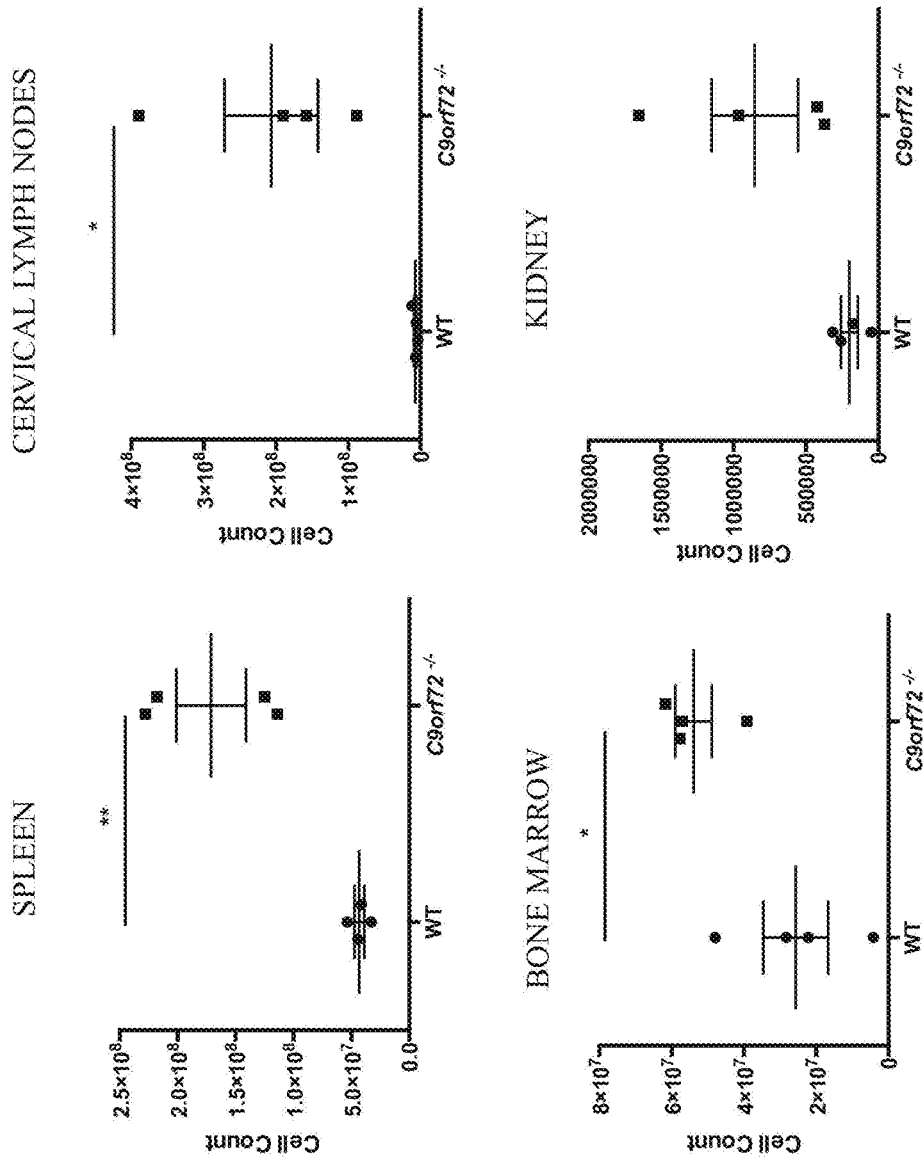
FIG. 3Q: exemplary total cell counts in spleen, cervical lymph nodes, bone marrow and kidney in wild type (WT) and C9orf72$^{-/-}$ mice. Cells were counted using a Cellometer Auto T4 Cell Viability Counter PRIOR to FACS analysis. This was done to calculate total number of cells positive for surface markers of interest in addition to presenting the data in percent of cells positive for said markers. As these counts were performed after red blood cell lysis, they are also representative of a huge immune infiltration (white blood cells) as total cell counts were increased in null mice compared with wild type.
Figure 3R:
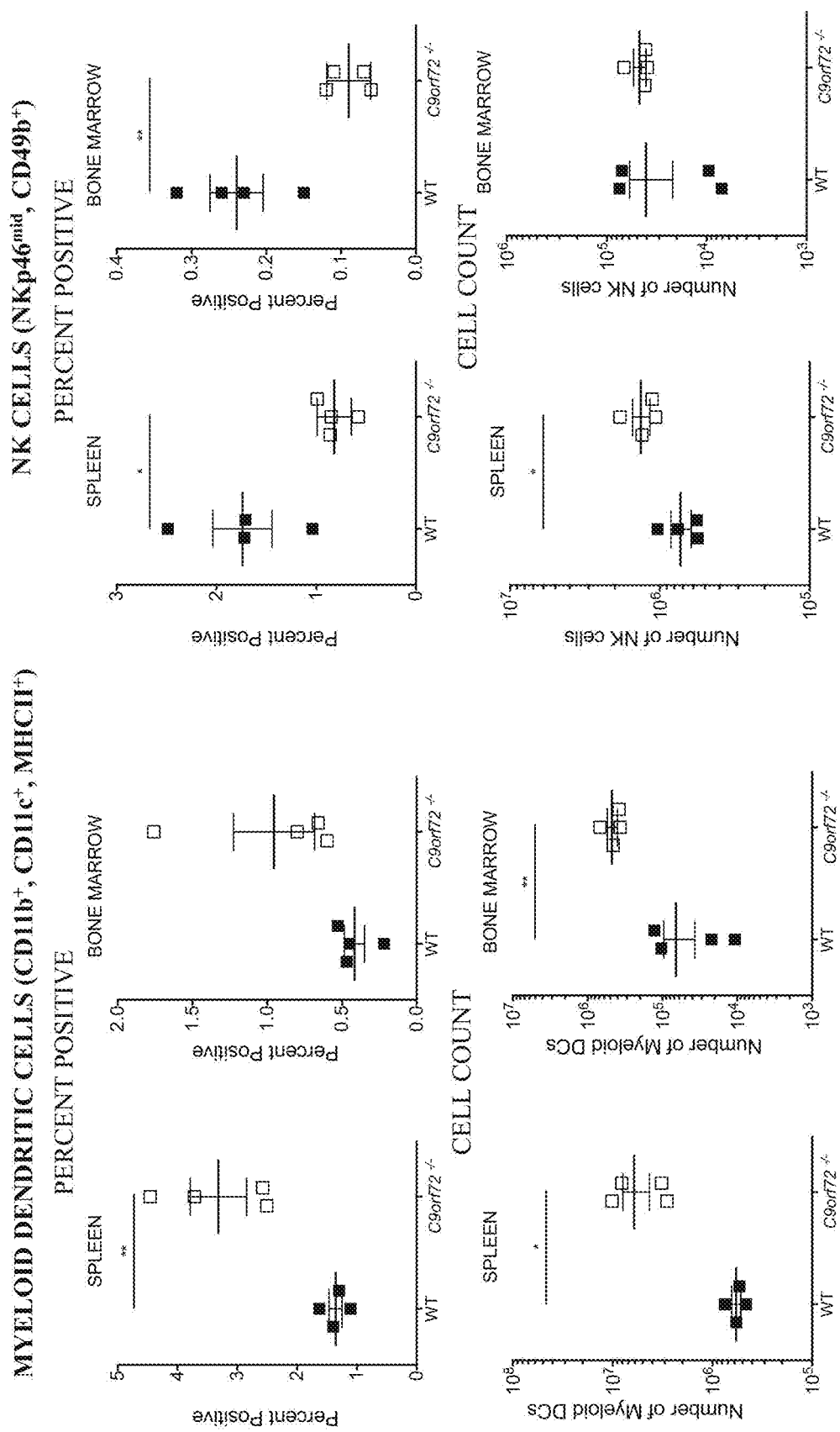
FIG. 3R: exemplary percent positive and cell counts of myeloid dendritic cells (left; CD11b$^+$, CD11c$^+$, MHCII$^+$) and NK cells (right; NKp46$^{mid}$, CD49b$^+$) in spleen and bone marrow for wild type (WT) and C9orf72$^{-/-}$ mice.
Figure 3S:
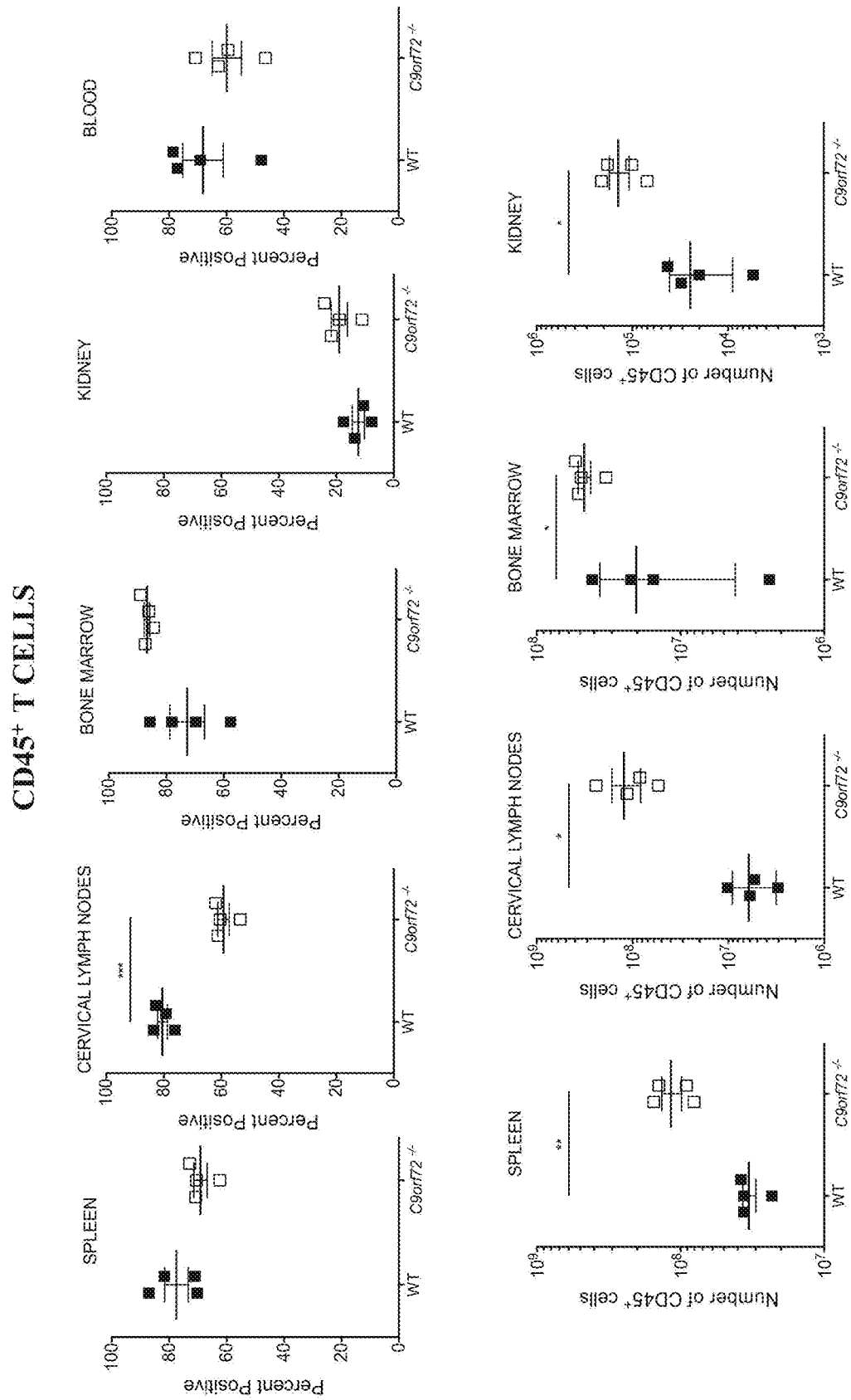
FIG. 3S: exemplary percent positive (top row) and total cell count (bottom row) for CD45$^+$ cells in various tissues of wild type (WT) and C9orf72$^{-/-}$ mice.

Total CD45$^+$ (common leukocyte antigen) cell counts were increased in all tissues examined from C9orf72$^{-/-}$ mice, which was consistent with immune infiltration observed. However, CD45$^+$ percentages compared to total cell populations assayed were either unchanged or reduced as compared to wild type (FIG. 3S). Specific antibody panels were employed to determine if homeostasis within leukocyte subsets was altered. Neutrophil (CD45$^+$CD11b$^+$Ly6G$^+$Ly6C$^{int}$CD115$^-$) and total monocyte (CD45$^+$CD11b$^+$CD115$^+$) percentages were variably increased in lymph node, spleen, and bone marrow of C9orf72$^{-/-}$ mice as compared to wild type (FIGS. 3K and 3L). Increase in F4/80$^+$ macrophages (CD45$^+$CD11b$^+$F4/80$^+$Ly6G$^-$) was additionally observed in the spleen, lymph node, kidney and blood (FIG. 3M). Interestingly, although more cells stained positively with F4/80 in tissues from C9orf72$^{-/-}$ mice, the overall signal was less intense than that observed in wild type mice, which indicates a more widespread but less concentrated F4/80 IHC profile (FIG. 3P). Ly6G and Ly6C staining revealed an increased percentage of inflammatory monocytes (CD45$^+$CD11b$^+$CD115$^+$Ly6G$^-$Ly6C$^{hi}$) in spleen, lymph node, kidney, and blood of C9orf72$^{-/-}$ mice.

Figure 3T:
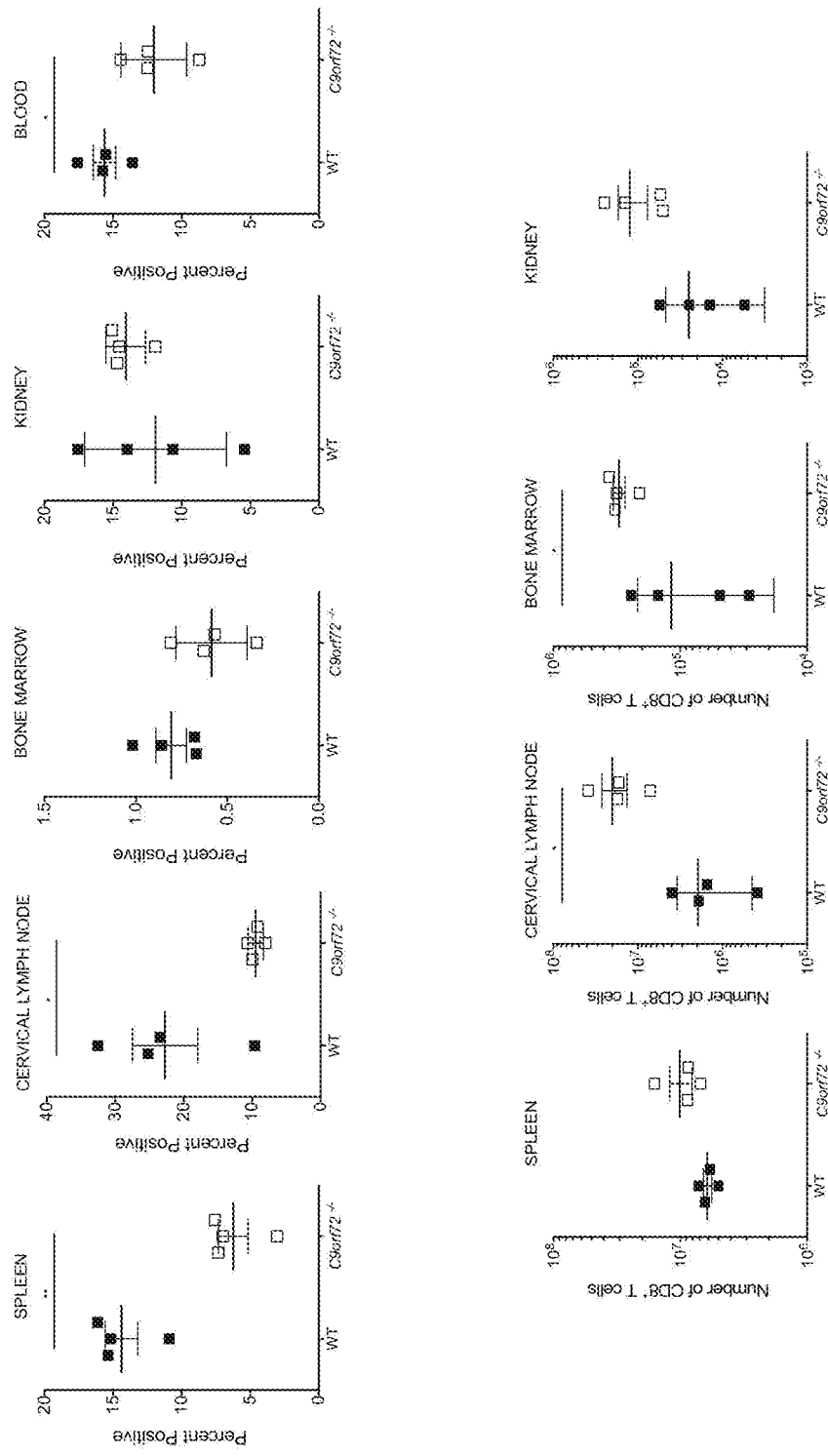
FIG. 3T: exemplary percent positive (top row) and total cell count (bottom row) for CD8+ T cells in various tissues of wild type (WT) and C9orf72−/− mice.

Additional FACS analysis was done on 30-35 week old females, a time point of specific interest as the majority of null mice have developed renal pathology but remained viable. As shown in FIG. 3Q, total cell counts performed on whole tissue demonstrated a significant increase in absolute cell counts by flow cytometry for various compartments in C9orf72$^{-/-}$ mice. The identity of such increases was determined using flow cytometry employing various markers for myeloid dendritic cells, NK cells, and T cells (FIGS. 3R-3AC). Myeloid dendritic cells (CD45$^+$CD11b$^+$CD11c$^+$MHCII$^+$) were increased by percent and total cell count in C9orf72$^{-/-}$ mice as compared to wild type whereas the NK cell (NKp46$^+$CD49b$^+$) fraction was decreased (FIG. 3R). Percent CD45$^+$ (leukocyte common antigen; stains all white blood cells) cells is comparable between wild type and C9orf72$^{-/-}$ mice tissues, however, total cell counts are significantly increased, which indicates a significant infiltration of immune cells (FIG. 3S). Staining with T cell-specific markers CD4$^+$ (helper T cell population) and CD8$^+$ (cytotoxic T cell population) demonstrated decreased percentages of T cell populations (FIGS. 3T-3AC). As shown by IHC, molecular profiling and CBC results, decreases observed in lymphocyte populations may reflect the increase in proportion of myeloid cells.

Figure 3U:
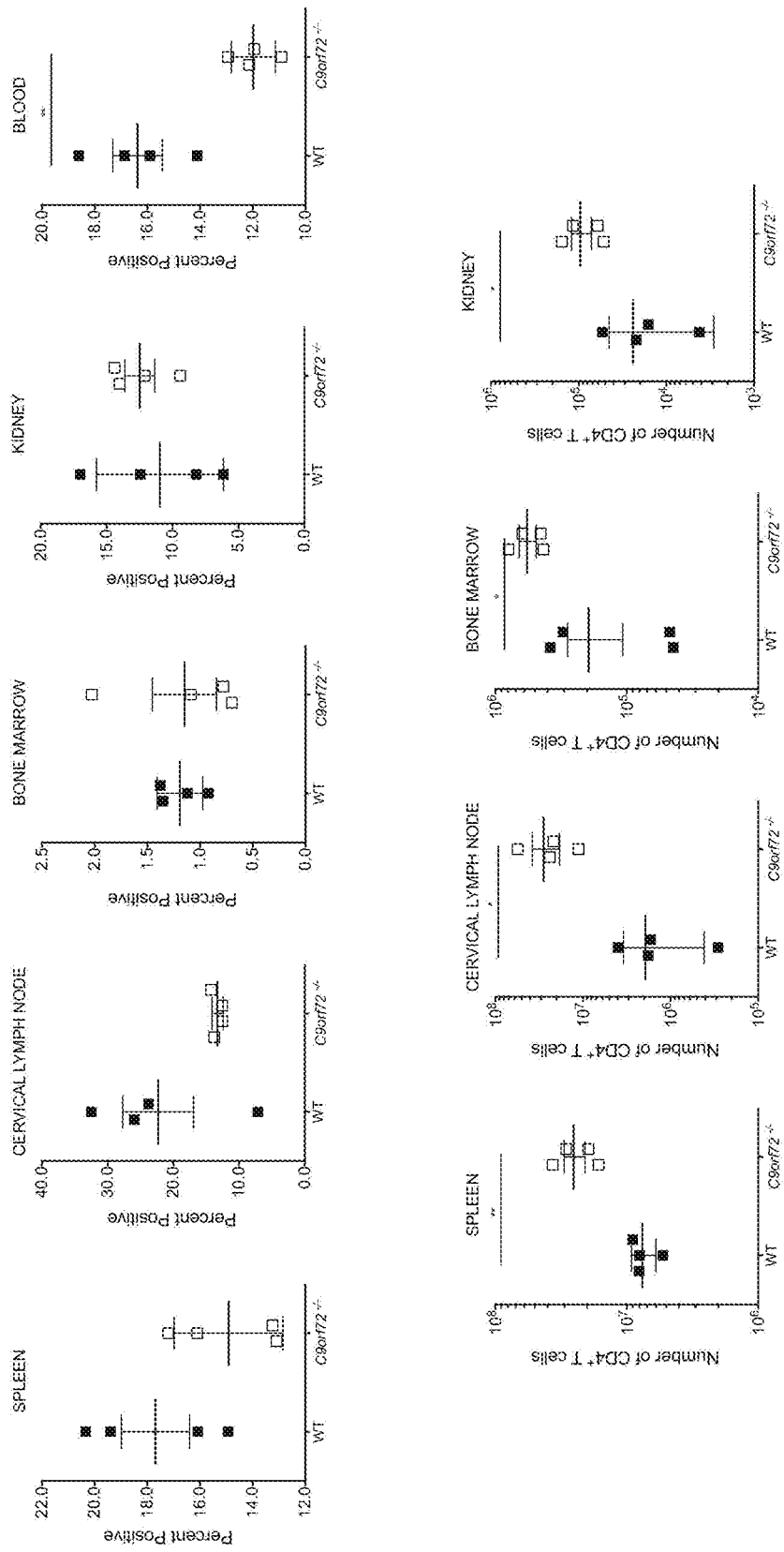
FIG. 3U: exemplary percent positive (top row) and total cell count (bottom row) for CD4+ T cells in various tissues of wild type (WT) and C9orf72−/− mice.
Figure 3V:
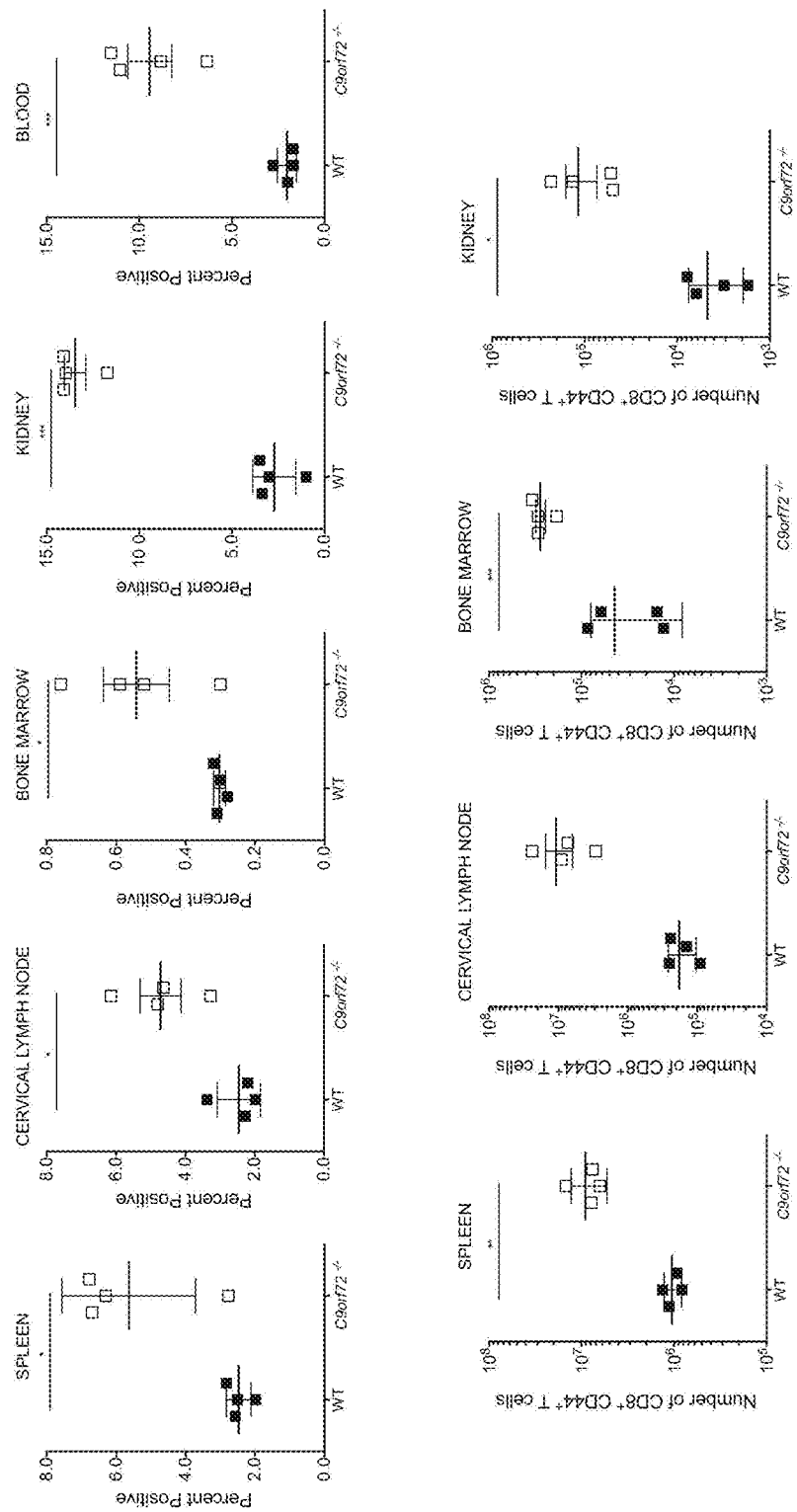
FIG. 3V: exemplary percent positive (top row) and total cell count (bottom row) for CD8+CD44+ T cells in various tissues of wild type (WT) and C9orf72−/− mice.
Figure 3W:
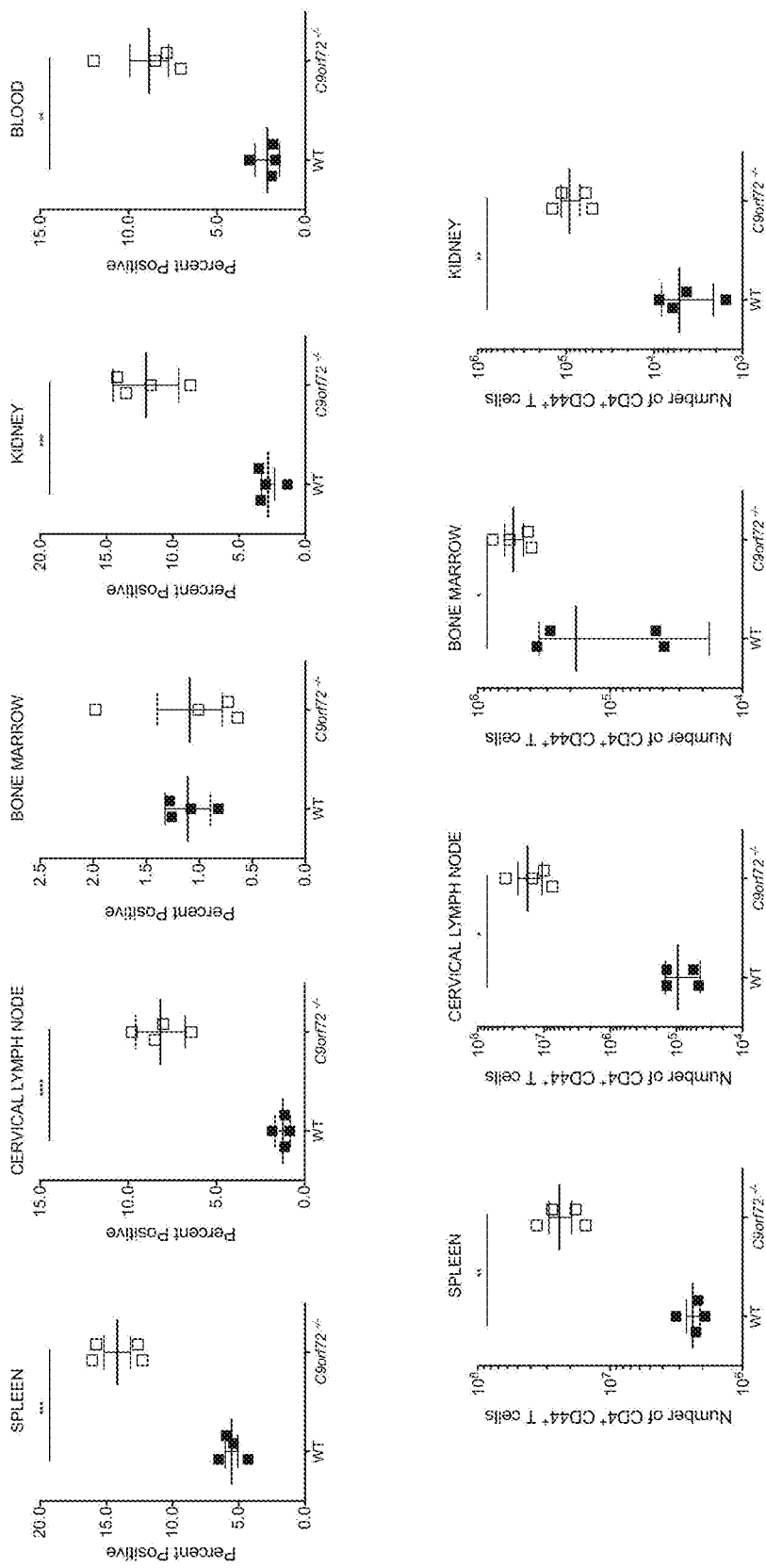
FIG. 3W: exemplary percent positive (top row) and total cell count (bottom row) for CD4+CD44− T cells in various tissues of wild type (WT) and C9orf72−/− mice.
Figure 3X:
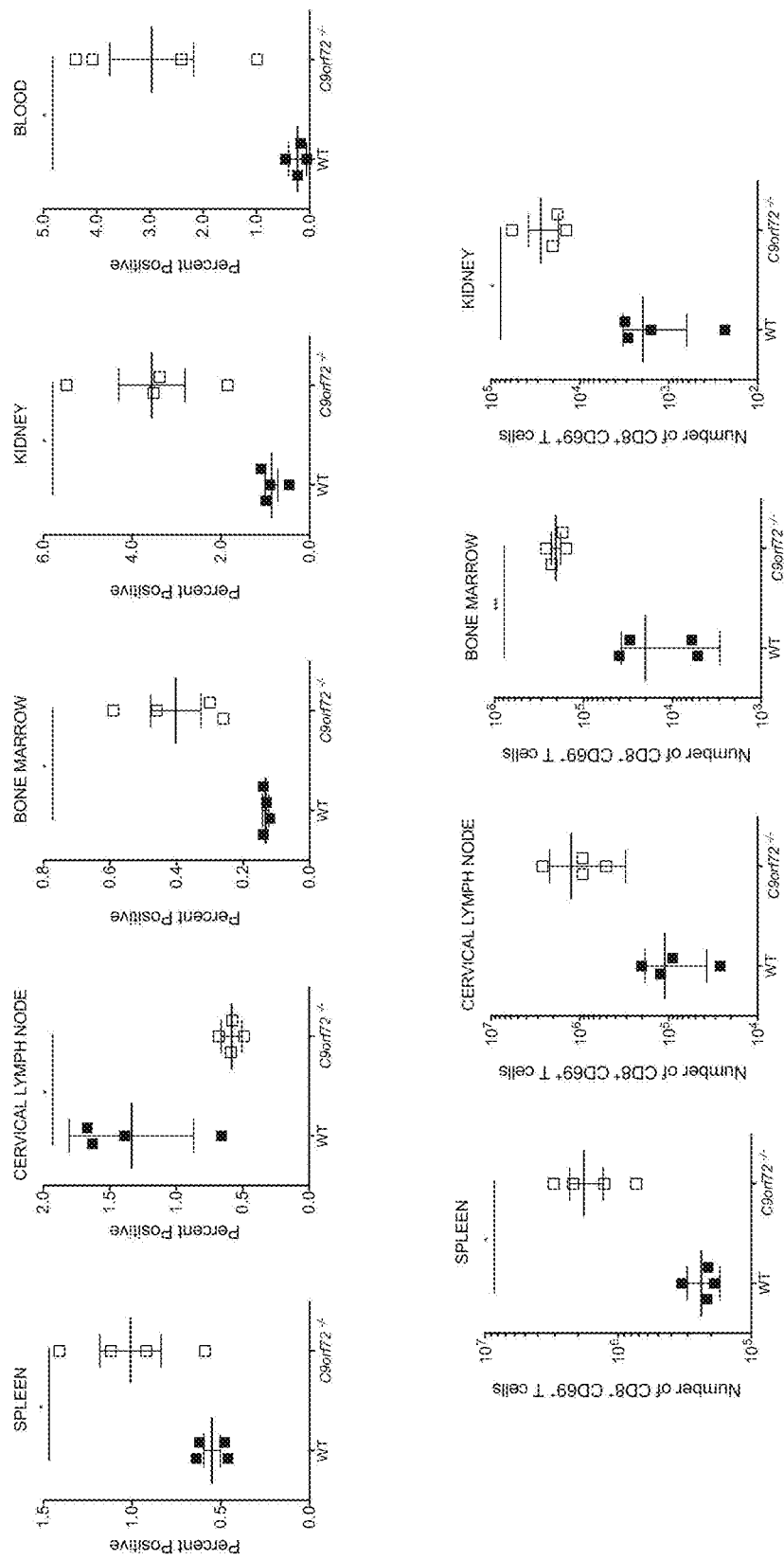
FIG. 3X: exemplary percent positive (top row) and total cell count (bottom row) for CD8+CD69+ T cells in various tissues of wild type (WT) and C9orf72−/− mice.
Figure 3Y:
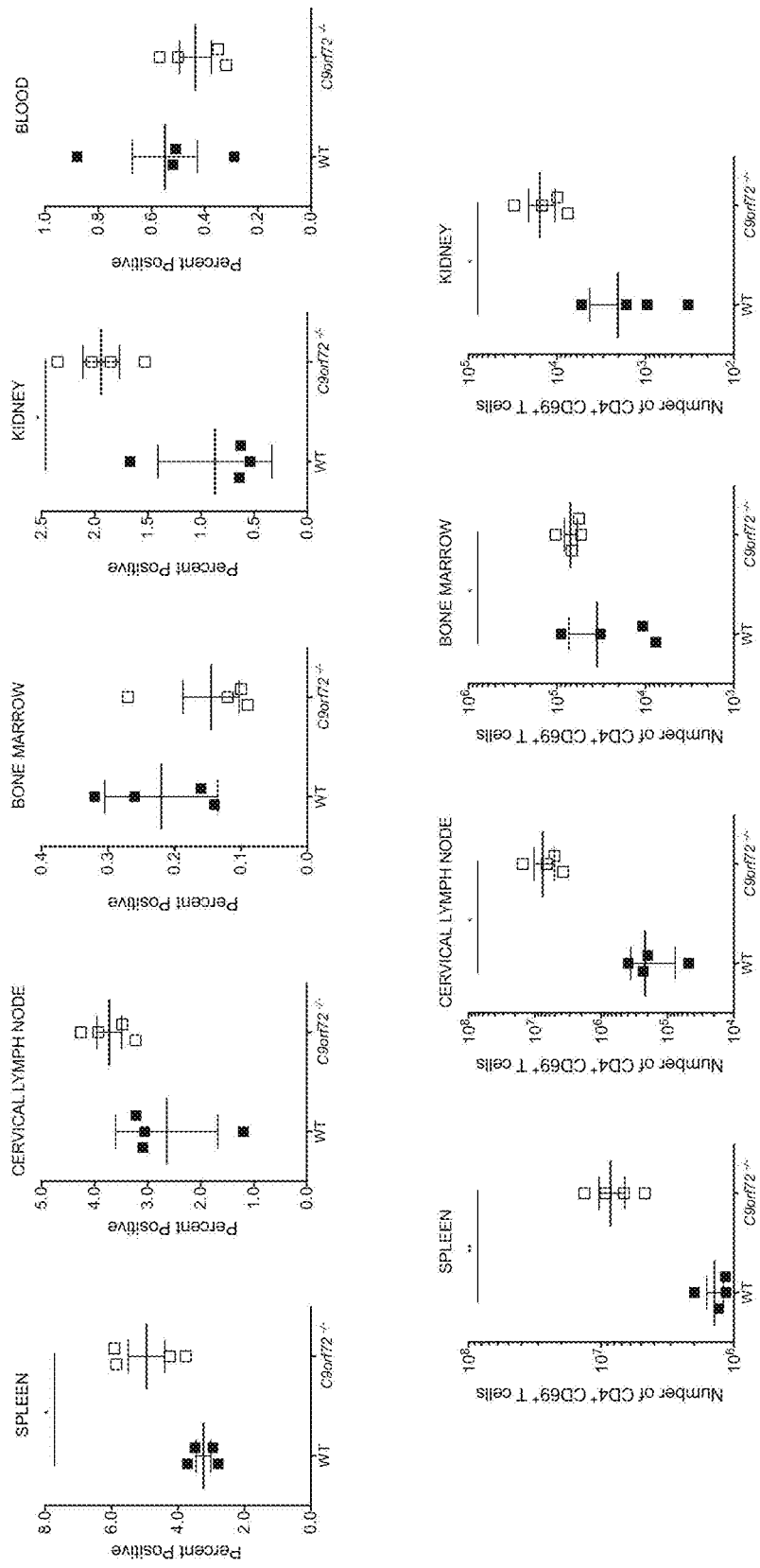
FIG. 3Y: exemplary percent positive (top row) and total cell count (bottom row) for CD4+CD69+ T cells in various tissues of wild type (WT) and C9orf72−/− mice.
Figure 3Z:
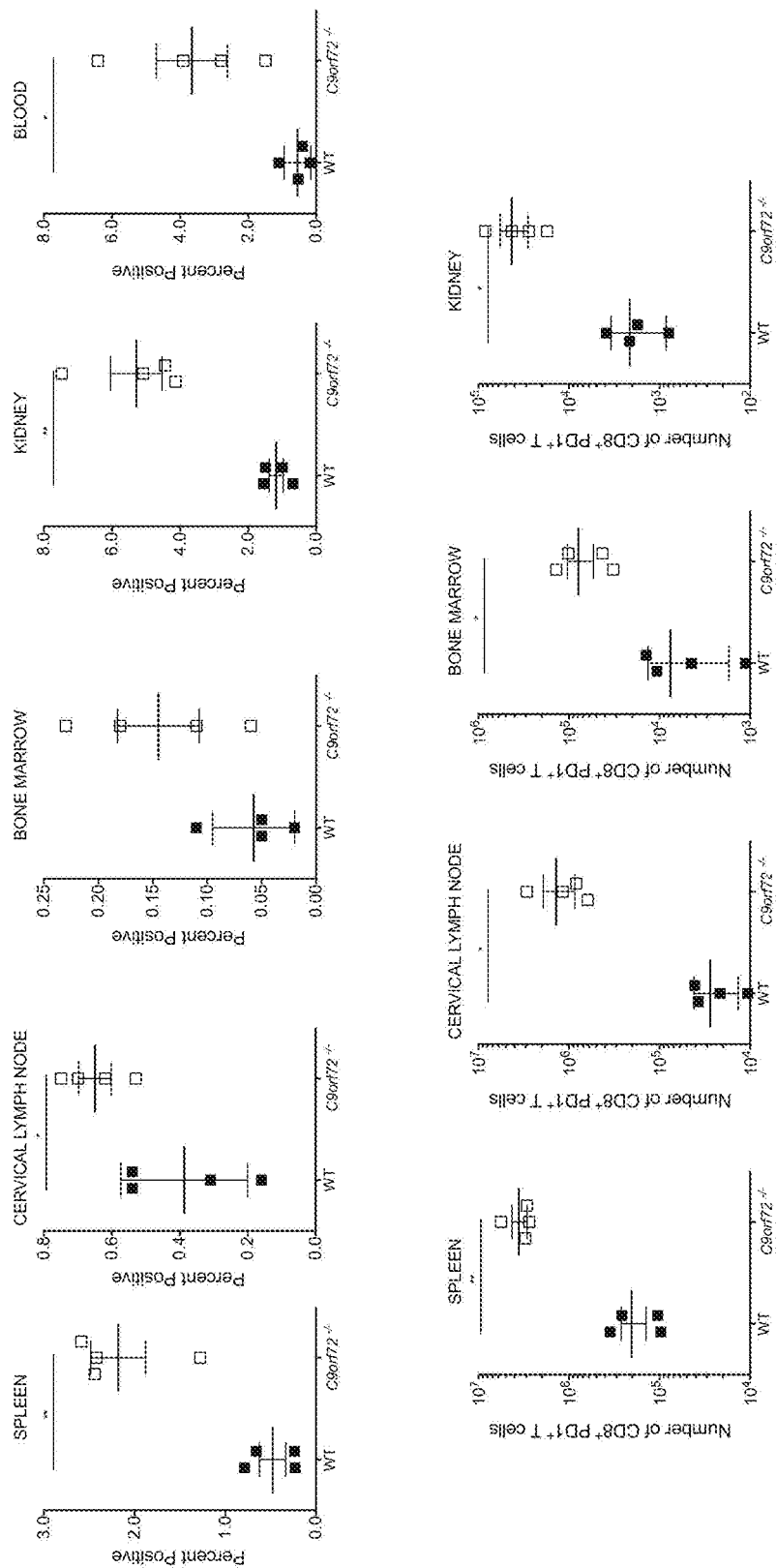
FIG. 3Z: exemplary percent positive (top row) and total cell count (bottom row) for CD8+PD1+ T cells in various tissues of wild type (WT) and C9orf72−/− mice.
Figure 3A:
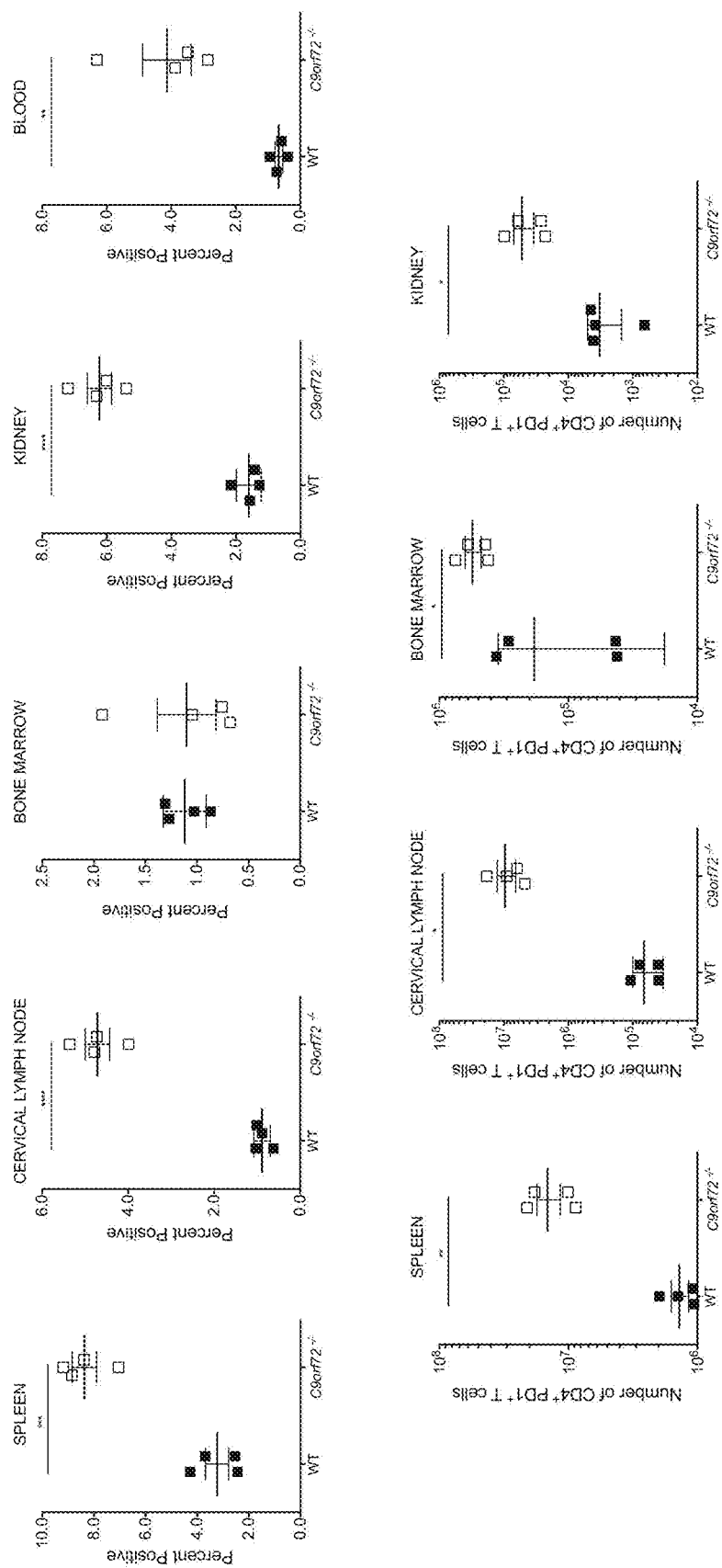
Figure 3A:
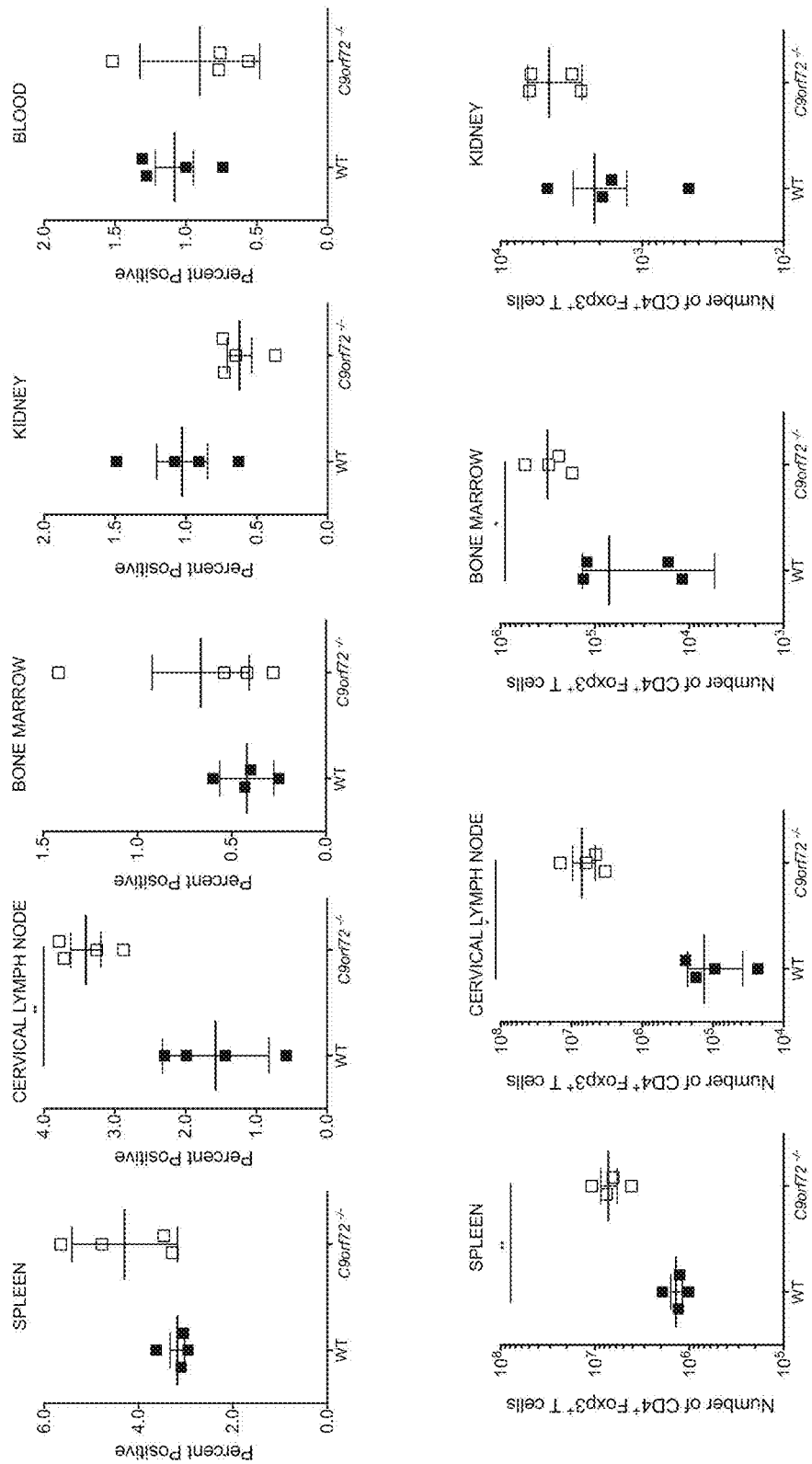
Figure 3A:
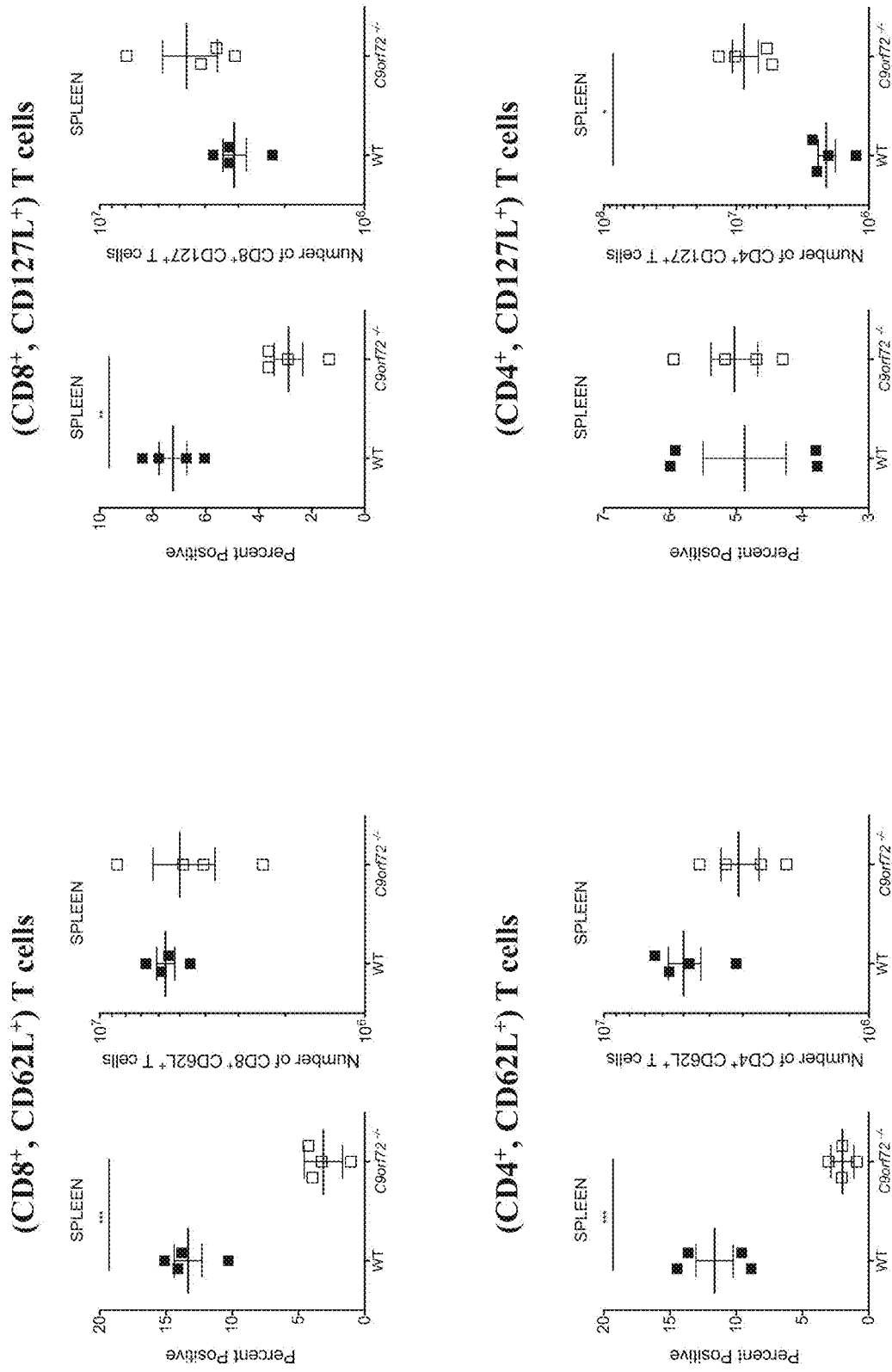
Figure 3A:
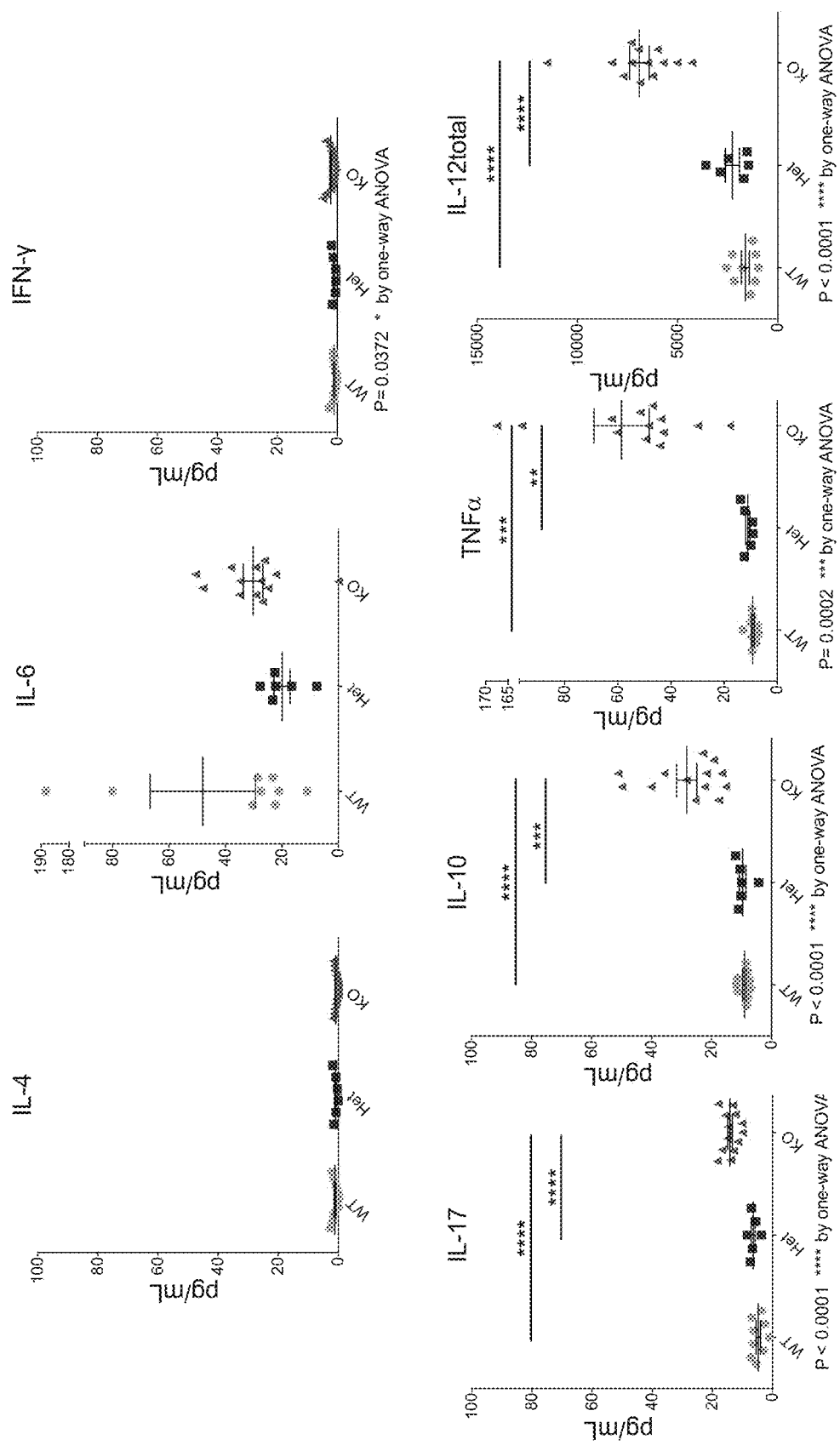
Figure 3A:
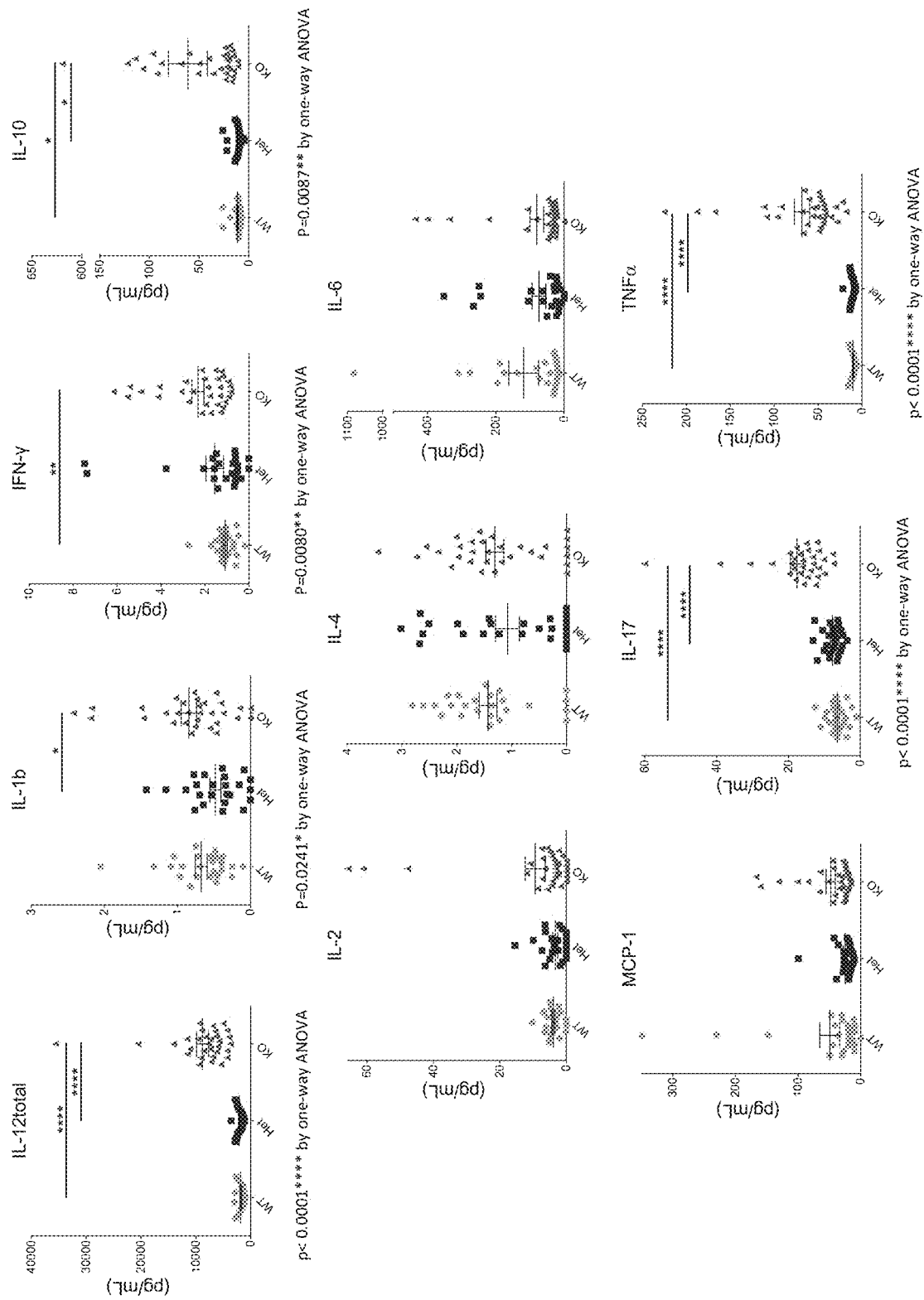
Figure 3A:
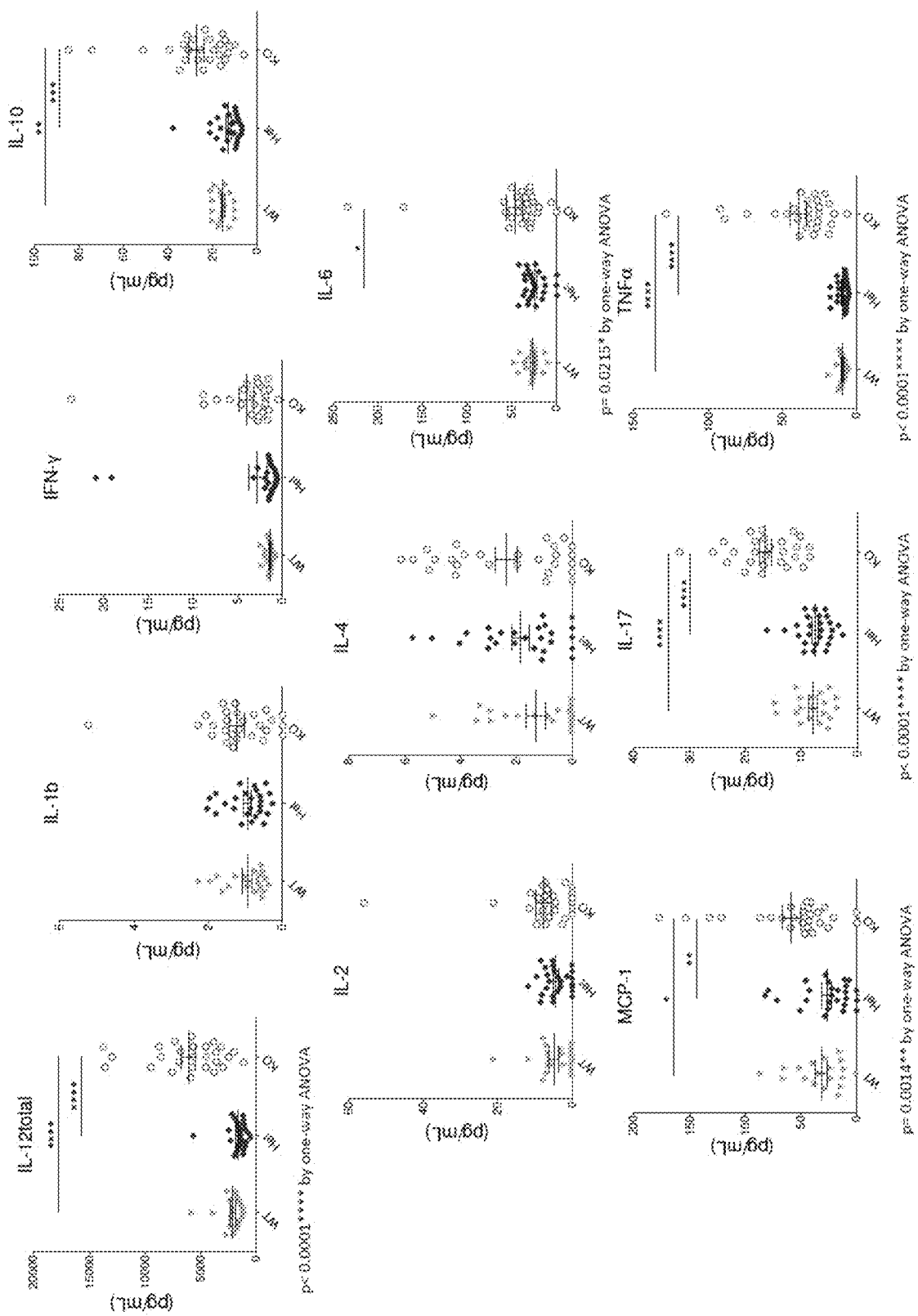
Figure 3A:
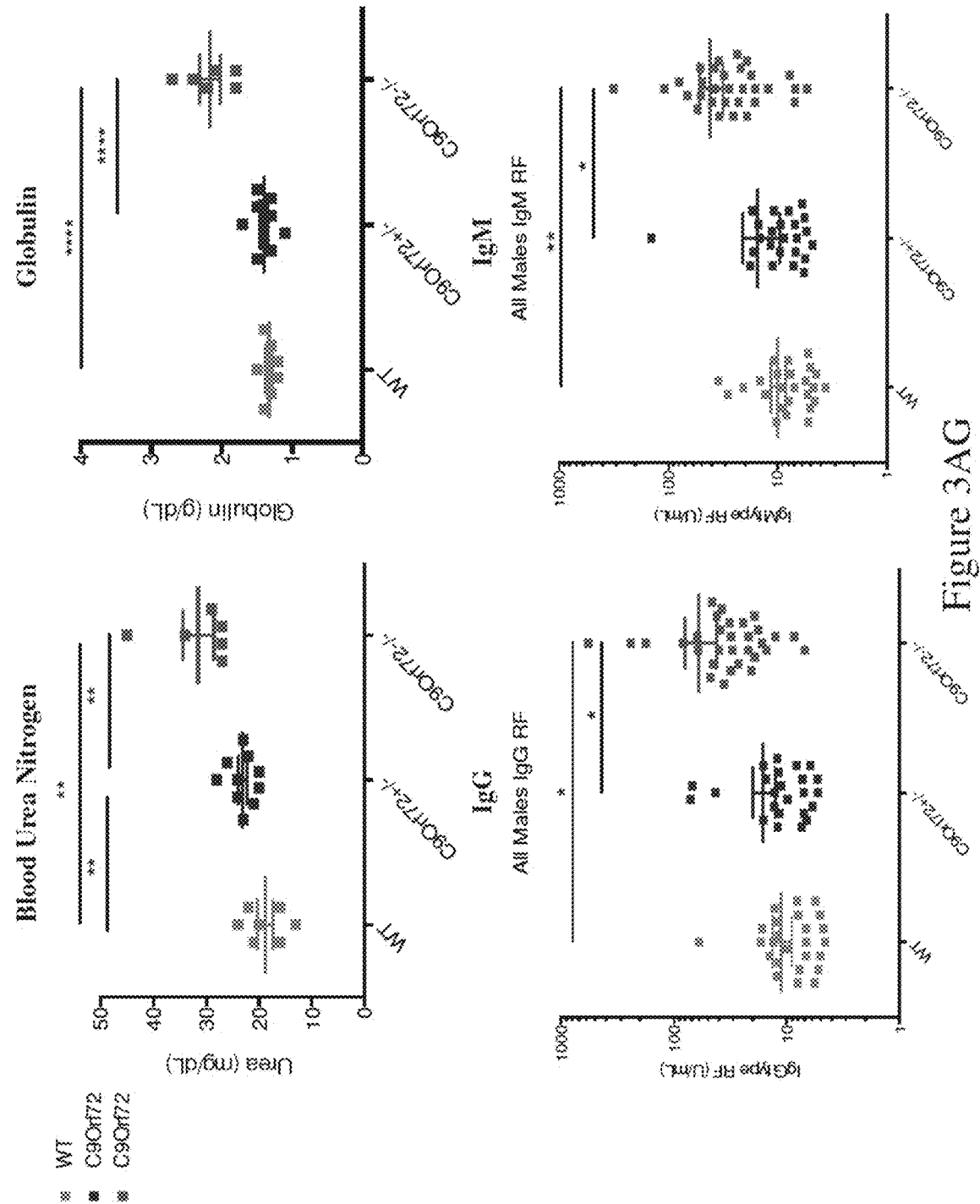
Figure 3A:
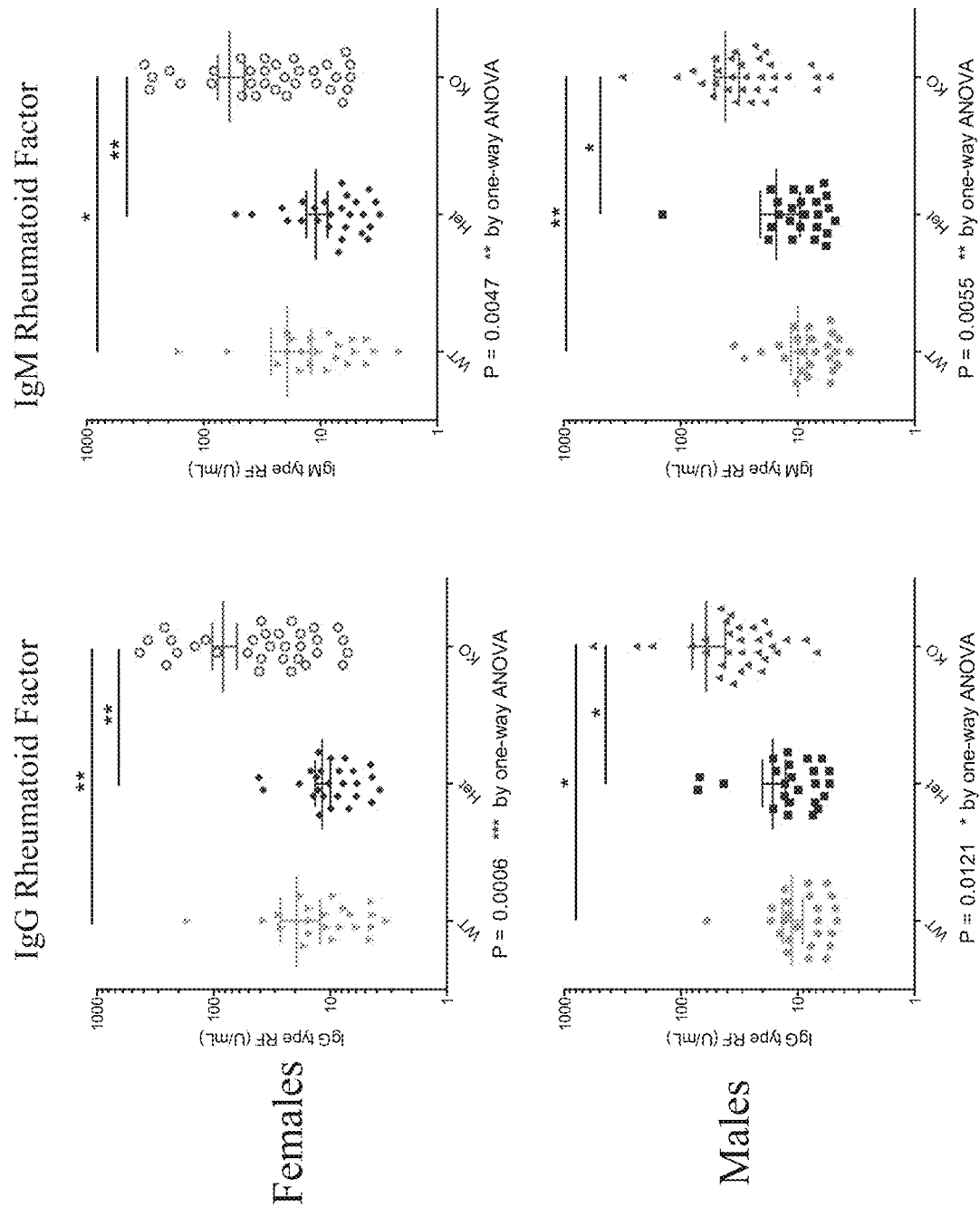
Figure 3A:
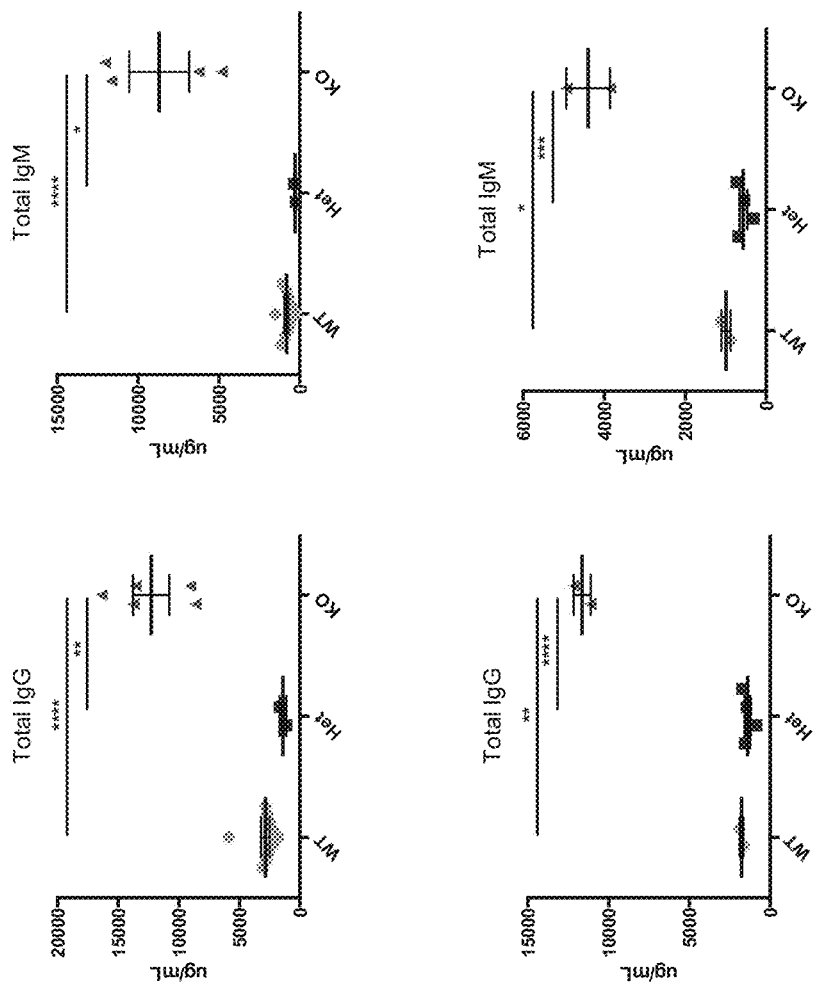
Figure 3A:
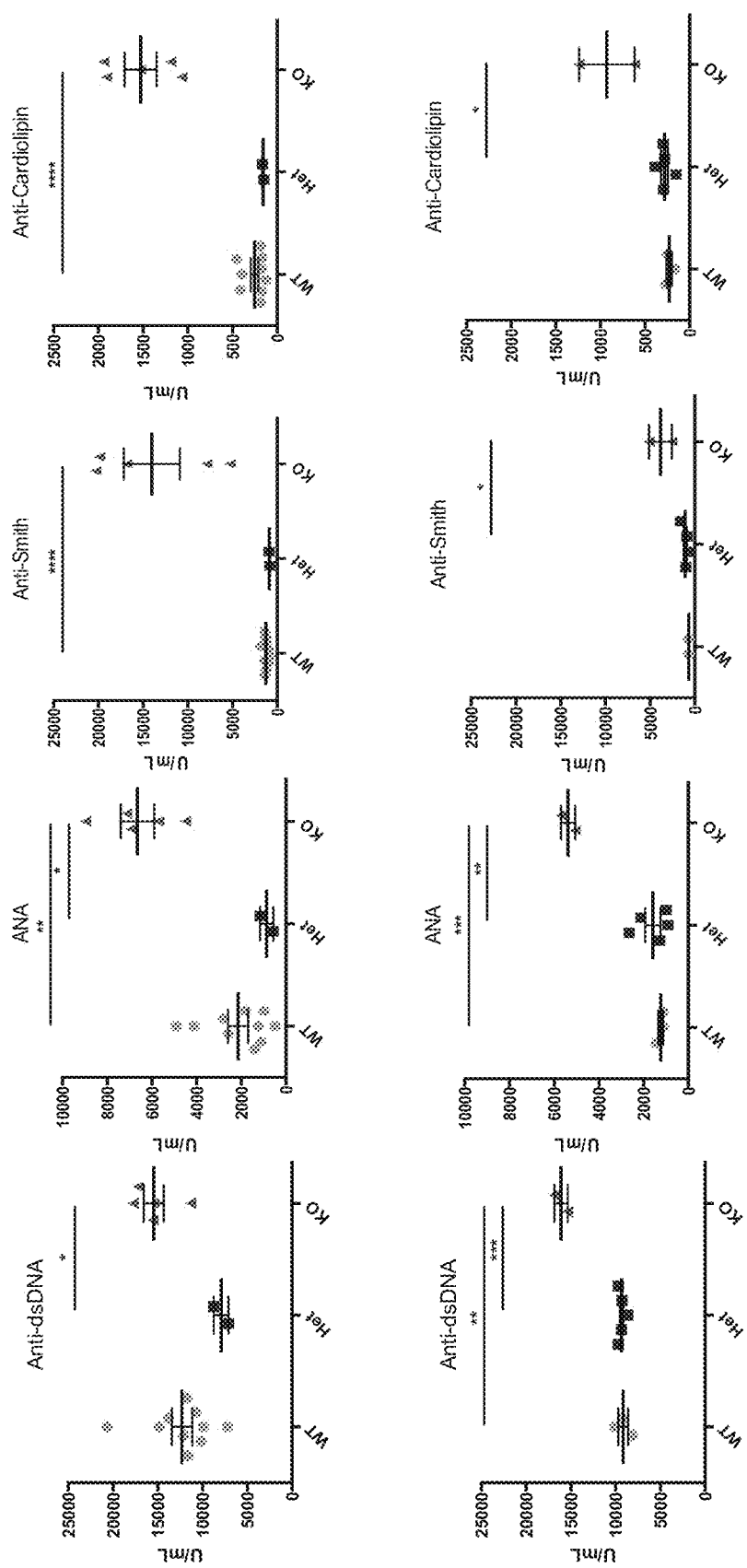
Figure 3A:
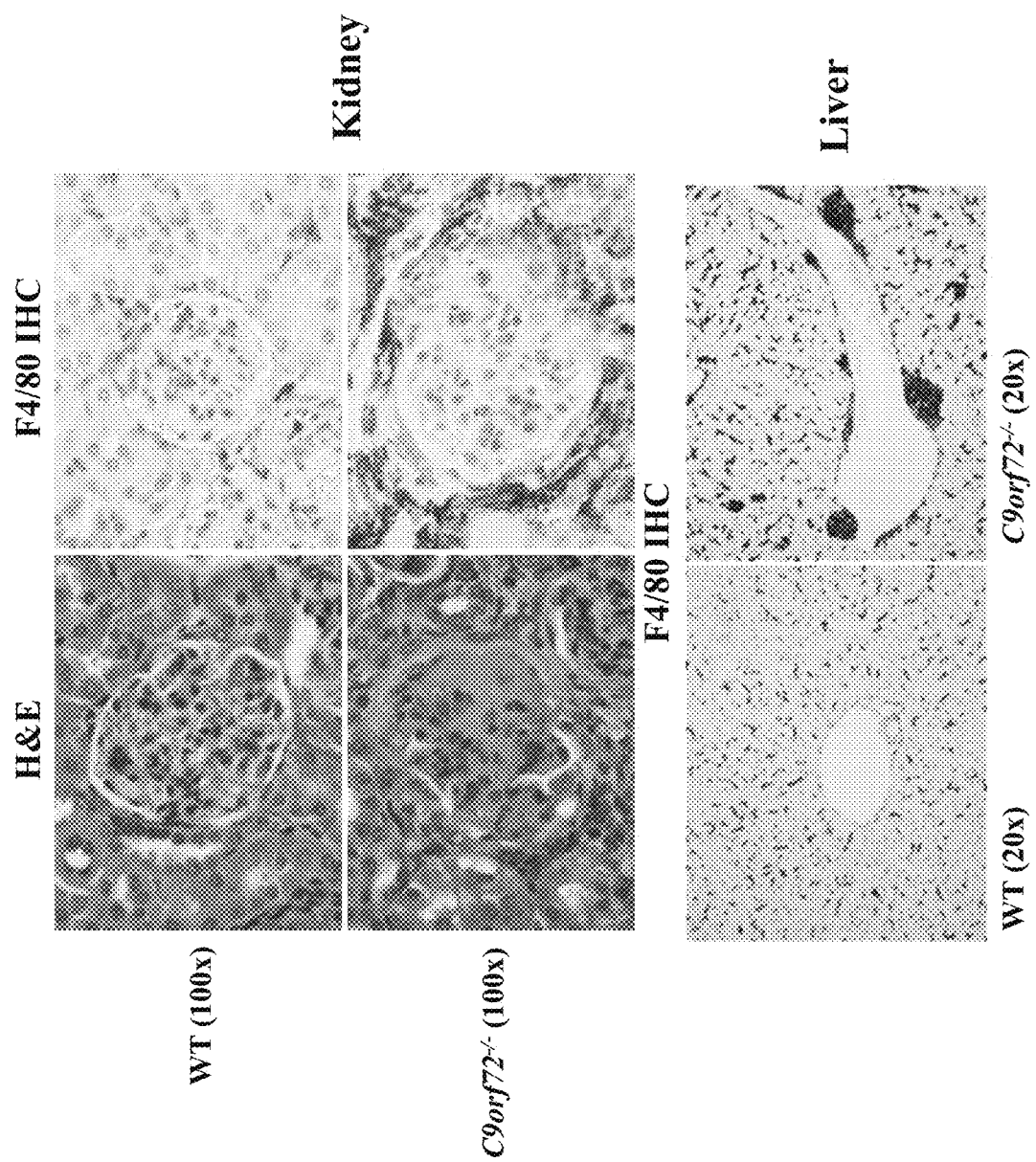
Figure 3A:
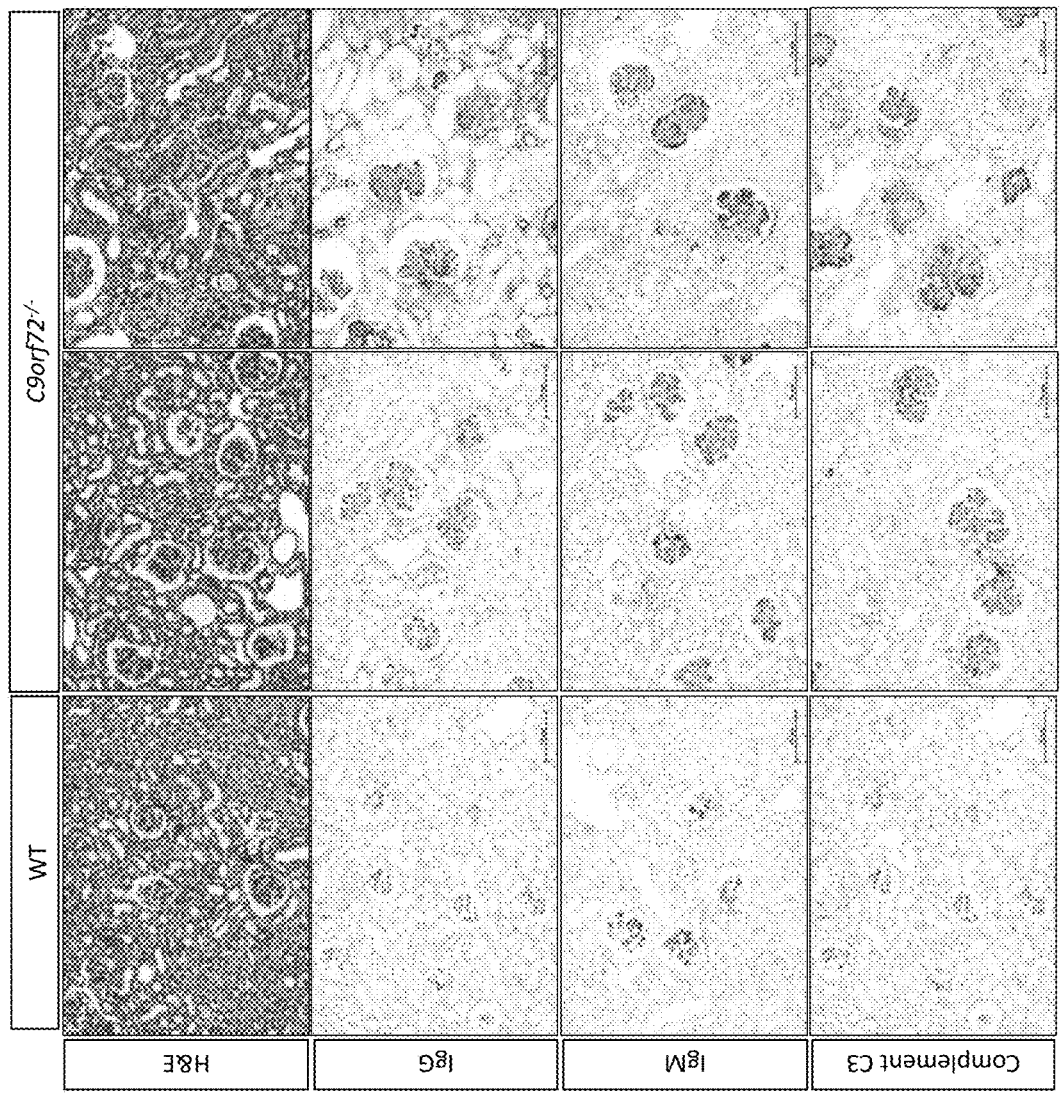

As shown above, percentages of CD45$^+$CD8$^+$ and CD45$^+$CD44$^+$ cells were overall reduced in C9orf72$^{-/-}$ mice as compared to wild type mice, which was likely a consequence of the increase in proportion of myeloid cells consistent with gene signature data. In contrast, total cell counts for these T cell populations were increased in C9orf72$^{-/-}$ mice. This was reflective of the gross expansion of lymphoid tissue and overt immune infiltration observed. CD8$^+$ and CD4$^+$ T cell populations were further subdivided based on the expression of additional surface activation markers (FIGS. 3V-3AC). For CD8$^+$ T cells, a significantly increased percentage of the early activation and effector memory T cell markers CD69 and CD44, respectively was observed in C9orf72$^{-/-}$ mice as compared to wild type (FIGS. 3V and 3X). Further, an increased percentage of T cells expressing PD-1, a co-inhibitory receptor that is upregulated on activated cells and plays an important role in down-regulating the immune system, was observed in C9orf72$^{-/-}$ mice as compared to wild type (FIG. 3Z). Cervical lymph nodes demonstrated increased expression of CD44 and PD-1 although CD69 expression was decreased (FIGS. 3V-3AA). For CD4$^+$ T cells, significant increases in the percentage of CD44, and PD1 in spleen, lymph nodes, kidney and blood were observed in C9orf72$^{-/-}$ mice as compared to wild type, with values comparable to wild type in the bone marrow (FIGS. 3U, 3W, 3AA). Percent CD69 expression was increased in spleen, cervical lymph nodes and kidney with varying significance (FIG. 3Y), Concomitant with the increase in activated T cells, increased percentages of CD4$^+$ FoxP3$^+$ regulatory T cells in spleens and lymph node was observed in C9orf72$^{-/-}$ mice as compared to wild type (FIG. 3AB). Also, the splenic compartment demonstrated a, reduced expression of CD62L and CD127 (FIG. 3AC), which are expressed on naïve or central memory T cells and are down regulated once T cells become activated. Cell count measurements also demonstrated significant increases in C9orf72$^{-/-}$ mice with varying significance.

Data from cytokine panels (FIGS. 3AD, 3AE and 3AF) demonstrated elevated cytokines in the serum of 8-58 week old C9orf72$^{-/-}$ mice. In particular, at 18 weeks of age, levels of IL-17, IL-10, TNF-α and IL-12 (total) were significantly increased in the serum of male C9orf72$^{-/-}$ mice as compared to wild type (FIG. 3AD). For these same cytokines, significant elevated levels were observed in C9orf72$^{-/-}$ mice as compared to C9orf72$^{+/-}$ mice. These data indicated systemic activation of macrophages in these mice. In all male mice analyzed (8-58 weeks old), C9orf72$^{-/-}$ mice demonstrate a significant increase in circulating levels of IFN-γ, IL-10, IL-12 (total), IL-17 and TNF-α as compared to wild type mice. In 8-38 week old female C9orf72$^{-/-}$ mice, a significant increase in circulating levels of IL-10, IL-12 (total), IL-17, TNF-α and MCP-1, as well as an increasing trend for IFN-γ, was observed as compared to wild type mice. IL-12 (total) was increased approximately 6-fold in C9orf72$^{-/-}$ mice as compared to wild type mice. IL-10, IL-17a, and TNF-α were also elevated, although to a lesser extent. No changes in the levels of IL-1β, IL-2, or IL-4 were observed, and while there was increased IL-6 in some C9orf72$^{-/-}$ mice as compared to wild type, this difference did not reach significance. Levels of the chemokine MCP-1 were significantly increased in female, but not male C9orf72$^{-/-}$ mice (FIGS. 3AE and 3AF), and IFN-γ was significantly increased in males with some females demonstrating a slight increase (FIGS. 3AE and 3AF). Thus, overall increased levels of pro-inflammatory cytokines are observed as early as 8 weeks in C9orf72$^{-/-}$ mice with varying significance as compared to wild type mice.

As shown in FIGS. 3AG-3AK, aging C9orf72$^{-/-}$ mice develop increased severity of glomerulonephritis. This result was confirmed in H&E staining and F4/80 IHC in liver and kidney (FIG. 3AK). For example, increased F4/80 staining by IHC on 8 week old C9orf72$^{-/-}$ liver demonstrated increased infiltration of macrophages, while large F4/80$^+$ macrophage cell infiltration was observed in the kidney of 38-week old female mice (FIG. 3AK). Increased blood urea nitrogen by serum chemistry correlated with kidney disease in C9orf72$^{-/-}$ mice, while increased serum globulin content indicated an inflammatory condition. Normal blood urea nitrogen in mice ranges from 8-33 mg/dL, while globulin levels normally range from 1-4 g/dL (see, e.g., Zaias, J. et al., 2009, J. Am. Assoc. Lab. Animal Sci. 48(4):387-390).

Further analysis of kidneys revealed large, F4/80$^+$ mononuclear cells that had characteristics of dendritic cells present in high numbers oriented around the glomeruli of 35-41 week old C9orf72$^{-/-}$ mice (FIG. 3AK). Mild to moderate degrees of glomerulonephritis in kidneys of 35-60 week-old C9orf72$^{-/-}$ mice was observed by H&E staining (FIG. 3AK). In more severely affected animals, glomeruli were enlarged, hypercellular, and showed mesangeal proliferation and leukocytic infiltration. Manifestation of immune-mediated disease was diverse with observed thickening of the capillary walls and proliferation of the parietal epithelium in some glomeruli, while others showed expansion of the mesangium with an acellular, eosinophilic hyaline material, consistent with glomerulosclerosis and a variable degree of periglomerular fibrosis. Interestingly, these areas did not prove positive for amyloid deposition upon Congo red staining. Tubular changes included cortical and medullary tubular dilatation and the presence of hyaline proteinaceous casts and tubular basophilia with degeneration/regeneration. Such changes were not observed in wild type mice. A serum chemistry panel revealing elevated blood urea nitrogen (e.g., FIG. 3AG) and decreased serum albumin was consistent with impaired glomerular filtration that correlated to histological renal findings in C9orf72$^{-/-}$ mice as compared to wild type mice.

Figure 9A:
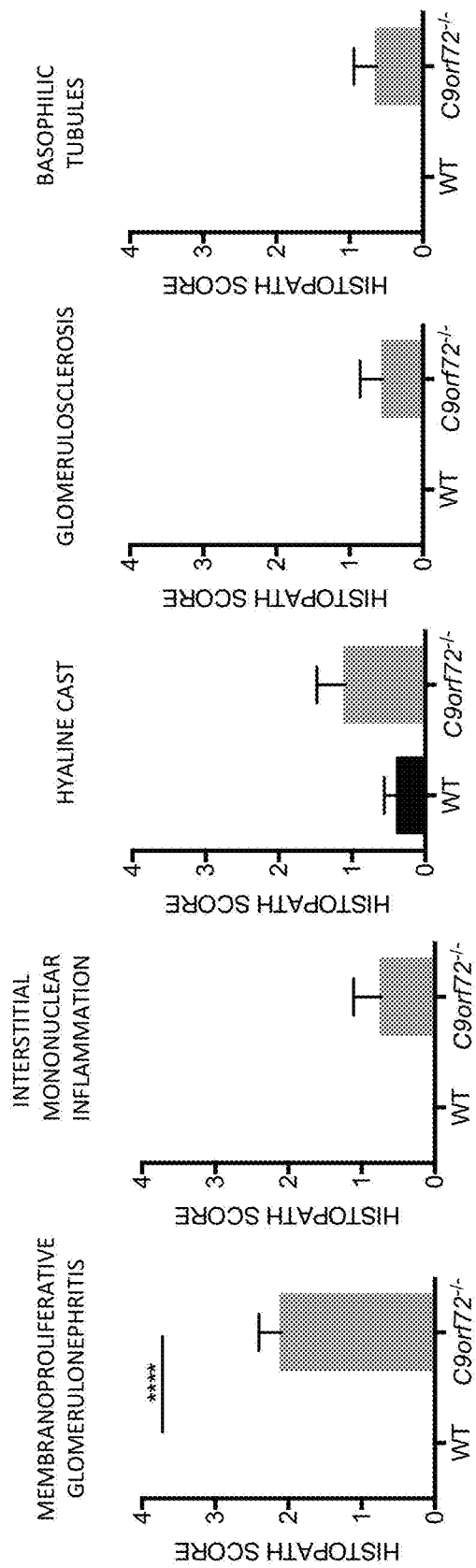
Figure 9C:
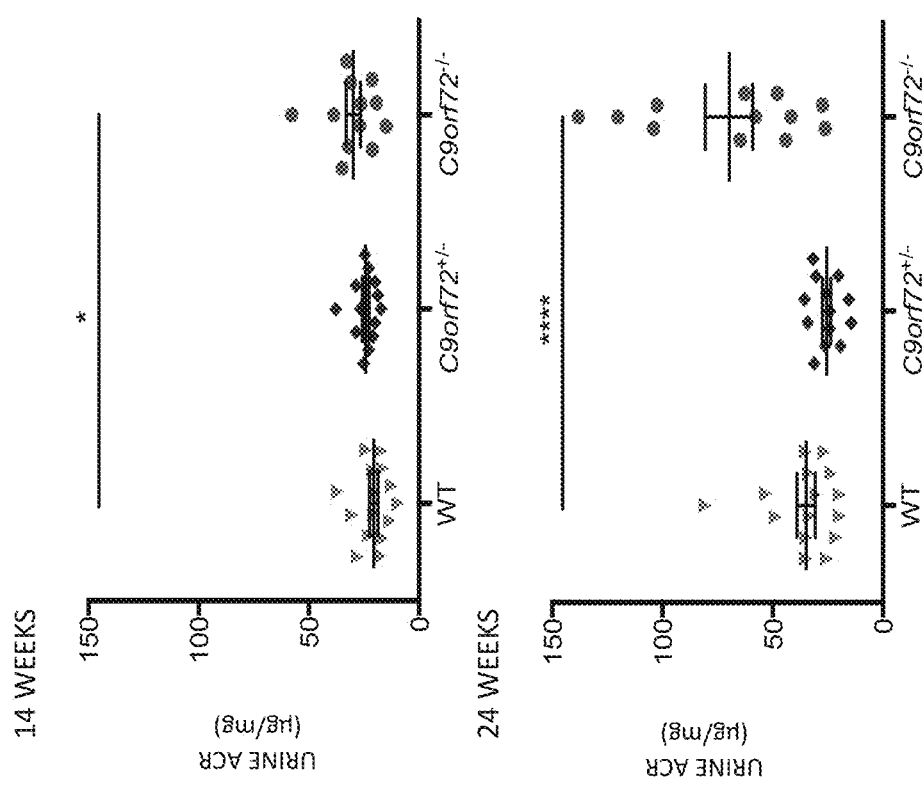

To further measure the severity of kidney disease observed in null mice, H&E stained kidney sections were blindly scored for membranoproliferative glomerulonephritis, interstitial mononuclear inflammation, hyaline cast formation, glomerulosclerosis, and basophilic tubules; categories of renal disease associated with immune mediated glomerulonephropathy. As shown in FIG. 9A, weighted graphs of histopathological scoring results demonstrate that the most significant renal changes observed in null mice are associated with membranoproliferative glomerulonephritis. Individual histopath scores are represented (FIG. 9B) to show that all null mice display minimal to severe membranoproliferative glomerulonephritis with occasional evidence of additional disease categories in more severely affected animals. Score of 0=none, 1=minimal, 2=mild, 3=moderate and 4=severe. Urine ACR measurements assayed at 14 week (FIG. 9C, top) and 24 week (FIG. 9C, bottom) time points from the same cohort of mice indicate onset of albuminuria in C9orf72-/- mice with age. Heterozygous mice displayed values comparable to WT consistent with the absence of an observed phenotype.

Also, C9orf72$^{-/-}$ mice demonstrated increased levels of total IgG and IgM autoantibodies by ELISA as compared to wild type mice, which indicated autoimmune disease (FIG. 3AI) and corresponds to increased serum globulin levels observed by serum chemistry (FIG. 3AG, top panel). Additionally, serum ELISA of C9orf72$^{-/-}$ mice indicated significantly elevated levels of circulating double stranded DNA (dsDNA) antibodies, antinuclear antibodies (ANA), anti-Smith (anti-Sm) antibodies and anti-Cardiolipin antibodies as compared to wild type mice. ANA are autoantibodies that bind contents of the cell nucleus. Anti-dsDNA antibodies are a type of ANA antibody that specifically binds double stranded DNA and anti-Cardiolipin antibodies are directed against phospholipid components of the mitochondrial membrane.

Further, C9orf72$^{-/-}$ mice demonstrated a significant increase in circulating rheumatoid factor (RF) antibodies as early as 8 weeks of age (FIG. 3AH). Increased serum globulin and autoantibody content may indicate any one of various disease conditions, for example, bone marrow disorder, autoimmune disease, chronic inflammatory condition (s), liver disease, kidney disease, infections, etc. To give but one example, systemic lupus erythematosus (SLE) is characterized by high titers of autoantibodies against many cell membrane and intracellular antigens. For example, anti-Sm antibodies, which are directed against core units of small nuclear ribonucleoproteins (snRNPs), are a, specific marker for SLE.

Figure 10:
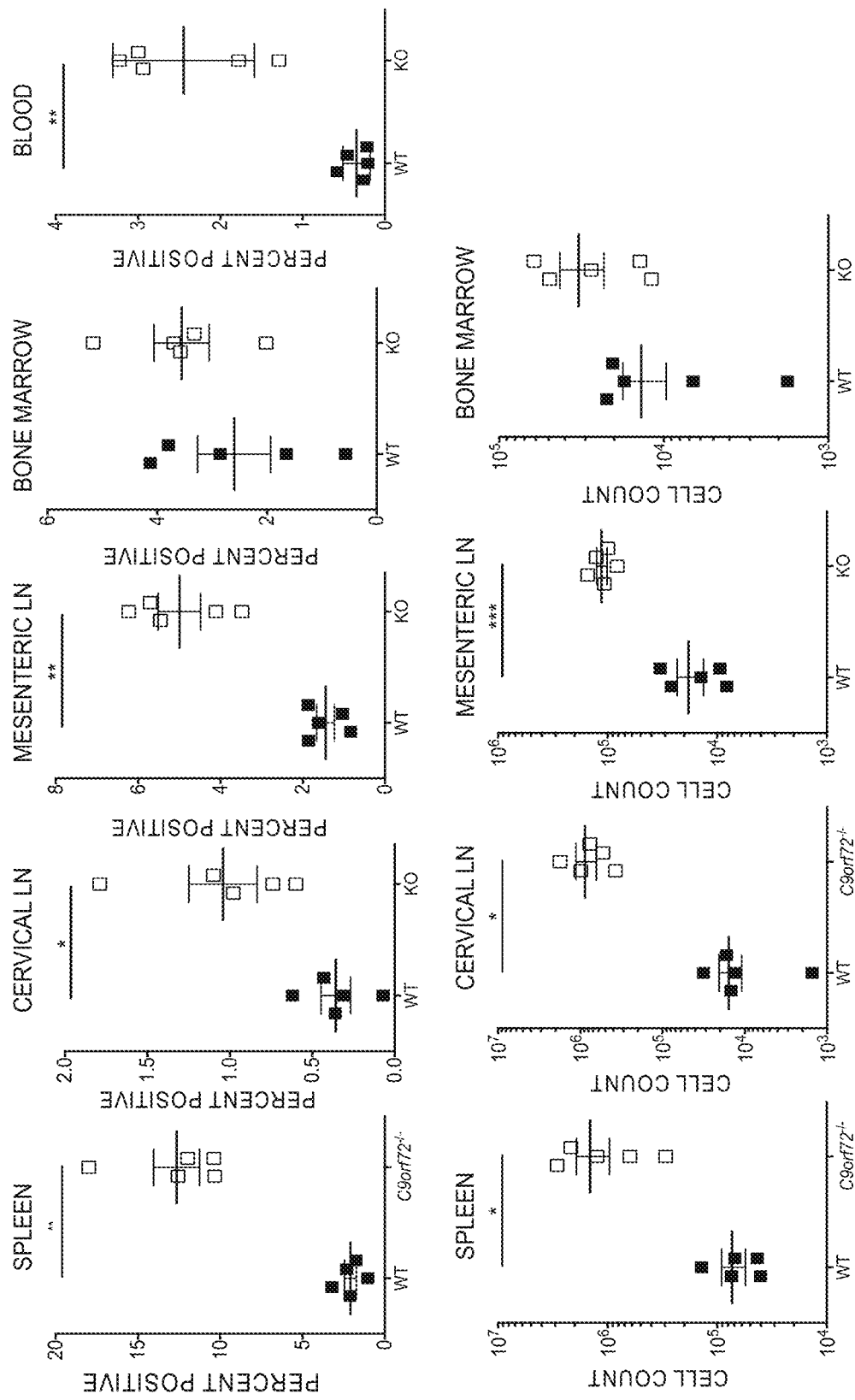
FIG. 10 demonstrates that T follicular helper (Tfh) cells (CD4+CXCR5+CD44+ICOS+PD-1+Bcl-6+) were significantly increased by percent and total cell count in C9orf72$^{-/-}$ spleen, CLN, MLN and blood. Graphs represent mean±s.e.m. (*P≤0.05, P≤0.01, *P≤0.001 by unpaired Students t-test), 26 week females, n=5 per genotype. Elevated Tfh cells were also observed in C9orf72$^{-/-}$ BM that did not reach significance.

Increased autoantibody titers in lupus patients are positively correlated with an increased frequency of circulating T follicular helper (Tfh) cells (Xu, H. et al. *Cell Immunol* 295, 46-51 (2015)). Interrogation of this specific cell population (CD4+CXCR5+CD44+ICOS+PD-1+Bcl-6+) in spleen, cervical LN, mesenteric LN, and blood by FACS analysis revealed significantly increased Tfh cell populations in C9orf72$^{-/-}$ tissues compared with controls (FIG. 10). Elevated Tfh cells were also observed in C9orf72$^{-/-}$ BM that did not reach significance (FIG. 10). Collectively, these observations support the notion that an immune response similar to human SLE occurs in the absence of C9orf72 expression.

Expansions in plasma cells and transitioning B cells/plasmablasts can be associated with specific neoplasms such as multiple myeloma and plasmacytoma, as well as autoimmune conditions. The spleen and lymph node of C9orf72$^{-/-}$ mice were enlarged and an immune infiltrate was notably obvious, however the infiltrating cells were negative for B cell markers (CD45R), and were F4/80$^+$ with characteristics of foamy macrophages. While the population of these cells was large, they occupied regional areas of these tissues considered appropriate for the lineage, and did not obliterate the basic architecture of these tissues. In addition, the mitotic index was low, with only rare mitoses observed. Thus, neoplasm seemed unlikely. There was, however, a population of plasma cells and occasional Mott cells present in these tissues, and evidence of glomerulonephritis, which indicated autoimmunity in C9orf72$^{-/-}$ mice. As shown above, both IgG and IgM-type anti-RF titers were significantly elevated in C9orf72$^{-/-}$ mice as compared to wild type and C9orf72$^{+/-}$ (heterozygous) mice (FIG. 3AH). Further, total serum levels of IgG and IgM were significantly elevated in C9orf72$^{-/-}$ mice starting at 8 weeks of age (FIGS. 3AG and 3AI) which was consistent with serum chemistry panels showing elevated globulin in C9orf72$^{-/-}$ mice.

Autoantibodies to glomerular basement membrane, or deposition of soluble immune complexes within the glomerular capillaries, followed by complement fixation and inflammation has been reported to cause renal disease (immune-mediated glorrerulonephritis). To determine if the observed increase in total immunoglobulin and autoantibody levels were contributing to glomerulonephritis, IHC was performed on kidney sections from 8-63 week old C9orf72$^{-/-}$ and wild type mice for total IgG and IgM (FIG. 3AL). As described herein, C9orf72$^{-/-}$ mice demonstrate clear evidence of glomerulonephritis at both the serum and histological level. In particular, kidneys from C9orf72$^{-/-}$ mice demonstrated increased IgG immunostaining as compared to wild type mice at all time points examined. Further, at 8 weeks, C9orf72$^{-/-}$ kidneys showed diffuse, intense IHC signal in the vasculature and tubular epithelium of the medulla and cortex. Correlating with the onset of glomerulonephritis pathology, a marked increase in glomerular IgG and IgM staining was observed by 38 weeks. Staining for both IgG and IgM was also frequently associated with the parietal layer of Bowman's capsule. Staining for IgG was occasionally observed in the urinary space and/or within proximal renal tubules, indicating impaired glomerular filtration function (i.e., leak that exceeds resorptive capacity). Intense IgG staining was present in tubule epithelial cells in animals with severe disease, consistent with reabsorption of abundant IgG. Similar yet less intense staining was observed for IgM less frequently. Staining in sclerotic glomeruli was diminished as compared to wild type, which was consistent with impaired blood flow to these units (i.e., vascular loops had been replaced with matrix or mesangial cells). However, glomeruli that retained clear vascular loops tended to have increased IgG as compared to wild type. Fine granular deposits and/or linear staining of IgG and IgM associated with vascular membranes was frequently observed under high magnification and suggests immune complex deposition.

Complement factor C3 deposition is commonly associated with immunoglobulin deposits on basement membranes in the kidney. IHC for complement factor C3 revealed increased staining in glomerular tufts of C9orf72$^{-/-}$ mice as compared to wild type (FIG. 3AL). Granular and linear staining was most prominent on the membranes of the visceral layer of glomerular capsule, prominently delineating the capillary loops and podocytes.

Gene signature data from molecular profiling in spleen and cervical lymph nodes (8-10 and 35 week wild type and C9orf72$^{-/-}$ mice) indicated infiltration of macrophage, monocyte, and granulocyte cell populations. Depletion of T & B cells was also observed, which may reflect the increase in proportion of myeloid cells present. Global hierarchical analyses primarily separated brain samples by gender and age, rather than genotype, indicating that profiling differences in this tissue were due to the basic biology of the samples and genotype. Only C9orf72 expression was consistently different in brain tissue across both ages and genders. In contrast, samples from spleen and lymph node clustered based on genotype, with age and sex only secondary, which indicated that transcriptome differences in these organs were the result of changes in C9orf72 expression. Further, over 100 loci associated with immune function demonstrated significant expression differences in C9orf72$^{-/-}$ mice as compared to wild type for both males and females at early and late time points. Spleen and lymph node gene signatures in C9orf72$^{-/-}$ mice indicated myeloid infiltration with a simultaneous decrease in the lymphocytic footprint, consistent with CBC data (see above) demonstrating comparable total leukocyte counts among strains due to a balance between elevated myeloid cells and decreased lymphocytes. In a comparison of biosets, the strongest profiling matches were to immune response signatures, mouse models of various inflammatory conditions, and human infectious diseases. As shown in this example, immunophenotyping data demonstrated that mice having a disruption in a C9orf72 locus (C9orf72$^{-/-}$) develop splenomegaly and lymphadenopathy as early as 8 weeks of age. In particular, CBC data showed an increase in circulating monocytes, neutrophils and eosinophils in C9orf72$^{-/-}$ mice as well as decreased lymphocytes in the blood beginning at 8 weeks. Also, cervical lymph nodes get progressively larger with age in male (58 weeks) and female (37 weeks) C9orf72$^{-/-}$ mice. This example also specifically demonstrates that C9orf72$^{-/-}$ mice develop glomerulonephritis (i.e., infiltration of F4/80$^+$ macrophages in the kidney) and autoimmune disease (i.e., significant elevated levels IgM and IgG autoantibodies) as they age. Thus, this example specifically described that rodents having a disruption in a C9orf72 locus as described in Example 1 demonstrate detectable abnormalities in the periphery and circulation as early as about 8 weeks of age. Irn particular, C9orf72 ablation lead to a chronic systemic immune response result-

Example 4. Administration of Neurotoxins to Non-Human Animals Having a Disruption in a C9orf72 Locus This experiment demonstrates that administration of various toxins to non-human animals described herein can exacerbate aspects of the observed ALS-like phenotype. In particular, this example specifically demonstrates that administration of various toxins to C9orf72$^{-/-}$ mice mildly exacerbates the ALS-like motor phenotype and increases oxidative stress on motor neurons, but does not affect the increased inactivity and gait abnormalities in these mice. This example also demonstrates that motor neurons of C9orf72$^{-/-}$ mice develop significant mitochondrial dysfunction.

Briefly, mouse embryonic stem cells are cultured and differentiated into motor neurons, during an eight-day period. The first day, previously frozen mouse embryonic stem cells are thawed and added to a 15 mL falcon tube with five mL of embryonic stem cell medium (ES medium: DMEM with 15% FBS, 1% pen/strep., 1% glutamine, 1% non-essential amino acids, 1% nucleosides, 0.1% β-mercaptoethanol, 1% sodium-pyruvate, and LIF at 10000 unit/mL), The tube is then centrifuged for five minutes at 800 rpm. The supernatant is aspirated and the cells suspended in 10 mL of ES medium. The cells are then plated on a T75 flask that is coated with 10 mL of 0.1% gelatin and incubated for 30 minutes at 37° C. to facilitate attachment to the flask bottom. The cells are then incubated overnight. The following day the medium exchanged with fresh medium for survival.

The following day medium is aspirated from the flask. The flask is washed with 10 mL of PBS, and then 5 mL of trypsin is added to detach the cells from the bottom of the flask. The cells are incubated for five minutes at 37° C. Detachment is confirmed by checking the flask under a microscope. Differentiation medium (10 mL DFNK medium: 44% advanced DMEM/F12, 44% neurobasal, 1% pen./strept., 1% glutamine, 0.1% β-mercaptoethanol, 10% knock-out serum replacement) is added to the flask in order to stop the trypsin reaction. The solution from the flask is collected into a falcon tube and centrifuged for five minutes at 800 rpm. The supernatant is aspirated and the cells suspended in 12 mL DFNK medium. The cells are then plated in cell culture dishes and put in an incubator overnight at 37° C. The following day, solution with the cells is transferred to a falcon tube and centrifuged for two minutes at 500 rpm. The supernatant is aspirated and the cells suspended in 12 mL DFNK medium. The cells are then plated in new cell culture dishes and put in an incubator overnight. The next day, medium from the dish is collected and transferred to a falcon tube. The tube is then centrifuged for two minutes at 500 rpm and then the supernatant aspirated. The cells are suspended in 36 mL DFNK medium, with retinoic acid at 1 μM and smoothened antagonist at 0.25 μM final concentration, for motor neuron differentiation. The medium is split to 12 mL per dish across three dishes.

Figure 4:
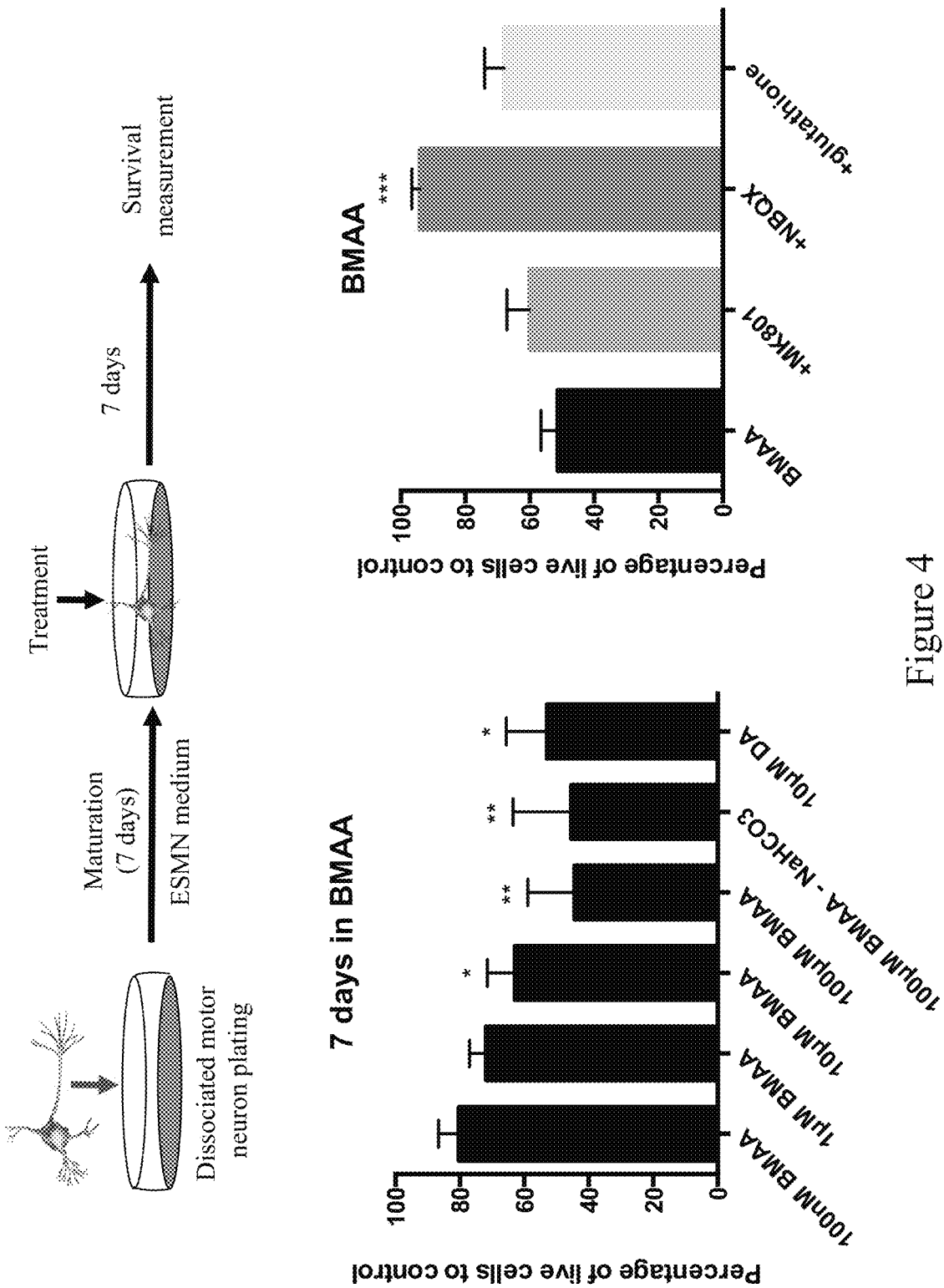
FIG. 4 shows exemplary percentage of live neurons to control (y-axis) in cultured wild type neurons treated with various concentrations of toxins. Top illustrates experimental design as described in Example 4. DA (domoic acid; AMPA/kainate receptor agonist), BMAA (β-Methylamino-L-alanine, 100 µM), MK801 (Dizocilpine, 10 µM; NMDA receptor antagonist), NBQX (2,3-dihydroxy-6-nitro-7-sulfamoyl-benzoquinoxaline-2,3-dione, 10 µM; AMPA/kainate receptor antagonist); Glutathione (10 µM, antioxidant). Statistical significance was determined using Student's unpaired t-test and one-way analysis of variance (ANOVA) a one-way ANOVA test. Cox, P. A. et al., 2003, Proc. Nat. Acad. Sci. U.S.A. 100(23):13380-13383; Murch, S. J. et al., 2004, Proc. Nat. Acad. Sci. U.S.A. 101(33):12228-12231; Cox, P. A. et al., 2005, Proc. Nat. Acad. Sci. U.S.A. 102(14):5074-5078; Erdner, D. L. et al., 2008, Environmental Health, 7(Suppl. 2):S2.

After three days embryoid bodies (EB) that form are dissociated. First, EBs are collected and transferred to a falcon tube. The cells are then centrifuged for two minutes at 500 rpm and the supernatant is aspirated. The cells are then washed with 4 mL of PBS-glucose. Next, 4 mL trypsin is added to the cells for chemical dissociation and are incubated for five minutes. Then, 1 mL of horse serum is added to stop the trypsin reaction. The EBs settle for five minutes and the supernatant is aspirated. 2 mL of PBS-glucose-DNase is added and the cells are mechanically dissociated ten times. The cells settle for 5 min and dissociated cells are transferred to a separate tube. 2 mL of PBS-glucose-DNase is added to non-dissociated cells and the mechanical dissociation is repeated. The cells settle for five minutes and then dissociated cells are transferred to a separate tube. The dissociated cells are centrifuged for five minutes at 800 rpm and then the supernatant is aspirated. The dissociated cells are suspended in 5 mL of embryonic-stem cell motor neuron medium (ESMN medium: neurobasal, 2% B27, 2% horse serum, 1% pen./istrept., 0.25% glutamine, 0.01% β-mercaptoethanol, 10 ng/mL BDNF, 10 ng/mL CNTF, 10 ng/mL GDNF). The cells are centrifuged for five minutes at 800 rpm. The supernatant is aspirated and the cells are suspended in ESMN medium. The cells are then counted using a Countess automatic cell counter (Life Technologies) and 0.5 to 1 million cells are plated with 2 mL ESMN medium per well in each six well plate. The cells remain in either ESMN (control) or ESMN with BMAA at 0.1-100 μM concentrations. Cell counts were taken using the with 0.4% trypan blue using a mean cell diameter setting of >20 μm (motor neurons). Exemplary results are set forth in FIG. 4.

Figure 5A:
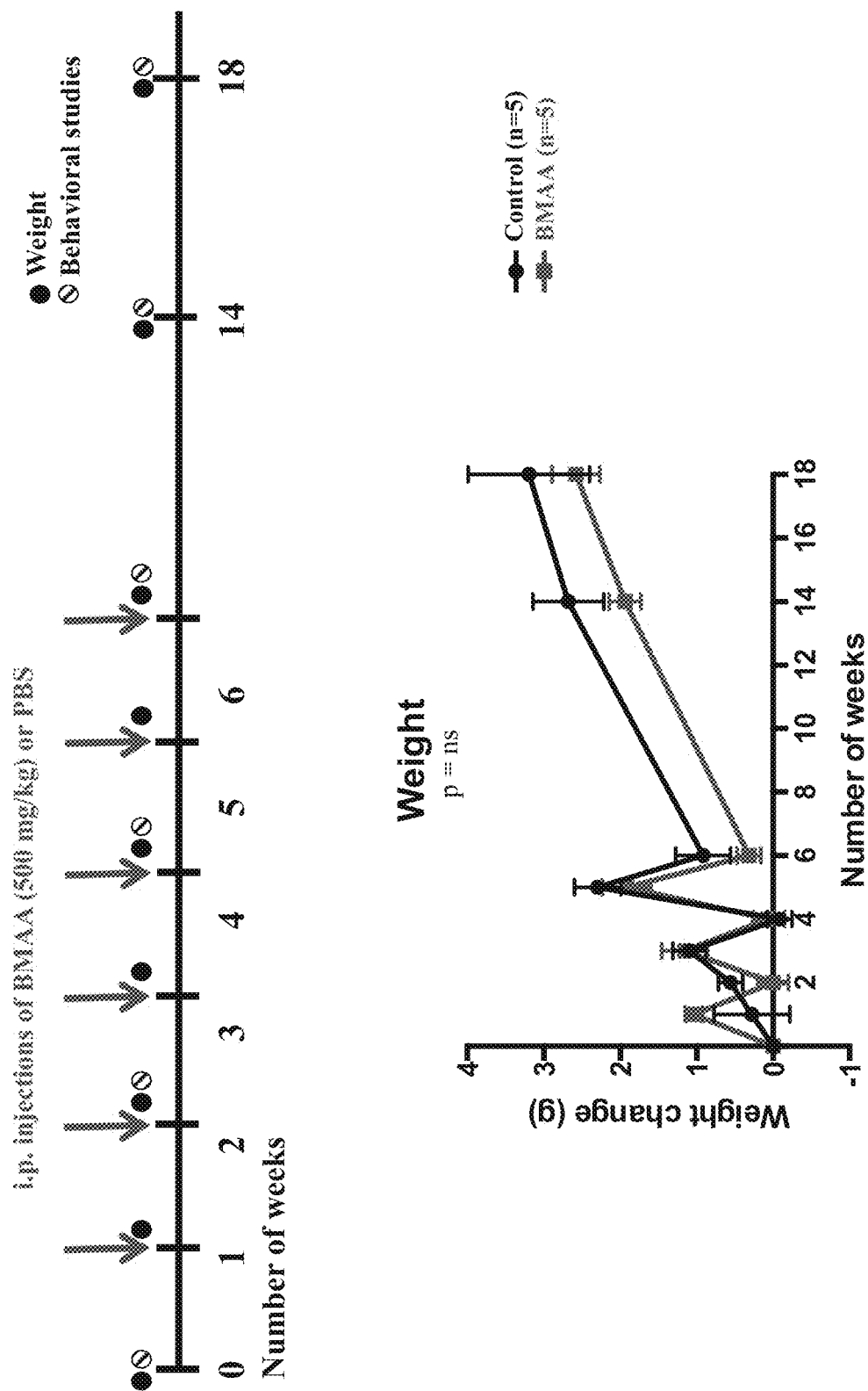
FIGS. 5A-5D show measurement of ALS-like phenotypes in wild type mice administered i.p. injections of BMMA (n=5) or PBS (control, n=5).
Figure 5B:
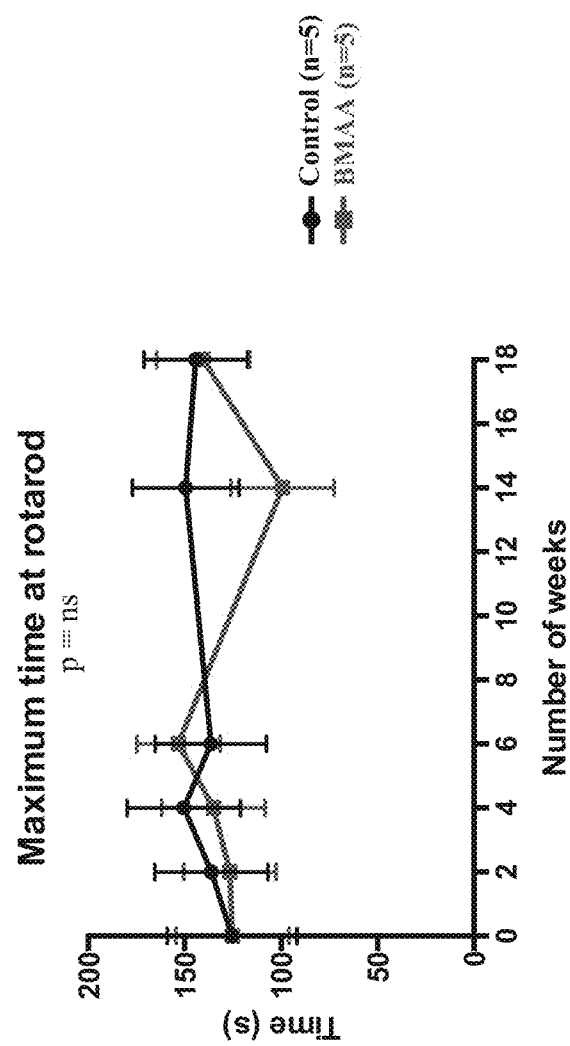
Figure 5C:
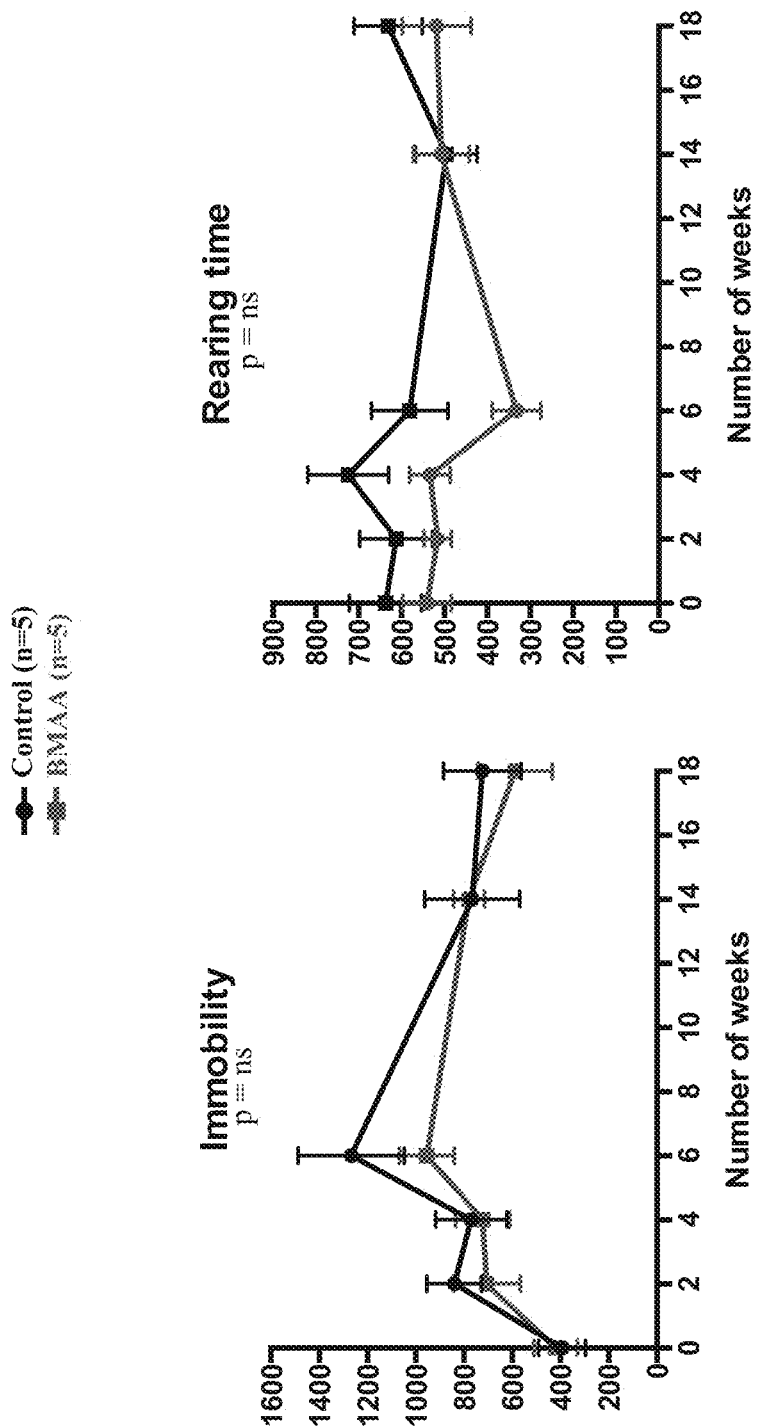
Figure 5D:
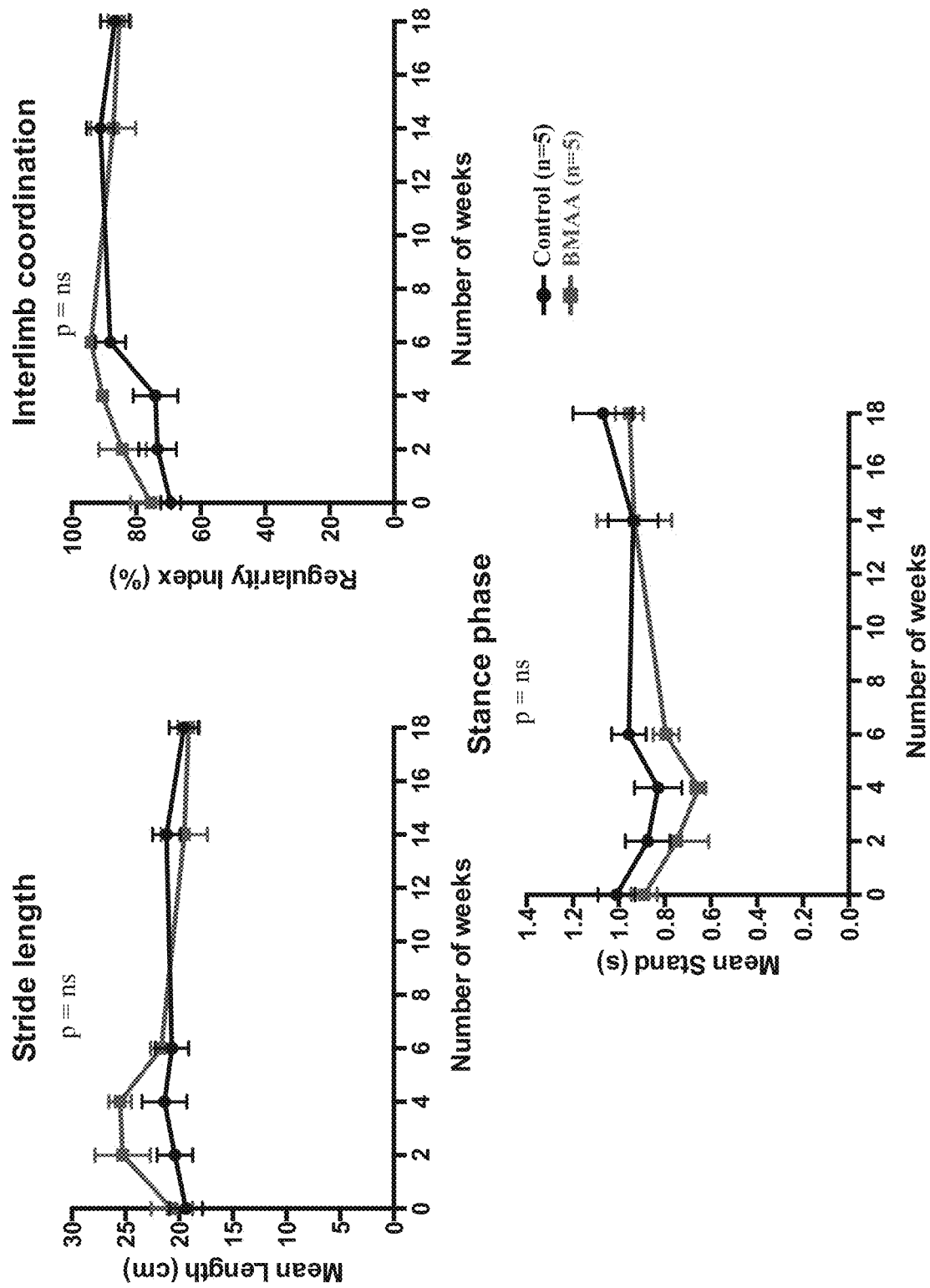
Figure 6A:
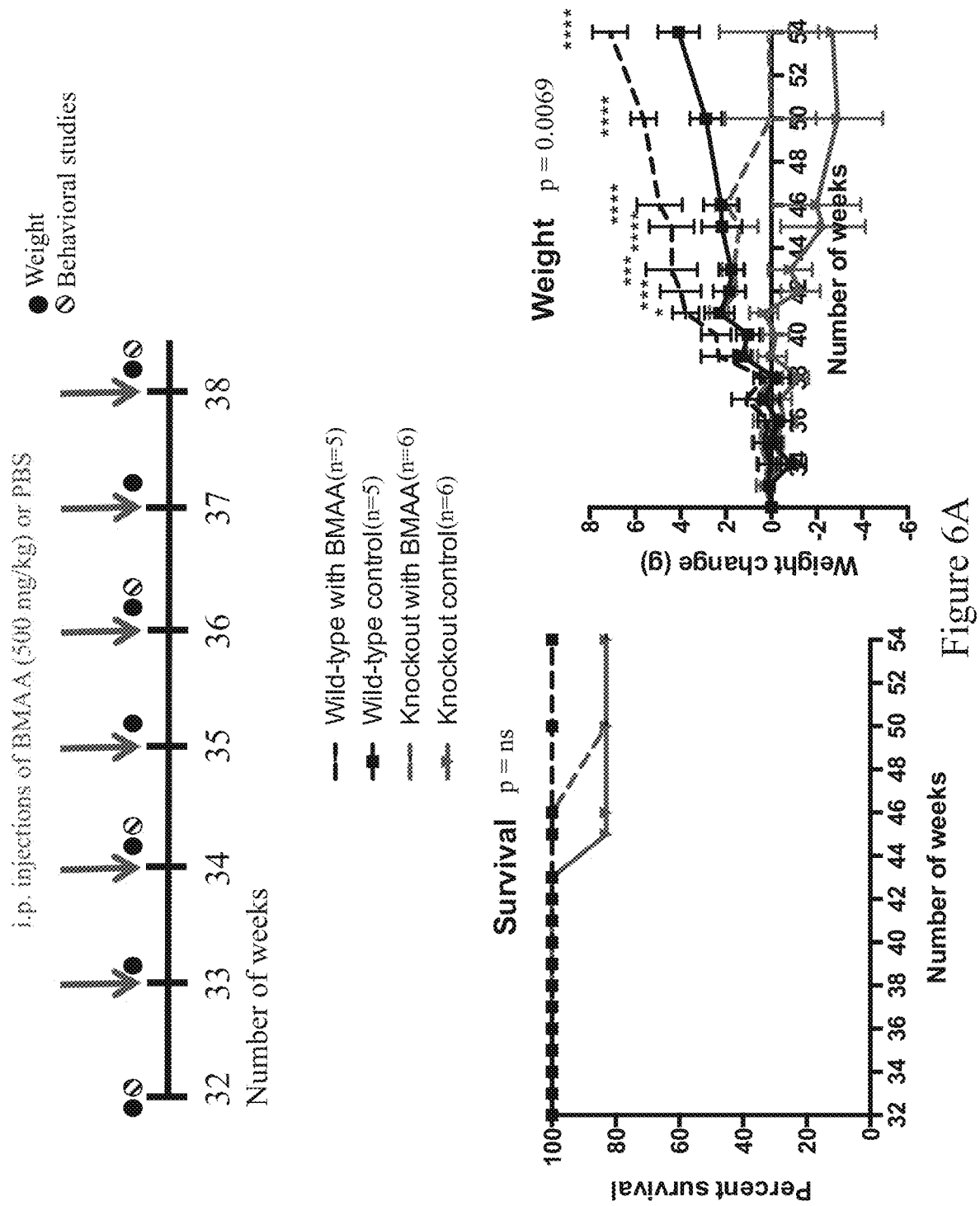
FIGS. 6A-6E show measurement of ALS-like phenotypes in wild type and C9orf72−/− mice administered i.p. injections of BMMA (wild type with BMAA: 3 males, 2 females; knockout with BMAA: 3 males, 3 females) or PBS (wild type control: 4 males, 1 female; knockout control: 5 males, 1 female).
Figure 6B:
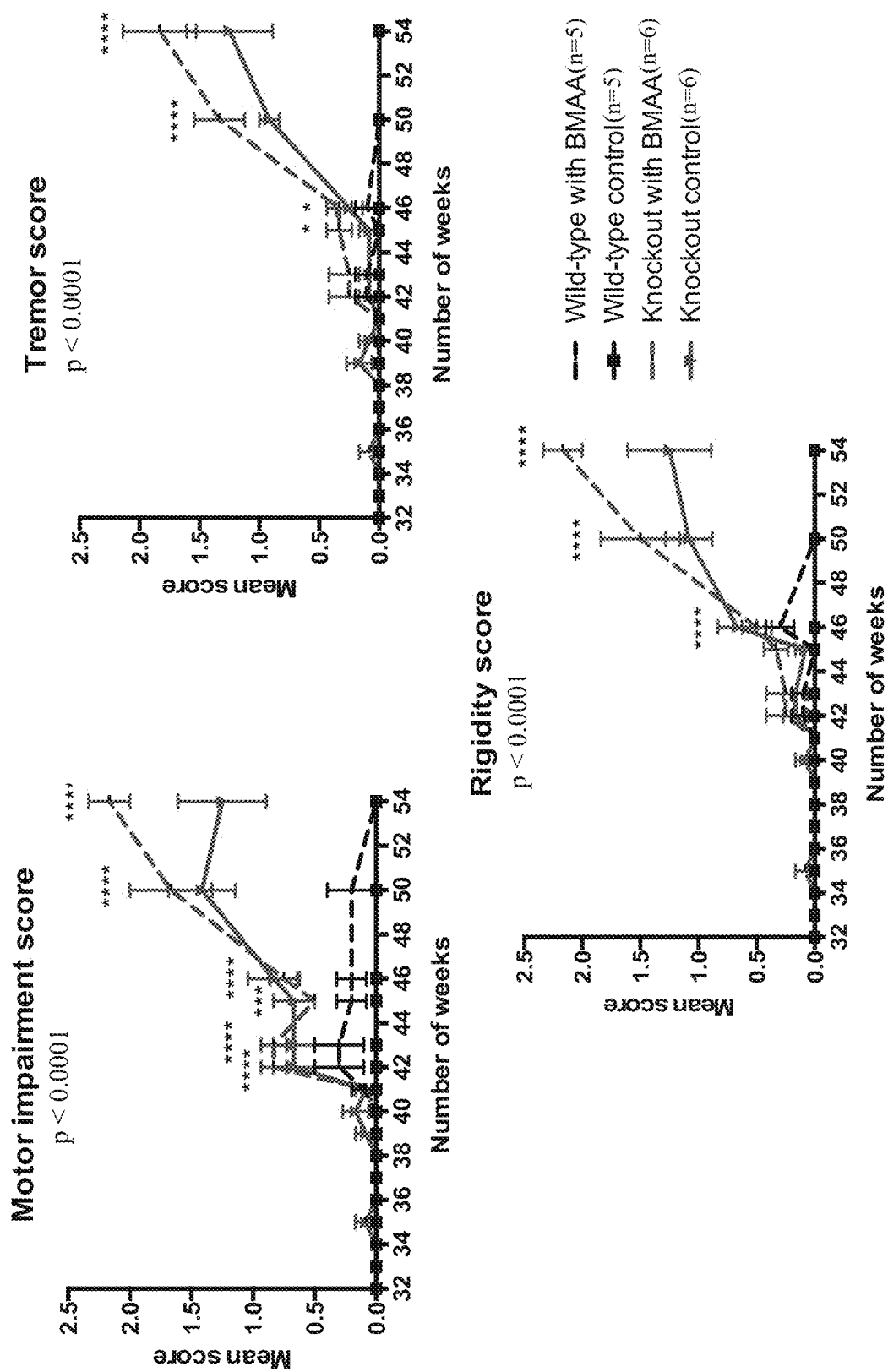
Figure 6C:
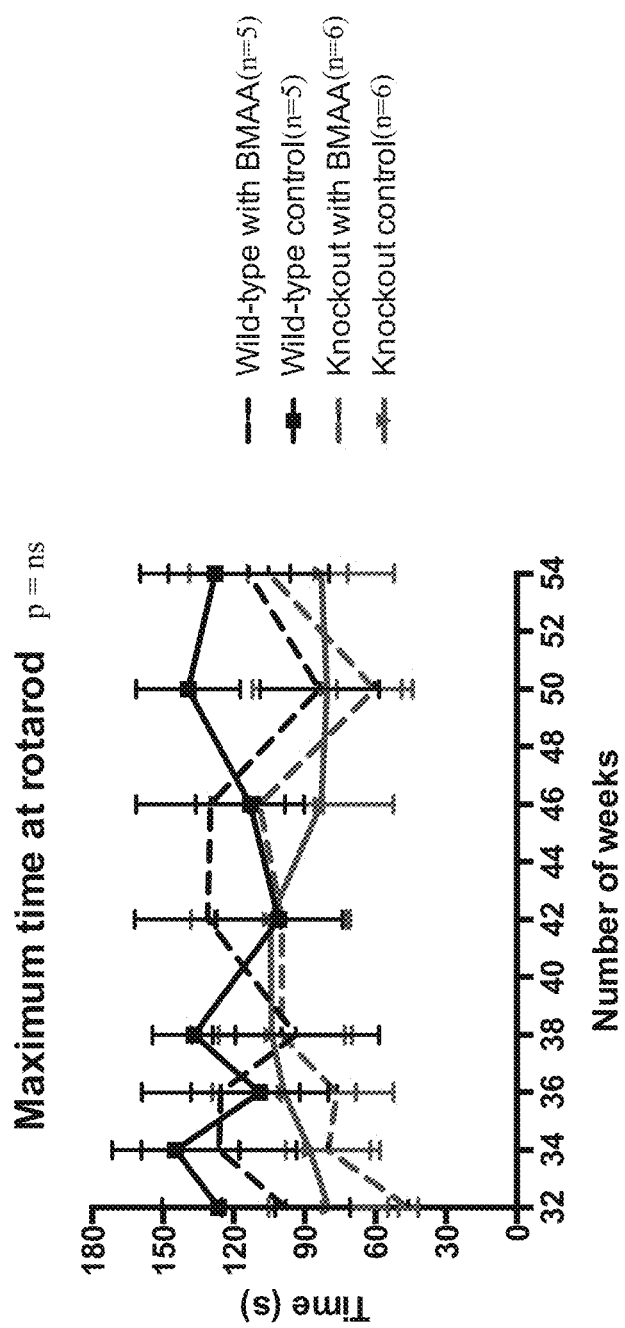
Figure 6D:
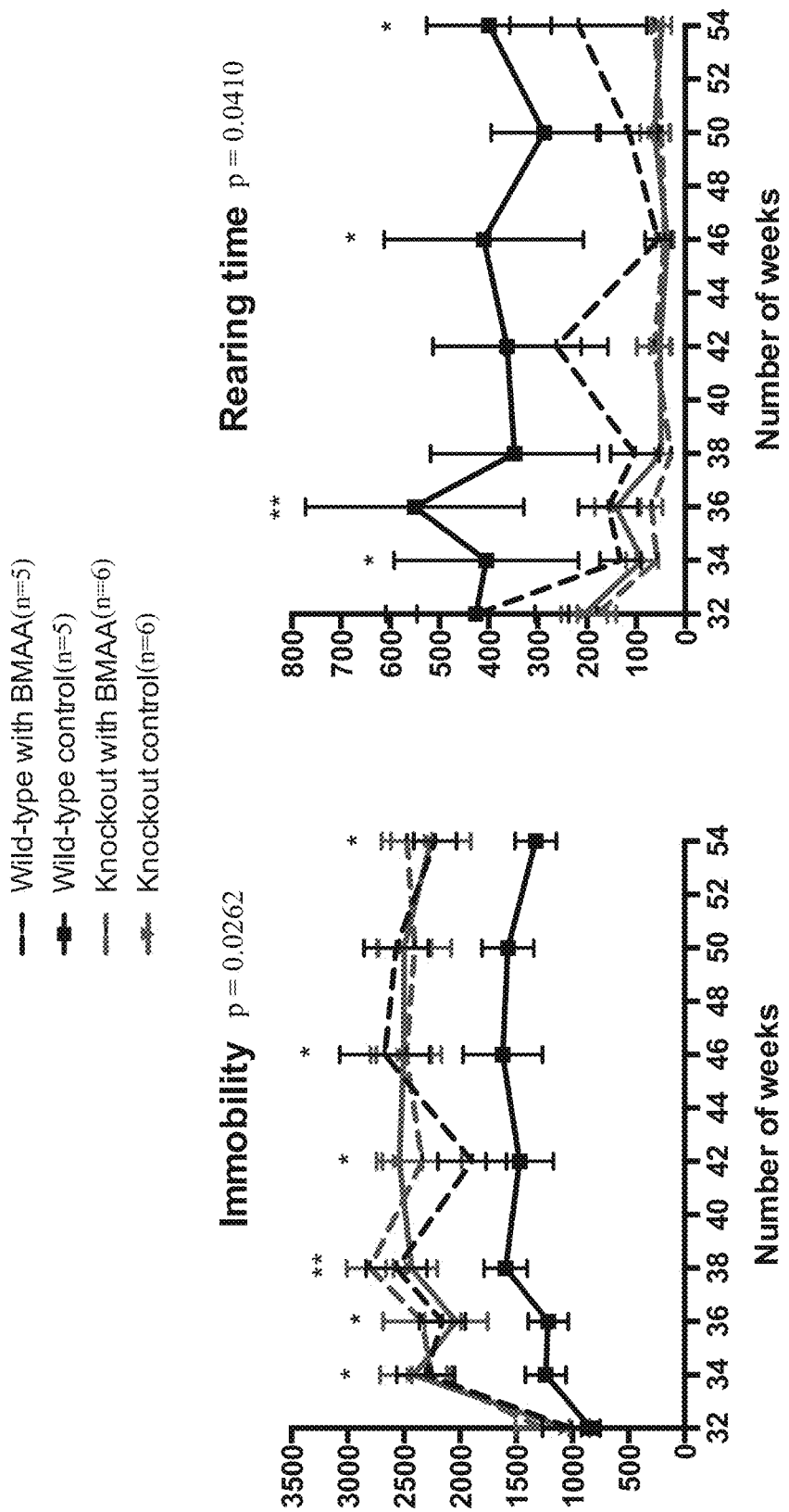
Figure 6E:
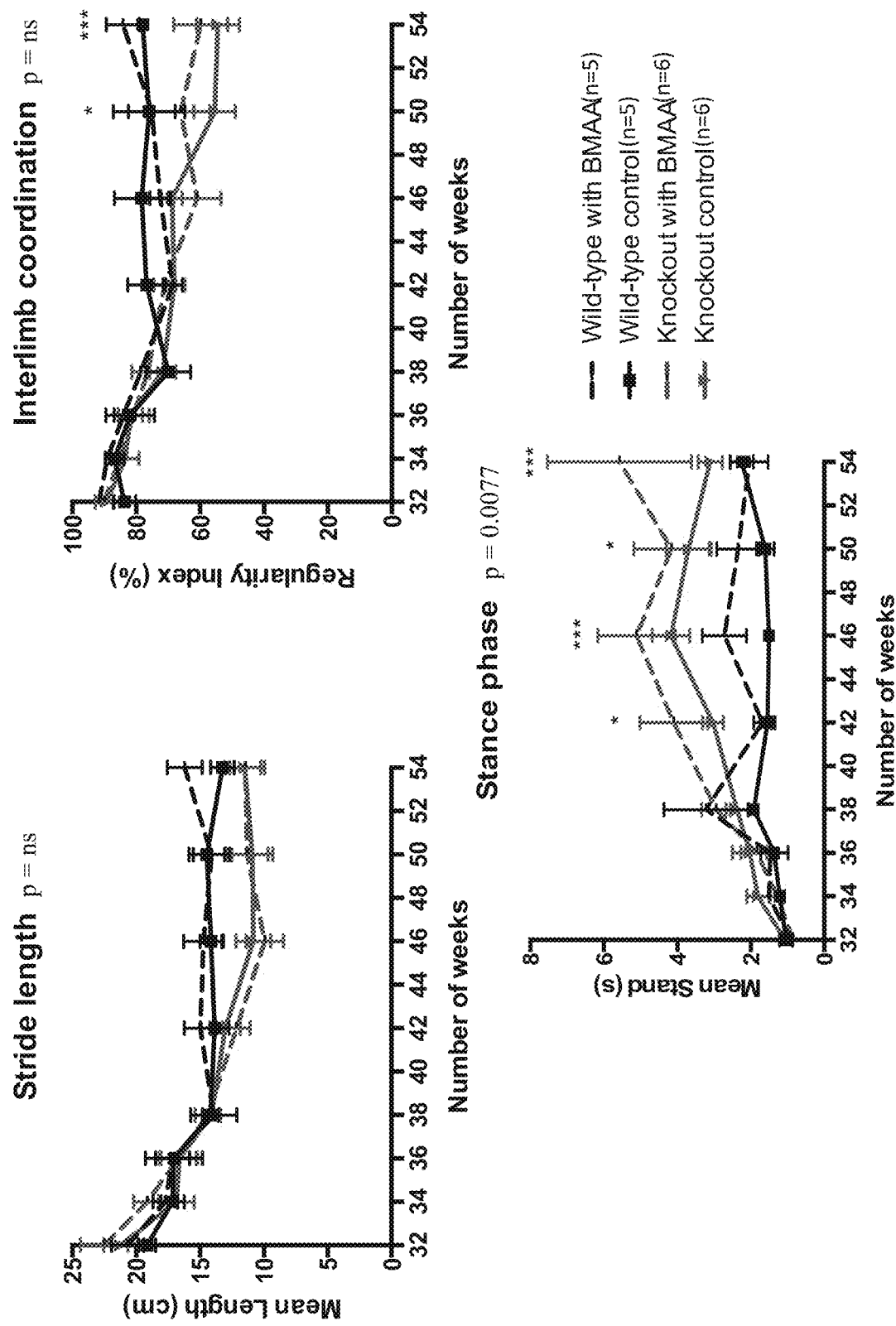

In another experiment, wild type mice were administered weekly i.p. injections of BMAA (500 mg/kg) or PBS (control) for six weeks starting at week 1 (FIG. 5A, top). Body weight measurements were recorded each week up to 6 weeks, week 14 and week 18. Analysis of motor impairment via rotarod, open field locomotor, and catwalk testing (as described above) were recorded at the start of the experiment (week 0, 10-weeks old), every other week up to 6 weeks, week 14 and week 18. Exemplary results are set forth in FIGS. 5A-5D.

For wild type mice, the data demonstrated that BMAA kills cultured wild type motor neurons in a dose-dependent manner via AMPA/kainite receptor-mediated pathway. Further, weekly injections (i.p.) of BMAA did not induce an ALS-like phenotype in wild type mice (FIGS. 5A-5D). Similar results were observed when using 100 mg/kg BMAA.

In another experiment, aged (i.e., 32-week old) wild type and C9orf72$^{-/-}$ mice were administered weekly i.p. injections of BMAA (500 mg/kg) or PBS (control) for six weeks. Body weight measurements were recorded each week up to 38 weeks starting at day zero (i.e., 32 weeks). Analysis of motor impairment via rotarod, open field locomotor, and catwalk testing (as described above) were also recorded at the start of the experiment (week 0, 10-weeks old) and every other week up to 38 weeks. Table 6 sets forth the scoring methodology related to motor impairment, tremor and rigidity of animals during testing. Exemplary results are set forth in FIGS. 6A-6E. The data demonstrated that administration of BMAA to C9orfF72$^{-/-}$ mice mildly exacerbates the ALS-like motor phenotype, but does not affect the increased inactivity and gait abnormalities of these mice.

Figure 7:
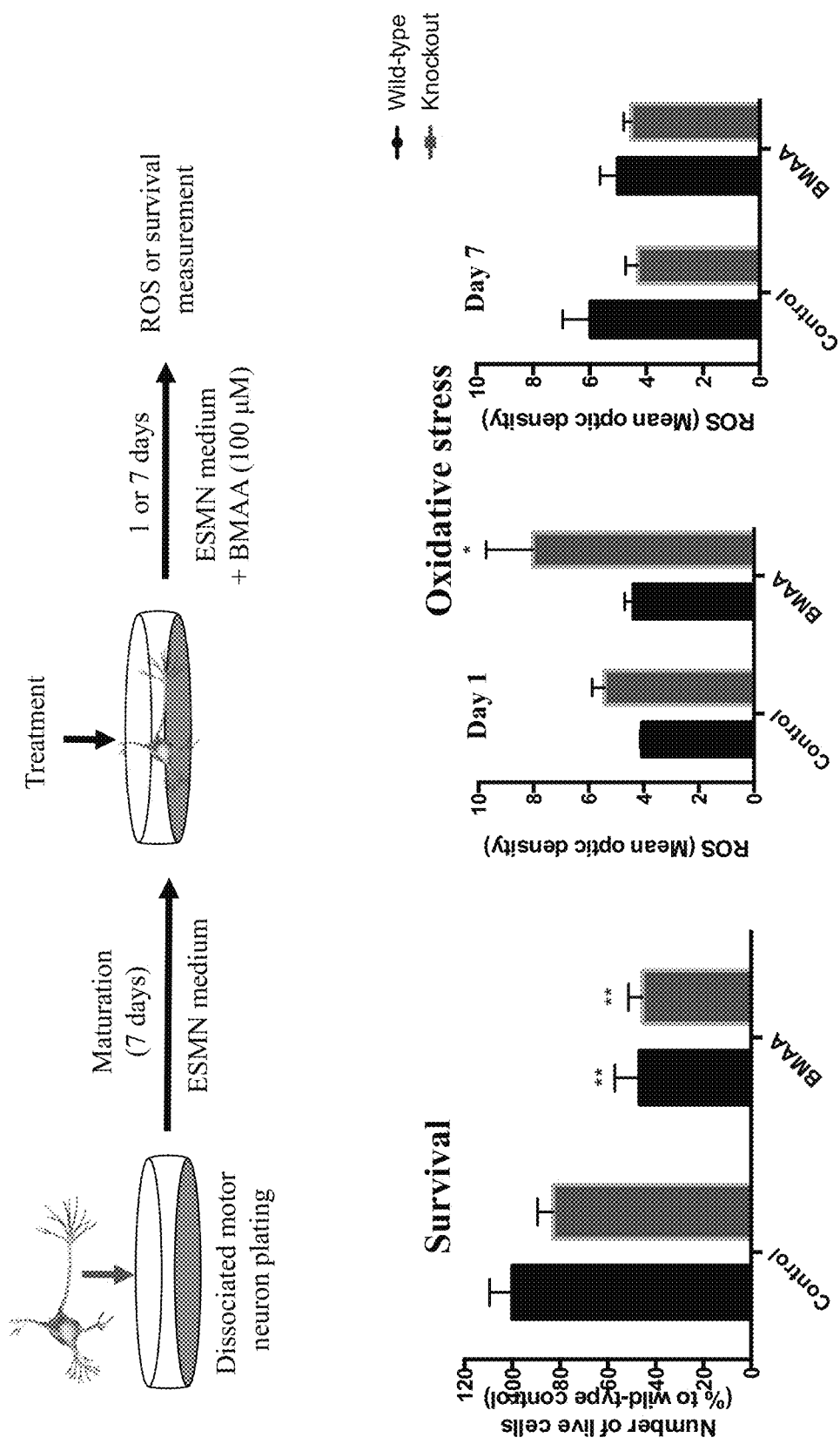
FIG. 7 shows the in vitro survival (bottom left) and oxidative stress (bottom right) of wild type and C9orf72$^{-/-}$ (knockout) motor neurons treated with BMAA. Top, schematic illustration of experimental design; Survival (bottom left) is presented as percentage of live neurons to wild type control (y-axis) in wild type (control) and C9orf72$^{-/-}$ (knockout) neurons treated with 100 mM B MAA. Oxidative stress at day 1 (left of bottom right) and day 7 (right of bottom right) is presented as mean optic density of ~485/520 nm fluorescence produced by a ROS-sensitive probe, Cell-ROX Green (Life Technologies). Statistical significance was determined using Student's unpaired t-test and one-way analysis of variance (ANOVA) test.

In another experiment, motor neurons from C9orfF72$^{-/-}$ mice were cultured as described above (see also FIG. 7) and treated with antisense oligonucleotides that selectively target sense strand repeat-containing RNAs and reduce sense-oriented RNA foci without affecting overall C9orf72 expression. Treatment was followed by addition of 100 mM BMAA. Survival and oxidative stress of cultured motor neurons were measured at days 1 and 7. Briefly, oxidative stress of plated embryonic stem cell-derived motor neurons (described above) was assessed by measuring the Reactive Oxygen Species (ROS) levels in the cells using Life Technologies' CellROX Oxidative Stress Green reagent at a final concentration of 5 μM and incubating for 30 minutes at 37° C. After incubation, cells were washed three times with PBS and fluorescence was measured using a standard microplate fluorometry. Exemplary results are set forth in FIG. 7. The data demonstrated that exposure of C9orfF72$^{-/-}$ motor neurons to BMAA causes increased oxidative stress.

In another experiment, mitochondrial function was determined in wild type and C9orf72$^{-/-}$ mice. Briefly, the ratio of mitochondrial to nuclear DNA of embryonic stem cell-derived motor neurons (described above) was measured by DNA isolation using DNAzol reagent (Invitrogen). Purity and quantity of DNA were assessed using Nanodrop 2000 spechtrophotometer (Thermo Scientific) and NovaQUANT mouse mitochondrial to nuclear ratio kit (Novagen) according to manufacturers specifications. Seahorse Bioscience XFe96 Analyzer was utilized to assess mitochondrial respiration of embryonic stem cell-derived motor neurons. Percent oxygen consumption rate to the first measurement of wild type mice was recorded for 12 measurements using the XFe96 Extracellular Flux Analyzer. The mean of first three measurements represented basal respiration, the next three after addition of oligomycin (1 μM) represented proton leak, the difference between basal respiration and proton leak represented ATP production, the next three measurements after the addition of FCCP (1 μM) represented maximal respiration, the difference between maximal and basal respiration represented spare respiratory capacity and the final three after the addition of rotenone/antimycin A (0.5 μM) represented non-mitochondrial respiration. All data were collected from at least three independent experiments and are reported as mean±SEM. Student's t-test was performed for statistical analysis comparing values of wild type mice to C9orf72$^{-/-}$ mice with * for P≤0.05,  for P≤0.01, and * for P≤0.001. Exemplary results are set forth in FIG. 8.

Figure 8:
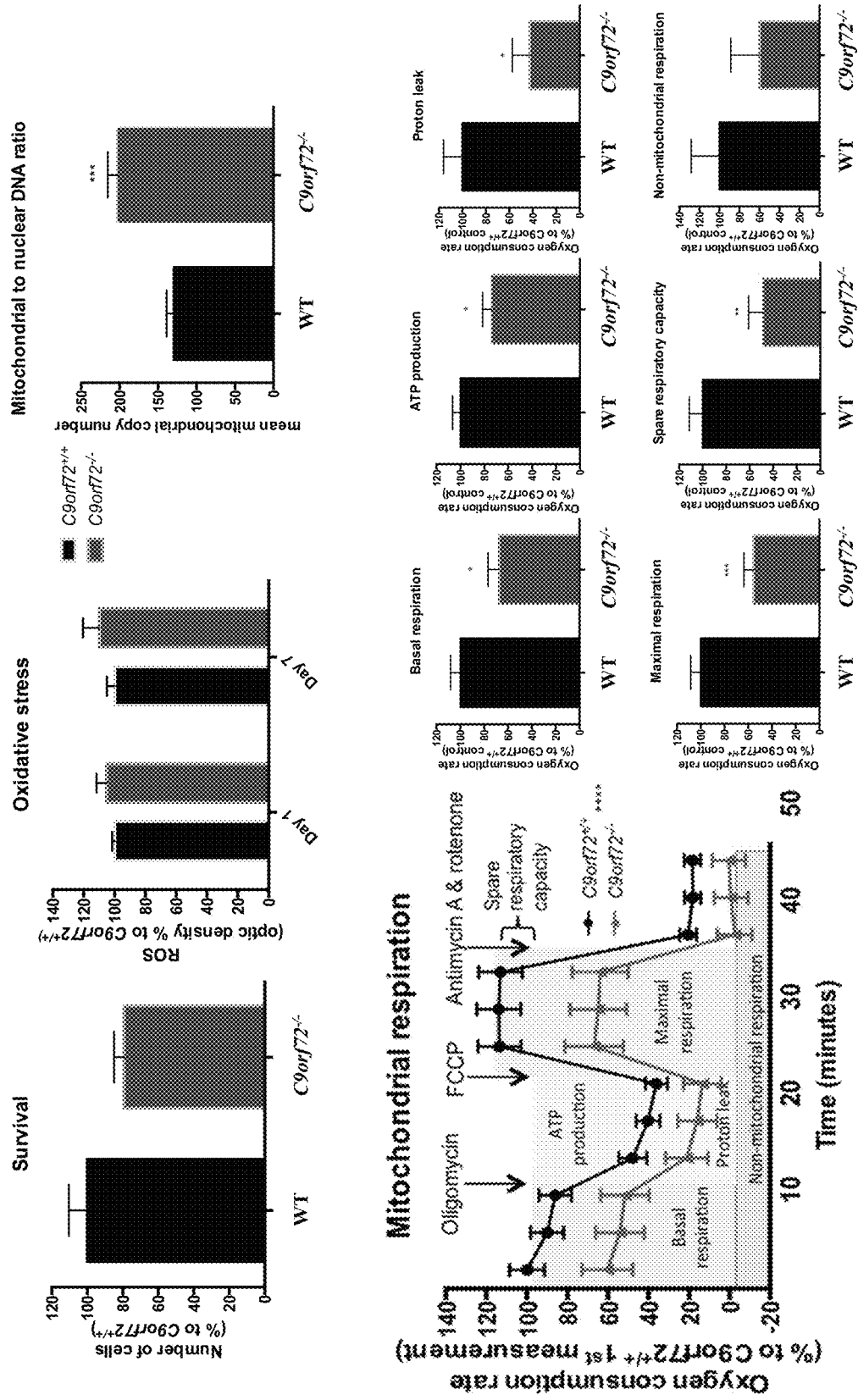
FIG. 8 shows exemplary survival (top left), oxidative stress (top middle), mitochondrial to nuclear DNA ratio (top right) and various measurements of mitochondrial function (bottom left to right) in wild type (WT) and C9orf72$^{-/-}$ motor neurons. Survival (top left) is presented as number of cells as percent to C9orf72$^{+/+}$; Oxidative stress at day 1 and day 7 is presented as Reactive Oxygen Species (ROS; optical density percent to C9orf72$^{+/+}$); Mitochondrial to nuclear DNA ratio is presented as mean mitochondrial copy number; Mitochondrial respiration is presented as oxygen consumption rate calculated as percent to C9orf72$^{+/+}$ 1$^{st}$ measurement; Basal respiration, ATP production, Proton leak, Maximal respiration, Spare respiratory capacity and Non-mitochondrial respiration are presented as oxygen consumption rate calculated as percent to C9orf72$^{+/+}$ control.

Previous reports have demonstrated that ATP depletion results in intracellular accumulation of Na$^+$, leading to pathological cellular hypertrophy (Liang D). et al., 2007, Neurosurg. Focus 22(5):E2). As shown in FIG. 8, using motor neurons differentiated from stem cells of wild type and C9orf72$^{-/-}$ mice (described above; see also Wichterle H. et al; 2002, Cell 110(3):385-97), C9orf72$^{-/-}$ mice demonstrated a failure in the Na—K ATPase pump due to lack of ATP and/or compromise of the cell membrane. In contrast, no difference in survival and oxidative stress was observed in wild type or C9orf72$^{-/-}$ neurons (FIG. 8, top). Interestingly, a greater amount of mitochondrial to nuclear DNA was observed in motor neurons from C9orf72$^{-/-}$ mice (FIG. 8, top right), as well as a significantly lower (P<0.0001) mitochondrial respiration rate as compared to wild type motor neurons (FIG. 8, bottom left). Further, basal respiration, ATP production, maximal respiration, proton leak and spare respiratory capacity were all significantly lower in C9orf72$^{-/-}$ motor neurons as compared to wild type (FIG. 8, lower right). Thus, motor neurons from C9orf72$^{-/-}$ mice demonstrate significant mitochondrial dysfunction that likely leads to cellular damage and hypertrophy.

The present example specifically demonstrates that C9orf72$^{-/-}$ mice show ALS-like motor deficits. Further, this example highlights that while BMAA kills motor neurons in an AMPA/kainate-mediated glutamate excitotoxicity pathway, exposure to BMAA is not enough to induce disease in vivo. Moreover, exposure to BMAA only mildly exacerbates the ALS-disease phenotype in C9orf72$^{-/-}$ mice. Therefore, the data presented herein suggest that, at least in some embodiments, the loss of C9orf72 protein in C9orf72$^{-/-}$ mice is not the prominent mechanism of ALS-FTD disease.

Taken together, the present disclosure specifically demonstrates that C9orf72$^{-/-}$ mice made according to Example 1 demonstrate complete ablation of the C9orf72 locus. Further, as described herein, C9orf72$^{-/-}$ mice develop several distinct phenotypes throughout development characterized by, for example, significant motor deficits and a disruption in immune system and mitochondrial function. For example, C9orf72$^{-/-}$ mice develop an autoimmune phenotype characterized by a significant increase in serum autoantibody concentration and infiltration of various immune cells into the spleen, lymph nodes, bone marrow, kidney and blood. Interestingly, immunophenotyping data described herein illustrate that C9orf72 gene product plays a critical role in immune system homeostasis and neuronal health. In particular, splenomegaly and lymphadenopathy in C9orf72$^{-/-}$ mice are a result of infiltration of a number of cell populations including plasma cells, monocytes, granulocytes, and most notably, F4/80$^+$ macrophages as early as 8 weeks of age and progressive through 60 weeks of age. Cytokine panel and molecular profiling data strongly suggest an increased Th1/Macrophage activating pathway in C9orf72$^{-/-}$ mice. Thus, the present disclosure specifically demonstrates that haploinsufficiency is unlikely the main cause of ALS-FTD pathology in the context of C9orf72 and provides a novel role for C9orf72 in immune function and homeostasis in a comprehensive phenotypic analysis of a non-human animal with global C9orf72 ablation.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

We claim:

1. A method of making a population of motor neurons that exhibit mitochondrial dysfunction and/or increased oxidative stress compared to wildtype motor neuron cells, the methods comprising
    establishing embryoid bodies from a genetically engineered rodent embryonic stem (ES) cell, wherein the ES cell comprises in its genome a deletion consisting of the full coding portion of exon 2 through the full coding portion of exon 11 of sequence in a C9orf72 locus, and differentiating the embryoid bodies into a population of motor neurons,
    wherein the population of motor neurons demonstrate mitochondrial dysfunction or increased oxidative stress compared to wildtype motor neurons.

2. The method of claim 1, wherein the C9orf72 locus comprises a reporter gene.

3. The method of claim 2, wherein the reporter gene is operably linked to the endogenous C9orf72 promoter at the endogenous C9orf72 locus.

4. The rodent of claim 2, wherein the reporter gene is operably linked to exon 1 of the C9orf72 locus.

5. The method of claim 1, wherein the rodent ES cell is a rat ES cell or a mouse ES cell.

6. The method of claim 1, wherein the rodent ES cell is homozygous for the deletion.

7. The method of claim 1, wherein the rodent ES cell is heterozygous for the deletion.

8. A method for screening a candidate agent for reducing mitochondrial dysfunction and/or oxidative stress in a motor neuron comprising (a) culturing the population of motor neurons made according to the method of claim 1 in the presence or absence of an agent;
    (b) determining whether the agent prevents, inhibits, and/or reduces mitochondrial dysfunction and/or oxidative stress in the population of motor neurons compared to a control population of motor neurons cultured in the absence of the agent; wherein the prevention, inhibition, and/or reduction of oxidative stress in the motor neurons is indicative of a candidate agent for reducing mitochondrial dysfunction and/or oxidative stress in a motor neuron.

* * * * *